(12) United States Patent
Starr et al.

(10) Patent No.: US 8,440,629 B2
(45) Date of Patent: May 14, 2013

(54) CYCLIC RECEPTOR-ASSOCIATED PROTEIN (RAP) PEPTIDES

(75) Inventors: Christopher M. Starr, Sonoma, CA (US); Todd C. Zankel, San Francisco, CA (US)

(73) Assignee: Raptor Pharmaceuticals Inc., Novato, CA (US)

( * ) Notice: Subject to any disclaimer, the term of this patent is extended or adjusted under 35 U.S.C. 154(b) by 415 days.

(21) Appl. No.: 12/600,786

(22) PCT Filed: Mar. 21, 2008

(86) PCT No.: PCT/US2008/057863
§ 371 (c)(1),
(2), (4) Date: Feb. 5, 2010

(87) PCT Pub. No.: WO2008/116171
PCT Pub. Date: Sep. 25, 2008

(65) Prior Publication Data
US 2010/0210517 A1 Aug. 19, 2010

Related U.S. Application Data

(60) Provisional application No. 60/919,238, filed on Mar. 21, 2007.

(51) Int. Cl.
*C07K 14/705* (2006.01)
*A61K 38/17* (2006.01)

(52) U.S. Cl.
USPC .......................... 514/21.3; 530/317; 424/9.1

(58) Field of Classification Search .................... 514/11, 514/21.3; 530/317; 424/9.1
See application file for complete search history.

(56) References Cited

U.S. PATENT DOCUMENTS

| | | | |
|---|---|---|---|
| 4,391,904 | A | 7/1983 | Litman et al. |
| 4,394,448 | A | 7/1983 | Szoka, Jr. et al. |
| 5,186,941 | A | 2/1993 | Callahan et al. |
| 5,962,012 | A | 10/1999 | Lin et al. |
| 5,994,129 | A | 11/1999 | Armstrong et al. |
| 6,048,729 | A | 4/2000 | Selden et al. |
| 6,063,630 | A | 5/2000 | Treco et al. |
| 6,069,167 | A | 5/2000 | Sokol |
| 6,261,595 | B1 | 7/2001 | Stanley et al. |
| 6,426,208 | B1 | 7/2002 | Kakkis et al. |
| 6,569,661 | B1 | 5/2003 | Qin et al. |
| 6,585,971 | B1 | 7/2003 | Kakkis |
| 6,596,762 | B2 | 7/2003 | Sokol |
| 2003/0211113 | A1 | 11/2003 | Kakkis et al. |
| 2004/0009906 | A1 | 1/2004 | Kakkis et al. |

FOREIGN PATENT DOCUMENTS

| | | |
|---|---|---|
| WO | WO-2005/002515 | 1/2005 |
| WO | WO-2006/138343 | 12/2006 |
| WO | WO-2008/036682 | 3/2008 |

OTHER PUBLICATIONS

Agrawal et al., Efficient differentiation of functional hepatocytes from human embryonic stem cells, *Stem Cells*, 26:1117-27 (2008).
Allinson et al., ADAMs family members as amyloid precursor protein alpha-secretases, *J. Neurosci. Res.*, 74:342-52 (2003).
Amour et al., The in vitro activity of ADAM-10 is inhibited by TIMP-1 and TIMP-3, *FEBS Lett.*, 473:275-9 (2000).
Andersen et al., Analysis of a two-domain binding site for the urokinase-type plasminogen activator-plasminogen activator inhibitor-1 complex in low-density-lipoprotein-receptor-related protein, *Biochem. J.*, 357(pt.1):289-96 (2001).
Andersen et al.. Ca2+ binding to complement-type repeat domains 5 and 6 from the low-density lipoprotein receptor-related protein, *BMC Biochem.*, 4:7 (2003).
Andersen et al., Differential binding of ligands to the apolipoprotein E receptor 2. *Biochemistry*, 42:9355-64 (2003).
Andersen et al., Dominant thermodynamic role of the third independent receptor binding site in the receptor-associated protein RAP, *Biochemistry*, 40:15408-17 (2001).
Andersen et al., Identification of the minimal functional unit in the low density lipoprotein receptor-related protein for binding the receptor-associated protein (RAP). A conserved acidic residue in the complement-type repeats is important for recognition of RAP. *J. Biol. Chem.*, 275:21017-24 (2000).
Andersen et al., Specific binding of alpha-macroglobulin to complement-type repeat CR4 of the low-density lipoprotein receptor-related protein, *Biochemistry*, 39:10627-33 (2000).
Armengol et al., Orthotopic implantation of human hepatocellular carcinoma in mice: analysis of tumor progression and establishment of the BCLC-9 cell line, *Clin. Cancer Res.*, 110:2150-7 (2004).
Bard et al., Peripherally administered antibodies against amyloid beta-peptide enter the central nervous system and reduce pathology in a mouse model of Alzheimer disease, *Nat. Med.*, 6:916-9 (2000).
Basu et al., CD91 is a common receptor for heat shock proteins gp96, hsp90, hsp70, and calreticulin, *Immunity*, 14:303-13 (2001).
Beisiegel et al., The LDL-receptor-related protein, LRP, is an apolipoprotein E-binding protein, *Nature*, 341:162-4 (1989).
Benchenane et al., Tissue-type plasminogen activator crosses the intact blood-brain barrier by low-density lipoprotein receptor-related protein-mediated transcytosis, *Circulation*, 111:2241-9 (2005).
Benjannet et al., Alpha1-antitrypsin Portland inhibits processing of precursors mediated by proprotein convertases primarily within the constitutive secretory pathway, *J. Biol. Chem.*, 272:26210-8 (1997).
IBickel et al., Delivery of peptides and proteins through the blood-brain barrier, *Adv. Drug Deliv. Rev.*, 46:247-79 (2001).
Bosshart et al., The cytoplasmic domain mediates localization of furin to the trans-Golgi network en route to the endosomal/lysosomal system, *J. Cell Biol.*, 126:1157-72 (1994).

(Continued)

*Primary Examiner* — Chih-Min Kam
(74) *Attorney, Agent, or Firm* — Marshall, Gerstein & Borun LLP

(57) ABSTRACT

The present invention relates generally to receptor-selective variants of the low-density lipoprotein receptor-associated protein (RAP) and compositions thereof, methods of generating such variants and methods of using such receptor-selective RAP variant compositions for therapeutic purposes.

20 Claims, 24 Drawing Sheets

OTHER PUBLICATIONS

Boucher et al., LRP: role in vascular wall integrity and protection from atherosclerosis, *Science*, 300:329-32 (2003).

Bu et al., RAP, a novel type of ER chaperone, *Trends Cell Biol.*, 8:272-6 (1998).

Cam et al., The low density lipoprotein receptor-related protein 1B retains beta-amyloid precursor protein at the cell surface and reduces amyloid-beta peptide production, *J. Biol. Chem.*, 279:29639-46 (2004).

Camarero et al,, Rescuing a destabilized protein fold through backbone cyclization, *J. Mol. Biol.*, 308:1045-62 (2001).

Casas et al., Massive CA1/2 neuronal loss with intraneuronal and N-terminal truncated Abeta42 accumulation in a novel Alzheimer transgenic model, *Am. J. Pathol.*, 165:1289-300 (2004).

Davies et al., The cyclization of peptides and depsipeptides, *J. Pept. Sci.*, 9:471-501 (2003).

Deane et al., LRP/amyloid beta-peptide interaction mediates differential brain efflux of Abeta isoforms, *Neuron*, 43:333-44 (2004).

Dehouck et al., A new function for the LDL receptor: transcytosis of LDL across the blood-brain barrier, *J. Cell Biol.*, 138:877-89 (1997).

Dolmer et al., Characterization of the calcium site in two complement-like domains from the low-density lipoprotein receptor-related protein (LRP) and comparison with a repeat from the low-density lipoprotein receptor, *Biochemistry*, 37:17016-23 (1998).

Dolmer et al., NMR solution structure of complement-like repeat CR3 from the low density lipoprotein receptor-related protein. Evidence for specific binding to the receptor binding domain of human alpha(2)-macroglobulin, *J. Biol. Chem.*, 275:3264-9 (2000).

Elmore et al., Comparative tissue-specific toxicities of 20 cancer preventive agents using cultured cells from 8 different normal human epithelia, *In Vitr. Mol. Toxicol.*, 14:191-207 (2001).

Fahrenholz et al., Alpha-secretase activity of the disintegrin metalloprotease ADAM 10. Influences of domain structure, *Ann. N Y Acad. Sci.*, 920:215-22 (2000).

Fillebeen et al., Receptor-mediated transcytosis of lactoferrin through the blood-brain barrier, *J. Biol. Chem.*, 274:7011-7 (1999).

Fisher et al., Structure of an LDLR-RAP complex reveals a general mode for ligand recognition by lipoprotein receptors, *Mol. Cell.*, 22:277-83 (2006).

Fitzgerald et al., *Pseudomonas* exotoxin-mediated selection yields cells with altered expression of low-density lipoprotein receptor-related protein, *J. Cell Biol.*, 129:1533-41 (1995).

Furukawa et al., Increased activity-regulating and neuroprotective efficacy of alpha-secretase-derived secreted amyloid precursor protein conferred by a C-terminal heparin-binding domain, *J. Neurochem.*, 67:1882-96 (1996).

Galkin et al., CVS-3983, a selective matriptase inhibitor, suppresses the growth of androgen independent prostate tumor xenografts, *Prostate*, 61:228-35 (2004).

Gong et al., Alzheimer's disease-affected brain: presence of oligomeric A beta ligands (ADDLs) suggests a molecular basis for reversible memory loss, *Proc. Natl. Acad. Sci. USA*, 100:10417-22 (2003).

Goudriaan et al., Protection from obesity in mice lacking the VLDL receptor, *Arterioscler. Thomb. Vasc. Biol.*, 21:1488-93 (2001).

Goudriaan et al., The VLDL receptor plays a major role in chylomicron metabolism by enhancing LPL-mediated triglyceride hydrolysis, *J. Lipid Res.*, 45:1475-81 (2004).

Hahn-Dantona et al., The low density lipoprotein receptor-related protein modulates levels of matrix metalloproteinase 9 (MMP-9) by mediating its cellular catabolism, *J. Biol. Chem.*, 276:15498-503 (2001).

Herz et al., Coaxin the LDL receptor family into the fold, *Cell*, 112:289-92 (2003).

Herz et al., Gene transfer and disruption strategies to elucidate hepatic lipoprotein receptor functions, *Atherosclerosis*, 118 Suppl:S37-41 (1995).

Herz et al., Lipoprotein receptors in the nervous system, *Annu. Rev. Biochem.*, 71:405-34 (2002).

Hickey et al., Apoptosis in Huntington's disease, *Prog. Neuropsychopharmacol. Biol. Psychiatry*, 27:255-65 (2003).

Hiltunen et al., Expression of LDL receptor, VLDL receptor, LDL receptor-related protein, and scavenger receptor in rabbit atherosclerotic lesions: marked induction of scavenger receptor and VLDL receptor expression during lesion development, *Circulation*, 97:1079-86 (1998).

Hoang et al., Expression of LDL receptor-related protein 5 (LRP5) as a novel marker for disease progression in high-grade osteosarcoma, *Int. J. Cancer*, 109:106-11 (2004).

Hoang et al., Gene expression profiling identifies matriptase overexpression in malignant mesothelioma, *Chest*, 125:1843-52 (2004).

Hoe et al., Multiple pathways of apolipoprotein E signaling in primary neurons, *J. Neurochem.*, 93:145-55 (2005).

Holmen et al., Essential role of beta-catenin in postnatal bone acquisition, *J. Biol. Chem.*, 280:21162-8 (2005).

Horn et al., Molecular analysis of ligand binding to the second cluster of complement-type repeats of the low density lipoprotein receptor-related protein. Evidence for an allosteric component in receptor-associated protein-mediated inhibition of ligand binding, *J. Biol. Chem.*, 272:13608-13 (1997).

Hsia et al., Plaque-independent disruption of neural circuits in Alzheimer's disease mouse models, *Proc. Natl. Acad. Sci. USA*, 96:3228-33 (1999).

Hsieh et al., Mesd encodes an LRP5/6 chaperone essential for specification of mouse embryonic polarity, *Cell*, 122:355-67 (2003).

Huang et al., NMR solution structure of complement-like repeat CR8 from the low density lipoprotein receptor-related protein, *J. Biol. Chem.*, 274:14130-6 (1999).

Hung et al., Assembly of adherens junctions is required for sphingosine 1-phosphate-induced matriptase accumulation and activation at mammary epithelial cell-cell contacts, *Am. J. Physiol. Cell Physiol.*, 286:C1159-69 (2004).

Hussain et al., Characterization of the ectodomain shedding of the beta-site amyloid precursor protein-cleaving enzyme 1 (BACE1), *J. Biol. Chem.*, 278:36264-8 (2003).

lInternational Preliminary Report on Patentability for corresponding International Application No. PCT/US2008/057863, dated Sep. 22, 2009.

International Search Report and Written Opinion for corresponding International Application No. PCT/US2008/057863, dated Jul. 31, 2008.

Irie et al., Transendothelial transport of macromolecules: the concept of tissue-blood harriers, *Cell Biol. Rev.*, 25:317-33, 340-1 (1991).

Isbell et al., Functional mimicry of the LDL receptor-associated protein through multimerization of a minimized third domain, *Biochem. Biophys. Res. Commun.*, 364:614-9 (2007).

Isbell et al., Minimization of the third domain of the LDL receptor-associated protein (RAP), *Biochem. Biophys. Res. Commun.*, 361:758-62 (2007).

Johnson et al., Possible role of matriptase in the diagnosis of ovarian cancer, *Expert Rev. Mol. Diagn.*, 3:331-8 (2003).

Kataoka et al., Role of cancer cell-stroma interaction in invasive growth of cancer cells, *Hum. Cell*, 16:1-14 (2003).

Kim et al., Gene transfer into human hepatoma cells by receptor-associated protein/polylysine conjugates, *Bioconjug. Chem.*, 15:326-32 (2004).

Lee et al., Increased expression of matriptase is associated with histopathologic grades of cervical neoplasia, *Hum. Pathol.*, 36:626-33 (2005).

Lee at al., RAP uses a histidine switch to regulate its interaction with LRP in the ER and Golgi, *Mol. Cell*, 22:423-30 (2006).

Li et al., Identification of a human follicular dendritic cell molecule that stimulates germinal center B cell growth, *J. Exp. Med.*, 191:1077-84 (2000).

Li et al., LRP6 expression promotes cancer cell proliferation and tumorigenesis by altering beta-catenin subcellular distribution, *Oncogene*, 23:9129-35 (2004).

Li et al., Novel follicular dendritic cell molecule, 8D6, collaborates with CD44 in supporting lymphomagenesis by a Burkitt lymphoma cell line, L3055, *Blood*, 104:815-21 (2004).

Lichtenthaler et al., Amyloid at the cutting edge: activation of alpha-secretase prevents amyloidogenesis in an Alzheimer disease mouse model, *J. Clin. Invest.*, 113:1384-7 (2004).

Lin et al., GDNF: a glial cell line-derived neurotrophic factor for midbrain dopaminergic neurons, *Science*, 260:1130-2 (1993).

Lisi et al., Impaired thyroglobulin (Tg) secretion by FRTL-5 cells transfected with soluble receptor associated protein (RAP): evidence for a role of RAP in the Tg biosynthetic pathway, *J. Endocrinol. Invest.*, 26:1105-10 (2003).

List et al., Deregulated matriptase causes ras-independent multistage carcinogenesis and promotes ras-mediated malignant transformation, *Genes Dev.*, 19:1934-50 (2005).

Lundgren et al., Tissue distribution of human gp330/megalin, a putative Ca(2+)-sensing protein, *J. Histochem. Cytochem.*, 45:383-92 (1997).

Marino et al., Role of megalin (gp330) in transcytosis of thyroglobulin by thyroid cells. A novel function in the control of thyroid hormone release, *J. Biol. Chem.*, 275:7125-37 (2000).

Martin et al., Involvement of the neurotensin receptor-3 in the neurotensin-induced migration of human microglia, *J. Neurosci.*, 23:1198-205 (2003).

May et al., Integration of endocytosis and signal transduction by lipoprotein receptors, Sci STKE 2003 (176): PE12.

Mayer et al., Sorting of furin in polarized epithelial and endothelial cells: expression beyond the Golgi apparatus, *J. Histochem. Cytochem.*, 52:567-79 (2004).

McCormick et al., Independent and cooperative roles of N-glycans and molecular chaperones in the folding and disulfide bond formation of the low-density lipoprotein (LDL) receptor-related protein, *Biochemistry*, 44:5794-803 (2005).

Medved et al., Domain organization of the 39-kDa receptor-associated protein, *J. Biol. Chem.*, 274:717-27 (1999).

Melman et al., High affinity binding of receptor-associated protein to heparin and low density lipoprotein receptor-related protein requires similar basic amino acid sequence motifs, *J. Biol. Chem.*, 276:29338-46 (2001).

Meziane et al., Memory-enhancing effects of secreted forms of the beta-amyloid precursor protein in normal and amnestic mice, *Proc. Natl. Acad. Sci. USA*, 95:12683-8 (1998).

Migliorini et al., Allosteric modulation of ligand binding to low density lipoprotein receptor-related protein by the receptor-associated protein requires critical lysine residues within its carboxyl-terminal domain, *J. Biol. Chem.*, 278:17986-92 (2003).

Miret et al., Comparison of in vitro assays of cellular toxicity in the human hepatic cell line HepG2, *J. Biomol. Screen.*, 11:184-93 (2006).

Mizuguchi et al., LRP5, low-density-lipoprotein-receptor-related protein 5, is a determinant for bone mineral density, *J. Hum. Genet.*, 49:80-6 (2004).

Moestrup et al., Distribution of the alpha 2-macroglobulin receptor/low density lipoprotein receptor-related protein in human tissues, *Cell Tissue Res.*, 269:375-82 (1992).

Moestrup et al., Megalin- and cubilin-mediated endocytosis of protein-bound vitamins, lipids, and hormones in polarized epithelia, *Annu. Rev. Nutr.*, 21:407-28 (2001).

Nagaike et al., Paradoxically enhanced immunoreactivity of hepatocyte growth factor activator inhibitor type 1 (HAI-1) in cancer cells at the invasion front, *Cancer Sci.*, 95:728-35 (2004).

Neels et al., Interaction between factor VIII and LDL receptor-related protein. Modulation of coagulation?, *Trends Cardiovasc. Med.*, 10:8-14 (2000).

Obermoeller et al., Differential functions of triplicated repeats suggest two independent roles for the receptor-associated protein as a molecular chaperone, *J. Biol. Chem.*, 272:10761-8 (1997).

Oberst et al., Expression of the serine protease matriptase and its inhibitor HAI-1 in ovarian cancer: correlation with clinical outcome and tumor clinicopathological parameters, *Clin. Cancer Res.*, 8:1101-7 (2002).

Oberst et al., Matriptase and HAI-1 are expressed by normal and malignant epithelial cells in vitro and in vivo, *Am. J. Pathol.*, 158:1301-11 (2001).

Oberst et al., The activation of matriptase requires its noncatalytic domains, serine protease domain, and its cognate inhibitor, *J. Biol. Chem.*, 278:26773-9 (2003).

Obunike et al., Transcytosis of lipoprotein lipase across cultured endothelial cells requires both heparan sulfate proteoglycans and the very low density lipoprotein receptor, *J. Biol. Chem.*, 276:8934-41 (2001).

Okubo et al., Orthotopic hepatocellular carcinoma model with a controlled and reproducible tumorigenicity, *J. Gastroenterol. Hepatol.*, 22:423-8 (2007).

Olsen, Life without perlecan has its problems, *J. Cell Biol.*, 147:909-12 (1999).

Orlando et al., Identification of the second cluster of ligand-binding repeats in megalin as a site for receptor-ligand interactions, *Proc. Natl. Acad. Sci. USA*, 94:2368-73 (1997).

Pan et al., Efficient transfer of receptor-associated protein (RAP) across the blood-brain barrier, *J. Cell Sci.*, 117(Pt. 21):5071-8 (2004).

Pfistermueller et al., Preferential recognition of the very low-density lipoprotein receptor ligand binding site by antibodies from phage display libraries, *FEBS Lett.*, 396:14-20 (1996).

Postina et al., A disintegrin-metalloproteinase prevents amyloid plaque formation and hippocampal defects in an Alzheimer disease mouse model, *J. Clin. Invest.*, 113:1456-64 (2004).

Prince et al., Lipoprotein receptor binding, cellular uptake, and lysosomal delivery of fusions between the receptor-associated protein (RAP) and alpha-L-iduronidase or acid alpha-glucosidase, *J. Biol. Chem.*, 279:35037-46 (2004).

Qiu et al., ApoE isoforms affect neuronal N-methyl-D-aspartate calcium responses and toxicity via receptor-mediated processes, *Neuroscience*, 122:291-303 (2003).

Qu et al., Role of VLDL receptor in the process of foam cell formation, *J. Huazhong Univ. Sci. Technology. Med. Sci.*, 24:1-4,8 (2004).

Rall et al., The domain structure of human receptor-associated protein. Protease sensitivity and guanidine HCl denaturation, *J. Biol. Chem.*, 273:24152-7 (1998).

Rohn et al., Bi-directional trafficking between the trans-Golgi network and the endosomal/lysosomal system, *J. Cell Sci.*, 113 (Pt. 12):2093-101 (2000).

Rosebrough et al., Biochemical modification of streptavidin and avidin: in vitro and in vivo analysis, *J. Nucl. Med.*, 37:1380-4 (1996).

Rudenko et al., Structure of the LDL receptor extracellular domain at endosomal pH, *Science*, 298:2353-8 (2002).

Santin et al., Gene expression profiles in primary ovarian serous papillary tumors and normal ovarian epithelium: identification of candidate molecular markers for ovarian cancer diagnosis and therapy, *Int. J. Cancer*, 112:14-25 (2004).

Santin et al., The novel serine protease tumor-associated differentially expressed gene-15 (matriptase/MT-SP1) is highly overexpressed in cervical carcinoma, *Cancer*, 98:1898-904 (2003).

Schenk et al., Immunization with amyloid-beta attenuates Alzheimer-disease-like pathology in the PDAPP mouse, *Nature*, 400:173-7 (1999).

Schmitz et al., Hippocampal neuron loss exceeds amyloid plaque load in a transgenic mouse model of Alzheimer's disease, *Am. J. Pathol.*, 164:1495-502 (2004).

Schneider et al., LDL receptor relatives at the crossroad of endocytosis and signaling, *Cell Mol. Life Sci.*, 60:892-903 (2003).

Selkoe, Amyloid beta-protein and the genetics of Alzheimer's disease, *J. Biol. Chem.*, 271:18295-8 (1996).

Shayo et al., The putative blood-brain barrier transporter for the beta-amyloid binding protein apolipoprotein j is saturated at physiological concentrations, *Life Sci.*, 60:PL115-8 (1997).

Shimizu et al., Regulation of adiponectin receptor expression in human liver and a hepatocyte cell line, *Metabolism*, 56:1478-85 (2007).

Sidhu et al., Phage display for selection of novel binding peptides, *Methods Enzymol.*, 328:333-63 (2000).

Simonovic et al., Calcium coordination and pH dependence of the calcium affinity of ligand-binding repeat CR7 from the LRP. Comparison with related domains from the LRP and the LDL receptor, *Biochemistry*, 40:15127-34 (2001).

Srour et al., TACE/ADAM-17 maturation and activation of sheddase activity require proprotein convertase activity, *FEBS Lett.*, 554:275-83 (2003).

Suzuki et al., Inhibition of tumor invasion by genomic down-regulation of matriptase through suppression of activation of receptor-bound pro-urokinase, *J. Biol. Chem.*, 279:14899-908 (2004).

Tacken et al., Living up to a name: the role of the VLDL receptor in lipid metabolism, *Curr. Opin. Lipidol.*, 12:275-9 (2001).

Takahashi et al., The very low density lipoprotein (VLDL) receptor—a peripheral lipoprotein receptor for remnant lipoproteins into fatty acid active tissues, *Mol. Cell. Biochem.*, 248:121-7 (2003).

Tanimoto et al., Ovarian tumor cells express a transmembrane serine protease: a potential candidate for early diagnosis and therapeutic intervention, *Tumour Biol.*, 22:104-14 (2001).

Tanimoto et al., Transmembrane serine protease TADG-15 (ST14/Matriptase/MT-SP1): expression and prognostic value in ovarian cancer, *Br. J. Cancer*, 92:278-83 (2005).

Thompson et al., Clustal W: improving the sensitivity of progressive multiple sequence alignment through sequence weighting, position-specific gap penalties and weight matrix choice, *Nucleic Acids Res.*, 22:4673-80 (1994).

Trabi et al., Circular proteins—no end in sight, *Trends Biochem. Sci.*, 27:132-8 (2002).

Tsai et al., Fibrillar amyloid deposition leads to local synaptic abnormalities and breakage of neuronal branches, *Nat. Neurosci.*, 7:1181-3 (2004).

Tsuzuki et al., Evidence for the occurrence of membrane-type serine protease 1/matriptase on the basolateral sides of enterocytes, *Biochem. J.*, 388(Pt.2):679-87 (2005).

Vash et al., Three complement-type repeats of the low-density lipoprotein receptor-related protein define a common binding site for RAP, PAI-1, and lactoferrin, *Blood*, 92:3277-85 (1998).

Verdaguer et al., X-ray structure of a minor group human rhinovirus bound to a fragment of its cellular receptor protein, *Nat. Struct. Mol. Biol.*, 11:429-34 (2004).

Wang et al., Role of calcium in protein folding and function of Tva, the receptor of subgroup A avian sarcoma and leukosis virus, *J. Virol.*, 75:2051-8 (2001).

Warshawsky et al., 39-kD protein inhibits tissue-type plasminogen activator clearance in vivo, *J. Clin. Invest.*, 92:937-44 (1993).

Westendorf et al., Wnt signaling in osteoblasts and bone diseases, *Gene*, 341:19-39 (2004).

Wilbur et al., Streptavidin in antibody pretargeting. Comparison of a recombinant streptavidin with two streptavidin mutant proteins and two commercially available streptavidin proteins, *Bioconjug. Chem.*, 9:100-7 (1998).

Wyne et al., Expression of the VLDL receptor in endothelial cells, *Arterioscler Thromb. Vasc. Biol.*, 16:407-15 (1996).

Xia et al., Intramembrane proteolysis by presenilin and presenilin-like proteases, *J. Cell Sci.*, 116(Pt. 14):2839-44 (2003).

Yagyu et al., Very low density lipoprotein (VLDL) receptor-deficient mice have reduced lipoprotein lipase activity. Possible causes of hypertriglyceridemia and reduced body mass with VLDL receptor deficiency, *J. Biol. Chem.*, 277:10037-43 (2002).

Yao et al., A novel orthotopic tumor model to study growth factors and oncogenes in hepatocarcinogenesis, *Clin. Cancer Res.*, 9:2719-26 (2003).

Zerbinatti et al., Increased soluble amyloid-beta peptide and memory deficits in amyloid model mice overexpressing the low-density lipoprotein receptor-related protein, *Proc. Natl. Acad. Sci. USA*, 101:1075-80 (2004).

Zhang et al. The LRP5 high-bone-mass G171V mutation disrupts LRP5 interaction with Mesd, *Mol. Cell. Biol.*, 24:4677-84 (2004).

Zheng et al., Organ distribution in rats of two members of the low-density lipoprotein receptor gene family, gp330 and LRP/alpha 2MR, and the receptor-associated protein (RAP), *J. Histochem. Cytochem.*, 42:531-42 (1994).

Zlokovic et al., Glycoprotein 330/megalin: probable role in receptor-mediated transport of apolipoprotein J alone and in a complex with Alzheimer disease amyloid beta at the blood-brain and blood-cerebrospinal fluid barriers, *Proc. Natl. Acad. Sci. USA*, 93:4229-34 (1996).

FIGURE 2

Figure 3
Native CR proteins
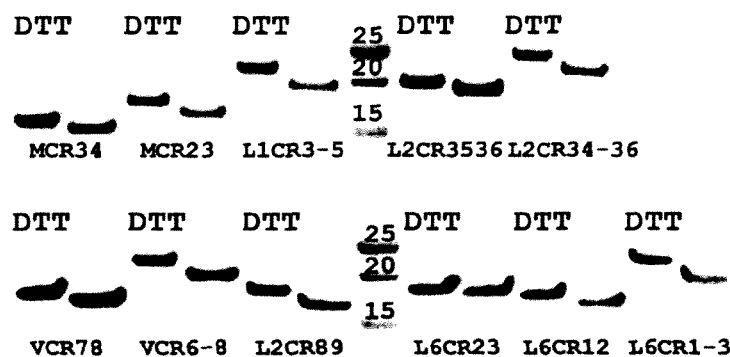
LRP2 CR89 variants
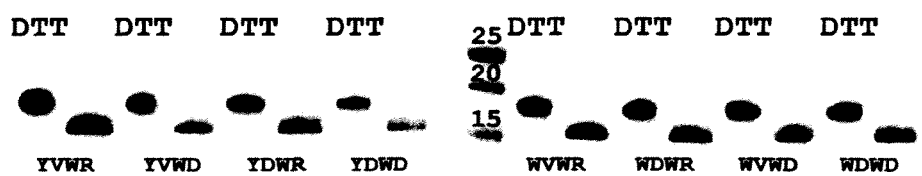

Figure 5B
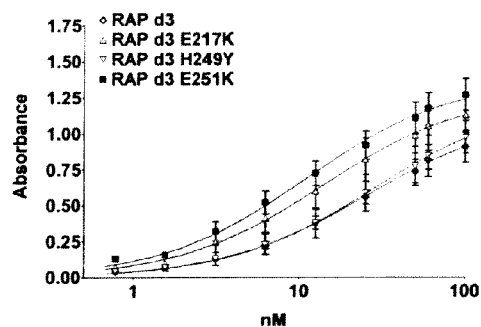
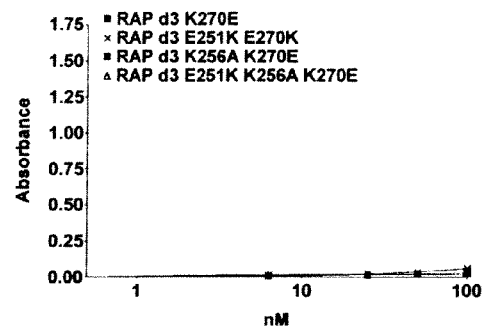
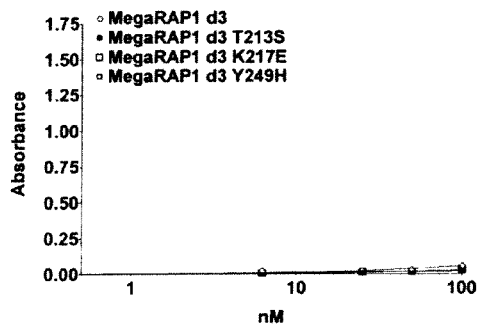
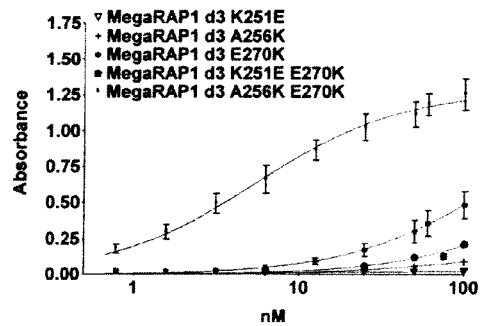

Figure 5C

| d3 sequence | variable positions | | | | | | LRP2 CR89 | | LRP1 CR3-5 | |
|---|---|---|---|---|---|---|---|---|---|---|
| | 213 | 217 | 249 | 251 | 256 | 270 | $K_d$ (nM) | % max | $K_d$ (nM) | % max |
| RAP | S | E | H | E | K | K | NF | 5% | 16 ± 4 | 76% |
| RAP E217K | S | K | H | E | K | K | NF | 5% | 9 ± 1 | 91% |
| RAP H249Y | S | E | Y | E | K | K | NF | 2% | 28 ± 8 | 90% |
| RAP E251K | S | E | H | K | K | K | NF | 5% | 7 ± 1 | 100% |
| RAP K270E | S | E | H | E | K | E | NF | 2% | NF | 4% |
| RAP K256A, K270E | S | E | H | E | A | E | NF | 3% | NF | 2% |
| RAP E251K, K270E | S | E | H | K | K | E | NF | 2% | NF | 4% |
| RAP E251K, K256A, K270E | S | E | H | K | A | E | 114 ± 32 | 40% | NF | 2% |
| MegaRAP1 | T | K | Y | K | A | E | 38 ± 3 | 88% | NF | 4% |
| MegaRAP1 T213S | S | K | Y | K | A | E | 19 ± 1 | 94% | NF | 2% |
| MegaRAP1 K217E | T | E | Y | K | A | E | 25 ± 1 | 88% | NF | 2% |
| MegaRAP1 Y249H | T | K | H | K | A | E | NF | 35% | NF | 2% |
| MegaRAP1 K251E | T | K | Y | E | A | E | NF | 11% | NF | 2% |
| MegaRAP1 A256K | T | K | Y | K | K | E | NF | 2% | NF | 6% |
| MegaRAP1 E270K | T | K | Y | K | A | K | 8 ± 1 | 100% | 114 ± 31 | 85% |
| MegaRAP1 A256K, E270K | T | K | Y | K | K | K | 72 ± 11 | 73% | 4 ± 0.3 | 93% |
| MegaRAP1 K251E, E270K | T | K | Y | E | A | K | 153 ± 104 | 16% | NF | 16% |

Figure 6A

| LRP2 CR89 variants | | | | RAP d3 | | MegaRAP1 d3 | |
|---|---|---|---|---|---|---|---|
| 1040 | 1047 | 1081 | 1088 | $K_d$ (nM) | % max bind | $K_d$ (nM) | % max bind |
| A | C | AÕ | CÕ | | | | |
| Y | V | W | R | NF | 7% | 33 ± 2 | 100% |
| Y | V | W | D | NF | 7% | 78 ± 25 | 55% |
| Y | D | W | D | NF | 6% | NF | 3% |
| Y | D | W | R | NF | 6% | NF | 11% |
| W | V | W | R | NF | 9% | NF | 5% |
| W | D | W | R | NF | 11% | NF | 3% |
| W | V | W | D | NF | 16% | NF | 4% |
| W | D | W | D | NF | 15% | NF | 1% |

Figure 6B

| d3 | CR | $K_d$ | 249 | 251 | 256 | 257 | 266 | 270 | 279 | 280 | 296 | 305 |
|---|---|---|---|---|---|---|---|---|---|---|---|---|
| RAP | LRP1 CR3-5 | 16 ± 4 | H | E | K | H | I | K | D | G | R | K |
| MegaRAP1 | LRP2 CR89 | 38 ± 3 | Y | K | A | | | E | | | | |
| VRAP2 | VLDLR CR78 | 44 ± 9 | | T | L | | | Y | | | L | |
| MatRAP1 | MAT CR12 | ND | | A | V | Y | F | W | | | | |
| MatRAP2 | MAT CR23 | ND | | G | R | | F | W | | S | | |
| 320RAP1 | 8D6 CR12 | ND | | A | S | | | S | Y | | | M |

Figure 8 Amino acid sequences of RAP d3 variants selected on CR pairs d3
LDRLRRVSHQGYSTEAEFEEPRVIDLWDLEQSANLTDKELEAFREELKHFEAKIEKHNHYQKQ
LEIAHEKLRHAESVGDGERVSRSREKHALLEGRTKELGYTVKKHLQDLSGRISRAR
(SEQ ID NO: 92)

MegaRAP1
LDRLRRVSHQGYSTEAEFEEPRVIDLWDLEQSANLTDKELEAFREELKHFKAKIEAHNHYQKQ
LEIAHEDLRHAESVGDGERVSRSREKHALLEGRTKELGYTVKKHLQDLSGRISRAR
(SEQ ID NO: 93)

VRAP2
LDRLRRVSHQGYSTEAEFEEPRVIDLWDLEQSANLTDKELEAFREELKHFTAKIEIHNHYQKQL
EIAHEELRHAESVGDGERVSRSREKHALLEGLTKELGYTVKKHLQDLSGRISRAR
(SEQ ID NO:113)

MatRAP1
LDRLRRVSHQGYSTEAEFEEPRVIDLWDLEQSANLTDKELEAFREELKHFAAKIEVYNHYQKQ
LEFAHEWLRHAESVGDGERVSRSREKHALLEGRTKELGYTVKKHLQDLSGRISRAR
(SEQ ID NO:114)

MatRAP2
LDRLRRVSHQGYSTEAEFEEPRVIDLWDLEQSANLTDKELEAFREELKHFGAKIERHNHYQKQ
LEFAHEWLRHAESVGDSERVSRSREKHALLEGRTKELGYTVKKHLQDLSGRISRAR
(SEQ ID NO:115)

320RAP1
LDRLRRVSHQGYSTEAEFEEPRVIDLWDLEQSANLTDKELEAFREELKHFAAKIESHNHYQKQL
EIAHESMRHAESVGYGERMSRSREKHALLEGRTKELGYTVTMHLQDLSG RISRAR
(SEQ ID NO:116)

Figure 9 Relative affinity of sequentially-truncated forms of MatRAP1 and MAT CR12.
(fnctn is the relative binding signal under isomolar conditions)

| fnct | ID | sequence | aa | SEQ ID NO |
|---|---|---|---|---|
| 0.22 | MR1 | ALDRLRRVSHQGYSTEAEFEEPRVIDLWDLEQSANLTDKELEAFREELKHFAAKIEVYNHYQKQLEFAHEWLRHAESVGDGERVSRSREKHALLEGRTKELGYTVKKHLQDLSGRISRARAEAE | 119 | 117 |
| 0.10 | 1 | -----------AGYSTEAEFEEPRVIDLWDLEQSANLTDKELEAFREELKHFAAKIEVYNHYQKQLEFAHEWLRHAESVGDGERVSRSREKHALLEGRTKELGYTVKKHLQDLSGRISRARAEAE | 109 | 118 |
| 0.35 | 2 | ---------------------ASANLTDKELEAFREELKHFAAKIEVYNHYQKQLEFAHEWLRHAESVGDGERVSRSREKHALLEGRTKELGYTVKKHLQDLSGRISRARAEAE | 98 | 119 |
| 0.65 | 3 | ----------------------------------AFREELKHFAAKIEVYNHYQKQLEFAHEWLRHAESVGDGERVSRSREKHALLEGRTKELGYTVKKHLQDLSGRISRARAEAE | 77 | 120 |
| 0 | 4 | ------------------------------------------AKIERHHYQKQLEFAHEWLRHAESVGDGERVSRSREKHALLEGRTKELGYTVKKHLQDLSGRISRARAEAE | 67 | 121 |
| 0 | 6 | ----------------------------------------------------------AKIERHHYQKQLEFAHEWLRHAESVGDGERVSRSREKHALLEGRTKELGYTVKKIILQDLSGRISRARAEAE | 53 | 122 |
| 0 | 7 | --------------------------------------------------AHEWLRHAESVGDGERVSRSREKHALLEGRTKELGYTVKKHLQDLSGRISRARAEAE | 55 | 123 |
| 0 | 8 | ----------------------------------------------------AEFAHEWLRHAESVGDGERVSRSREKHALLEGRTKELGYTVKKHLQDLSGRISRARAEAE | 52 | 124 |
| 1.3 | 3R1 | ----------------------------------AFREELKHFAAKIEVYNHYQKQLEFAHEWLRHAESVGDGERVSRSREKHALLEGRTKELGYTVKKHLQDLSGRISRAFB | 77 | 125 |
| 2.7 | 3R2 | ----------------------------------AFREELKHFAAKIEVYNHYQKQLEFAHEWLRHAESVGDGERVSRSREKHALLEGRTKELGYTVKKHLQDLSGB | 71 | 126 |
| 0 | 3R4 | ----------------------------------AFREELKHFAAKIEVYNHYQKQLEFAHEWLRHAESVGDGERVSRSRSB | 52 | 127 |
| 0 | 3R5 | ----------------------------------AFREELKHFAAKIEVYNHYQKQLEFAHEWLRHAESVGDGERVSRSB | 44 | 128 |
| 0 | 3R6 | ----------------------------------AFREELKHFAAKIEVYNHYQKQLEFAHEMLRHAESB | 34 | 129 |

A - MHHHHHSSGLVPRGSGMKETAAAKFERQHMDSPDLGTDDDDKAMADIGS (SEQ ID NO: 130)

B - KLAAALEHHHHHH (SEQ ID NO: 131)

C - GPLGS (SEQ ID NO: 13)

Figure 10 Binding of a RAP variant (320RAP) and its 71 amino acid truncated form (see Figure 14 for identical truncation of MATRAP1) selected on the FDC-8D6 antigen CR pair.
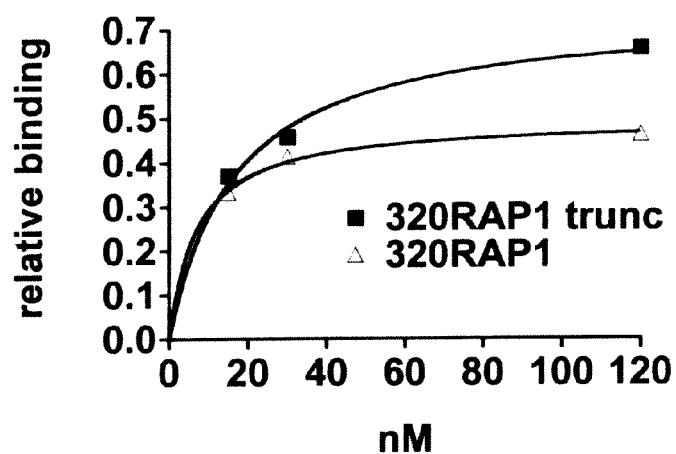

Binding of peptides to rhLRP1 cluster 2

Binding of peptides to rmVLDLR

Heptide-Octa-difluoromethylornithine

SEQUENCE LISTING

<160> NUMBER OF SEQ ID NOS: 132

<210> SEQ ID NO 1
<211> LENGTH: 1493
<212> TYPE: DNA
<213> ORGANISM: Homo sapiens

<400> SEQUENCE: 1

```
tgagcggggg atgatggcgc cgcggagggt caggtcgttt ctgcgcgggc tcccggcgct      60
gctactgctg ctgctcttcc tcgggccctg gcccgctgcg agccacggcg gcaagtactc     120
gcgggagaag aaccagccca agccgtcccc gaaacgcgag tccggagagg agttccgcat     180
ggagaagttg aaccagctgt gggagaaggc ccagcgactg catcttcctc ccgtgaggct     240
ggccgagctc cacgctgatc tgaagataca ggagagggac gaactcgcct ggaagaaact     300
aaagcttgac ggcttggacg aagatgggga aaggaagcg agactcatac gcaacctcaa     360
tgtcatcttg gccaagtatg gtctggacg aaagaaggac gctcggcagg tgaccagcaa     420
ctccctcagt ggcacccagg aagacgggct ggatgacccc aggctggaaa agctgtggca     480
caaggcgaag acctctggga aattctccgg cgaagaactg gacaagctct ggcgggagtt     540
cctgcatcac aaagagaaag ttcacgagta caacgtcctg ctggagaccc tgagcaggac     600
cgaagaaatc cacgagaacg tcattagccc ctcggacctg agcgacatca agggcagcgt     660
```

```
cctgcacagc aggcacacgg agctgaagga gaagctgcgc agcatcaacc agggcctgga    720
ccgcctgcgc agggtcagcc accagggcta cagcactgag gctgagttcg aggagcccag    780
ggtgattgac ctgtgggacc tggcgcagtc cgccaacctc acggacaagg agctggaggc    840
gttccgggag gagctcaagc acttcgaagc caaaatcgag aagcacaacc actaccagaa    900
gcagctggag attgcgcacg agaagctgag gcacgcagag agcgtgggcg acggcgagcg    960
tgtgagccgc agccgcgaga agcacgccct gctggagggg cggaccaagg agctgggcta   1020
cacggtgaag aagcatctgc aggacctgtc cggcaggatc tccagagctc ggcacaacga   1080
actctgaagg cactggggag cccagcccgg cagggaagag gccagcgtga aggacctggg   1140
ctcttggccg tggcatttcc gtggacagcc cgccgtcagg gtggctgggg ctggcacggg   1200
tgtcgaggca ggaaggattg tttctggtga ctgcagccgc tgccgtcgcg acacagggct   1260
tggtggtggt agcatttggg tctgagatcg gcccagctct gactgaaggg gcttggcttc   1320
cactcagcat cagcgtggca gtcaccaccc cagtgaggac ctcgatgtcc agctgctgtc   1380
aggtctgata gtcctctgct aaaacaacac gatttacata aaaaatctta cacatctgcc   1440
accggaaata ccatgcacag agtccttaaa aaatagagtg cagtatttaa acc          1493
```

<210> SEQ ID NO 2
<211> LENGTH: 357
<212> TYPE: PRT
<213> ORGANISM: Homo sapiens

<400> SEQUENCE: 2

```
Met Ala Pro Arg Arg Val Arg Ser Phe Leu Arg Gly Leu Pro Ala Leu
1               5                   10                  15

Leu Leu Leu Leu Phe Leu Gly Pro Trp Pro Ala Ala Ser His Gly
            20                  25                  30

Gly Lys Tyr Ser Arg Glu Lys Asn Gln Pro Lys Pro Ser Pro Lys Arg
        35                  40                  45

Glu Ser Gly Glu Glu Phe Arg Met Glu Lys Leu Asn Gln Leu Trp Glu
    50                  55                  60

Lys Ala Gln Arg Leu His Leu Pro Pro Val Arg Leu Ala Glu Leu His
65                  70                  75                  80

Ala Asp Leu Lys Ile Gln Glu Arg Asp Glu Leu Ala Trp Lys Lys Leu
                85                  90                  95

Lys Leu Asp Gly Leu Asp Glu Asp Gly Glu Lys Glu Ala Arg Leu Ile
            100                 105                 110

Arg Asn Leu Asn Val Ile Leu Ala Lys Tyr Gly Leu Asp Gly Lys Lys
        115                 120                 125

Asp Ala Arg Gln Val Thr Ser Asn Ser Leu Ser Gly Thr Gln Glu Asp
    130                 135                 140

Gly Leu Asp Asp Pro Arg Leu Glu Lys Leu Trp His Lys Ala Lys Thr
145                 150                 155                 160

Ser Gly Lys Phe Ser Gly Glu Glu Leu Asp Lys Leu Trp Arg Glu Phe
                165                 170                 175

Leu His His Lys Glu Lys Val His Glu Tyr Asn Val Leu Leu Glu Thr
            180                 185                 190

Leu Ser Arg Thr Glu Glu Ile His Glu Asn Val Ile Ser Pro Ser Asp
        195                 200                 205

Leu Ser Asp Ile Lys Gly Ser Val Leu His Ser Arg His Thr Glu Leu
    210                 215                 220

Lys Glu Lys Leu Arg Ser Ile Asn Gln Gly Leu Asp Arg Leu Arg Arg
```

```
            225                 230                 235                 240
Val Ser His Gln Gly Tyr Ser Thr Glu Ala Glu Phe Glu Glu Pro Arg
                245                 250                 255

Val Ile Asp Leu Trp Asp Leu Ala Gln Ser Ala Asn Leu Thr Asp Lys
            260                 265                 270

Glu Leu Glu Ala Phe Arg Glu Glu Leu Lys His Phe Glu Ala Lys Ile
        275                 280                 285

Glu Lys His Asn His Tyr Gln Lys Gln Leu Glu Ile Ala His Glu Lys
        290                 295                 300

Leu Arg His Ala Glu Ser Val Gly Asp Gly Glu Arg Val Ser Arg Ser
305                 310                 315                 320

Arg Glu Lys His Ala Leu Leu Glu Gly Arg Thr Lys Glu Leu Gly Tyr
                325                 330                 335

Thr Val Lys Lys His Leu Gln Asp Leu Ser Gly Arg Ile Ser Arg Ala
            340                 345                 350

Arg His Asn Glu Leu
        355

<210> SEQ ID NO 3
<211> LENGTH: 66
<212> TYPE: DNA
<213> ORGANISM: Artificial sequence
<220> FEATURE:
<223> OTHER INFORMATION: Synthetic primer - LRP6CR1F

<400> SEQUENCE: 3
gcgataggat ccccaacatg ttctcctcag cagtttactt gtttcacggg ggaaattgac      60
tgtatc                                                                66

<210> SEQ ID NO 4
<211> LENGTH: 70
<212> TYPE: DNA
<213> ORGANISM: Artificial sequence
<220> FEATURE:
<223> OTHER INFORMATION: Synthetic primer - LRP6CR2R

<400> SEQUENCE: 4
gcgataaagc ttttatcaaa gcacttcaca gttcttctca tctgatttgt cctggcagtt      60
tgcatctcca                                                            70

<210> SEQ ID NO 5
<211> LENGTH: 65
<212> TYPE: DNA
<213> ORGANISM: Artificial sequence
<220> FEATURE:
<223> OTHER INFORMATION: Synthetic primer - LRP6CR2F

<400> SEQUENCE: 5
gcgataggat ccctgtatg ctcagagtcc cagttccagt gtgccagtgg gcagtgtatt       60
gatgg                                                                 65

<210> SEQ ID NO 6
<211> LENGTH: 63
<212> TYPE: DNA
<213> ORGANISM: Artificial sequence
<220> FEATURE:
<223> OTHER INFORMATION: Synthetic primer - LPR6CR3R

<400> SEQUENCE: 6
gcgataaagc tttcactaag tcggataaca atccagttca tctgacttgt cactgcaatc      60
```

```
cac                                                              63

<210> SEQ ID NO 7
<211> LENGTH: 60
<212> TYPE: DNA
<213> ORGANISM: Artificial sequence
<220> FEATURE:
<223> OTHER INFORMATION: Synethic primer - VLDLRCR6F

<400> SEQUENCE: 7
gcgataggat cccacaccaa gtgtccagcc agcgaaatcc agtgcggctc tggcgagtgc     60

<210> SEQ ID NO 8
<211> LENGTH: 51
<212> TYPE: DNA
<213> ORGANISM: Artificial sequence
<220> FEATURE:
<223> OTHER INFORMATION: Synthetic primer - VLDLRCR7F

<400> SEQUENCE: 8
gcgataggat ccacttgccg acctgaccaa tttgaatgtg aggatggcag c              51

<210> SEQ ID NO 9
<211> LENGTH: 64
<212> TYPE: DNA
<213> ORGANISM: Artificial sequence
<220> FEATURE:
<223> OTHER INFORMATION: Synthetic primer - VLDLRCR8R

<400> SEQUENCE: 9
gcgataaagc ttttatcatt cgtttatatg acactctttc agggctcat cactccagtc      60 cctg                                                                  64

<210> SEQ ID NO 10
<211> LENGTH: 57
<212> TYPE: DNA
<213> ORGANISM: Artificial sequence
<220> FEATURE:
<223> OTHER INFORMATION: Synthetic primer - LRP2CR8F

<400> SEQUENCE: 10
gcgataggat cccccacgga gcagtgtggc ttattttcct tcccctgtaa aaatggc        57

<210> SEQ ID NO 11
<211> LENGTH: 73
<212> TYPE: DNA
<213> ORGANISM: Artificial sequence
<220> FEATURE:
<223> OTHER INFORMATION: Synthetic primer - LRP2CR9R

<400> SEQUENCE: 11
gcgataaagc ttttatcatg cgtgggtggg gcagttgtgc tcatcactgc catccacaca     60
gtcgttgcgt ttg                                                        73

<210> SEQ ID NO 12
<211> LENGTH: 70
<212> TYPE: DNA
<213> ORGANISM: Artificial sequence
<220> FEATURE:
<223> OTHER INFORMATION: Synthetic primer - LRP2CR34F

<400> SEQUENCE: 12
gcgataggat ccgatggtgc atactgccag gctactatgt tcgaatgcaa aaaccatgtt     60
tgtatcccgc                                                            70
```

```
<210> SEQ ID NO 13
<211> LENGTH: 63
<212> TYPE: DNA
<213> ORGANISM: Artificial sequence
<220> FEATURE:
<223> OTHER INFORMATION: Synthetic primer - LRP2CR35F

<400> SEQUENCE: 13
gcgataggat ccgatgttcc ctgtaattca ccaaaccgtt tccggtgtga caacaatcgc    60
tgc                                                                 63

<210> SEQ ID NO 14
<211> LENGTH: 70
<212> TYPE: DNA
<213> ORGANISM: Artificial sequence
<220> FEATURE:
<223> OTHER INFORMATION: Synthetic primer - LRP2CR36R

<400> SEQUENCE: 14
gcgataaagc ttttatcata tattttcagc acatgttctt tcttttcctt tattgcaacc    60
cagttcatcg                                                          70

<210> SEQ ID NO 15
<211> LENGTH: 54
<212> TYPE: DNA
<213> ORGANISM: Artificial sequence
<220> FEATURE:
<223> OTHER INFORMATION: Synthetic primer - ST14F1

<400> SEQUENCE: 15
gcgataggat ccccatgccc ggggcagttc acgtgccgca cggggcggtg tatc          54

<210> SEQ ID NO 16
<211> LENGTH: 54
<212> TYPE: DNA
<213> ORGANISM: Artificial sequence
<220> FEATURE:
<223> OTHER INFORMATION: Synthetic primer - ST14F2

<400> SEQUENCE: 16
gcgataggat cctgcgacgc cggccaccag ttcacgtgca agaacaagtt ctgc          54

<210> SEQ ID NO 17
<211> LENGTH: 53
<212> TYPE: DNA
<213> ORGANISM: Artificial sequence
<220> FEATURE:
<223> OTHER INFORMATION: Synthetic primer - ST14F3

<400> SEQUENCE: 17
gcgataggat ccagttgtcc ggcccagacc ttcaggtgtt ccaatgggaa gtg           53

<210> SEQ ID NO 18
<211> LENGTH: 59
<212> TYPE: DNA
<213> ORGANISM: Artificial sequence
<220> FEATURE:
<223> OTHER INFORMATION: Synthetic primer - ST14R1

<400> SEQUENCE: 18
gcgataaagc ttttatcaac ccctgctcgt cgctgttgtc tccgcagtcg ttcacactg     59

<210> SEQ ID NO 19
<211> LENGTH: 43
<212> TYPE: DNA
```

```
<213> ORGANISM: Artificial sequence
<220> FEATURE:
<223> OTHER INFORMATION: Synthetic primer - ST14R2

<400> SEQUENCE: 19
gcgataaagc ttttatcaac tgcacccctg ctcgtcgctg ttg                43

<210> SEQ ID NO 20
<211> LENGTH: 64
<212> TYPE: DNA
<213> ORGANISM: Artificial sequence
<220> FEATURE:
<223> OTHER INFORMATION: Synthetic primer - ST14R3

<400> SEQUENCE: 20
gcgataaagc ttttatcagt cgcagtcctt ctcatctgag ccgtcgctac agtcctcctt    60
cccg                                                              64

<210> SEQ ID NO 21
<211> LENGTH: 39
<212> TYPE: DNA
<213> ORGANISM: Artificial sequence
<220> FEATURE:
<223> OTHER INFORMATION: Synthetic primer - LRP1CR3F

<400> SEQUENCE: 21
gcgataggat cccccagtg ccagccaggc gagtttgcc                         39

<210> SEQ ID NO 22
<211> LENGTH: 45
<212> TYPE: DNA
<213> ORGANISM: Artificial sequence
<220> FEATURE:
<223> OTHER INFORMATION: Synthetic primer - LRP1CR5R

<400> SEQUENCE: 22
gcgataagct tcaataggc acacgaagca gactcatcag agcgg                   45

<210> SEQ ID NO 23
<211> LENGTH: 56
<212> TYPE: DNA
<213> ORGANISM: Artificial sequence
<220> FEATURE:
<223> OTHER INFORMATION: Synthetic primer - 8D6AF

<400> SEQUENCE: 23
gcgataggat cctcgtgccc acccaccaag ttccagtgcc gcaccagtgg cttatg      56

<210> SEQ ID NO 24
<211> LENGTH: 50
<212> TYPE: DNA
<213> ORGANISM: Artificial sequence
<220> FEATURE:
<223> OTHER INFORMATION: Synthetic primer - 8D65AR

<400> SEQUENCE: 24
gcgataaagc ttttatcatc cacagccgag ctcgtcgctg gagtcgggac             50

<210> SEQ ID NO 25
<211> LENGTH: 28
<212> TYPE: DNA
<213> ORGANISM: Artificial sequence
<220> FEATURE:
<223> OTHER INFORMATION: Synthetic primer - CR89YWF

<400> SEQUENCE: 25
```

```
gtgcccaatt actggctctg tgatggag                                              28

<210> SEQ ID NO 26
<211> LENGTH: 28
<212> TYPE: DNA
<213> ORGANISM: Artificial sequence
<220> FEATURE:
<223> OTHER INFORMATION: Synthetic primer - CR89YWR

<400> SEQUENCE: 26
ctccatcaca gagccagtaa ttgggcac                                              28

<210> SEQ ID NO 27
<211> LENGTH: 31
<212> TYPE: DNA
<213> ORGANISM: Artificial sequence
<220> FEATURE:
<223> OTHER INFORMATION: Synthetic primer - CR89V1047DF

<400> SEQUENCE: 27
ctctgtgatg gagacgatga ttgtcatgat a                                          31

<210> SEQ ID NO 28
<211> LENGTH: 31
<212> TYPE: DNA
<213> ORGANISM: Artificial sequence
<220> FEATURE:
<223> OTHER INFORMATION: Synthetic primer - CR89V1047DR

<400> SEQUENCE: 28
tatcatgaca atcatcgtct ccatcacaga g                                          31

<210> SEQ ID NO 29
<211> LENGTH: 41
<212> TYPE: DNA
<213> ORGANISM: Artificial sequence
<220> FEATURE:
<223> OTHER INFORMATION: Synthetic primer - CR89R1088DF

<400> SEQUENCE: 29
cacactggcg ctgtgacaaa gacaacgact gtgtggatgg c                               41

<210> SEQ ID NO 30
<211> LENGTH: 41
<212> TYPE: DNA
<213> ORGANISM: Artificial sequence
<220> FEATURE:
<223> OTHER INFORMATION: Synthetic primer - CR89R1088DR

<400> SEQUENCE: 30
gccatccaca cagtcgttgt ctttgtcaca gcgccagtgt g                               41

<210> SEQ ID NO 31
<211> LENGTH: 36
<212> TYPE: DNA
<213> ORGANISM: Artificial sequence
<220> FEATURE:
<223> OTHER INFORMATION: Synthetic primer - RAP2KXF

<400> SEQUENCE: 31
ccctcggacg tcagcgacat caagggcagc gtcctg                                     36

<210> SEQ ID NO 32
<211> LENGTH: 65
<212> TYPE: DNA
<213> ORGANISM: Artificial sequence
<220> FEATURE:
```

<223> OTHER INFORMATION: Synthetic primer - RAP2KX2
<220> FEATURE:
<221> NAME/KEY: misc_feature
<222> LOCATION: (29)..(30)
<223> OTHER INFORMATION: n is a, c, g, or t

<400> SEQUENCE: 32
ctccagctgc ttctggtagt ggttgtgvnn ctcctcgatt ttggcttcga agtgcttgag    60
ctcct                                                                65

<210> SEQ ID NO 33
<211> LENGTH: 58
<212> TYPE: DNA
<213> ORGANISM: Artificial sequence
<220> FEATURE:
<223> OTHER INFORMATION: Synthetic primer - RAP2KX1
<220> FEATURE:
<221> NAME/KEY: misc_feature
<222> LOCATION: (25)..(26)
<223> OTHER INFORMATION: n is a, c, g, or t

<400> SEQUENCE: 33
aagcagctgg agattgcgca cgagnnbctg aggcacgcag agagcgtggg cgaacggc    58

<210> SEQ ID NO 34
<211> LENGTH: 19
<212> TYPE: DNA
<213> ORGANISM: Artificial sequence
<220> FEATURE:
<223> OTHER INFORMATION: Synthetic primer - RAPmut1R

<400> SEQUENCE: 34
ggtgcggggc ctcaccggt                                                 19

<210> SEQ ID NO 35
<211> LENGTH: 29
<212> TYPE: DNA
<213> ORGANISM: Artificial sequence
<220> FEATURE:
<223> OTHER INFORMATION: Synthetic primer - MORPHF4

<400> SEQUENCE: 35
ggcccagatc taccggtttc tgcctcggc                                      29

<210> SEQ ID NO 36
<211> LENGTH: 76
<212> TYPE: DNA
<213> ORGANISM: Artificial sequence
<220> FEATURE:
<223> OTHER INFORMATION: Synthetic primer - D3HALFR2
<220> FEATURE:
<221> NAME/KEY: misc_feature
<222> LOCATION: (38)..(39)
<223> OTHER INFORMATION: n is a, c, g, or t
<220> FEATURE:
<221> NAME/KEY: misc_feature
<222> LOCATION: (53)..(54)
<223> OTHER INFORMATION: n is a, c, g, or t

<400> SEQUENCE: 36
gtgcgcaatc tcgagctgct tctggtagtg gttgtgvnnc tcgattttgg cvnngaagtg    60
cttgagctcc tcccgg                                                    76

<210> SEQ ID NO 37
<211> LENGTH: 67
<212> TYPE: DNA
<213> ORGANISM: Artificial sequence
<220> FEATURE:

-continued

<223> OTHER INFORMATION: Synthetic primer - D3HALFF2
<220> FEATURE:
<221> NAME/KEY: misc_feature
<222> LOCATION: (35)..(36)
<223> OTHER INFORMATION: n is a, c, g, or t

<400> SEQUENCE: 37
ccactaccag aagcagctcg agattgcgca cgagnnbctg aggcacgcag agagcgtggg    60
cgacggc                                                             67

<210> SEQ ID NO 38
<211> LENGTH: 33
<212> TYPE: DNA
<213> ORGANISM: Artificial sequence
<220> FEATURE:
<223> OTHER INFORMATION: Synthetic primer - MORPHR3

<400> SEQUENCE: 38
gagtgcggcc gcaagcttat cttctgcctc ggc                                33

<210> SEQ ID NO 39
<211> LENGTH: 40
<212> TYPE: DNA
<213> ORGANISM: Artificial sequence
<220> FEATURE:
<223> OTHER INFORMATION: Synthetic primer - d3 Rescue F

<400> SEQUENCE: 39
gcgataggat ccctggaccg cctgcgcagg gtcagccacc                          40

<210> SEQ ID NO 40
<211> LENGTH: 42
<212> TYPE: DNA
<213> ORGANISM: Artificial sequence
<220> FEATURE:
<223> OTHER INFORMATION: Synthetic primer - d3 Rescue R

<400> SEQUENCE: 40
gcgataaagc ttttatcaag atctaccggt ttctgcctcg gc                      42

<210> SEQ ID NO 41
<211> LENGTH: 56
<212> TYPE: DNA
<213> ORGANISM: Artificial sequence
<220> FEATURE:
<223> OTHER INFORMATION: Synthetic primer - V2AR1

<400> SEQUENCE: 41
agggtcagcc accagggcta cagcactgag gctaagttcg aggagcccag ggtgat       56

<210> SEQ ID NO 42
<211> LENGTH: 56
<212> TYPE: DNA
<213> ORGANISM: Artificial sequence
<220> FEATURE:
<223> OTHER INFORMATION: Synthetic primer - V2AR2

<400> SEQUENCE: 42
cagccaccag ggctacacca ctgaggctga gttcgaggag cccagggtga ttgacc       56

<210> SEQ ID NO 43
<211> LENGTH: 56
<212> TYPE: DNA
<213> ORGANISM: Artificial sequence
<220> FEATURE:
<223> OTHER INFORMATION: Synthetic primer - V2AR3

```
<400> SEQUENCE: 43
ggaggcgttc cgggaggagc tcaagcactt caaagccaaa attgaggccc acaacc        56

<210> SEQ ID NO 44
<211> LENGTH: 56
<212> TYPE: DNA
<213> ORGANISM: Artificial sequence
<220> FEATURE:
<223> OTHER INFORMATION: Synthetic primer - V2AR4

<400> SEQUENCE: 44
cgttccggga ggagctcaag tacttcgaag ccaaaattga gcccacaac cactac         56

<210> SEQ ID NO 45
<211> LENGTH: 58
<212> TYPE: DNA
<213> ORGANISM: Artificial sequence
<220> FEATURE:
<223> OTHER INFORMATION: Synthetic primer - V2AR5

<400> SEQUENCE: 45
gctcaagtac ttcaaagcca aaattgagaa gcacaaccac taccagaagc agctggag     58

<210> SEQ ID NO 46
<211> LENGTH: 58
<212> TYPE: DNA
<213> ORGANISM: Artificial sequence
<220> FEATURE:
<223> OTHER INFORMATION: Synthetic primer - V2AR6

<400> SEQUENCE: 46
agaagcagct ggagattgcg cacgagaagc tgaggcacgc agagagcgtg ggcgacgg     58

<210> SEQ ID NO 47
<211> LENGTH: 56
<212> TYPE: DNA
<213> ORGANISM: Artificial sequence
<220> FEATURE:
<223> OTHER INFORMATION: Synthetic primer - V2ARR1

<400> SEQUENCE: 47
atcaccctgg gctcctcgaa cttagcctca gtgctgtagc cctggtggct gaccct        56

<210> SEQ ID NO 48
<211> LENGTH: 56
<212> TYPE: DNA
<213> ORGANISM: Artificial sequence
<220> FEATURE:
<223> OTHER INFORMATION: Synthetic primer - V2ARR2

<400> SEQUENCE: 48
ggtcaatcac cctgggctcc tcgaactcag cctcagtggt gtagccctgg tggctg        56

<210> SEQ ID NO 49
<211> LENGTH: 56
<212> TYPE: DNA
<213> ORGANISM: Artificial sequence
<220> FEATURE:
<223> OTHER INFORMATION: Synthetic primer - V2ARR3

<400> SEQUENCE: 49
ggttgtgggc tcaattttgc tttgaagt gcttgagctc ctcccggaac gcctcc         56

<210> SEQ ID NO 50
<211> LENGTH: 56
<212> TYPE: DNA
```

<213> ORGANISM: Artificial sequence
<220> FEATURE:
<223> OTHER INFORMATION: Synthetic primer - V2ARR4

<400> SEQUENCE: 50
gtagtggttg tgggcctcaa ttttggcttc gaagtacttg agctcctccc ggaacg    56

<210> SEQ ID NO 51
<211> LENGTH: 58
<212> TYPE: DNA
<213> ORGANISM: Artificial sequence
<220> FEATURE:
<223> OTHER INFORMATION: Synthetic primer - V2ARR5

<400> SEQUENCE: 51
ctccagctgc ttctggtagt ggttgtgctt ctcaattttg ctttgaagt acttgagc    58

<210> SEQ ID NO 52
<211> LENGTH: 58
<212> TYPE: DNA
<213> ORGANISM: Artificial sequence
<220> FEATURE:
<223> OTHER INFORMATION: Synthetic primer - V2ARR6

<400> SEQUENCE: 52
ccgtcgccca cgctctctgc gtgcctcagc ttctcgtgcg caatctccag ctgcttct    58

<210> SEQ ID NO 53
<211> LENGTH: 41
<212> TYPE: DNA
<213> ORGANISM: Artificial sequence
<220> FEATURE:
<223> OTHER INFORMATION: Synthetic primer - K256AF

<400> SEQUENCE: 53
cttcgaagcc aaaatcgagg cgcacaacca ctaccagaag c    41

<210> SEQ ID NO 54
<211> LENGTH: 41
<212> TYPE: DNA
<213> ORGANISM: Artificial sequence
<220> FEATURE:
<223> OTHER INFORMATION: Synthetic primer - K256AR

<400> SEQUENCE: 54
gcttctggta gtggttgtgc gcctcgattt tggcttcgaa g    41

<210> SEQ ID NO 55
<211> LENGTH: 39
<212> TYPE: DNA
<213> ORGANISM: Artificial sequence
<220> FEATURE:
<223> OTHER INFORMATION: Synthetic primer - K270EF

<400> SEQUENCE: 55
gctggagatt gcgcacgagg agctgaggca cgcagagag    39

<210> SEQ ID NO 56
<211> LENGTH: 39
<212> TYPE: DNA
<213> ORGANISM: Artificial sequence
<220> FEATURE:
<223> OTHER INFORMATION: Synthetic primer - K270ER

<400> SEQUENCE: 56
ctctctgcgt gcctcagctc ctcgtgcgca atctccagc    39

```
<210> SEQ ID NO 57
<211> LENGTH: 42
<212> TYPE: DNA
<213> ORGANISM: Artificial sequence
<220> FEATURE:
<223> OTHER INFORMATION: Synthetic primer - d3E251KF

<400> SEQUENCE: 57
gaggagctca agcacttcaa agccaaaatc gagaagcaca ac            42

<210> SEQ ID NO 58
<211> LENGTH: 42
<212> TYPE: DNA
<213> ORGANISM: Artificial sequence
<220> FEATURE:
<223> OTHER INFORMATION: Synthetic primer - d3E251KF

<400> SEQUENCE: 58
gttgtgcttc tcgattttgg ctttgaagtg cttgagctcc tc            42

<210> SEQ ID NO 59
<211> LENGTH: 42
<212> TYPE: DNA
<213> ORGANISM: Artificial sequence
<220> FEATURE:
<223> OTHER INFORMATION: Synthetic primer - d3E217KF

<400> SEQUENCE: 59
cagggctaca gcactgaggc taagttcgag gagcccaggg tg            42

<210> SEQ ID NO 60
<211> LENGTH: 42
<212> TYPE: DNA
<213> ORGANISM: Artificial sequence
<220> FEATURE:
<223> OTHER INFORMATION: Synthetic primer - d3E217KR

<400> SEQUENCE: 60
caccctgggc tcctcgaact tagcctcagt gctgtagccc tg            42

<210> SEQ ID NO 61
<211> LENGTH: 40
<212> TYPE: DNA
<213> ORGANISM: Artificial sequence
<220> FEATURE:
<223> OTHER INFORMATION: Synthetic primer - d3H249YF

<400> SEQUENCE: 61
gttccgggag gagctcaagt acttcgaagc caaaatcgag            40

<210> SEQ ID NO 62
<211> LENGTH: 40
<212> TYPE: DNA
<213> ORGANISM: Artificial sequence
<220> FEATURE:
<223> OTHER INFORMATION: Synthetic primer - d3H249YR

<400> SEQUENCE: 62
ctcgattttg gcttcgaagt acttgagctc ctcccggaac            40

<210> SEQ ID NO 63
<211> LENGTH: 8
<212> TYPE: PRT
<213> ORGANISM: Artificial sequence
<220> FEATURE:
<223> OTHER INFORMATION: LDLR CR1
```

```
<400> SEQUENCE: 63

Trp Val Cys Asp Gly Ser Ala Glu
1               5

<210> SEQ ID NO 64
<211> LENGTH: 8
<212> TYPE: PRT
<213> ORGANISM: Artificial sequence
<220> FEATURE:
<223> OTHER INFORMATION: LDLR CR3

<400> SEQUENCE: 64

Phe Val Cys Asp Ser Asp Arg Asp
1               5

<210> SEQ ID NO 65
<211> LENGTH: 8
<212> TYPE: PRT
<213> ORGANISM: Artificial sequence
<220> FEATURE:
<223> OTHER INFORMATION: LDLR CR5

<400> SEQUENCE: 65

Trp Arg Cys Asp Gly Gly Pro Asp
1               5

<210> SEQ ID NO 66
<211> LENGTH: 8
<212> TYPE: PRT
<213> ORGANISM: Artificial sequence
<220> FEATURE:
<223> OTHER INFORMATION: LDLR CR6

<400> SEQUENCE: 66

Arg Gln Cys Asp Arg Glu Tyr Asp
1               5

<210> SEQ ID NO 67
<211> LENGTH: 8
<212> TYPE: PRT
<213> ORGANISM: Artificial sequence
<220> FEATURE:
<223> OTHER INFORMATION: LDLR CR7

<400> SEQUENCE: 67

Lys Val Cys Asn Met Ala Arg Asp
1               5

<210> SEQ ID NO 68
<211> LENGTH: 8
<212> TYPE: PRT
<213> ORGANISM: Artificial sequence
<220> FEATURE:
<223> OTHER INFORMATION: TVA  CR

<400> SEQUENCE: 68

Trp Leu Cys Asp Gly His Pro Asp
1               5

<210> SEQ ID NO 69
<211> LENGTH: 44
<212> TYPE: PRT
<213> ORGANISM: Artificial sequence
<220> FEATURE:
<223> OTHER INFORMATION: LRP1CR3

<400> SEQUENCE: 69
```

Arg Pro Gln Cys Gln Pro Gly Glu Phe Ala Cys Ala Asn Ser Arg Cys
1               5                   10                  15

Ile Gln Glu Arg Trp Lys Cys Asp Gly Asp Asn Asp Cys Leu Asp Asn
                20                  25                  30

Ser Asp Glu Ala Pro Ala Leu Cys His Gln His Thr
            35                  40

<210> SEQ ID NO 70
<211> LENGTH: 41
<212> TYPE: PRT
<213> ORGANISM: Artificial sequence
<220> FEATURE:
<223> OTHER INFORMATION: LRP1CR4

<400> SEQUENCE: 70

Cys Pro Ser Asp Arg Phe Lys Cys Glu Asn Asn Arg Cys Ile Pro Asn
1               5                   10                  15

Arg Trp Leu Cys Asp Gly Asp Asn Asp Cys Gly Asn Ser Glu Asp Glu
                20                  25                  30

Ser Asn Ala Thr Cys Ser Ala Arg Thr
            35                  40

<210> SEQ ID NO 71
<211> LENGTH: 38
<212> TYPE: PRT
<213> ORGANISM: Artificial sequence
<220> FEATURE:
<223> OTHER INFORMATION: LRP1CR5

<400> SEQUENCE: 71

Cys Pro Pro Asn Gln Phe Ser Cys Ala Ser Gly Arg Cys Ile Pro Ile
1               5                   10                  15

Ser Trp Thr Cys Asp Leu Asp Asp Asp Cys Gly Asp Arg Ser Asp Glu
                20                  25                  30

Ser Ala Ser Cys Ala Tyr
            35

<210> SEQ ID NO 72
<211> LENGTH: 42
<212> TYPE: PRT
<213> ORGANISM: Artificial sequence
<220> FEATURE:
<223> OTHER INFORMATION: VLDLRCR6

<400> SEQUENCE: 72

His Thr Lys Cys Pro Ala Ser Glu Ile Gln Cys Gly Ser Gly Glu Cys
1               5                   10                  15

Ile His Lys Lys Trp Arg Cys Asp Gly Asp Pro Asp Cys Lys Asp Gly
                20                  25                  30

Ser Asp Glu Val Asn Cys Pro Ser Arg Thr
            35                  40

<210> SEQ ID NO 73
<211> LENGTH: 40
<212> TYPE: PRT
<213> ORGANISM: Artificial sequence
<220> FEATURE:
<223> OTHER INFORMATION: VLDLRCR7

<400> SEQUENCE: 73

Cys Arg Pro Asp Gln Phe Glu Cys Glu Asp Gly Ser Cys Ile His Gly
1               5                   10                  15

Ser Arg Gln Cys Asn Gly Ile Arg Asp Cys Val Asp Gly Ser Asp Glu

```
                20                  25                  30
Val Asn Cys Lys Asn Val Asn Gln
            35                  40

<210> SEQ ID NO 74
<211> LENGTH: 42
<212> TYPE: PRT
<213> ORGANISM: Artificial sequence
<220> FEATURE:
<223> OTHER INFORMATION: VLDLRCR8

<400> SEQUENCE: 74

Cys Leu Gly Pro Gly Lys Phe Lys Cys Arg Ser Gly Glu Cys Ile Asp
1               5                   10                  15
Ile Ser Lys Val Cys Asn Gln Glu Gln Asp Cys Arg Asp Trp Ser Asp
            20                  25                  30
Glu Pro Leu Lys Glu Cys His Ile Asn Glu
        35                  40

<210> SEQ ID NO 75
<211> LENGTH: 36
<212> TYPE: PRT
<213> ORGANISM: Artificial sequence
<220> FEATURE:
<223> OTHER INFORMATION: MATCR1

<400> SEQUENCE: 75

Pro Cys Pro Gly Gln Phe Thr Cys Arg Thr Gly Arg Cys Ile Arg Lys
1               5                   10                  15
Glu Leu Arg Cys Asp Gly Trp Ala Asp Cys Thr Asp His Ser Asp Glu
            20                  25                  30
Leu Asn Cys Ser
        35

<210> SEQ ID NO 76
<211> LENGTH: 37
<212> TYPE: PRT
<213> ORGANISM: Artificial sequence
<220> FEATURE:
<223> OTHER INFORMATION: MATCR2

<400> SEQUENCE: 76

Cys Asp Ala Gly His Gln Phe Thr Cys Lys Asn Lys Phe Cys Lys Pro
1               5                   10                  15
Leu Phe Trp Val Cys Asp Ser Val Asn Asp Cys Gly Asp Asn Ser Asp
            20                  25                  30
Glu Gln Gly Cys Ser
        35

<210> SEQ ID NO 77
<211> LENGTH: 42
<212> TYPE: PRT
<213> ORGANISM: Artificial sequence
<220> FEATURE:
<223> OTHER INFORMATION: MATCR3

<400> SEQUENCE: 77

Cys Pro Ala Gln Thr Phe Arg Cys Ser Asn Gly Lys Cys Leu Ser Lys
1               5                   10                  15
Ser Gln Gln Cys Asn Gly Lys Asp Asp Cys Gly Asp Gly Ser Asp Glu
            20                  25                  30
Ala Ser Cys Pro Lys Val Asn Val Val Thr
        35                  40
```

<210> SEQ ID NO 78
<211> LENGTH: 37
<212> TYPE: PRT
<213> ORGANISM: Artificial sequence
<220> FEATURE:
<223> OTHER INFORMATION: MATCR4

<400> SEQUENCE: 78

```
Cys Thr Lys His Thr Tyr Arg Cys Leu Asn Gly Leu Cys Leu Ser Lys
1               5                   10                  15
Gly Asn Pro Glu Cys Asp Gly Lys Glu Asp Cys Ser Asp Gly Ser Asp
            20                  25                  30
Glu Lys Asp Cys Asp
        35
```

<210> SEQ ID NO 79
<211> LENGTH: 45
<212> TYPE: PRT
<213> ORGANISM: Artificial sequence
<220> FEATURE:
<223> OTHER INFORMATION: LRP2CR8

<400> SEQUENCE: 79

```
Pro Thr Glu Gln Cys Gly Leu Phe Ser Phe Pro Cys Lys Asn Gly Arg
1               5                   10                  15
Cys Val Pro Asn Tyr Tyr Leu Cys Asp Gly Val Asp Asp Cys His Asp
            20                  25                  30
Asn Ser Asp Glu Gln Leu Cys Gly Thr Leu Asn Asn Thr
        35                  40                  45
```

<210> SEQ ID NO 80
<211> LENGTH: 40
<212> TYPE: PRT
<213> ORGANISM: Artificial sequence
<220> FEATURE:
<223> OTHER INFORMATION: LRP2CR9

<400> SEQUENCE: 80

```
Cys Ser Ser Ser Ala Phe Thr Cys Gly His Gly Glu Cys Ile Pro Ala
1               5                   10                  15
His Trp Arg Cys Asp Lys Arg Asn Asp Cys Val Asp Gly Ser Asp Glu
            20                  25                  30
His Asn Cys Pro Thr His Ala Phe
        35                  40
```

<210> SEQ ID NO 81
<211> LENGTH: 41
<212> TYPE: PRT
<213> ORGANISM: Artificial sequence
<220> FEATURE:
<223> OTHER INFORMATION: LRP2CR27

<400> SEQUENCE: 81

```
Cys Arg Leu Gly Gln Phe Gln Cys Ser Asp Gly Asn Cys Thr Ser Pro
1               5                   10                  15
Gln Thr Leu Cys Asn Ala His Gln Asn Cys Pro Asp Gly Ser Asp Glu
            20                  25                  30
Asp Arg Leu Leu Cys Glu Asn His His
        35                  40
```

<210> SEQ ID NO 82
<211> LENGTH: 39

```
<212> TYPE: PRT
<213> ORGANISM: Artificial sequence
<220> FEATURE:
<223> OTHER INFORMATION: LRP2CR28

<400> SEQUENCE: 82

Cys Asp Ser Asn Glu Trp Gln Cys Ala Asn Lys Arg Cys Ile Pro Glu
1               5                   10                  15

Ser Trp Gln Cys Asp Thr Phe Asn Asp Cys Glu Asp Asn Ser Asp Glu
            20                  25                  30

Asp Ser Ser His Cys Ala Ser
            35

<210> SEQ ID NO 83
<211> LENGTH: 42
<212> TYPE: PRT
<213> ORGANISM: Artificial sequence
<220> FEATURE:
<223> OTHER INFORMATION: LRP2CR30

<400> SEQUENCE: 83

Leu Cys Asp Asn Phe Thr Glu Phe Ser Cys Lys Thr Asn Tyr Arg Cys
1               5                   10                  15

Ile Pro Lys Trp Ala Val Cys Asn Gly Val Asp Asp Cys Arg Asp Asn
            20                  25                  30

Ser Asp Glu Gln Gly Cys Glu Gly Arg Thr
            35                  40

<210> SEQ ID NO 84
<211> LENGTH: 40
<212> TYPE: PRT
<213> ORGANISM: Artificial sequence
<220> FEATURE:
<223> OTHER INFORMATION: LRP2CR31

<400> SEQUENCE: 84

Cys His Pro Val Gly Asp Phe Arg Cys Lys Asn His His Cys Ile Pro
1               5                   10                  15

Leu Arg Trp Gln Cys Asp Gly Leu Asn Asp Cys Gly Asp Asn Ser Asp
            20                  25                  30

Glu Glu Asn Cys Ala Pro Arg Glu
            35                  40

<210> SEQ ID NO 85
<211> LENGTH: 45
<212> TYPE: PRT
<213> ORGANISM: Artificial sequence
<220> FEATURE:
<223> OTHER INFORMATION: LRP2CR34

<400> SEQUENCE: 85

Asp Gly Ala Tyr Cys Gln Ala Thr Met Phe Glu Cys Lys Asn His Val
1               5                   10                  15

Cys Ile Pro Pro Tyr Trp Lys Cys Asp Gly Asp Asp Cys Gly Asp
            20                  25                  30

Gly Ser Asp Glu Glu Leu His Leu Cys Leu Asp Val Pro
            35                  40                  45

<210> SEQ ID NO 86
<211> LENGTH: 45
<212> TYPE: PRT
<213> ORGANISM: Artificial sequence
<220> FEATURE:
<223> OTHER INFORMATION: LRP2CR35
```

<400> SEQUENCE: 86

Cys Asn Ser Pro Asn Arg Phe Arg Cys Asp Asn Asn Arg Cys Ile Tyr
1               5                   10                  15

Ser His Glu Val Cys Asn Gly Val Asp Asp Cys Gly Asp Gly Thr Asp
            20                  25                  30

Glu Thr Glu Glu His Cys Arg Lys Pro Thr Pro Lys Pro
        35                  40                  45

<210> SEQ ID NO 87
<211> LENGTH: 47
<212> TYPE: PRT
<213> ORGANISM: Artificial sequence
<220> FEATURE:
<223> OTHER INFORMATION: LRP2CR36

<400> SEQUENCE: 87

Cys Thr Glu Tyr Glu Tyr Lys Cys Gly Asn Gly His Cys Ile Pro His
1               5                   10                  15

Asp Asn Val Cys Asp Asp Ala Asp Asp Cys Gly Asp Trp Ser Asp Glu
            20                  25                  30

Leu Gly Cys Asn Lys Gly Lys Glu Arg Thr Cys Ala Glu Asn Ile
        35                  40                  45

<210> SEQ ID NO 88
<211> LENGTH: 41
<212> TYPE: PRT
<213> ORGANISM: Artificial sequence
<220> FEATURE:
<223> OTHER INFORMATION: LRP6CR1

<400> SEQUENCE: 88

Pro Thr Cys Ser Pro Gln Gln Phe Thr Cys Phe Thr Gly Glu Ile Asp
1               5                   10                  15

Cys Ile Pro Val Ala Trp Arg Cys Asp Gly Phe Thr Glu Cys Glu Asp
            20                  25                  30

His Ser Asp Glu Leu Asn Cys Pro Val
        35                  40

<210> SEQ ID NO 89
<211> LENGTH: 38
<212> TYPE: PRT
<213> ORGANISM: Artificial sequence
<220> FEATURE:
<223> OTHER INFORMATION: LRP6CR2

<400> SEQUENCE: 89

Cys Ser Glu Ser Gln Phe Gln Cys Ala Ser Gly Gln Cys Ile Asp Gly
1               5                   10                  15

Ala Leu Arg Cys Asn Gly Asp Ala Asn Cys Gln Asp Lys Ser Asp Glu
            20                  25                  30

Lys Asn Cys Glu Val Leu
        35

<210> SEQ ID NO 90
<211> LENGTH: 38
<212> TYPE: PRT
<213> ORGANISM: Artificial sequence
<220> FEATURE:
<223> OTHER INFORMATION: LRP6CR3

<400> SEQUENCE: 90

Cys Leu Ile Asp Gln Phe Arg Cys Ala Asn Gly Gln Cys Ile Gly Lys

```
                1               5                   10                  15
His Lys Lys Cys Asp His Asn Val Asp Cys Ser Asp Lys Ser Asp Glu
            20                  25                  30

Leu Asp Cys Tyr Pro Thr
            35
```

<210> SEQ ID NO 91
<211> LENGTH: 118
<212> TYPE: PRT
<213> ORGANISM: Artificial sequence
<220> FEATURE:
<223> OTHER INFORMATION: 8D6 CR12

<400> SEQUENCE: 91

```
Gly Ser Ser Cys Pro Pro Thr Lys Phe Gln Cys Arg Thr Ser Gly Leu
1               5                   10                  15

Cys Val Pro Leu Thr Trp Arg Cys Asp Arg Asp Leu Asp Cys Ser Asp
            20                  25                  30

Gly Ser Asp Glu Glu Cys Arg Ile Glu Pro Cys Thr Gln Lys Gly
            35                  40                  45

Gln Cys Pro Pro Pro Gly Leu Pro Cys Pro Cys Thr Gly Val Ser
50                  55                  60

Asp Cys Ser Gly Gly Thr Asp Lys Lys Leu Arg Asn Cys Ser Arg Leu
65                  70                  75                  80

Ala Cys Leu Ala Gly Glu Leu Arg Cys Thr Leu Ser Asp Asp Cys Ile
            85                  90                  95

Pro Leu Thr Trp Arg Cys Asp Gly His Pro Asp Cys Pro Asp Ser Ser
            100                 105                 110

Asp Glu Leu Gly Cys Gly
            115
```

<210> SEQ ID NO 92
<211> LENGTH: 119
<212> TYPE: PRT
<213> ORGANISM: Homo sapiens

<400> SEQUENCE: 92

```
Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
            35                  40                  45

His Phe Glu Ala Lys Ile Glu Lys His Asn His Tyr Gln Lys Gln Leu
50                  55                  60

Glu Ile Ala His Glu Lys Leu Arg His Ala Glu Ser Val Gly Asp Gly
65              70                  75                  80

Glu Arg Val Ser Arg Ser Arg Gly Lys His Ala Leu Leu Glu Gly Arg
            85                  90                  95

Thr Lys Glu Leu Gly Tyr Thr Val Lys Lys His Leu Gln Asp Leu Ser
            100                 105                 110

Gly Arg Ile Ser Arg Ala Arg
            115
```

<210> SEQ ID NO 93
<211> LENGTH: 119
<212> TYPE: PRT
<213> ORGANISM: Homo sapiens

```
<400> SEQUENCE: 93

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
        35                  40                  45

His Phe Lys Ala Lys Ile Glu Ala His Asn His Tyr Gln Lys Gln Leu
    50                  55                  60

Glu Ile Ala His Glu Asp Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg
        115

<210> SEQ ID NO 94
<211> LENGTH: 118
<212> TYPE: PRT
<213> ORGANISM: Homo sapiens

<400> SEQUENCE: 94

Gly Ser Ser Cys Pro Pro Thr Lys Phe Gln Cys Arg Thr Ser Gly Leu
1               5                   10                  15

Cys Val Pro Leu Thr Trp Arg Cys Asp Arg Asp Leu Asp Cys Ser Asp
            20                  25                  30

Gly Ser Asp Glu Glu Cys Arg Ile Glu Pro Cys Thr Gln Lys Gly
        35                  40                  45

Gln Cys Pro Pro Pro Gly Leu Pro Cys Pro Cys Thr Gly Val Ser
    50                  55                  60

Asp Cys Ser Gly Gly Thr Asp Lys Lys Leu Arg Asn Cys Ser Arg Leu
65                  70                  75                  80

Ala Cys Leu Ala Gly Glu Leu Arg Cys Thr Leu Ser Asp Asp Cys Ile
                85                  90                  95

Pro Leu Thr Trp Arg Cys Asp Gly His Pro Asp Cys Pro Asp Ser Ser
            100                 105                 110

Asp Glu Leu Gly Cys Gly
        115

<210> SEQ ID NO 95
<211> LENGTH: 323
<212> TYPE: PRT
<213> ORGANISM: homo sapiens

<400> SEQUENCE: 95

Tyr Ser Arg Glu Lys Asn Gln Pro Lys Pro Ser Pro Lys Arg Glu Ser
1               5                   10                  15

Gly Glu Glu Phe Arg Met Glu Lys Leu Asn Gln Leu Trp Glu Lys Ala
            20                  25                  30

Gln Arg Leu His Leu Pro Pro Val Arg Leu Ala Glu Leu His Ala Asp
        35                  40                  45

Leu Lys Ile Gln Glu Arg Asp Glu Leu Ala Trp Lys Lys Leu Lys Leu
    50                  55                  60

Asp Gly Leu Asp Glu Asp Gly Glu Lys Glu Ala Arg Leu Ile Arg Asn
65                  70                  75                  80
```

```
Leu Asn Val Ile Leu Ala Lys Tyr Gly Leu Asp Gly Lys Lys Asp Ala
                85                  90                  95

Arg Gln Val Thr Ser Asn Ser Leu Ser Gly Thr Gln Glu Asp Gly Leu
            100                 105                 110

Asp Asp Pro Arg Leu Glu Lys Leu Trp His Lys Ala Lys Thr Ser Gly
        115                 120                 125

Lys Phe Ser Gly Glu Glu Leu Asp Lys Leu Trp Arg Glu Phe Leu His
130                 135                 140

His Lys Glu Lys Val His Glu Tyr Asn Val Leu Leu Glu Thr Leu Ser
145                 150                 155                 160

Arg Thr Glu Glu Ile His Glu Asn Val Ile Ser Pro Ser Asp Leu Ser
                165                 170                 175

Asp Ile Lys Gly Ser Val Leu His Ser Arg His Thr Glu Leu Lys Glu
            180                 185                 190

Lys Leu Arg Ser Ile Asn Gln Gly Leu Asp Arg Leu Arg Arg Val Ser
        195                 200                 205

His Gln Gly Tyr Ser Thr Glu Ala Glu Phe Glu Glu Pro Arg Val Ile
210                 215                 220

Asp Leu Trp Asp Leu Ala Gln Ser Ala Asn Leu Thr Asp Lys Glu Leu
225                 230                 235                 240

Glu Ala Phe Arg Glu Glu Leu Lys His Phe Glu Ala Lys Ile Glu Lys
                245                 250                 255

His Asn His Tyr Gln Lys Gln Leu Glu Ile Ala His Glu Lys Leu Arg
            260                 265                 270

His Ala Glu Ser Val Gly Asp Gly Glu Arg Val Ser Arg Ser Arg Glu
        275                 280                 285

Lys His Ala Leu Leu Glu Gly Arg Thr Lys Glu Leu Gly Tyr Thr Val
290                 295                 300

Lys Lys His Leu Gln Asp Leu Ser Gly Arg Ile Ser Arg Ala Arg His
305                 310                 315                 320

Asn Glu Leu

<210> SEQ ID NO 96
<211> LENGTH: 123
<212> TYPE: PRT
<213> ORGANISM: Homo sapiens

<400> SEQUENCE: 96

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Ala Gln Ser
            20                  25                  30

Ala Asn Leu Thr Asp Lys Glu Leu Glu Ala Phe Arg Glu Glu Leu Lys
        35                  40                  45

His Phe Glu Ala Lys Ile Glu Lys His Asn His Tyr Gln Lys Gln Leu
    50                  55                  60

Glu Ile Ala His Glu Lys Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg His Asn Glu Leu
        115                 120
```

<210> SEQ ID NO 97
<211> LENGTH: 71
<212> TYPE: PRT
<213> ORGANISM: Homo sapiens

<400> SEQUENCE: 97

Phe Arg Glu Glu Leu Lys His Phe Glu Ala Lys Ile Glu Lys His Asn
1               5                   10                  15

His Tyr Gln Lys Gln Leu Glu Ile Ala His Glu Lys Leu Arg His Ala
            20                  25                  30

Glu Ser Val Gly Asp Gly Glu Arg Val Ser Arg Ser Arg Glu Lys His
        35                  40                  45

Ala Leu Leu Glu Gly Arg Thr Lys Glu Leu Gly Tyr Thr Val Lys Lys
    50                  55                  60

His Leu Gln Asp Leu Ser Gly
65                  70

<210> SEQ ID NO 98
<211> LENGTH: 55
<212> TYPE: PRT
<213> ORGANISM: Homo sapiens

<400> SEQUENCE: 98

His Phe Glu Ala Lys Ile Glu Lys His Asn His Tyr Gln Lys Gln Leu
1               5                   10                  15

Glu Ile Ala His Glu Lys Leu Arg His Ala Glu Ser Val Gly Asp Gly
            20                  25                  30

Glu Arg Val Ser Arg Ser Arg Glu Lys His Ala Leu Leu Glu Gly Arg
        35                  40                  45

Thr Lys Glu Leu Gly Tyr Thr
    50                  55

<210> SEQ ID NO 99
<211> LENGTH: 75
<212> TYPE: PRT
<213> ORGANISM: Artificial Sequence
<220> FEATURE:
<223> OTHER INFORMATION: Synthetic peptide

<400> SEQUENCE: 99

Cys Gly Phe Arg Glu Glu Leu Lys His Phe Glu Ala Lys Ile Glu Lys
1               5                   10                  15

His Asn His Tyr Gln Lys Gln Leu Glu Ile Ala His Glu Lys Leu Arg
            20                  25                  30

His Ala Glu Ser Val Gly Asp Gly Glu Arg Val Ser Arg Ser Arg Glu
        35                  40                  45

Lys His Ala Leu Leu Glu Gly Arg Thr Lys Glu Leu Gly Tyr Thr Val
    50                  55                  60

Lys Lys His Leu Gln Asp Leu Ser Gly Gly Cys
65                  70                  75

<210> SEQ ID NO 100
<211> LENGTH: 67
<212> TYPE: PRT
<213> ORGANISM: Artificial sequence
<220> FEATURE:
<223> OTHER INFORMATION: Synthetic peptide

<400> SEQUENCE: 100

Cys Gly Lys His Phe Glu Ala Lys Ile Glu Lys His Asn His Tyr Gln
1               5                   10                  15

```
Lys Gln Leu Glu Ile Ala His Glu Lys Leu Arg His Ala Glu Ser Val
            20                  25                  30

Gly Asp Gly Glu Arg Val Ser Arg Ser Arg Glu Lys His Ala Leu Leu
        35                  40                  45

Glu Gly Arg Thr Lys Glu Leu Gly Tyr Thr Val Lys Lys His Leu Gln
    50                  55                  60

Asp Gly Cys
65

<210> SEQ ID NO 101
<211> LENGTH: 60
<212> TYPE: PRT
<213> ORGANISM: Artificial sequence
<220> FEATURE:
<223> OTHER INFORMATION: Synthetic peptide

<400> SEQUENCE: 101

Cys Glu Ala Lys Ile Glu Lys His Asn His Tyr Gln Lys Gln Leu Glu
1               5                   10                  15

Ile Ala His Glu Lys Leu Arg His Ala Glu Ser Val Gly Asp Gly Glu
            20                  25                  30

Arg Val Ser Arg Ser Arg Glu Lys His Ala Leu Leu Glu Gly Arg Thr
        35                  40                  45

Lys Glu Leu Gly Tyr Thr Val Lys Lys His Gly Cys
    50                  55                  60

<210> SEQ ID NO 102
<211> LENGTH: 5
<212> TYPE: PRT
<213> ORGANISM: Artificial sequence
<220> FEATURE:
<223> OTHER INFORMATION: Synthetic peptide

<400> SEQUENCE: 102

Gly Gly Ser Gly Gly
1               5

<210> SEQ ID NO 103
<211> LENGTH: 68
<212> TYPE: PRT
<213> ORGANISM: Artificial Sequence
<220> FEATURE:
<223> OTHER INFORMATION: Synthetic Peptide

<400> SEQUENCE: 103

Cys Gly Lys His Phe Glu Ala Lys Ile Glu Lys His Asn His Tyr Gln
1               5                   10                  15

Lys Gln Leu Glu Ile Ala His Glu Lys Leu Arg His Ala Glu Ser Val
            20                  25                  30

Gly Asp Ala Glu Arg Val Ser Arg Ser Arg Glu Lys His Ala Leu Leu
        35                  40                  45

Glu Gly Arg Thr Lys Glu Leu Gly Tyr Thr Val Lys Lys His Leu Gln
    50                  55                  60

Asp Ala Cys Gly
65

<210> SEQ ID NO 104
<211> LENGTH: 73
<212> TYPE: PRT
<213> ORGANISM: Artificial Sequence
<220> FEATURE:
<223> OTHER INFORMATION: Synthetic Peptide
```

<400> SEQUENCE: 104

Gly Gly Ser Gly Gly Cys Gly Lys His Phe Glu Ala Lys Ile Glu Lys
1               5                   10                  15

His Asn His Tyr Gln Lys Gln Leu Glu Ile Ala His Glu Lys Leu Arg
            20                  25                  30

His Ala Glu Ser Val Gly Asp Ala Glu Arg Val Ser Arg Ser Arg Glu
        35                  40                  45

Lys His Ala Leu Leu Glu Gly Arg Thr Lys Glu Leu Gly Tyr Thr Val
    50                  55                  60

Lys Lys His Leu Gln Asp Ala Cys Gly
65                  70

<210> SEQ ID NO 105
<211> LENGTH: 73
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Xaa is glycine modified with SU6668

<400> SEQUENCE: 105

Xaa Gly Ser Gly Gly Cys Gly Lys His Phe Glu Ala Lys Ile Glu Lys
1               5                   10                  15

His Asn His Tyr Gln Lys Gln Leu Glu Ile Ala His Glu Lys Leu Arg
            20                  25                  30

His Ala Glu Ser Val Gly Asp Ala Glu Arg Val Ser Arg Ser Arg Glu
        35                  40                  45

Lys His Ala Leu Leu Glu Gly Arg Thr Lys Glu Leu Gly Tyr Thr Val
    50                  55                  60

Lys Lys His Leu Gln Asp Ala Cys Gly
65                  70

<210> SEQ ID NO 106
<211> LENGTH: 74
<212> TYPE: PRT
<213> ORGANISM: Artificial Sequence
<220> FEATURE:
<223> OTHER INFORMATION: Synthetic Peptide
<220> FEATURE:
<221> NAME/KEY: MOD_RES
<222> LOCATION: (1)..(1)
<223> OTHER INFORMATION: Xaa is lysine modified with
      octa-difluoromethylornithine

<400> SEQUENCE: 106

Xaa Gly Gly Ser Gly Gly Cys Gly Lys His Phe Glu Ala Lys Ile Glu
1               5                   10                  15

Lys His Asn His Tyr Gln Lys Gln Leu Glu Ile Ala His Glu Lys Leu
            20                  25                  30

Arg His Ala Glu Ser Val Gly Asp Ala Glu Arg Val Ser Arg Ser Arg
        35                  40                  45

Glu Lys His Ala Leu Leu Glu Gly Arg Thr Lys Glu Leu Gly Tyr Thr
    50                  55                  60

Val Lys Lys His Leu Gln Asp Ala Cys Gly
65                  70

<210> SEQ ID NO 107
<211> LENGTH: 75

```
<212> TYPE: PRT
<213> ORGANISM: Artificial Sequence
<220> FEATURE:
<223> OTHER INFORMATION: Synthetic Peptide

<400> SEQUENCE: 107

Ser Gly Phe Arg Glu Glu Leu Lys His Phe Glu Ala Lys Ile Glu Lys
1               5                   10                  15

His Asn His Tyr Gln Lys Gln Leu Glu Ile Ala His Glu Lys Leu Arg
            20                  25                  30

His Ala Glu Ser Val Gly Asp Gly Glu Arg Val Ser Arg Ser Arg Glu
        35                  40                  45

Lys His Ala Leu Leu Glu Gly Arg Thr Lys Glu Leu Gly Tyr Thr Val
    50                  55                  60

Lys Lys His Leu Gln Asp Leu Ser Gly Gly Ser
65                  70                  75

<210> SEQ ID NO 108
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 108

His Asn Glu Leu
1

<210> SEQ ID NO 109
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 109

Tyr Trp Thr Asp
1

<210> SEQ ID NO 110
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (5)..(5)
<223> OTHER INFORMATION: Xaa can be any naturally occurring amino acid

<400> SEQUENCE: 110

Phe Asp Asn Pro Xaa Tyr
1               5

<210> SEQ ID NO 111
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 111

Arg Lys Lys Arg
1

<210> SEQ ID NO 112
```

```
<211> LENGTH: 6
<212> TYPE: PRT
<213> ORGANISM: Artificial Sequence
<220> FEATURE:
<223> OTHER INFORMATION: Synthetic polypeptide

<400> SEQUENCE: 112

Ala Glu Ala Glu Thr Gly
1               5

<210> SEQ ID NO 113
<211> LENGTH: 119
<212> TYPE: PRT
<213> ORGANISM: Homo sapiens

<400> SEQUENCE: 113

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
        35                  40                  45

His Phe Thr Ala Lys Ile Glu Ile His Asn His Tyr Gln Lys Gln Leu
    50                  55                  60

Glu Ile Ala His Glu Glu Leu Arg His Ala Glu Ser Val Gly Asp Gly
65                  70                  75                  80

Glu Arg Val Ser Arg Ser Arg Glu Lys His Ala Leu Leu Glu Gly Leu
                85                  90                  95

Thr Lys Glu Leu Gly Tyr Thr Val Lys Lys His Leu Gln Asp Leu Ser
            100                 105                 110

Gly Arg Ile Ser Arg Ala Arg
        115

<210> SEQ ID NO 114
<211> LENGTH: 119
<212> TYPE: PRT
<213> ORGANISM: Homo sapiens

<400> SEQUENCE: 114

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Glu Gln Ser
            20                  25                  30

Ala Asn Leu Thr Asp Lys Glu Leu Glu Ala Phe Arg Glu Glu Leu Lys
        35                  40                  45

His Phe Ala Ala Lys Ile Glu Val Tyr Asn His Tyr Gln Lys Gln Leu
    50                  55                  60

Glu Phe Ala His Glu Trp Leu Arg His Ala Glu Ser Val Gly Asp Gly
65                  70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg
        115

<210> SEQ ID NO 115
<211> LENGTH: 119
<212> TYPE: PRT
<213> ORGANISM: Homo sapiens
```

<400> SEQUENCE: 115

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Gln Ser
            20                  25                  30

Ala Asn Leu Thr Asp Lys Glu Leu Glu Ala Phe Arg Glu Glu Leu Lys
            35                  40                  45

His Phe Gly Ala Lys Ile Glu Arg His Asn His Tyr Gln Lys Gln Leu
        50                  55                  60

Glu Phe Ala His Glu Trp Leu Arg His Ala Glu Ser Val Gly Asp Ser
65              70                  75                  80

Glu Arg Val Ser Arg Ser Arg Glu Lys His Ala Leu Leu Glu Gly Arg
                85                  90                  95

Thr Lys Glu Leu Gly Tyr Thr Val Lys Lys His Leu Gln Asp Leu Ser
            100                 105                 110

Gly Arg Ile Ser Arg Ala Arg
            115

<210> SEQ ID NO 116
<211> LENGTH: 113
<212> TYPE: PRT
<213> ORGANISM: Homo sapiens

<400> SEQUENCE: 116

Leu Asp Arg Leu Arg Arg Val Ser His Gln Gly Tyr Ser Thr Glu Ala
1               5                   10                  15

Glu Phe Glu Glu Pro Arg Val Ile Asp Leu Trp Asp Leu Gln Ser
            20                  25                  30

Ala Asn Leu Thr Asp Lys Glu Leu Glu Ala Phe Arg Glu Glu Leu Lys
            35                  40                  45

His Phe Ala Ala Lys Ile Glu Ser His Asn His Tyr Gln Lys Gln Leu
        50                  55                  60

Glu Ile Ala His Glu Ser Met Arg His Ala Glu Ser Val Gly Tyr Gly
65              70                  75                  80

Glu Arg Met Ser Arg Ser Arg Glu Lys His Ala Leu Leu Glu Gly Arg
                85                  90                  95

Thr Lys Glu Leu Gly Tyr Thr Val Thr Met His Leu Gln Asp Leu Ser
            100                 105                 110

Gly

<210> SEQ ID NO 117
<211> LENGTH: 173
<212> TYPE: PRT
<213> ORGANISM: Artificial Sequence
<220> FEATURE:
<223> OTHER INFORMATION: Synthetic polypeptide

<400> SEQUENCE: 117

Met His His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile
            35                  40                  45

Gly Ser Leu Asp Arg Leu Arg Arg Val Ser His Gln Gly Tyr Ser Thr
        50                  55                  60

Glu Ala Glu Phe Glu Glu Pro Arg Val Ile Asp Leu Trp Asp Leu Glu
65                  70                  75                  80

Gln Ser Ala Asn Leu Thr Asp Lys Glu Leu Ala Phe Arg Glu Glu
            85                  90                  95

Leu Lys His Phe Ala Ala Lys Ile Glu Val Tyr Asn His Tyr Gln Lys
            100                 105                 110

Gln Leu Glu Phe Ala His Glu Trp Leu Arg His Ala Glu Ser Val Gly
            115                 120                 125

Asp Gly Glu Arg Val Ser Arg Ser Arg Glu Lys His Ala Leu Leu Glu
        130                 135                 140

Gly Arg Thr Lys Glu Leu Gly Tyr Thr Val Lys Lys His Leu Gln Asp
145                 150                 155                 160

Leu Ser Gly Arg Ile Ser Arg Ala Arg Ala Glu Ala Glu
                165                 170

<210> SEQ ID NO 118
<211> LENGTH: 163
<212> TYPE: PRT
<213> ORGANISM: Artificial Sequence
<220> FEATURE:
<223> OTHER INFORMATION: Synthetic polypeptide

<400> SEQUENCE: 118

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Gly Tyr Ser Thr Glu Ala Glu Phe Glu Glu Pro Arg Val Ile
    50                  55                  60

Asp Leu Trp Asp Leu Glu Gln Ser Ala Asn Leu Thr Asp Lys Glu Leu
65                  70                  75                  80

Glu Ala Phe Arg Glu Glu Leu Lys His Phe Ala Ala Lys Ile Glu Val
                85                  90                  95

Tyr Asn His Tyr Gln Lys Gln Leu Glu Phe Ala His Glu Trp Leu Arg
            100                 105                 110

His Ala Glu Ser Val Gly Asp Gly Glu Arg Val Ser Arg Ser Arg Glu
            115                 120                 125

Lys His Ala Leu Leu Glu Gly Arg Thr Lys Glu Leu Gly Tyr Thr Val
        130                 135                 140

Lys Lys His Leu Gln Asp Leu Ser Gly Arg Ile Ser Arg Ala Arg Ala
145                 150                 155                 160

Glu Ala Glu

<210> SEQ ID NO 119
<211> LENGTH: 142
<212> TYPE: PRT
<213> ORGANISM: Artificial Sequence
<220> FEATURE:
<223> OTHER INFORMATION: Synthetic polypeptide

<400> SEQUENCE: 119

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile

```
                35                  40                  45
Gly Ser Ser Ala Asn Leu Thr Asp Lys Glu Leu Glu Ala Phe Arg Glu
 50                  55                  60

Glu Leu Lys His Phe Ala Ala Lys Ile Glu Val Tyr Asn His Tyr Gln
 65                  70                  75                  80

Lys Gln Leu Glu Phe Ala His Glu Trp Leu Arg His Ala Glu Ser Val
                 85                  90                  95

Gly Asp Gly Glu Arg Val Ser Arg Ser Arg Lys His Ala Leu Leu
            100                 105                 110

Glu Gly Arg Thr Lys Glu Leu Gly Tyr Thr Val Lys Lys His Leu Gln
            115                 120                 125

Asp Leu Ser Gly Arg Ile Ser Arg Ala Arg Ala Glu Ala Glu
130                 135                 140

<210> SEQ ID NO 120
<211> LENGTH: 131
<212> TYPE: PRT
<213> ORGANISM: Artificial Sequence
<220> FEATURE:
<223> OTHER INFORMATION: Synthetic polypeptide

<400> SEQUENCE: 120

Met His His His His His Ser Ser Gly Leu Val Pro Arg Gly Ser
 1               5                  10                  15

Gly Met Lys Glu Thr Ala Ala Ala Lys Phe Glu Arg Gln His Met Asp
                 20                  25                  30

Ser Pro Asp Leu Gly Thr Asp Asp Asp Lys Ala Met Ala Asp Ile
             35                  40                  45

Gly Ser Phe Arg Glu Glu Leu Lys His Phe Ala Ala Lys Ile Glu Val
 50                  55                  60

Tyr Asn His Tyr Gln Lys Gln Leu Glu Phe Ala His Glu Trp Leu Arg
 65                  70                  75                  80

His Ala Glu Ser Val Gly Asp Gly Glu Arg Val Ser Arg Ser Arg Glu
                 85                  90                  95

Lys His Ala Leu Leu Glu Gly Arg Thr Lys Glu Leu Gly Tyr Thr Val
            100                 105                 110

Lys Lys His Leu Gln Asp Leu Ser Gly Arg Ile Ser Arg Ala Arg Ala
            115                 120                 125

Glu Ala Glu
130

<210> SEQ ID NO 121
<211> LENGTH: 121
<212> TYPE: PRT
<213> ORGANISM: Artificial Sequence
<220> FEATURE:
<223> OTHER INFORMATION: Synthetic polypeptide

<400> SEQUENCE: 121

Met His His His His His Ser Ser Gly Leu Val Pro Arg Gly Ser
 1               5                  10                  15

Gly Met Lys Glu Thr Ala Ala Ala Lys Phe Glu Arg Gln His Met Asp
                 20                  25                  30

Ser Pro Asp Leu Gly Thr Asp Asp Asp Lys Ala Met Ala Asp Ile
             35                  40                  45

Gly Ser Lys Ile Glu Arg His Asn His Tyr Gln Lys Gln Leu Glu Phe
 50                  55                  60

Ala His Glu Trp Leu Arg His Ala Glu Ser Val Gly Asp Gly Glu Arg
```

```
                65                  70                  75                  80
Val Ser Arg Ser Arg Glu Lys His Ala Leu Leu Glu Gly Arg Thr Lys
                    85                  90                  95

Glu Leu Gly Tyr Thr Val Lys Lys His Leu Gln Asp Leu Ser Gly Arg
                100                 105                 110

Ile Ser Arg Ala Arg Ala Glu Ala Glu
                115                 120

<210> SEQ ID NO 122
<211> LENGTH: 117
<212> TYPE: PRT
<213> ORGANISM: Artificial Sequence
<220> FEATURE:
<223> OTHER INFORMATION: Synthetic polypeptide

<400> SEQUENCE: 122

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
            35                  40                  45

Gly Ser His Asn His Tyr Gln Lys Gln Leu Glu Phe Ala His Glu Trp
    50                  55                  60

Leu Arg His Ala Glu Ser Val Gly Asp Gly Glu Arg Val Ser Arg Ser
65                  70                  75                  80

Arg Glu Lys His Ala Leu Leu Glu Gly Arg Thr Lys Glu Leu Gly Tyr
                85                  90                  95

Thr Val Lys Lys His Leu Gln Asp Leu Ser Gly Arg Ile Ser Arg Ala
                100                 105                 110

Arg Ala Glu Ala Glu
        115

<210> SEQ ID NO 123
<211> LENGTH: 109
<212> TYPE: PRT
<213> ORGANISM: Artificial Sequence
<220> FEATURE:
<223> OTHER INFORMATION: Synthetic polypeptide

<400> SEQUENCE: 123

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
            35                  40                  45

Gly Ser Glu Phe Ala His Glu Trp Leu Arg His Ala Glu Ser Val Gly
    50                  55                  60

Asp Gly Glu Arg Val Ser Arg Ser Arg Glu Lys His Ala Leu Leu Glu
65                  70                  75                  80

Gly Arg Thr Lys Glu Leu Gly Tyr Thr Val Lys Lys His Leu Gln Asp
                85                  90                  95

Leu Ser Gly Arg Ile Ser Arg Ala Arg Ala Glu Ala Glu
                100                 105

<210> SEQ ID NO 124
<211> LENGTH: 106
<212> TYPE: PRT
```

<213> ORGANISM: Artificial Sequence
<220> FEATURE:
<223> OTHER INFORMATION: Synthetic polypeptide

<400> SEQUENCE: 124

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser His Glu Trp Leu Arg His Ala Glu Ser Val Gly Asp Gly Glu
    50                  55                  60

Arg Val Ser Arg Ser Arg Glu Lys His Ala Leu Leu Glu Gly Arg Thr
65                  70                  75                  80

Lys Glu Leu Gly Tyr Thr Val Lys Lys His Leu Gln Asp Leu Ser Gly
                85                  90                  95

Arg Ile Ser Arg Ala Arg Ala Glu Ala Glu
            100                 105

<210> SEQ ID NO 125
<211> LENGTH: 140
<212> TYPE: PRT
<213> ORGANISM: Artificial Sequence
<220> FEATURE:
<223> OTHER INFORMATION: Synthetic polypeptide

<400> SEQUENCE: 125

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

Ser Pro Asp Leu Gly Thr Asp Asp Asp Lys Ala Met Ala Asp Ile
        35                  40                  45

Gly Ser Phe Arg Glu Glu Leu Lys His Phe Ala Ala Lys Ile Glu Val
    50                  55                  60

Tyr Asn His Tyr Gln Lys Gln Leu Glu Phe Ala His Glu Trp Leu Arg
65                  70                  75                  80

His Ala Glu Ser Val Gly Asp Gly Glu Arg Val Ser Arg Ser Arg Glu
                85                  90                  95

Lys His Ala Leu Leu Glu Gly Arg Thr Lys Glu Leu Gly Tyr Thr Val
            100                 105                 110

Lys Lys His Leu Gln Asp Leu Ser Gly Arg Ile Ser Arg Ala Arg Lys
        115                 120                 125

Leu Ala Ala Ala Leu Glu His His His His His
    130                 135                 140

<210> SEQ ID NO 126
<211> LENGTH: 134
<212> TYPE: PRT
<213> ORGANISM: Artificial Sequence
<220> FEATURE:
<223> OTHER INFORMATION: Synthetic polypeptide

<400> SEQUENCE: 126

Met His His His His His Ser Ser Gly Leu Val Pro Arg Gly Ser
1               5                   10                  15

Gly Met Lys Glu Thr Ala Ala Ala Lys Phe Glu Arg Gln His Met Asp
            20                  25                  30

```
Ser Pro Asp Leu Gly Thr Asp Asp Asp Lys Ala Met Ala Asp Ile
        35                  40                  45

Gly Ser Phe Arg Glu Glu Leu Lys His Phe Ala Ala Lys Ile Glu Val
    50                  55                  60

Tyr Asn His Tyr Gln Lys Gln Leu Glu Phe Ala His Glu Trp Leu Arg
 65                  70                  75                  80

His Ala Glu Ser Val Gly Asp Gly Glu Arg Val Ser Arg Ser Arg Glu
                 85                  90                  95

Lys His Ala Leu Leu Glu Gly Arg Thr Lys Glu Leu Gly Tyr Thr Val
                100                 105                 110

Lys Lys His Leu Gln Asp Leu Ser Gly Lys Leu Ala Ala Ala Leu Glu
                115                 120                 125

His His His His His His
        130
```

<210> SEQ ID NO 127
<211> LENGTH: 115
<212> TYPE: PRT
<213> ORGANISM: Artificial Sequence
<220> FEATURE:
<223> OTHER INFORMATION: Synthetic polypeptide

<400> SEQUENCE: 127

```
Met His His His His His His Ser Ser Gly Leu Val Pro Arg Gly Ser
 1               5                  10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
        35                  40                  45

Gly Ser Phe Arg Glu Glu Leu Lys His Phe Ala Ala Lys Ile Glu Val
    50                  55                  60

Tyr Asn His Tyr Gln Lys Gln Leu Glu Phe Ala His Glu Trp Leu Arg
 65                  70                  75                  80

His Ala Glu Ser Val Gly Asp Gly Glu Arg Val Ser Arg Ser Arg Glu
                 85                  90                  95

Lys His Ala Leu Leu Glu Lys Leu Ala Ala Ala Leu Glu His His His
                100                 105                 110

His His His
        115
```

<210> SEQ ID NO 128
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 128

```
Met His His His His His His Ser Ser Gly Leu Val Pro Arg Gly Ser
 1               5                  10                  15

Gly Met Lys Glu Thr Ala Ala Ala Lys Phe Glu Arg Gln His Met Asp
                20                  25                  30

Ser Pro Asp Leu Gly Thr Asp Asp Asp Lys Ala Met Ala Asp Ile
        35                  40                  45

Gly Ser Phe Arg Glu Glu Leu Lys His Phe Ala Ala Lys Ile Glu Val
    50                  55                  60

Tyr Asn His Tyr Gln Lys Gln Leu Glu Phe Ala His Glu Trp Leu Arg
 65                  70                  75                  80
```

His Ala Glu Ser Val Gly Asp Gly Glu Arg Val Ser Arg Ser Lys Leu
            85                  90                  95

Ala Ala Ala Leu Glu His His His His His
            100                 105

<210> SEQ ID NO 129
<211> LENGTH: 97
<212> TYPE: PRT
<213> ORGANISM: Artificial Sequence
<220> FEATURE:
<223> OTHER INFORMATION: Synthetic polypeptide

<400> SEQUENCE: 129

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
            35                  40                  45

Gly Ser Phe Arg Glu Glu Leu Lys His Phe Ala Ala Lys Ile Glu Val
            50                  55                  60

Tyr Asn His Tyr Gln Lys Gln Leu Glu Phe Ala His Glu Trp Leu Arg
65                  70                  75                  80

His Ala Glu Ser Lys Leu Ala Ala Ala Leu Glu His His His His
            85                  90                  95

His

<210> SEQ ID NO 130
<211> LENGTH: 50
<212> TYPE: PRT
<213> ORGANISM: Artificial Sequence
<220> FEATURE:
<223> OTHER INFORMATION: Synthetic polypeptide

<400> SEQUENCE: 130

Met His His His His His Ser Ser Gly Leu Val Pro Arg Gly Ser
1               5                   10                  15

Gly Met Lys Glu Thr Ala Ala Lys Phe Glu Arg Gln His Met Asp
            20                  25                  30

Ser Pro Asp Leu Gly Thr Asp Asp Asp Lys Ala Met Ala Asp Ile
            35                  40                  45

Gly Ser
    50

<210> SEQ ID NO 131
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 131

Lys Leu Ala Ala Ala Leu Glu His His His His His
1               5                   10

<210> SEQ ID NO 132
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 132

Gly Pro Leu Gly Ser
1               5

CYCLIC RECEPTOR-ASSOCIATED PROTEIN (RAP) PEPTIDES

This application is a 35 U.S.C. 371 national phase application of PCT/US2008/57863, filed Mar. 21, 2008, which claims the priority benefit of U.S. Provisional Patent Application No. 60/919,238, filed Mar. 21, 2007, herein incorporated by reference in its entirety.

FIELD OF THE INVENTION

The present invention relates to cyclic peptides of the low-density lipoprotein receptor-associated protein (RAP), including analogs thereof, compositions thereof, and methods of generating and methods of using such cyclic RAP peptides.

BACKGROUND OF THE INVENTION

Receptor-associated protein (RAP), also known as alpha-2-macroglobulin/low density lipoprotein receptor-related protein-associated protein 1 (Uniprot accession P30533, Pfam accession numbers PF06400 and PF06401), is a unique 39 kD protein that binds to almost all members of the low-density lipoprotein receptor (LDLR) family. Localized in the endoplasmic reticulum and Golgi (Bu and Schwartz, Trends Cell. Biol. 8 (7):272-6, 1998), RAP acts as a chaperone for these family members. For example, RAP binds tightly to LRP in these compartments preventing premature association of the receptor with co-expressed ligands (Herz and Willnow, Atherosclerosis 118 Suppl:S37-41, 1995).

Full length human RAP including its signal sequence is 357 amino acids. Mature RAP contains 323 amino acids, of which the last four amino acids (HNEL (SEQ ID NO: 108)) constitute an endoplasmic reticulum retention signal. RAP has been reported to be composed of three weakly homologous domains (d1, d2 and d3). All three domains are capable of binding LRP, although d3 binds with the highest affinity. Different publications have reported slightly different assignment of the boundaries of the three domains of RAP (residues 1-100, 101-200 and 201-323, or 18-112, 113-218 and 219-323), and the domains appear to have slightly different binding characteristics. For example, d1 has been reported to inhibit binding of alpha-2-macroglobulin to LRP, while d3 has been reported to promote proper folding of LRP. (See Obermoeller et al., J. Biol. Chem. 272(16):10761-100768 (1997).) An alternative four-domain assignment (residues 1-92, 93-163, 164-216 and 217-323) has been reported by Medved et al., J. Biol. Chem., 274(2):717-727 (1999).

Truncated and/or mutated versions of RAP have been studied. Melman et al., J. Biol. Chem., 276 (31):29338-29346 (2001) reported the generation of a number of GST/RAP fragment fusions including residues 221-323, 221-275, 276-323, 221-290, 221-300 and 221-310 of mature RAP, which all exhibited no or low affinity binding to LRP. From this data, Melman et al. concluded that residues 201-210 were required for high affinity LRP binding. Melman et al. also generated RAP mutants containing mutations within positions 203-206 (site A), 282-289 (site B) and 314-319 (site C); mutations within site A alone or site B alone produced a small reduction in LRP binding activity, while mutations within both sites A and B significantly decreased LRP binding activity. Medved et al., supra, generated two GST/RAP C-terminal fragments fusions, one consisting of residues 216-323 of mature RAP and another consisting of residues 206-323. Rall et al., J. Biol. Chem., 273 (37):24152-24157 (1998) reported proteolytic cleavage of mature RAP into a variety of fragments and identified residues 223-323 as a highly protease resistant region. Obermoeller et al., supra, also generated a RAP fragment consisting of residues 191-323 of mature RAP and studied binding interactions with various domains of LRP. McCormick et al., Biochemistry, 44:5794-803 (2005) constructed a GSP/RAP fragment fusion containing residues 221-323 of RAP and evaluated its binding to endoplasmic reticulum chaperone ERp57. Andersen et al., Biochemistry 42, 9355-64 (2003) tested RAP domain fragments for binding to apoE receptor 2 and reported that only the third domain (residues 216-323) bound. Andersen et al., J Biol Chem 275, 21017-24 (2000) tested RAP d3 (residues 216-323) for binding to various fragments of LRP. Andersen et al., Biochemistry 40, 15408-17 (2001) also tested a variant of RAPd3, C-terminally truncated to residues 219-309, for ability to bind to an LRP fragment fused to ubiquitin (U-CR56), and observed a significant decrease in affinity for U-CR56. Lee et al. Mol Cell 22, 423-30 (2006) constructed mutants of full length RAP in which each conserved histidine was mutated to alanine, all histidines in domain 1 were mutated to alanine, all histidines in domain 2 were mutated to alanine, and all histidines in domain 3 were mutated to alanine. Migliorini et al., J Biol Chem 278, 17986-92 (2003) constructed a library containing clones with random mutations within residues 206-323 of RAP and reported that mutation of the lysine at position 256 or the lysine at position 270 of RAP abolished binding of RAP to LRP.

The lipoprotein receptor-related protein (LRP) receptor family comprises a group of cell-surface, transmembrane proteins that mediate a wide variety of physiological phenomena. All of the receptors are homologous to LDLR and share a similar domain organization, which includes groups of LDL receptor class A domains, or complement-type repeats (CR), that are part of a large family of conserved protein sequences. Structural data on members of this family suggests that CR sequences adopt a characteristic fold, the LDL receptor-like module (Structural Classification of Proteins, SCOP, terminology). CR sequences are found in a variety of different types of proteins including the LDLR family and the type II transmembrane serine protease (matriptase) family.

Mechanisms of action of LRP family members include both endocytosis of bound ligands and signal transduction from the extracellular space (1). LRP participate in various cellular functions, including but not limited to the metabolism of lipoproteins (2, 3), control of matrix metalloproteases and coagulation factors (4-6), specification of cell fate (3, 7), guidance of neural cell migration (7, 8), induction of proliferation in tumor cells (9, 10), binding of rhinovirus (11, 12), signalling by neurotransmitters (13, 14), acquisition of antigens by antigen presenting cells (15), trancytosis of ligands across the blood-brain barrier (16-19), recovery of proteins from glomerular filtrate (20), transport of endocrine hormones (21), efflux of amyloid β peptide from the brain (22), activation of bone deposition (23) and regulation of endothelial cell proliferation (24). The capacity of the LDLR to serve in so many roles derives in part from the diverse set of ligands to which these receptors are able to bind. Another feature of this receptor family is the diverse, and often unique, tissue distribution patterns of each LDLR.

The type II transmembrane serine protease family includes corin and the matriptases ST14, matriptase-2 and matriptase-3. Matriptase (MT-SP1, ST14, TADG-15) is overexpressed in a variety of epithelial tumors (carcinomas) (25-33). Following transactivation facilitated by hepatocyte activator inhibitor-1 (HAI-1), matriptase promotes tumor growth and metastasis by degrading extracellular matrix components directly or by activating other proteases, such as urokinase plasminogen activator (uPA), resulting in matrix-degradative events (26, 34, 35). In addition to the LDLR and matriptase families, a variety of other proteins have CR domains. One such protein, the FDC-8D6 antigen (CD320) has a pair of such domains and plays an important role in B-cell differentiation in lymphatic follicles (36, 37).

The important roles that CR-containing proteins play in pathophysiological processes, along with the unique tissue-distribution profiles of some members of these families, make these proteins useful drug targets. Protein-selective drugs could directly impact the function of a targeted protein, diminishing the supporting effects that the protein has on a particular disease state. Alternatively, the drug could take advantage of the tissue distribution of the targeted protein to efficiently deliver other therapeutic molecules to a particular tissue affected by a disease. Despite considerable evidence of the importance of CR-containing proteins in mammalian physiology and pathophysiology, there are few examples of drugs that act selectively on particular members of the LDLR or CR-containing protein families. The ability to create molecules that bind specific members of these families would provide a means of developing such drugs.

For example, WO 2006/138343 (Zankel et al.) reports data showing that a fusion of GDNF to RAP (which crosses the blood brain barrier) produced a conjugate that retained the disulfide-linked homodimeric conformation of GDNF. The RAP-GDNF conjugate bound and activated the receptor for GDNF (GFRα-1) with the same affinity (Kd) as GDNF, and retained biological activity in vitro as evidenced by RAP-GDNF induced neurite outgrowth in PC12 cells in culture.

Given the widespread participation of CR-containing proteins throughout mammalian physiology, there exists a need for RAP fragments and variants that retain the original binding characteristics of RAP, or that have improved binding selectivity for specific CR-containing proteins, and also exhibit other desirable properties such as improved stability or ease of production and manufacturing.

SUMMARY OF THE INVENTION

Complement-type repeats (CR) are a large family of conserved protein sequences that adopt a characteristic fold. CR-containing proteins include members of the LDL receptor family, the type II transmembrane serine protease (matriptase) family, and other proteins such as FDC-8D6 antigen (CD320). Receptor-associated protein (RAP) binds to many of these CR-containing proteins with high affinity. The 323 amino acid sequence of mature RAP is set forth in SEQ ID NO: 95. The amino acid sequence of domain 3 of mature RAP (amino acids 201-323), 123 amino acids in length, is set forth in SEQ ID NO: 96. Amino acids 243-313 are set forth in SEQ ID NO: 97. Amino acids 249-303 of RAP are set forth in SEQ ID NO: 98.

The invention provides cyclic RAP peptides (including analogs or derivatives) that bind CR-containing proteins with high affinity, conjugates and compositions comprising such cyclic peptides, and therapeutic and diagnostic uses of such peptides, for example, as inhibitors or enhancers of such CR-containing proteins, or for the targeted delivery of diagnostic or therapeutic agents to tissues expressing such CR-containing proteins. The cyclic RAP peptides may exhibit desirable properties such as improved affinity, improved binding selectivity for a CR-containing protein, improved stability, and/or ease of manufacturing.

The cyclic RAP peptides of the invention are based on the amino acid sequence of mature RAP, preferably domain 3, are preferably less than 123 amino acids in length and contain a covalent bond between two non-consecutive amino acids. In some embodiments, the covalent bond stabilizes the three-dimensional structure of the RAP peptide. In some embodiments, the covalent bond provides an improvement in binding affinity so that the cyclic RAP peptide binds to a CR-containing protein with a Kd of about $1 \times 10^{-8}$ M or less (less meaning better affinity). Such binding affinities can be measured by any method known in the art, such as radioimmunoassay, ELISA, surface plasmon resonance (SPR) based technology (e.g., Biacore) analysis, or kinetic exclusion assay (e.g., KinExA). The affinity data may be analyzed, for example, by the method of Scatchard et al., Ann N.Y. Acad. Sci., 51:660 (1949). In exemplary embodiments, the binding affinity for a CR-protein is about $1 \times 10^{-9}$, $10^{-10}$, $10^{-11}$, $10^{-12}$, $10^{-13}$, $10^{-14}$ M or less. The invention provides cyclic RAP peptides of various sizes, including about 103, about 99, about 95, about 90, about 85, about 82, about 80, about 78, about 76, 75, 74, 73, 72, 71, 70, 69, 68, 67, 66, 65, 64, 63, 62, 61, 60, 59, 58, 57, or 56 amino acids in length or less. In some embodiments, the covalent bond is formed between amino acids that are separated by about 76, 75, 74, 73, 72, 71, 70, 69, 68, 67, 66, 65, 64, 63, 62, 61, 60, 59, 58, 57, or 56 amino acids.

The cyclic RAP peptides of the invention may comprise an amino acid sequence based on mature human RAP sequence (SEQ ID NO: 95). In one embodiment the amino acid sequence of the cyclic RAP peptide is missing at least 200 and up to 243 amino acids from the N-terminus of mature RAP. Thus, the cyclic RAP peptide may be missing amino acids 1-200, 1-220, 1-225, 1-230, 1-235, 1-240, 1-241, 1-242, 1-243, or alternatively 1-244, 1-245, 1-246, 1-247, or 1-248 of mature RAP. In a related embodiment, the RAP peptide amino acid sequence is further missing at least 4 and up to 11 amino acids from the C-terminus of mature RAP. Thus, the cyclic RAP peptide may be missing amino acids 314-323 or 313-323, or alternatively 304-323, 305-323, 306-323, 307-323, 308-323, 309-323, 310-323, 311-323, or 312-323 of mature RAP. In another embodiment the RAP peptide amino acid sequence comprises a continuous portion of mature RAP that is (a) at least 71 amino acids in length and (b) comprises amino acids 256-270. In a related embodiment, the RAP peptide amino acid sequence comprises a continuous portion of mature RAP domain 3 that is (a) at least 71 amino acids in length and (b) comprises amino acids 256-270. Exemplary portions of RAP which may form the basis for a cyclic RAP peptide include amino acids 200-323, 221-323, 200-319, 221-319, 243-319, 244-319, 249-319, 200-313, 221-313, 243-313, 244-313, 249-313, 200-303, 221-303, 243-303, 244-303, 246-311, 246-313, or 249-303 of mature RAP (SEQ ID NO: 95).

As described herein, cyclic RAP peptides can be prepared that exhibit affinity for and selectivity for CR-containing proteins that is similar to that of native RAP (e.g., about 5-fold difference or less compared to native RAP). Cyclic RAP peptides can also be prepared that exhibit improved affinity for and/or altered selectivity for one or more CR-containing proteins, compared to native RAP. In one embodiment, the cyclic RAP peptide exhibits at least 1.5-fold, 2-fold, 2.5-fold, 3-fold, 4-fold, 5-fold, 7-fold, 10-fold, or 20-fold improved affinity (relative to native RAP) and/or improved binding selectivity for a CR-containing protein selected from the group consisting of LDLR (P01130), LRP1 (P98157), LRP1B (Q9NZR2), LRP2 (P98164), LRP3 (O75074), LRP4 (O75096), LRP5 (O75197), LRP6 (O75581), LRP8 (Q14114), Sortilin-related receptor, SorLA (Q92673), LRP10 (Q7Z4F1), LRP11 (Q86VZ4), LRP12 (Q9Y561), FDC-8D6 (CD320), VLDLR (P98155), TADG-15 (ST14, Q8WVC1), TMPS3 (P57727), TMPS4 (Q9NRS4), TMPS6

(Q8IU80), Q6ICC2, Q6PJ72, Q76B61, Q7RTY8, Q7Z7K9, Q86YD5, Q8NAN7, Q8NBJ0, Q8WW88, Q96NT6, Q9BYE1, Q9BYE2, Q9NPF0 and corin (Q8IZR7). Such binding selectivity may be calculated, e.g., by the ratio of the peptide's binding affinity for a particular CR-containing protein relative to the peptide's binding affinity for at least one other CR-containing protein. The peptide may exhibit binding selectivity for a CR-containing protein relative to 1, 2, 3, 4, 5, 6, 7, or 8 other CR-containing proteins.

The cyclic RAP peptides of the invention may be composed of native RAP sequence or may include mutations to the native sequence. In exemplary embodiments, the cyclic RAP peptides of the invention comprise an amino acid sequence at least 60%, 65%, 70%, 75%, 80%, 85%, 90%, 91%, 92%, 93%, 94%, 95%, 96%, 97%, 98% or 99% identical to either SEQ ID NO: 97 or SEQ ID NO: 98. In some embodiments, the cyclic RAP peptide is less than about 85 amino acids in length, comprises 50 contiguous amino acids that are at least 70% identical to SEQ ID NO: 98, and binds to a CR-containing protein with a binding affinity Kd of about $1\times10^{-8}$ M or less. In some embodiments, the cyclic RAP peptide includes a mutation at one, two, three, four, five, or six or more positions within any one of the regions selected from: amino acids 200-319, 300-319, or 247-257 of mature RAP. In exemplary embodiments, the cyclic RAP peptide includes a mutation at one, two, three, four, five, six or more positions selected from the group consisting of 175, 205, 213, 217, 226, 230, 232, 239, 241, 242, 246, 247, 249, 250, 251, 256, 257, 261, 266, 267, 268, 270, 273, 279, 280, 287, 290, 294, 296, 297, 298, 305, 308, 311, 312, 313, 314, or 315 of mature RAP (SEQ ID NO: 95). In other embodiments, the cyclic RAP peptide comprises a mutation at three or more of the following positions: 205, 217, 249, 251, 256, 257, 266, 270, 294, 296, 297, 305. In one embodiment, the cyclic RAP peptide contains at least one mutation at positions 251, 256 and 270 of mature RAP.

In one aspect, the cyclic RAP peptide binds selectively to a matriptase protein. It is contemplated that a matriptase-specific peptide may comprise amino acids 243-313 or 249-303 of mature RAP (SEQ ID NO: 95) and further contains a mutation at any one of positions 251, 256, 257, 266, 270 or 280 of mature RAP. It is further contemplated that the matriptase-specific RAP peptides contain at least one, two, three, four, five or six mutations at positions 251, 256, 257, 266, 270 and/or 280 of mature RAP.

In another aspect, the cyclic RAP peptide binds selectively to a VLDLR protein. It is contemplated that a VLDLR-specific peptide may comprise amino acids 243-313 or 249-303 of mature RAP (SEQ ID NO: 95) and further contains a mutation at any one of positions 251, 256, 270 or 296 of RAP. It is further contemplated that the VLDLR-specific RAP peptides contain at least one, two, three, or four mutations at positions 251, 256, 270 and/or 296 of mature RAP.

In a further aspect, the cyclic RAP peptide binds selectively to an FDC-8D6 (CD320) protein. It is contemplated that the FDC-8D6-specific peptide may comprise amino acids 243-313 or 249-303 of mature RAP (SEQ ID NO: 95) and further contains a mutation at any one of positions 251, 256, 270, 279 or 305 of RAP. It is further contemplated that the FDC-8D6-specific RAP peptides contain at least one, two, three, four or five mutations at positions 251, 256, 270, 279 and/or 305 of mature RAP.

Any of the preceding mutations may include replacement of an amino acid from the acidic group (D, E) with an amino acid from the basic group (K, R), or vice versa. Any of the preceding mutations may also include replacement of an amino acid from the group (A, C, D, E, G, I, K, L, M, N, P, Q, R, S, T, V) with an amino acid from the group (F, Y, W, H). In a further embodiment, the cyclic RAP peptide comprises three, four, five, six or more of the following mutations: V175L, R2055, S213T, E217K, L226M, H249Y, E230V, S232P, E239G, E246G, E251L, E251K, E251T, E251G, E251P, E251N, E251R, K256R, K256V, K256A, K256I, K256P, K256L, I266F, I266T, K257Y, Q261R, A267V, H268R, K270P, K270D, K270N, K270G, K270E, K270W, L271M, H273Y, D279Y, V283M, R287H, H290Y, H290L, E294V, R296L, T297I, K298R, K305T, K306M, S312F, G313D, E246C, L247G, G280A, L311A, S312C, Q309C, F250C, L308G, L311G, E241C, and I315C compared to mature RAP (SEQ ID NO: 95).

In any of the preceding embodiments, the RAP peptides may contain a cysteine at or near the N-terminus of the peptide and a cysteine at or near the C-terminus of the peptide, allowing cyclization of the peptide and stabilization of the alpha-helices through disulfide bond formation between the two cysteines. Optionally, a glycine or proline may be interposed between the cysteines and the alpha-helices (e.g. Cys-Gly at the N-terminus and Gly-Cys at the C-terminus). Introduction of glycines allows a break in the alpha-helix for an adjacent non-native inter-helical disulfide bond.

The invention also contemplates oligomeric combinations or arrays of at least 2, 3, 4, 5, or 6 cyclic RAP peptides of the invention. The arrays may be repeating arrays of the same cyclic RAP peptide or arrays of different cyclic RAP peptides. The various combinations may be contiguous or separated by peptide linkers (e.g., 1, 2, 3, 4 or 5 amino acids in length) that display each cyclic RAP peptide in a 3-dimensional configuration that allows the domains to bind different CR pairs within the same CR-containing protein or to bind CR pairs of different CR-containing proteins.

In another aspect, the invention provides a conjugate comprising the cyclic RAP peptide (or array of cyclic RAP peptides) conjugated to a diagnostic or therapeutic agent. In one embodiment, the polypeptide and diagnostic or therapeutic agent are linked through a linker. In a further embodiment, said linker is a peptide linker. In another embodiment, the conjugate comprising the polypeptide of the invention is transcytosed in vivo. In exemplary embodiments, the therapeutic agent linked to the polypeptide of the invention is selected from the group consisting of a glial cell-derived neuronal growth factor (GDNF), brain-derived neuronal growth factor (BDNF), neuronal growth factor (NGF), or other neural growth factors known in the art, a disintegrin and metalloproteinase domain 10 [*Homo sapiens*] ADAM10, or other proteases acting on APP or Abeta, MESD (a chaperone protein for LRP5/6 that is required for transport of the receptors to cell surfaces), cancer chemotherapeutic agents, protease inhibitors, pro-apoptotic molecules, autoimmune antigens or lysosomal enzymes. In a related embodiment, the conjugate comprising the cyclic RAP peptide (or array of cyclic RAP peptides) is conjugated to an active agent. In a further embodiment, the active agent is a chemotherapeutic agent. In a still further embodiment, the chemotherapeutic agent is a radioisotope.

In yet another aspect, the invention contemplates a method of delivering the diagnostic or therapeutic agent to a particular tissue of a subject by administering to that subject a conjugate comprising said agent and a cyclic RAP peptide (or array thereof) of the invention. In one embodiment, the diagnostic or therapeutic agent conjugated to a cyclic RAP peptide is delivered to a specific tissue by transcytosis across epithelial or endothelial barriers. In one embodiment, the agent is delivered across the blood-brain barrier. In a related embodiment, the subject is suffering from a neurological disease including but not limited to Alzheimer's disease, Parkinson's disease, Multiple Sclerosis, Amylotrophic Lateral Sclerosis, other demyelination related disorders, a central nervous system cancer, traumatic brain injury, spinal cord injury, stroke or cerebral ischemia, plaque sclerosis, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal damyotrophy, progressive supranuclear palsy, dystonia, muscle spasticity, tremor, retinitis pigmentosa, senile dementia, subcortical dementia, arteriosclerotic dementia, AIDS-associated dementia, or other dementias, striatonigral degeneration, mitochondrial encephalo-myopathies, neuronal ceroid lipofuscinosis, lysosomal storage disorders with central nervous system involvement, leukodystrophies, urea cycle defect disorders, hepatic encephalopathies, renal encephalopathies, metabolic encephalopathies, porphyria, poisonings with neurotoxic compounds, radiation-induced brain damage, or psychiatric disorders such as psychosis, anxiety, depression, attention deficits, memory disorders, cognitive disorders, appetite disorders, obesity, addiction, appetence, or drug dependence. The invention further provides a method of delivering a therapeutic protein to a lysosomal compartment in a cell within a particular tissue of a subject, comprising contacting said cell with an effective amount of a conjugate comprising said therapeutic protein conjugated to a cyclic RAP peptide of the invention. In one embodiment, the subject is suffering from a lysosomal storage disease (LSD).

In another embodiment, the invention contemplates a method of treating cancer or metastatic cancer, or a method of reducing tumorigenic or metastatic effects associated with a CR-containing protein. Such methods involve administering to a subject a cyclic RAP peptide (or array thereof) that selectively binds to the tumorigenic CR-containing protein, or a conjugate comprising a cancer therapeutic agent conjugated to said cyclic RAP peptide (or array). Such tumorigenic CR-containing proteins include, but are not limited to, LRP5, LRP6, any of the matriptases or FDC-8D6 antigen. The cyclic RAP peptide of the invention may diminish the tumorigenic effects associated with the target CR-containing protein by directly interfering with its functions, for example by blocking binding or active sites. Alternatively, the conjugate comprising the cyclic RAP peptide of the invention conjugated to a cancer therapeutic agent may be used to target tissues that overexpress these CR-containing proteins with the anti-tumor drug. For example, tissues that overexpress matriptase include carcinomas, for example ovarian, cervical, prostate, breast, lung, colon or gastric carcinomas.

In another embodiment, the invention contemplates a method of delivering therapeutic agents to the liver to treat liver disorders, including hepatitis or liver cancer. Such methods involve administering to a subject a conjugate comprising a therapeutic agent conjugated to a cyclic RAP peptide (or array thereof) that retains the binding characteristics of native RAP or that selectively binds with even higher affinity to LRP1. In some embodiments, the methods include delivery of chemotherapeutic/cytotoxic agents to liver to treat hepatocellular carcinoma and other liver diseases.

In yet another embodiment, the invention contemplates a method of treating osteoporosis or other disease associated with reduced osteoblast and/or increased osteoclast activity, comprising administering a cyclic RAP peptide or conjugate comprising an active agent conjugated to a cyclic RAP peptide, that selectively binds to LRP5 and thereby inhibits factors that antagonize osteoblast differentiation and bone deposition as well as promote osteoclast activity. Such treatment methods are expected to increase osteoblast and/or reduce osteoclast activity, thus reducing bone loss or promoting bone strengthening.

In a related aspect, the invention provides a pharmaceutical composition comprising a conjugate comprising a cyclic RAP peptide conjugated to a diagnostic or therapeutic agent, and a pharmaceutically acceptable carrier, diluent or excipient.

In a different aspect, the invention provides a cyclic RAP peptide conjugated to a detectable moiety or label. Where the cyclic RAP peptide has binding selectivity for a particular CR-containing protein, the cyclic RAP peptide may be used to detect the presence of such CR-containing protein. It may also be used to detect expression patterns of the CR-containing protein, including, for example, overexpression associated with tumorigenicity. The invention further provides methods of using such cyclic RAP peptide to diagnose conditions associated with overexpression or underexpression of a CR-containing protein.

In other aspects, the present invention features a method of producing a RAP peptide, synthetically or by recombinant means, that can naturally cyclize or can be further chemically modified to cyclize via covalent linkage. The invention provides nucleic acids that encode any of the foregoing RAP peptides, vectors comprising such nucleic acids, host cells containing such nucleic acids or vectors, and methods of producing such peptides comprising the steps of culturing the host cells in suitable culture medium and isolating the peptide from said host cells or culture medium.

Other features and advantages of the invention will become apparent from the following detailed description. It should be understood, however, that the detailed description and the specific examples, while indicating preferred embodiments of the invention, are given by way of illustration only, because various changes and modifications within the spirit and scope of the invention will become apparent to those skilled in the art from this detailed description.

BRIEF DESCRIPTION OF THE FIGURES

FIG. 2 shows an alignment of CR sequences selected for binding analysis and RAP mutant or CR-antibody selection. The specific pairs and triplets used are indicated by brackets on the left. The panning substrate (LRP2 CR89) is indicated by the red (lighter colored) bracket. The AxcBxCxD motif within the alignment is indicated, with positions A and C for each CR sequence underlined. The text string concatenation of amino acids at A, C, A', and C' for each CR pair are indicated on the right. Amino acids in shading are identical to the predominant amino acid at the aligned position; amino acids in bold are homologous to the predominant amino acid at the aligned position. Sequences were aligned with Clustal W (44) and formatted with BOXSHADE.

FIG. 3 shows an SDS-PAGE analysis of CR proteins. Purified, refolded proteins were denatured in SDS loading buffer in the presence or absence of 2 mM DTT. Treated samples were resolved in 12% NuPAGE Bis-Tris gels as described in Methods. Gels were stained with Coomassie Brilliant Blue. Each pair of lanes is labeled at the bottom with the associated CR protein tested. Molecular weight marker sizes are indicated. Typical results are shown. Abbreviations: L1 is LRP1; L2 is LRP2; L6 is LRP6; M is MAT (matriptase, ST14); V is VLDLR; YVWR=LRP2 CR89; YVWD=LRP2 CR89 R1088D; YDWR=LRP2 CR89 V1047D; YDWD=LRP2 CR89 V1047D R1088D; WVWR=LRP2 CR89 Y1042W; WDWR=LRP2 CR89 Y1042W V1047D; WVWD=LRP2 CR89 Y1042W R1088D; WDWD=LRP2 CR89 Y1042W V1047D R1088D.

FIG. 5A-B depict binding of RAP d3, MegaRAP1 d3 (RAPv2A d3) and intermediate sequence variants to LRP2 CR89 and LRP1 CR3-5. FIG. 5A illustrates binding of RAP d3 mutants and RAPv2A d3 revertants to LRP2 CR89. FIG. 5B illustrates binding of RAP d3 mutants and RAPv2A d3 revertants to LRP1 CR3-5. Data were plotted and fitted by non-linear regression with the assumption of a single binding site (GraphPad Prism). $K_d$ values with standard deviations were derived from the regression analysis.

FIG. 5C shows data for binding of RAP d3 and RAP v2 (RAP v2A) variants to LRP1 CR3-5 and LRP2 CR89. NF indicates that binding could not be measured or that data could not be reliably fit using non-linear regression with the assumption of a single binding site. Percent of maximum binding is the ratio of the OD at the highest concentration tested for each ligand and the highest OD measured for all such ligands at that concentration.

FIG. 6A shows data for binding of RAP d3 and RAPv2A d3 to LRP2 CR89 variants. NF indicates that binding could not be measured or that data could not be reliably fit using non-linear regression with the assumption of a single binding site. Percent of maximum binding is the ratio of the OD at the highest concentration tested for each ligand and the highest OD measured for all such ligands at that concentration.

FIG. 6B shows RAP d3 variant sequences isolated by panning mutant phage libraries on different CR pairs. Only variable positions are shown. Amino acid numbering corresponds with mature RAP. Variant name (d3), CR pair used for affinity-selection (CR), apparent dissociation constant (Kd) for complex between variant and target CR pair (when determined), and amino acid identities at variable positions are shown.

FIG. 8 shows the complete amino acid sequences of RAP d3 variants isolated herein.

FIG. 9 shows the positive effect that truncation of the MatRAP1 variant at both the N-terminus and C-terminus has on binding affinity. Truncated variants were produced as described for full-length variants.

FIG. 10 shows the binding of 320RAP1 and the corresponding truncated variant to the target CR pair from FDC-8D6 antigen.

DETAILED DESCRIPTION

Figure 1:
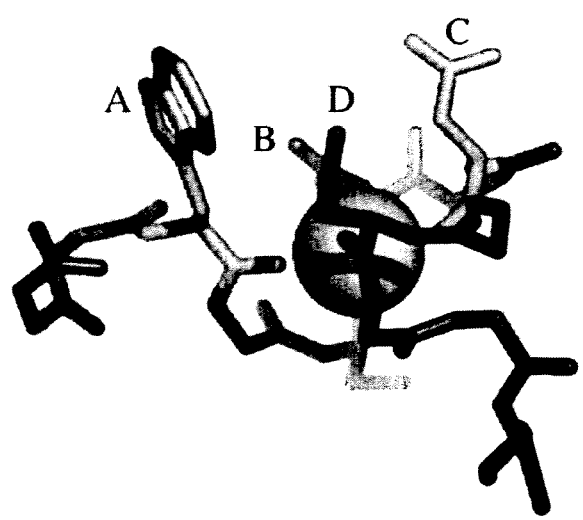
FIG. 1 is a representative illustration of a complement-type repeat, and is based on the sequence of the seventh complement-type repeat of the low-density lipoprotein receptor-related protein 1 (LRP1 CR7, PDB 1J8E), as determined by Simonovic et al. (43), showing the surface of the calcium-binding loop formed by residues at positions marked A, B, C, D. Calcium is represented as a sphere.

RAP is functionally bidentate, with both the first and third domains (d1 and d3) binding with low nanomolar affinity to particular tandem pairs of complement-type repeats (CR) within LDLR. Domain 3, consisting of approximately 110 amino acids, has been shown to have the highest affinity for relevant CR pairs. To minimize immunogenicity, maximize production efficiency and improve potency, it is useful to minimize RAP to those sequences that participate directly in receptor binding. However, stable folding of d3 has been shown to require sequences within RAP that do not participate directly in forming the receptor contact surface. These additional sequences, found within the N-terminal region of d3 and the C-terminal region of d2, are therefore necessary to ensure stable folding and high-affinity receptor binding. Isolated d3 does not bind as tightly to receptor as does d3 within the context of full-length RAP. Truncated versions of d3 that lack the fold-stabilizing sequences also bind poorly to receptor. Structural data derived from the complex between RAP d3 and LDLR CR34 indicates that the receptor-binding sequences of RAP d3 are found within two anti-parallel alpha-helices of approximately equal length joined by a flexible loop. The paired helical ensemble has a pronounced counter-clockwise twist and resembles a stretched, twisted "U".

The invention provides a substantially truncated form of RAP d3 stabilized by a single, intramolecular covalent bond, e.g. a disulfide bond. The truncated uncyclized form, without the intramolecular covalent bond, has reduced binding affinity for LRP1. In contrast, the cyclic RAP peptide has improved receptor-binding affinities indistinguishable from those of full-length RAP d3. The ability to stabilize the three-dimensional helical structure within a fragment of RAP d3 with a single, non-native covalent bond, instead of the large peptidic regions present in native RAP, provides improved affinity and results in a number of advantages. The invention permits rapid manufacturing of the small RAP peptides, e.g. by solid phase peptide synthesis, without the need for recombinant organisms, permits potential reduced immunogenicity, and provides greater ease of conjugation to active agents.

Cyclic RAP peptides of the invention have potential pharmaceutical applications based on two general properties of the target receptors: First, a number of the receptors have roles in the establishment and progression of disease states. Reagents that selectively bind to such receptors, therefore, may be used to alter the behavior of the receptors and the pathophysiological effects, which they support. Second, a number of the receptors have unique tissue distributions. Reagents that selectively bind to such receptors, therefore, may be used to selectively carry other drug substances to those tissues in which a targeted receptor is predominantly expressed. The invention also contemplates the use of such compositions in the prevention, management and treatment of disease, including but not limited to cellular proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, autoimmune diseases, enzyme deficiency diseases, lysosomal storage diseases such as those described above, and the like.

Members of the LDLR family are well expressed on capillary endothelium and on CNS cell types including neurons and astrocytes (e.g., LDL receptor, Megalin, LRP1). The LDL receptor family endocytose bound ligand and have been demonstrated to transcytose ligands across polarized epithelial cells in the kidney, thyroid and across capillary endothelial cells in the brain. LDLR therefore comprises a pool of compositionally and functionally related receptors expressed at different levels in different tissues. Examples include the VLDLR expressed on muscle tissue, LRP1B expressed on neuronal tissue, Megalin expressed on both kidney and neuronal tissue and LRP1 expressed on liver and vascular smooth muscle tissue. Cyclic RAP peptides of the invention can be used to target any of these receptors, as well as tissues expressing other CR-containing proteins as described herein.

In more general embodiments, receptor-selective cyclic RAP peptides of the invention, alone, in arrays, or conjugated to therapeutic agents, constitute a means by which CR-containing proteins might be specifically modulated (activated or inhibited). There are least four mechanisms by which modulation could be effected: Competitive blockade of ligand binding by direct association of cyclic RAP peptide with ligand binding sites; non-competitive blockade of ligand binding by cyclic RAP peptide-induced allosteric modification of ligand binding sites; clearance of receptors or other CR-containing protein from the cell surface following cross-linking between the same or different receptors induced by the binding of a cyclic RAP peptide; or alternatively delivery to tissues of active agents attached to a selective cyclic RAP peptide (e.g. proteases, protease inhibitors, other enzymes, radioisotopes, pro-apoptotic agents, toxins, therapeutic molecules (drugs), other receptor binding moieties, etc.).

A. Definitions

Unless otherwise defined, all technical and scientific terms used herein have the same meaning as commonly understood by one of ordinary skill in the art to which this invention belongs. The following references provide one of skill with a general definition of many of the terms used in this invention: Singleton, et al., DICTIONARY OF MICROBIOLOGY AND MOLECULAR BIOLOGY (2d ed. 1994); THE CAMBRIDGE DICTIONARY OF SCIENCE AND TECHNOLOGY (Walker ed., 1988); THE GLOSSARY OF GENETICS, 5TH ED., R. Rieger, et al. (eds.), Springer Verlag (1991); and Hale and Marham, THE HARPER COLLINS DICTIONARY OF BIOLOGY (1991).

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

As used herein, the following terms have the meanings ascribed to them unless specified otherwise.

A "cyclic RAP peptide" as used herein means a peptide less than about 100 amino acids in length and at least 80%, 85%, 90%, 95%, 97%, 98%, 99% or more identical or similar to SEQ ID NO: 98 (amino acids 249-303), and that contains a covalent bond between two non-consecutive amino acids. In exemplary embodiments, the covalent bond is a disulfide bond between two cysteines.

A "RAP conjugate" or "conjugate" refers to a compound comprising a cyclic RAP peptide of the invention attached to an active agent. As used herein, the term "conjugated" means that the therapeutic agent(s) and cyclic RAP peptide are physically linked by, for example, by covalent chemical bonds, physical forces such van der Waals or hydrophobic interactions, encapsulation, embedding, or combinations thereof.

The term "mutation" as used herein means insertion, deletion or substitution of an amino acid in a peptide sequence. A peptide having one or more mutations relative to the native or wild type amino acid sequence is considered to be an "analog."

The term "derivative" when refers to covalent modification of peptides, e.g. by conjugation to therapeutic or diagnostic agents, labeling (e.g., with radionuclides or various enzymes), covalent polymer attachment such as pegylation (derivatization with polyethylene glycol) and insertion or substitution by chemical synthesis of non-natural amino acids. Derivatives of the invention will retain the binding properties of underivatized molecules of the invention. Conjugation of cancer-targeting antibodies to cytotoxic agent, for example, radioactive isotopes (e.g., I131, I125, Y90 and Re186), chemotherapeutic agents, or toxins, may enhance destruction of cancerous cells.

A "Complement-repeat" or "CR", also known as a low-density lipoprotein receptor class A domain (LDL-A, Pfam), is a member of a family of protein domains defined by six cysteines and a cluster of acidic amino acids, among other features. A number of complement-repeats have been found to fold into a defined structure termed the LDL receptor-like module (Structural Classification of Proteins, SCOP). CR domains constitute the ligand-binding determinant of many receptors, including receptors belonging to the LDLR. A linear sequence of amino acids within each CR, with the motif AxcBxCxD, where c is a conserved cysteine, x is any amino acid, and B and D are either aspartate, glutamate or asparagine, has been demonstrated to participate in calcium binding and in the binding of ligands. Immediately adjacent pairs of particular CR domains have been demonstrated to bind to RAP. Amino acids at positions A and C in both of the two CR domains of a RAP-binding CR pair (A, C, A' and C') have been demonstrated to participate in RAP binding.

A "CR-containing protein" is a protein that contains one or more CRs. Nonlimiting examples of CR-containing proteins include: LDLR (P01130), LRP1 (P98157), LRP1B (Q9NZR2), LRP2 (P98164), LRP3 (O75074), LRP4 (O75096), LRP5 (O75197), LRP6 (O75581), LRP8

(Q14114), Sortilin-related receptor, SorLA (Q92673), LRP10 (Q7Z4F1), LRP11 (Q86VZ4), LRP12 (Q9Y561), FDC-8D6 (CD320), VLDLR (P98155), TADG-15 (ST14/matriptase/MT-SP1, Q8WVC1), TMPS3 (P57727), TMPS4 (Q9NRS4), TMPS6 (Q8IU80), Q6ICC2, Q6PJ72, Q76B61, Q7RTY8, Q7Z7K9, Q86YD5, Q8NAN7, Q8NBJ0, Q8WW88, Q96NT6, Q9BYE1, Q9BYE2, Q9NPF0 and corin (Q8IZR7). The Uniprot accession number reference identifying each of these proteins is provided.

Binding affinity Kd is measured by methods conventionally known in the art.

"Selectivity," "binding selectivity" or "binds selectively", refers to differences in the affinity of a ligand for different receptors. A ligand is selective for a particular receptor if it binds that receptor with an affinity that is at least 3-fold greater than other receptors. For example, RAP binds to LRP1, LRP1B, LRP2, SorLA, apoER2 and VLDLR with almost identical affinities. Therefore, RAP is not selective for one of these receptors over another. However, while RAP binds strongly to LRP1, LRP1B, LRP2, SorLA, apoER2 and VLDLR, with dissociation constants of less than 5 nM, it binds only weakly to LDLR, LRP5 and LRP6, with affinities that are at least 10-fold lower than for LRP1. Therefore, RAP is selective for LRP1, LRP1B, LRP2, SorLA, apoER2 and VLDLR relative to LDLR, LRP5 and LRP6. HRV2 coat protein binds strongly to VLDLR but does not bind to other LDLR. Therefore, HRV2 coat protein shows selectivity in its binding, with a preference for VLDLR over other LDLR. Reelin binds to apoER2 and VLDLR but not to other LDLR. Therefore, reelin is selective for apoER2 and VLDLR over other LDLR.

"Increasing relative delivery" as used herein refers to the effect whereby the accumulation at the intended delivery site (e.g., brain, or tissue expressing a CR-containing protein) of a conjugate comprising an active agent conjugated to a cyclic RAP peptide of the invention is increased relative to the accumulation of the unconjugated active agent.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA produced by that gene produces the protein in a cell or other biological system. Both the coding strand, the nucleotide sequence of which is identical to the mRNA sequence and is usually provided in sequence listings, and non-coding strand, used as the template for transcription, of a gene or cDNA can be referred to as encoding the protein or other product of that gene or cDNA. Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Recombinant polynucleotide" refers to a polynucleotide having sequences that are not naturally joined together. A host cell that comprises the recombinant polynucleotide is referred to as a "recombinant host cell." The gene is expressed in the recombinant host cell to produce, e.g., a "recombinant polypeptide."

"Expression control sequence" refers to a nucleotide sequence in a polynucleotide that regulates the expression (transcription and/or translation) of a nucleotide sequence operatively linked thereto. "Operatively linked" refers to a functional relationship between two parts in which the activity of one part (e.g., the ability to regulate transcription) results in an action on the other part (e.g., transcription of the sequence). Expression control sequences can include, for example and without limitation, sequences of promoters (e.g., inducible or constitutive), enhancers, transcription terminators, a start codon (i.e., ATG), splicing signals for introns, and stop codons.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in vitro expression system. Expression vectors include all those known in the art, such as cosmids, plasmids (e.g., naked or contained in liposomes) and viruses that incorporate the recombinant polynucleotide.

"Amplification" refers to any means by which a polynucleotide sequence is copied and thus expanded into a larger number of polynucleotide molecules, e.g., by reverse transcription, polymerase chain reaction, and ligase chain reaction.

"Stringent hybridization" and "stringent hybridization wash conditions" in the context of nucleic acid hybridization experiments are sequence dependent, and are different under different environmental parameters. An extensive guide to the hybridization of nucleic acids is found in Tijssen (1993) Laboratory Techniques in Biochemistry and Molecular Biology—Hybridization with Nucleic Acid Probes part I chapter 2 "Overview of principles of hybridization and the strategy of nucleic acid probe assays", Elsevier, New York. Generally, highly stringent hybridization and wash conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Very stringent conditions are selected to be equal to the Tm for a particular probe.

An example of highly stringent wash conditions is 0.15 M NaCl at 72° C. for about 15 minutes. An example of stringent wash conditions is a 0.2×SSC wash at 65° C. for 15 minutes (see, Sambrook et al. for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. In general, a signal to noise ratio of 2× (or higher) than that observed for an unrelated probe in the particular hybridization assay indicates detection of a specific hybridization.

"Polypeptide" or "peptide" refers to a polymer composed of amino acid residues linked via peptide bonds, naturally occurring structural variants, and non-naturally occurring analogs thereof. Synthetic polypeptides can be synthesized, for example, using an automated polypeptide synthesizer. The term "protein" typically refers to large polypeptides. The term "peptide" typically refers to short polypeptides.

The terms "identical" or "percent identity," in the context of two or more polynucleotide or polypeptide sequences, refer to two or more sequences or subsequences that are the same or have a specified percentage of nucleotides or amino acid residues that are the same, when compared and aligned for maximum correspondence, as measured using one of the following sequence comparison algorithms or by visual inspection. Preferably, the percent identity exists over a region of the sequences that is at least about 50 residues in length, at least about 100 residues, at least about 150 residues, or over the entire length of either or both comparison biopolymers.

Optimal alignment of sequences for comparison can be conducted, e.g., by the local homology algorithm of Smith and Waterman, Adv. Appl. Math. 2:482 (1981), by the homology alignment algorithm of Needleman and Wunsch, J. Mol. Biol. 48:443 (1970), by the search for similarity method of Pearson and Lipman, Proc. Natl. Acad. Sci. USA 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection.

Another example of algorithm that is suitable for determining percent sequence identity and sequence similarity is the BLAST algorithm, which is described in Altschul et al., J. Mol. Biol. 215:403-410 (1990).

The term "percent similarity" when used with respect to polypeptide sequence describes the percentage of amino acid residues that are (1) the same or (2) differ only by conservative substitutions (i.e. are similar) when compared and aligned for maximum correspondence, as measured using conventional sequence comparison algorithms or by visual inspection.

"Substantially pure" or "isolated" means an object species is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80%, 90%, 95%, 99% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. In some embodiments, the conjugates of the invention are substantially pure or isolated. In some embodiments, a pharmaceutical composition of the invention comprises a substantially purified or isolated cyclic RAP peptide or conjugate thereof with an active agent.

"Naturally-occurring" as applied to an object refers to the fact that the object can be found in nature. For example, a polypeptide or polynucleotide sequence that is present in an organism that can be isolated from a source in nature and which has not been intentionally modified by man in the laboratory is naturally-occurring.

"Detecting" refers to determining the presence, absence, or amount of an analyte in a sample, and can include quantifying the amount of the analyte in a sample or per cell in a sample.

"Detectable moiety" or a "label" refers to a composition detectable by spectroscopic, photochemical, biochemical, immunochemical, or chemical means. For example, useful labels include $^{32}P$, $^{35}S$, fluorescent dyes, electron-dense reagents, enzymes (e.g., as commonly used in an ELISA), biotin-streptavidin, dioxigenin, haptens and proteins for which antisera or monoclonal antibodies are available, or nucleic acid molecules with a sequence complementary to a target. The detectable moiety often generates a measurable signal, such as a radioactive, chromogenic, or fluorescent signal, that can be used to quantitate the amount of bound detectable moiety in a sample. The detectable moiety can be incorporated in or attached to a primer or probe either covalently, or through ionic, van der Waals or hydrogen bonds, e.g., incorporation of radioactive nucleotides, or biotinylated nucleotides that are recognized by streptavadin. The detectable moiety may be directly or indirectly detectable. Indirect detection can involve the binding of a second directly or indirectly detectable moiety to the detectable moiety. For example, the detectable moiety can be the ligand of a binding partner, such as biotin, which is a binding partner for streptavadin, or a nucleotide sequence, which is the binding partner for a complementary sequence, to which it can specifically hybridize. The binding partner may itself be directly detectable, for example, an antibody may be itself labeled with a fluorescent molecule. The binding partner also may be indirectly detectable, for example, a nucleic acid having a complementary nucleotide sequence can be a part of a branched DNA molecule that is in turn detectable through hybridization with other labeled nucleic acid molecules. (See, e.g., P D. Fahrlander and A. Klausner, Bio/Technology (1988) 6:1165.) Quantitation of the signal is achieved by, e.g., scintillation counting, densitometry, or flow cytometry.

"Linker" refers to a molecule that joins two other molecules, either covalently, or through ionic, van der Waals or hydrogen bonds, e.g., a nucleic acid molecule that hybridizes to one complementary sequence at the 5' end and to another complementary sequence at the 3' end, thus joining two non-complementary sequences.

"Tumors" or "neoplasia" or "cancer" as used herein includes both primary tumors and/or metastases. Such tumors are generally solid tumors, or they are diffuse tumors with localized accumulations. Many types of such tumors and neoplasia are known. Primary brain tumors include glioma, meningioma, neurinoma, pituitary adenoma, medulloblastoma, craniopharyngioma, hemangioma, epidermoid, sarcoma and others. Carcinomas include, for example, ovarian, cervical, prostate, breast, lung, colon or gastric carcinomas. Hepatocellular carcinoma, or hepatoma, is the fifth most common cancer in the world and incidence rates have been climbing steadily. Hepatocellular carcinoma is a disease of hepatocytes. Fifty percent of all intracranial tumors are intracranial metastasis. Brain tumors and neoplasia may be associated with the brain and neural tissue, or they may be associated with the meninges, skull, vasculature or any other tissue of the head or neck. ized to the head. Tumors or neoplasia for treatment according to the invention may be malignant or benign, and may have been treated previously with chemotherapy, radiation and/or other treatments.

The term "effective amount" means a dosage sufficient to produce a desired result on a health condition, pathology, and disease of a subject or for a diagnostic purpose. The desired result may comprise a subjective or objective improvement in the recipient of the dosage. "Therapeutically effective amount" refers to that amount of an agent effective to produce the intended beneficial effect on health.

"Small organic molecule" refers to organic molecules of a size comparable to those organic molecules generally used in pharmaceuticals. The term excludes organic biopolymers (e.g., proteins, nucleic acids, etc.). Preferred small organic molecules range in size up to about 5,000 Da, up to about 2,000 Da, or up to about 1,000 Da.

A "subject" of diagnosis or treatment is a human or non-human animal, including a mammal or a primate.

"Treatment" refers to prophylactic treatment or therapeutic treatment or diagnostic treatment.

A "prophylactic" treatment is a treatment administered to a subject who does not exhibit signs of a disease or exhibits only early signs for the purpose of decreasing the risk of developing pathology. The conjugate compounds of the invention may be given as a prophylactic treatment to reduce the likelihood of developing a pathology or to minimize the severity of the pathology, if developed.

A "therapeutic" treatment is a treatment administered to a subject who exhibits signs or symptoms of pathology for the purpose of diminishing or eliminating those signs or symptoms. The signs or symptoms may be biochemical, cellular, histological, functional, subjective or objective. The conjugate compounds of the invention may be given as a therapeutic treatment or for diagnosis.

"Diagnostic" means identifying the presence or nature of a pathologic condition. Diagnostic methods differ in their specificity and selectivity. While a particular diagnostic method may not provide a definitive diagnosis of a condition, it suffices if the method provides a positive indication that aids in diagnosis.

"Pharmaceutically acceptable carrier" refers to any of the standard pharmaceutical carriers, buffers, and excipients, such as a phosphate buffered saline solution, 5% aqueous solution of dextrose, and emulsions, such as an oil/water or water/oil emulsion, and various types of wetting agents and/or adjuvants, that are approvable by a competent regulatory authority as suitable for administration to humans. Suitable pharmaceutical carriers and formulations are described in Remington's Pharmaceutical Sciences, 19th Ed. (Mack Publishing Co., Easton, 1995). Preferred pharmaceutical carriers depend upon the intended mode of administration of the active agent. Typical modes of administration include enteral (e.g., oral) or parenteral (e.g., subcutaneous, intramuscular, intravenous, intraperitoneal or intrathecal injection; or topical, transdermal, or transmucosal including intrapulmonary administration). A "pharmaceutically acceptable salt" is a salt that can be formulated into a compound for pharmaceutical use including, e.g., metal salts (sodium, potassium, magnesium, calcium, etc.) and salts of ammonia or organic amines.

A. CR-Containing Proteins and their Role

"LDLR" refers to members of the low-density lipoprotein receptor family including the low-density lipoprotein receptor-related protein 1 (LRP1). LRP1 is a large protein of 4525 amino acids (600 kDa), which is cleaved by furin to produce two subunits of 515-(alpha) kD and 85-(β) kDa that remain non-covalently bound. LRP1 is expressed on most tissue types, but is primarily found in the liver. Other members of the low-density lipoprotein (LDL) receptor family include LDL-R (132 kDa); LRP2 (megalin, gp330); LRP/LRP1 and LRP1B (600 kDa); VLDL-R (130 kDa); LRP5; LRP6; apoER-2 (LRP-8, 130 kDa); Mosaic LDL-R (LR11, 250 KDa); and other members such as LRP3, LRP6, and LRP-7. Characteristic features of the family include cell-surface expression; extracellular ligand binding domain repeats (Dx-SDE); a requirement of Ca++ for ligand binding; binding of RAP and apoE; EGF precursor homology domain repeats (YWTD (SEQ ID NO: 109)); a single membrane spanning region; internalization signals in the cytoplasmic domain (FDNPXY (SEQ ID NO: 110)); and receptor mediated endocytosis of various ligands. Some members of the family, including LRP1, LRP5, LRP6, apoER2 and VLDLR, participate in signal transduction pathways.

RAP d3 is folded as an antiparallel helical hairpin. The first helix, approximately D237-V277, is connected by a turn, comprised by residues G278-G280, to a second helix, residues E281-R317. The two helices are proximate, in a right leg (helix 2)-crossed-over-left leg (helix 1) configuration. CR3 of the LDLR contacts RAP d3 primarily at K270, while CR4 forms contacts with RAP d3 primarily at K256. K256 and K270 are both on the same face of helix 2. RAP R282 and R285 are directed at the negatively-charged calcium-chelating pocket of CR3, while RAP K253 plays a similar role in binding CR4. The LDLR CR pair only associates with residues between approximately H249-T303 of the RAP d3 antiparallel helical hairpin. Outside of this region is an N-terminal extension of helix 1 and a C-terminal extension of helix 2. These portions of helix 1 and 2 presumably help stabilize the helical bundle. In addition, helix 1 is preceded by a turn, S232-T236, a short helix and some additional sequence, comprising residues between R206-Q231. It has been suggested that the short helix, and the additional sequences, are also important for the folding stability of RAP d3.

i. LRP1-Selective RAP Peptides

Native RAP binds strongly to LRP1, which is highly expressed on hepatocytes. One aspect of the invention contemplates conjugation of chemotherapeutic drugs or other agents for treating liver disorders to cyclic RAP peptides to deliver therapeutic compounds to the liver for the treatment of liver disease. Administration of a RAP conjugate to treat liver disease would solve several problems associated with treatment of liver diseases, such as clearance of the agent by the liver, since a majority of the drug would be delivered directly to hepatocytes almost immediately after injection. Additionally, because the RAP conjugate would be endocytosed via LRP1, drug resistance mechanisms in the plasma membrane (MDR, P-glycoprotein) would be bypassed.

ii. LRP2-Selective RAP Peptides

LRP2 has been shown to be expressed on brain capillary endothelium and to mediate transport of apoJ into the parenchyma of the brain (Lundgren, et al., (1997) J Histochem Cytochem 45, 383-392; Zlokovic, et al., (1996) Proc Natl Acad Sci USA 93, 4229-4234; Shayo, et al., (1997) Life Sci 60, PL115-118). Cyclic RAP peptides of the invention and conjugates thereof that selectively bind to LRP2 with greater affinity than other LDLR are expected to have enhanced distribution to the brain. For example, GDNF has been demonstrated to promote survival and growth of nigrostriatal neurons in subjects with Parkinson's disease (Lin, et al., (1993) Science 260, 1130-1132). However, GDNF does not cross into the brain from the vasculature. Fusions of LRP2-selective RAP peptides to GDNF would be expected to increase the distribution of GDNF to the brain.

iii. VLDLR-Selective RAP Peptides

Similarly, VLDLR has been shown to be expressed on brain capillary endothelium and to mediate transport of lipoprotein lipase across the endothelium of the aorta (Wyne, et al., (1996) Arterioscler Thromb Vasc Biol 16, 407-415; Obunike, et al., (2001) J Biol Chem 276, 8934-8941). Cyclic RAP peptides of the invention and conjugates thereof that selectively bind to VLDLR are expected to have enhanced distribution to the brain. VLDLR has also been implicated in foam cell formation by mediating uptake of excess free fatty acids (FFA) into vascular macrophages (Hiltunen, et al., (1998) Circulation 97, 1079-1086; Qu, et al., (2004) J Huazhong Univ Sci Technolog Med Sci 24, 1-4, 8). Cyclic RAP peptides and conjugates thereof that selectively bind to VLDLR would be expected to block association of lipoprotein particles with macrophages and inhibit foam cell formation. Such cyclic RAP peptides and conjugates thereof would also be expected to limit transfer of FFA from circulating lipoprotein into adipocytes, slowing the progression toward obesity in susceptible subjects (Goudriaan, et al., (2001) Arterioscler Thromb Vasc Biol 21, 1488-1493; Goudriaan, et al. (2004) J Lipid Res 45, 1475-1481; Tacken, et al., (2001) Curr Opin Lipidol 12, 275-279; Yagyu, et al., (2002) J Biol Chem 277, 10037-10043). The high level of expression of VLDLR on the luminal surface of muscle endothelium, along with the low level of expression of VLDLR in liver, would be expected to drive distribution of cyclic RAP peptides and conjugates thereof to muscle tissue after intravenous administration. Agents with therapeutic effects on muscle tissue could be attached to VLDLR-selective cyclic RAP peptides to improve distribution of such agents to muscle.

iv. CR-Containing Proteins Associated with Tumors or Metastasis

Overexpression of at least three CR-containing proteins, LRP5, LRP6 and ST14 (TADG-15), has been independently associated with increased tumorigenicity or carcinogenesis (Li, et al., (2004) Oncogene 23, 9129-9135; Hoang, et al., (2004) Int J Cancer 109, 106-111; Tanimoto, et al., (2005) Br J Cancer 92, 278-283; Santin, et al., (2004) Int J Cancer 112, 14-25; Santin, et al., (2003) Cancer 98, 1898-1904; Tanimoto, et al., (2001) Tumour Biol 22, 104-114). Cyclic RAP peptides of the invention or conjugates thereof that bind selectively to these proteins would be expected to provide a means of diminishing their tumorigenic effects. Cyclic RAP peptides may interfere with the function(s) of the CR-containing protein directly. Alternatively, the cyclic RAP peptide may be conjugated to a cancer therapeutic agent to target delivery to tissues that overexpress the CR-containing protein. For example, matriptase (MT-SP1, ST14, TADG-15) is overexpressed in a variety of epithelial tumors (carcinomas) (25-33).

Following transactivation facilitated by hepatocyte activator inhibitor-1 (HAI-1), matriptase promotes tumor growth and metastasis by degrading extracellular matrix components directly or by activating other proteases, such as urokinase plasminogen activator (uPA), resulting in matrix-degradative events (26, 34, 35). The protease domain adjacent to the CR array in the ectodomain of matriptase (ST14) has been implicated in the enhanced invasiveness and tumorigenicity of cells that overexpress matriptase (ST14). Matriptase is anchored in the lateral or basolateral membranes of epithelial cells through an N-terminal type II transmembrane domain (Pfistermueller, et al. (1996) FEBS Lett 396, 14-20). The membrane-embedded sequence is followed by an extracellular SEA domain, two CUB domains, four CR domains and a trypsin domain at the C-terminus of the protein. Mutagenesis of the CR sequences within matriptase results in a failure of the resulting protease mutant to become activated (Qiu, et al. (2003) Neuroscience 122, 291-303). Similarly, an antibody that binds to the third CR domain of matriptase blocks activation of the enzyme (Basu, et al. (2001) Immunity 14, 303-13). A cyclic RAP peptide with affinity for one of the two CR pairs within matriptase that include the third CR domain would be expected to interfere with proteolytic activation, in a manner similar to the observed inhibition by the antibody to this region. Such a RAP peptide would be expected to diminish the metastatic and tumorigenic effects of matriptase overexpression in affected tissues. A conjugate comprising a matriptase-selective cyclic RAP peptide and a protease inhibitor would also be expected to specifically block those effects of matriptase related to its proteolytic activity.

LRP6-selective cyclic RAP peptides could be designed to down-regulate LRP6 on tumor cells, either by inducing endocytosis of LRP6 or by interfering with the Wnt signal transduction events mediated by LRP6. Similarly, LRP6-selective cyclic RAP peptides conjugated to therapeutic agents (e.g. cancer chemotherapeutic drugs) or diagnostic agents can be used to target deliver to tissues that overexpress LRP6.

v. LRP5-Selective RAP Peptides and Bone Diseases

Enhanced Wnt signaling through LRP5 has been demonstrated to increase osteoblast differentiation, inhibit osteoclast activity and enhance bone deposition (Westendorf, et al., (2004) Gene 341, 19-39; Zhang, et al., (2004) Mol Cell Biol 24, 4677-4684). This signaling mechanism has been validated with osteoblast-specific APC (adenomatous polyposis coli) knockout mice and with LRP5 mutants that are insensitive to DKK (Dickkopf)-1 and sclerostin-mediated inhibition (Zhang, et al., (2004) Mol Cell Biol 24, 4677-4684; Holmen, et al., (2005) J Biol Chem). LRP5-specific cyclic RAP peptides that interfere with inhibitor binding, or which enhance Wnt signaling through other means (e.g. stabilizing LRP5 without blocking Wnt binding), would be expected to have similar effects. For example, fusions between cyclic RAP peptides specific for either of the two LRP5 CR pairs and the beta-propeller chaperone protein Mesd would be expected to interfere with DKK-1-mediated antagonism of Wnt signaling through LRP5 (Hsieh, et al., (2003) Cell 112, 355-367; Herz, et al., (2003) Cell 112, 289-292). These cyclic RAP peptides that interfere with inhibition of LRP5 (e.g. reduce DKK-1 binding to or inhibition of LRP5) and conjugates thereof are expected to have therapeutic effects in the treatment of osteoporosis or other diseases associated with reduced osteoblast activity and/or increased osteoclast activity. Similarly, cyclic RAP peptides that inhibit Wnt signaling through LRP5 are expected to have therapeutic effects in the treatment of diseases associated with increased osteoblast activity, such as osteopetrosis.

vi. FDC-8D6-Selective RAP Peptides

The FDC-8D6 antigen (CD320) has a pair of such domains and plays an important role in B-cell differentiation in lymphatic follicles (36, 37).

Non-Hodgkin's lymphoma (NHL) involves the proliferation and extranodal migration of a class of immune cells called B-cells. NHL is the leading cause of death from cancer in males between the ages of 20 and 39. Studies have shown that the FDC-8D6 antigen protein (CD320) facilitates neoplastic B-cell growth (36, 37). 8D6 antigen contains a single pair of CR domains. Agents, such as cyclic RAP peptides, that bind to and block the function of 8D6 are expected to slow the progression of non-Hodgkin's lymphoma in humans.

B. Treatment

The specific disease conditions treatable by administration of the cyclic RAP peptides or conjugates of the invention are as varied as the types of CR-containing proteins targeted and the drug moieties that can be present in the conjugate. Thus, disease conditions include cellular proliferative diseases, such as neoplastic diseases, autoimmune diseases, cardiovascular diseases, hormonal abnormality diseases, degenerative diseases, diseases of aging, diseases of the central nervous system (e.g., Alzheimer's disease, epilepsy, hyperlipidemias), psychiatric diseases and conditions (e.g., schizophrenia, mood disorders such as depression and anxiety), infectious diseases, enzyme deficiency diseases, lysosomal storage diseases such as those described above, and the like.

Treatment is meant to encompass any beneficial outcome to a subject associated with administration of a conjugate including a reduced likelihood of acquiring a disease, prevention of a disease, slowing, stopping or reversing, the progression of a disease or an amelioration of the symptoms associated with the disease condition afflicting the host, where amelioration or benefit is used in a broad sense to refer to at least a reduction in the magnitude of a parameter, e.g., symptom, associated with the pathological condition being treated, such as inflammation and pain associated therewith. As such, treatment also includes situations where the pathological condition, or at least symptoms associated therewith, are comi. Lysosomal Storage Diseases In some embodiments, the disorder being treated is a lysosomal storage disease and the conjugate is administered as a pharmaceutical composition in an amount effective to decrease the amount of storage granules present in the brain tissue of said mammal. Typically, the symptoms of such a disorder are monitored through routine assessment of history, physical examination, echocardiography, electrocardiography, magnetic resonance imaging, polysomnography, skeletal survey, range of motion measurements, corneal photographs, and skin biopsy. Administration of a cyclic RAP peptide or conjugate thereof in such a disorder results in normalization of developmental delay and regression in said subject, reduction in high pressure hydrocephalus, reduction in spinal cord compression in said subject, and reduction in number and/or size of perivascular cysts around the brain vessels of said subject. Methods of monitoring and assessing such sequelae are known to those of skill in the art. Those of skill in the art are referred to U.S. Pat. No. 6,585,971; U.S. Pat. No. 6,569,661 and U.S. Pat. No. 6,426,208 and U.S. Patent Publication No. 20040009906 for additional descriptions of such sequelae.

In preferred embodiments, the animal is suffering from mucopolysaccharidosis I and has about 50% or less of a normal α-L-iduronidase activity. In such embodiments, it would be desirable to administered an effective dose of between about 0.001 mg/kg body weight and 0.5 mg/kg body weight of human α-L-iduronidase as part of the conjugate e.g., weekly to a subject suffering from a deficiency thereof. In other embodiments, the subject is given a dose of between about 0.01 mg/15 cc of CSF to about 5.0 mg/15 cc of CSF in the mammal of said human α-L-iduronidase weekly. The therapies contemplated herein promote the breakdown of glycosaminoglycan (GAG) in a brain cell of a subject having lysosomal storage disease. The brain cell may be a neuron, a neuroglial cell, an ependymal cell. Typically, the brain cells in which granule accumulation occurs and should be ameliorated by administering a conjugate of the invention include neurons, glial cells, microglial cells, astrocytes, oligodendroglial cells, perivascular cells, perithelial cells, meningeal cells, ependymal cells, arachnid granulation cells, arachnoid membranes, dura mater, pia mater and choroid plexus cells. The therapy in preferred embodiments reduces storage granules in meningeal cells as compared to the number of lysosomal storage granules present in a similar cell in the absence of administration of said conjugate. This produces the therapeutic effects of relieving the symptoms of high pressure hydrocephalus in some subjects. and said administering reduces the amount of CSF fluid in the meningeal tissue of said subject.

Nonlimiting examples of lysosomal storage diseases treatable with the conjugates of the invention include Mucopolysaccharidosis type I, Mucopolysaccharidosis type II Hunter syndrome, Mucopolysaccharidosis type IIIA Sanfilippo syndrome, Mucopolysaccharidosis type IIIB Sanfilippo syndrome, Mucopolysaccharidosis type IIIC Sanfilippo syndrome, Mucopolysaccharidosis type IIID Sanfilippo syndrome, Mucopolysaccharidosis type IVA Morquio syndrome, Mucopolysaccharidosis type IVB Morquio syndrome, Mucopolysaccharidosis type VI, Mucopolysaccharidosis type VII Sly syndrome, Mucopolysaccharidosis type IX, Aspartylglucosaminuria, Cholesterol ester storage disease/Wolman disease, Cystinosis, Danon disease, Fabry disease, Farber Lipogranulomatosis/Farber disease, Fucosidosis, Galactosialidosis types I/II, Gaucher disease types I/IIIII Gaucher disease, Globoid cell leukodystrophy/Krabbe disease, Glycogen storage disease II/Pompe disease, GM1-Gangliosidosis types I/II/III, GM2-Gangliosidosis type I/Tay Sachs disease, GM2-Gangliosidosis type II Sandhoff disease, GM2-Gangliosidosis, α-Mannosidosis types I/II, β-Mannosidosis, Metachromatic leukodystrophy, Metachromatic leukodystrophy, Mucolipidosis type I/Sialidosis types I/II, Mucolipidosis types II/III I-cell disease, Mucolipidosis type IIIC pseudo-Hurler polydystrophy, Multiple sulfatase deficiency, Neuronal Ceroid Lipofuscinosis, CLN1 Batten disease, Neuronal Ceroid Lipofuscinosis, CLN2 Batten disease, Niemann-Pick disease types A/B Niemann-Pick disease, Niemann-Pick disease type C1 Niemann-Pick disease, Niemann-Pick disease type C2 Niemann-Pick disease, Pycnodysostosis, Schindler disease types I/II Schindler disease, or Sialic acid storage disease.

ii. Neurological Disorders

In other embodiments, the disorder being treated is a neurological disease and the conjugate is administered as a pharmaceutical composition in an amount effective to prevent, manage or treat such neurological disorder. A neurological disorder includes but is not limited to Alzheimer's disease, Parkinson's disease, Multiple Sclerosis, Amylotrophic Lateral Sclerosis, other demyelination related disorders, a central nervous system cancer, traumatic brain injury, spinal cord injury, stroke or cerebral ischemia, plaque sclerosis, cerebral vasculitis, epilepsy, Huntington's disease, Tourette's syndrome, Guillain Barre syndrome, Wilson disease, Pick's disease, neuroinflammatory disorders, encephalitis, encephalomyelitis or meningitis of viral, fungal or bacterial origin, or other central nervous system infections, prion diseases, cerebellar ataxias, cerebellar degeneration, spinocerebellar degeneration syndromes, Friedreichs ataxia, ataxia telangiectasia, spinal damyotrophy, progressive supranuclear palsy, dystonia, muscle spasticity, tremor, retinitis pigmentosa, senile dementia, subcortical dementia, arteriosclerotic dementia, AIDS-associated dementia, or other dementias, striatonigral degeneration, mitochondrial encephalo-myopathies, neuronal ceroid lipofuscinosis, lysosomal storage disorders with central nervous system involvement, leukodystrophies, urea cycle defect disorders, hepatic encephalopathies, renal encephalopathies, metabolic encephalopathies, porphyria, poisonings with neurotoxic compounds, radiation-induced brain damage, or psychiatric disorders such as psychosis, anxiety, depression, attention deficits, memory disorders, cognitive disorders, appetite disorders, obesity, addiction, appetence, or drug dependence.

Alzheimer's Disease

In a preferred embodiment, the disorder being treated is Alzheimer's disease, which is linked to elevated levels of a 40-42 amino acid peptide, amyloid beta (Aβ), within the brains of affected patients (Selkoe, et al. (1996) *J Biol Chem* 271, 18295-18298). Following its generation by a series of sequential proteolytic events, Aβ oligomerizes and ultimately accumulates in insoluble plaques within the neuronal interstitium. Both soluble and insoluble forms of Aβ have been demonstrated to be neurotoxic in vitro and in vivo (Zerbinatti, et al., (2004) *Proc Natl Acad Sci USA* 101, 1075-1080; Tsai, et al., (2004) *Nat Neurosci*; Schmitz, et al. (2004) *Am J Pathol* 164, 1495-1502; Gong, et al. (2003) *Proc Natl Acad Sci USA* 100, 10417-10422; Bard, et al. (2000) *Nat Med* 6, 916-919; Schenk, et al. (1999) *Nature* 400, 173-177; Hsia, et al. (1999) *Proc Natl Acad Sci USA* 96, 3228-3233). Soluble Aβ monomers and oligomers have also been demonstrated to reversibly induce memory deficits by inhibiting long-term potentiation (Gong, et al. (2003) *Proc Natl Acad Sci USA* 100, 10417-10422).

Aβ is a proteolytic fragment of the amyloid precursor protein or APP, a cell surface membrane protein of undetermined function. Aβ formation is initiated within the neuronal secretory pathway or through endocytosis of APP by LRP1, a member of the LDLR family of receptors (Cam, et al., (2004) *J Biol Chem* 279, 29639-29646). Upon reaching the endosomal system, APP is cleaved by the beta-site APP-cleaving enzyme, or BACE, a membrane protease. BACE cuts APP at position 671, just N-terminal to the transmembrane domain. The remaining portion of APP is then cut a second time by a complex of three proteins, presenilin-1, presenilin-2 and nicastrin, which constitute the gamma-secretase complex (Xia, et al. (2003) *J Cell Sci* 116, 2839-2844). Presenilins cleave their substrates within the inner leaflet of the lipid bilayer. The gamma-secretase cleavage step occurs between positions 711 and 713, within the transmembrane domain of APP. Gamma-secretase cleavage releases Aβ, which is either retained within the neuron or secreted into the extracellular space. In either location, Aβ is toxic to neurons (Casas, et al. (2004) *Am J Pathol* 165, 1289-1300).

The sequential cleavage of APP by beta and gamma-secretases is termed the amyloidogenic pathway. An alternate pathway predominates in the normal brain: The entire ectodomain of APP is released through receptor shedding, a proteolytic process catalyzed by alpha-secretase. The released ectodomain is termed sAPPα and has been demonstrated to have neuroprotective and memory-enhancing effects (Furukawa, et al. (1996) *J Neurochem* 67, 1882-1896; Meziane, et al. (1998) *Proc Natl Acad Sci USA* 95, 12683-12688). APP ectodomain release is the key event in the nonamyloidogenic pathway. Proteolysis in this case occurs at position 688, within the region of APP that becomes Aβ during amyloidogenesis (Allinson, et al. (2003) *J Neurosci Res* 74, 342-352). Therefore, the amyloidogenic and nonamyloidogenic pathways are mutually exclusive. Release of sAPPα is catalyzed by an alpha-secretase, ADAM10, also a membrane-bound protease (Fahrenholz, et al. (2000) *Ann N Y Acad Sci* 920, 215-222). ADAM10 is a disintegrin and metalloproteinase, part of a family of "sheddase" enzymes including the Notch cleaving enzyme (Kuzbanian) and the TNF-alpha precursor-cleaving enzyme (TACE, ADAM17). ADAM10 has been found to be responsible for shedding the ectodomain of BACE (Hussain, et al. (2003) *J Biol Chem* 278, 36264-36268).

Like the other members of the ADAM family, ADAM10 has an N-terminal prodomain, a catalytic protease domain, a disintegrin domain, a transmembrane domain and a cytoplasmic tail. The prodomain associates tightly with the catalytic domain, a requirement for proper folding of the enzyme. This association also allows a cysteine in the prodomain to reversibly bind to a zinc atom in the active site, masking the proteolytic activity of the enzyme while it is transiting the secretory pathway. Upon reaching the trans-Golgi, the proprotein convertase furin in the constitutive secretory pathway recognizes residues 211-214 (RKKR (SEQ ID NO: 111)) of ADAM10, cleaving off the prodomain and rendering the enzyme proteolytically active.

An increase in Aβ release by beta and gamma-secretases, at the expense of sAPPα release by ADAM10, is believed to be the basis for Alzheimer's disease. A number of programs are underway to develop pharmacological inhibitors of BACE or the gamma-secretase complex, in order to shift APP processing away from amyloidogenic pathway. A complementary approach is to increase sAPPα production at the expense of Aβ by increasing levels of alpha-secretase in the brain interstitium. The imbalance in the proteolytic processing of APP has been corrected in animal models by modestly supplementing the endogenous levels of a particular neuronal protease, ADAM10. The benefits of increased ADAM10 levels in brain have been validated in mouse models of Alzheimer's disease (Postina, et al. (2004) *J Clin Invest* 113, 1456-1464; Lichtenthaler, et al. (2004) *J Clin Invest* 113, 1384-1387). Slight increases in brain ADAM10 levels have been found to prevent the disease phenotype.

The invention contemplates treating Alzheimer's diseases based on intravenous administration of a fusion between cyclic RAP peptide and ADAM10. A preferred embodiment is a method of treating Alzheimer's Disease comprising administering an ADAM10-cyclic RAP peptide conjugate and increasing brain alpha-secretase activity, wherein said administering is via intravenous, intracarotid, or intrathecal administration. Increases in alpha-secretase levels, in turn, are expected to divert APP processing away from the amyloidogenic pathway. The enhanced production of sAPPα and its corollary, the diminished production of Aβ, are predicted to have a therapeutic effect on patients suffering from Alzheimer's disease. Alternatively, the invention contemplates treatments for Alzheimer's disease comprising administration of fusions between a cyclic RAP peptide and other proteases that act on APP or Abeta, or with inhibitors of beta-secretase or with inhibitors of gamma-secretase.

In a related aspect, the invention contemplates minimizing the peripheral effects of an intravenously injected active sheddase enzyme by using ADAM10-RAP fusions with the prodomain attached. Intact pro-ADAM10-RAP can isolated from standard production lines by co-expression with the furin inhibitor, α1-antitrypsin Portland (Srour, et al. (2003) *FEBS Lett* 554, 275-283; Benjannet, et al. (1997) *J Biol Chem* 272, 26210-26218). Activation of the fusion will then occur by removal of the prodomain after clearance into tissue, either during transcytosis or upon reaching the brain interstitium. During transcytosis, the fusion becomes membrane associated due to association with LRP. The fusion-receptor complex then transits the cell within an endosome. Previous studies in vivo and in vitro have demonstrated partial proteolysis of some proteins in transit during transcytosis (Lisi, et al. (2003) *J Endocrinol Invest* 26, 1105-1110). Endocytosis of ADAM10-RAP conjugate either upon initial endocytosis into endothelial cells or on final endocytosis into neurons will expose the fusion to furin in the early endosome (Mayer, et al. (2004) *J Histochem Cytochem* 52, 567-579; Bosshart, et al. (1994) *J Cell Biol* 126, 1157-1172; Rohn, et al. (2000) *J Cell Sci* 113 (Pt 12), 2093-2101). An alternative approach to delayed activation of ADAM10 is replacement of the furin-sensitive peptide linker connecting the prodomain and catalytic domain with an ADAM-sensitive peptide linker. To the extent that the modified prodomain is cleaved in production lines, this reaction can be inhibited by culture in the presence of hydroxamate inhibitors or by co-expression with TIMP1 or TIMP3 (Amour, et al. (2000) *FEBS Lett* 473, 275-279). While the half-life of RAP fusions in the periphery is short, accumulation of an ADAM-sensitive pro-ADAM10-RAP fusion will result in exposure of the fusion to endogenous, active ADAM10 at the neuron surface within the interstitial space. A proteolytic chain-reaction might then be predicted, with each activated ADAM10-RAP fusion subsequently activating more ADAM10-RAP. Intracarotid co-administration with mannitol, as well as intrathecal administration, may not require inactive ADAM10.

Additional neurological disorders contemplated by the invention are described below. For example, Parkinson's Disease is characterized by tremors and reduced motor neuron function, rigidity, and akinesia. These neurologic signs are due to malfunction of the major efferent projection of the substantia nigra, i.e., the nigrostriatal tract. The cell bodies of neurons in the dopaminergic system are the primary cells involved in PD progression. Examples of primary parkinsonian syndromes include Parkinson's disease (PD), progressive supranuclear palsy (PSP), and striatonigral degeneration (SND), which is included with olivopontocerebellear degeneration (OPCD) and Shy Drager syndrome (SDS) in a syndrome known as multiple system atrophy (MSA).

Amyotrophic lateral sclerosis (ALS), often referred to as "Lou Gehrig's disease," is a progressive neurodegenerative disease that attacks motor neurons in the brain and spinal cord. The progressive degeneration of the motor neurons in ALS eventually leads to their death, reducing the ability of the brain to initiate and control muscle movement.

Huntington's disease (HD), although a genetically heritable disease, results in the degeneration of neurons in the striatal medium spiny GABAergic neurons (Hickey et al., Prog Neuropsychopharmacol Biol Psychiatry. 27:255-65, 2003). This degeneration causes uncontrolled movements, loss of intellectual faculties, and emotional disturbance.

Multiple Sclerosis (MS) is a frequent and invalidating disease of the young adult. This disease is characterized by an inflammatory reaction, probably of an autoimmune type, and a demyelination frequently associated with a loss of oligodendrocytes, the myelin forming cell in the central nervous system. Current available treatments address the inflammatory factor of MS, but have little, if any, efficacy on remyelination.

The compositions of the invention are useful to treat cancers of the brain. The most common brain tumors are gliomas, which begin in the glial tissue. Astrocytomas, which arise from small, star-shaped cells called astrocytes, most often arise in the adult cerebrum. A grade III astrocytoma is sometimes called anaplastic astrocytoma. A grade IV astrocytoma is usually called glioblastoma multiforme. Brain stem gliomas occur in the lowest, stem-like part of the brain. The brain stem controls many vital functions. Most brain stem gliomas are high-grade astrocytomas. Ependymomas usually develop in the lining of the ventricles. They may also occur in the spinal cord. Oligodendrogliomas arise in the cells that produce myelin, the fatty covering that protects nerves. These tumors usually arise in the cerebrum. They grow slowly and usually do not spread into surrounding brain tissue. Medulloblastomas develop from primitive nerve cells that normally do not remain in the body after birth. For this reason, medulloblastomas are sometimes called primitive neuroectodermal tumors (PNET). Most medulloblastomas arise in the cerebellum; however, they may occur in other areas as well. Meningiomas grow from the meninges. They are usually benign. Because these tumors grow very slowly, the brain may be able to adjust to their presence; meningiomas often grow quite large before they cause symptoms. Schwannomas are benign tumors that begin in Schwann cells, which produce the myelin that protects the acoustic nerve. Acoustic neuromas are a type of schwannoma. Craniopharyngiomas develop in the region of the pituitary gland near the hypothalamus. They are usually benign; however, they are sometimes considered malignant because they can press on or damage the hypothalamus and affect vital functions. Germ cell tumors arise from primitive (developing) sex cells, or germ cells. The most frequent type of germ cell tumor in the brain is the germinoma. Pineal region tumors occur in or around the pineal gland. The tumor can be slow growing pineocytoma or fast growing (pineoblastoma). The pineal region is very difficult to reach, and these tumors often cannot be removed.

Treatment for a brain tumor depends on a number of factors. Among these are the type, location, and size of the tumor, as well as the patient's age and general health. Normally brain tumors are treated with surgery, radiation therapy, and chemotherapy. In one aspect, the invention provides a method of inhibiting growth and progression of neuroblastoma and neural tumors comprising administering to a subject having a neuroblastoma or neuronal tumor a composition comprising a cyclic RAP peptide. In additional aspect the cyclic RAP peptide may be conjugated to an agent useful to treat neural tumors.

GDNF

In another preferred embodiment, the invention contemplates a method of treating neurodegenerative disease by administering cyclic RAP peptide conjugated to a neuronal growth factor such as glial cell line-derived neurotrophic factor (GDNF). Such neurodegenerative diseases include but are not limited to Parkinson Disease. GDNF was originally purified from a rat glioma cell-line supernatant as a trophic factor for embryonic midbrain dopamine neurons. In vivo, GDNF homodimer binds to its receptor GFRα-1 (probably also a dimer), then the GDNF-GFRα-1 complex binds to the Ret protein, which dimerizes. The dimerization of Ret causes the autophosphorylation of tyrosine 1062. Studies showed that GDNF has pronounced effects on other neuronal subpopulations. Because GDNF protects dopamine neurons in animal models of Parkinson's disease, and rescues motoneurons in vivo, hopes have been raised that GDNF could be used as a therapeutic agent to treat several neurodegenerative diseases. However, GDNF does not cross the blood brain barrier. The present invention provides a method of transporting GDNF across the blood brain barrier comprising administering cyclic RAP peptide conjugated to GDNF.

iii. Liver Disorders

Liver disease contemplated for treatment using the cyclic RAP peptide or conjugates of the invention include, but are not limited to, those disorders discussed below. Hepatocellular carcinoma, or hepatoma, is the fifth most common cancer in the world and incidence rates have been climbing steadily. Hepatocellular carcinoma is a disease of hepatocytes. Tumorigenic hepatocytes retain high levels of LRP1 expression. Hepatocellular carcinoma does not respond well to chemotherapy because the tumor cells show high rates of drug resistance and because the chemotherapies used have serious toxicities, especially in the heart and kidney, due to systemic (intravenous) administration.

Hepatitis is a generic term for inflammation of the liver. Hepatitis can be acute or chronic and includes acute or chronic liver failure, e.g., due to virus (e.g., hepatitis A, B, C, D or E or non-ABCDE, CMV, Epstein-Barr), fungal, rickettsial or parasitic infections, alcohol, chemical toxins, drugs (e.g. acetaminophen, amiodarone, isoniazid, halothane, chlorpromazine, erythromycin), metabolic liver disease (e.g., Wilson's disease, alpha1-antitrypsin deficiency), cancer, idiopathic autoimmune liver disease, cirrhosis (e.g. primary biliary cirrhosis), biliary obstruction. Infection of the liver by Hepatitis A, B and/or C virus can lead to slowly progressing liver disease leading to liver failure. Acute hepatitis infection is most commonly caused by hepatitis A. Both hepatitis B and hepatitis C infection can persist in the body and become longstanding infections (chronic). Hepatitis C can cause critical conditions including cirrhosis and cancer.

Additional liver disorders or conditions contemplated that are treatable using compositions conjugated to cyclic RAP peptide include hepatic steatis (U.S. Pat. No. 6,596,762), cholestasis (U.S. Pat. No. 6,069,167), liver cirrhosis, toxic liver damage, post-hepatectomy conditions, biliary obstruction.

Candidate drugs for conjugation to cyclic RAP peptide for the treatment of liver disease include, but are not limited to: 5-fluorouracil, doxorubicin (adriamycin), mitomycin C, cisplatin, epirubicin, daunorubicin, etoposide, and other chemotherapeutic agents set out in Table 1, adefovir, lamivudine, entecavir, ribavirin, interferon alpha, pegylated interferon alpha-2a, interferon alpha-2b and other antivirals, Vitamin E, ursodeoxycholic acid, and other agents used to treat liver disorders.

TABLE 1

| Alkylating agents |
| --- |
| Nitrogen mustards |
| mechlorethamine<br>cyclophosphamide<br>ifosfamide<br>melphalan<br>chlorambucil<br>Nitrosoureas |
| carmustine (BCNU)<br>lomustine (CCNU)<br>semustine (methyl-CCNU)<br>Ethylenimine/Methyl-melamine |
| thriethylenemelamine (TEM)<br>triethylene thiophosphoramide<br>(thiotepa)<br>hexamethylmelamine<br>(HMM, altretamine)<br>Alkyl sulfonates |
| busulfan<br>Triazines |
| dacarbazine (DTIC) |
| Antimetabolites |
| Folic Acid analogs |
| methotrexate<br>Trimetrexate<br>Pemetrexed<br>(Multi-targeted antifolate)<br>Pyrimidine analogs |
| 5-fluorouracil<br>fluorodeoxyuridine<br>gemcitabine<br>cytosine arabinoside<br>(AraC, cytarabine)<br>5-azacytidine<br>2,2'-difluorodeoxy-cytidine<br>Purine analogs |
| 6-mercaptopurine<br>6-thioguanine<br>azathioprine<br>2'-deoxycoformycin<br>(pentostatin)<br>erythrohydroxynonyl-adenine (EHNA)<br>fludarabine phosphate<br>2-chlorodeoxyadenosine<br>(cladribine, 2-CdA) |
| Type I Topoisomerase Inhibitors |
| camptothecin<br>topotecan<br>irinotecan |

TABLE 1-continued

| Biological response modifiers |
| --- |
| G-CSF<br>GM-CSF |
| Differentiation Agents |
| retinoic acid derivatives |
| Hormones and antagonists |
| Adrenocorticosteroids/antagonists<br>prednisone and equivalents<br>dexamethasone<br>ainoglutethimide<br>Progestins |
| hydroxyprogesterone caproate<br>medroxyprogesterone acetate<br>megestrol acetate<br>Estrogens |
| diethylstilbestrol<br>ethynyl estradiol/equivalents<br>Antiestrogen |
| tamoxifen<br>Androgens |
| testosterone propionate<br>fluoxymesterone/equivalents<br>Antiandrogens |
| flutamide<br>gonadotropin-releasing<br>hormone analogs<br>leuprolide<br>Nonsteroidal antiandrogens |
| flutamide |
| Natural products |
| Antimitotic drugs<br>Taxanes |
| paclitaxel<br>Vinca alkaloids<br>vinblastine (VLB)<br>vincristine<br>vinorelbine<br>Taxotere ® (docetaxel)<br>estramustine<br>estramustine phosphate<br>Epipodophylotoxins |
| etoposide<br>teniposide<br>Antibiotics |
| actimomycin D<br>daunomycin (rubido-mycin)<br>doxorubicin (adria-mycin)<br>mitoxantroneidarubicin<br>bleomycin<br>splicamycin (mithramycin)<br>mitomycinC<br>dactinomycin<br>aphidicolin<br>Enzymes |
| L-asparaginase<br>L-arginase |
| Radiosensitizers |
| metronidazole<br>misonidazole<br>desmethylmisonidazole<br>pimonidazole |

TABLE 1-continued etanidazole
nimorazole
RSU 1069
EO9
RB 6145
SR4233
nicotinamide
5-bromodeozyuridine
5-iododeoxyuridine
bromodeoxycytidine

Miscellaneous agents

Platinium coordination complexes cisplatin
Carboplatin
oxaliplatin
Anthracenedione
mitoxantrone
Substituted urea hydroxyurea
Methylhydrazine derivatives N-methylhydrazine (MIH)
procarbazine
Adrenocortical suppressant mitotane (o,p'-DDD)
ainoglutethimide

Cytokines interferon (α, β, γ)
interleukin-2

Photosensitizers hematoporphyrin derivatives
Photofrin ®
benzoporphyrin derivatives
Npe6
tin etioporphyrin (SnET2)
pheoboride-a
bacteriochlorophyll-a
naphthalocyanines
phthalocyanines
zinc phthalocyanines

Radiation

X-ray
ultraviolet light
gamma radiation
visible light
infrared radiation
microwave radiation iv. Cancer Matriptase is overexpressed on epithelial cancers, for example carcinomas such as ovarian, cervical, prostate, breast, lung, colon or gastric carcinomas. Other examples include lung mesothelioma, melanoma, non-small cell lung cancer, glioma, hepatocellular (liver) carcinoma, thyroid tumor, bladder cancer, glioblastoma, endometrial cancer, kidney cancer, pancreatic cancer, or non-melanoma skin cancer. Cyclic RAP peptides can be used to inhibit matriptase activity or as targeting agents for delivery of cytotoxic or other cancer therapeutic agents.

LRP6 has been determined to be overexpressed in colon and breast cancer. Cyclic RAP peptides can be used to inhibit LRP6 activity or as targeting agents for delivery of cytotoxic or other cancer therapeutic agents.

Other examples of cancers that may be treated using the cyclic RAP peptides or conjugates of the invention include lymphoma including Burkitt's lymphoma, Non-Hodgkins lymphoma, B-cell lymphoma, T-cell lymphoma and leukemia.

v. Bone Metabolism Disorders

Bone metabolism disorders that may be treated using the cyclic RAP peptides and conjugates of the invention include disorders of bone (e.g. abnormal bone deposition, abnormal bone loss or bone weakening) associated with osteoporosis, osteopetrosis, inflammation of bone, arthritis, rheumatoid arthritis, osteoarthritis, hypercortisolism, hypogonadism, primary or secondary hyperparathyroidism, or hyperthyroidism; hypercalcemia; vitamin D deficiency states (e.g., rickets/osteomalacia, scurvy, malnutrition), malabsorption syndromes, chronic renal failure (renal osteodystrophy), chronic liver disease (hepatic osteodystrophy), aging or immobility; osteoporosis resulting from drugs (glucocorticoids or steroids, heparin, alcohol) or hereditary diseases (e.g., osteogenesis imperfecta, homocystinuria), bone metastatic cancer, myeloma, bone fractures, bone grafts, fibrous dysplasia, and/or Paget's disease.

C. Conjugates of Cyclic RAP Peptide and Active Agent

A cyclic RAP peptide and an active agent may be attached through any means known in the art. They may be physically linked by, for example, by covalent chemical bonds, physical forces such van der Waals or hydrophobic interactions, encapsulation, embedding, or combinations thereof. In preferred embodiments, the therapeutic agent(s) and the cyclic RAP peptide are physically linked by covalent chemical bonds. As such, preferred chemotherapeutic agents contain a functional group such as an alcohol, acid, carbonyl, thiol or amine group to be used in the conjugation to RAP peptide. Adriamycin is in the amine class and there is also the possibility to link through the carbonyl as well. Paclitaxel is in the alcohol class. Chemotherapeutic agents without suitable conjugation groups may be further modified to add such a group. All these compounds are contemplated in this invention. In the case of multiple therapeutic agents, a combination of various conjugations can be used.

In some embodiments, a covalent chemical bond that may be either direct (no intervening atoms) or indirect (through a linker e.g., a chain of covalently linked atoms) joins the RAP peptide and the active agent. In some embodiments, the RAP peptide and the active agent moiety of the conjugate are directly linked by covalent bonds between an atom of the RAP peptide and an atom of the active agent. In other embodiments, RAP peptide is connected to the active agent moiety by a linker that comprises a covalent bond or a peptide of virtually any amino acid sequence or any molecule or atoms capable of connecting the RAP peptide to the active agent moiety.

In some embodiments, the linker comprises a chain of atoms from 1 to about 60, or 1 to 30 atoms or longer, 2 to 5 atoms, 2 to 10 atoms, 5 to 10 atoms, or 10 to 20 atoms long. In some embodiments, the chain atoms are all carbon atoms. In some embodiments, the chain atoms are selected from the group consisting of C, O, N, and S. Chain atoms and linkers may be selected according to their expected solubility (hydrophilicity) so as to provide a more soluble conjugate. In some embodiments, the linker provides a functional group that is subject to enzymatic attack in a lysosome. In some embodiments, the linker provides a functional group which is subject to attack by an enzyme found in the target tissue or organ and which upon attack or hydrolysis severs the link between the active agent and the RAP peptide. In some embodiments, the linker provides a functional group that is subject to hydrolysis under the conditions found at the target site (e.g., low pH of a lysosome). A linker may contain one or more such functional groups. In some embodiments, the length of the linker is long enough to reduce the potential for steric hindrance (when an active agent is large) between one or both of the RAP peptide binding site and the active agent active binding site.

If the linker is a covalent bond or a peptide and the active agent is a polypeptide, the entire conjugate can be a fusion protein. Such peptidyl linkers may be any length. Exemplary linkers are from about 1 to 50 amino acids in length, 5 to 50, 3 to 5, 5 to 10, 5 to 15, or 10 to 30 amino acids in length. Such fusion proteins may be produced by recombinant genetic engineering methods known to one of ordinary skill in the art. In some embodiments, the RAP peptide portion of the conjugate is formulated to rapidly degrade or be cleaved so as to release the active compound. In other embodiments, the linker is subject to cleavage under intracellular, or more preferably, lysosomal environmental conditions to release or separate the active agent portion from the RAP peptide portion.

The conjugate can comprise one or more active agents linked to the same RAP peptide. For example, conjugation reactions may conjugate from 1 to 5, about 5, about 1 to 10, about 5 to 10, about 10 to 20, about 20 to 30, or 30 or more molecules of an active agent to the RAP peptide. These formulations can be employed as mixtures, or they may be purified into specific stoichiometric formulations. Those skilled in the art are able to determine which format and which stoichiometric ratio is preferred. Further, more than one type of active agent may be linked to the RAP peptide where delivery of more than one type of an agent to a target site or compartment is desired. A plurality of active agent species may be attached to the same RAP peptide e.g., adriamycin-cisplatinum RAP peptide conjugates. Thus, the conjugates may consist of a range of stoichiometric ratios and incorporate more than one type of active agent. These, too, may be separated into purified mixtures or they may be employed in aggregate.

The cyclic RAP peptides of the invention, or conjugates thereof, may also be modified as desired to enhance stability or pharmacokinetic properties (e.g., by PEGylation).

It is contemplated that RAP peptides of the invention may be fused or linked to therapeutic proteins such as glial cell-derived neuronal growth factor (GDNF), brain-derived neuronal growth factor (BDNF), neuronal growth factor (NGF), other neurotrophic factors known to the art, ADAM10, other protease acting on APP or Abeta, MESD, cancer chemotherapeutic agents, protease inhibitors, autoimmune antigens, pro-apoptotic molecules, lysosomal enzymes, DNA or siRNA. It is contemplated that fusion of these agents to cyclic RAP peptides with improved affinity or binding selectivity for CR-containing proteins will facilitate increased transport across the blood-brain barrier or to other tissue sites. In one aspect, it is contemplated that conjugation to a cyclic RAP peptide results in altered tissue distribution or improved delivery of the conjugate after intravenous, subcutaneous, intramuscular, intraventricular, intrathecal or intraparenchymal administration of the conjugate.

It is further provided that conjugation to the cyclic RAP peptide results in alterations in the pharmacological activity of the active agent caused by one or more of the following effects: Increased potency, diminished binding to receptors or tissues that are different from the intended target receptor or tissue, increased binding to receptors or tissues that are the intended target receptor or tissue, increased access to receptors or tissues that are the intended target receptor or tissue, altered rates of clearance from the body, and, altered characteristics of the immune response to the protein.

It is further provided that cyclic RAP peptides of the invention may be conjugated to therapeutic nucleic acids, such as DNA or siRNA, in order to improve the tissue-selective distribution of said nucleic acids and facilitate endocytosis of said nucleic acids into cells (Kim et al., (2004) Bioconjugate Chemistry 15, 326-332).

D. Active Agents

Active agents according to the invention include agents that can affect a biological process. Particularly preferred active agents for use in the compounds compositions and methods of the invention are therapeutic agents, including drugs and diagnostic agents. The term "drug" or "therapeutic agent" refers to an active agent that has a pharmacological activity or benefits health when administered in a therapeutically effective amount. Particularly preferred agents are naturally occurring biological agents (e.g., enzymes, proteins, polynucleotides, antibodies, polypeptides, nanoparticles, glycoconjugates). Examples of drugs or therapeutic agents include substances that are used in the prevention, diagnosis, alleviation, treatment or cure of a disease or condition. It is particularly contemplated that the agent is not an agent that causes a disease.

i. Protein Active Agents

The active agent can be a non-protein or a protein. The active agent can be a protein or enzyme or any fragment of such that still retains some, substantially all, or all of the therapeutic or biological activity of the protein or enzyme. In some embodiments, the protein or enzyme is one that, if not expressed or produced or if substantially reduced in expression or production, would give rise to a disease, including but not limited to, lysosomal storage diseases. Preferably, the protein or enzyme is derived or obtained from a human or mouse.

In preferred embodiments of the invention, when the active agent conjugated to cyclic RAP peptide is a protein or enzyme, or fragment thereof possessing a biological activity of the protein or enzyme, the active agent has an amino acid sequence identical to the amino acid sequence to the corresponding portion of the human or mammalian protein or enzyme. In other embodiments, the active agent moiety of the conjugate is a protein or enzyme native to the species of the human or mammal. In other embodiments, the protein or enzyme, or fragment thereof, is substantially homologous (i.e., at least 80%, 85%, 90%, 95%, more preferably 98%, or most preferably 99% identical in amino acid sequence over a length of at least 10, 25, 50, 100, 150, or 200 amino acids, or the entire length of the active agent) to a native sequence of the corresponding human or mammal protein or enzyme.

If the compound is a protein, the compound can be an enzyme, or any fragment of an enzyme that still retains some, substantially all, or all of the activity of the enzyme. Preferably, in the treatment of lysosomal storage diseases, the enzyme is an enzyme that is found in a cell that if not expressed or produced or is substantially reduced in expression or production would give rise to a lysosomal storage disease. Preferably, the enzyme is derived or obtained from a human or mouse. Preferably, the enzyme is a lysosomal storage enzyme, such as α-L-iduronidase, iduronate-2-sulfatase, heparan N-sulfatase, α-N-acetylglucosaminidase, arylsulfatase A, galactosylceramidase, acid-alpha-glucosidase, tripeptidyl peptidase, hexosaminidase alpha, acid sphingomyelinase, β-galactosidase, or any other lysosomal storage enzyme.

In some embodiments, therefore, in the treatment of human Lysosomal Storage Diseases (LSDs), the cyclic RAP peptide conjugate comprises an active agent protein or enzyme that is deficient in the lysosomes of a subject or patient to be treated. Such enzymes, include for example, alpha-L-iduronidase, iduronate-2-sulfatase, heparan N-sulfatase, alpha-N-acetyl-glucosaminidase, Arylsulfatase A, Galactosylceramidase, acid-alpha-glucosidase, thioesterase, hexosaminidase A, Acid Spingomyelinase, alpha-galactosidase, or any other lysosomal storage enzyme. A table of lysosomal storage diseases and the proteins deficient therein, which are useful as active agents, follows:

| Lysosomal Storage Disease | Protein deficiency |
|---|---|
| Mucopolysaccharidosis type I | L-Iduronidase |
| Mucopolysaccharidosis type II Hunter syndrome | Iduronate-2-sulfatase |
| Mucopolysaccharidosis type IIIA Sanfilippo syndrome | Heparan-N-sulfatase |
| Mucopolysaccharidosis type IIIB Sanfilippo syndrome | α-N-Acetylglucosaminidase |
| Mucopolysaccharidosis type IIIC Sanfilippo syndrome | AcetylCoA:N-acetyltransferase |
| Mucopolysaccharidosis type IIID Sanfilippo syndrome | N-Acetylglucosamine 6-sulfatase |
| Mucopolysaccharidosis type IVA Morquio syndrome | Galactose 6-sulfatase |
| Mucopolysaccharidosis type IVB Morquio syndrome | β-Galactosidase |
| Mucopolysaccharidosis type VI | N-Acetylgalactosamine 4-sulfatase |
| Mucopolysaccharidosis type VII Sly syndrome | β-Glucuronidase |
| Mucopolysaccharidosis type IX | hyaluronoglucosaminidase |
| Aspartylglucosaminuria | Aspartylglucosaminidase |
| Cholesterol ester storage disease/Wolman disease | Acid lipase |
| Cystinosis | Cystine transporter |
| Danon disease | Lamp-2 |
| Fabry disease | α-Galactosidase A |
| Farber Lipogranulomatosis/Farber disease | Acid ceramidase |
| Fucosidosis | α-L-Fucosidase |
| Galactosialidosis types I/II | Protective protein |
| Gaucher disease types I/IIIII Gaucher disease | Glucocerebrosidase (β-glucosidase) |
| Globoid cell leukodystrophy/Krabbe disease | Galactocerebrosidase |
| Glycogen storage disease II/Pompe disease | α-Glucosidase |
| GM1-Gangliosidosis types I/II/III | β-Galactosidase |
| GM2-Gangliosidosis type I/Tay Sachs disease | β-Hexosaminidase A |
| GM2-Gangliosidosis type II Sandhoff disease | β-Hexosaminidase A |
| GM2-Gangliosidosis | GM2-activator deficiency |
| α-Mannosidosis types I/II | α-D-Mannosidase |
| β-Mannosidosis | β-D-Mannosidase |
| Metachromatic leukodystrophy | Arylsulfatase A |
| Metachromatic leukodystrophy | Saposin B |
| Mucolipidosis type I/Sialidosis types I/II | Neuraminidase |
| Mucolipidosis types II/III I-cell disease | Phosphotransferase |
| Mucolipidosis type IIIC pseudo-Hurler polydystrophy | Phosphotransferase γ-subunit |
| Multiple sulfatase deficiency | Multiple sulfatases |
| Neuronal Ceroid Lipofuscinosis, CLN1 Batten disease | Palmitoyl protein thioesterase |
| Neuronal Ceroid Lipofuscinosis, CLN2 Batten disease | Tripeptidyl peptidase I |
| Niemann-Pick disease types A/B Niemann-Pick disease | Acid sphingomyelinase |
| Niemann-Pick disease type C1 Niemann-Pick disease | Cholesterol trafficking |
| Niemann-Pick disease type C2 Niemann-Pick disease | Cholesterol trafficking |
| Pycnodysostosis | Cathepsin K |
| Schindler disease types I/II Schindler disease | α-Galactosidase B |
| Sialic acid storage disease | sialic acid transporter |

Thus, the lysosomal storage diseases that can be treated or prevented using the methods of the present invention include, but are not limited to, Mucopolysaccharidosis I (MPS I), MPS II, MPS IIIA, MPS IIIB, Metachromatic Leukodystrophy (MLD), Krabbe, Pompe, Ceroid Lipofuscinosis, Tay-Sachs, Niemann-Pick A and B, and other lysosomal diseases.

Thus, per the above table, for each disease the conjugated agent would preferably comprise a specific active agent enzyme deficient in the disease. For instance, for methods involving MPS I, the preferred compound or enzyme is α-L-iduronidase. For methods involving MPS II, the preferred compound or enzyme is iduronate-2-sulfatase. For methods involving MPS IIIA, the preferred compound or enzyme is heparan N-sulfatase. For methods involving MPS IIIB, the preferred compound or enzyme is α-N-acetylglucosaminidase. For methods involving Metachromatic Leukodystropy (MLD), the preferred compound or enzyme is arylsulfatase A. For methods involving Krabbe, the preferred compound or enzyme is galactosylceramidase. For methods involving Pompe, the preferred compound or enzyme is acid α-glucosidase. For methods involving CLN, the preferred compound or enzyme is tripeptidyl peptidase. For methods involving Tay-Sachs, the preferred compound or enzyme is hexosaminidase alpha. For methods involving Niemann-Pick A and B the preferred compound or enzyme is acid sphingomyelinase.

The cyclic RAP peptide conjugate can comprise one or more active agent moieties (e.g., 1 to 10 or 1 to 4 or 2 to 3 moieties) linked to the cyclic RAP peptide. For example, conjugation reactions may conjugate from 1 to 4 or more molecules of alpha-L-iduronidase to a single cyclic RAP peptide. These formulations can be employed as mixtures, or they may be purified into specific cyclic RAP peptide-agent stoichiometric formulations. Those skilled in the art are able to determine which format and which stoichiometric ratio is preferred. Further, one or more different active agents may be linked to any given molecule of a cyclic RAP peptide to facilitate a more complete degradation of the stored substrates. These cyclic RAP peptide conjugated agents may consist of a range of stoichiometric ratios. These, too, may be separated into purified mixtures or they may be employed in aggregate. It may be the order of cyclic RAP peptide and the LSD in the fusion is important. Therefore, in some embodiments, the cyclic RAP peptide is N-terminal to the LSD enzyme, and in other embodiments, the cyclic RAP peptide is C-terminal to the LSD enzyme.

The cyclic RAP peptide conjugated active agents can enter or be transported into or end up residing in the lysosomes of a cell within or without the CNS. The rate of passage of the conjugated agent can be modulated by any compound or protein that can modulate receptor transport activity. The cell can be from any tissue or organ system affected by the lysosomal storage disease. The cell can be, for instance, an endothelial, epithelial, muscle, heart, bone, lung, fat, kidney, or liver cell. In some embodiments, the cell is preferably a cell found within the BBB. In some embodiments, the cell is a neuron or a brain cell. In other embodiments, the cell is a cell of the periphery or one that is not isolated from the general circulation by an endothelium such as that of the BBB.

ii. Drug Active Agents

Generally, the drug active agent may be of any size. Preferred drugs are small organic molecules that are capable of binding to the target of interest. A drug moiety of the conjugate, when a small molecule, generally has a molecular weight of at least about 50 D, usually at least about 100 D, where the molecular weight may be as high as 500 D or higher, but will usually not exceed about 2000 D.

The drug moiety is capable of interacting with a target in the host into which the conjugate is administered during practice of the subject methods. The target may be a number of different types of naturally occurring structures, where targets of interest include both intracellular and extracellular targets, where such targets may be proteins, phospholipids, nucleic acids and the like, where proteins are of particular interest. Specific proteinaceous targets of interest include, without limitation, enzymes, e.g., kinases, phosphatases, reductases, cyclooxygenases, proteases and the like, targets comprising domains involved in protein-protein interactions, such as the SH2, SH3, PTB and PDZ domains, structural proteins, e.g., actin, tubulin, etc., membrane receptors, immunoglobulins, e.g., IgE, cell adhesion receptors, such as integrins, etc., ion channels, transmembrane pumps, transcription factors, signaling proteins, and the like.

In some embodiments, the active agent or drug has a hydroxyl or an amino group for reacting with the isocyanate reagent or the active agent is chemically modified to introduce a hydroxyl or an amino group for reacting with the isocyanate reagent.

In some embodiments, the active agent or drug comprises a region that may be modified and/or participate in covalent linkage, preferably, without loss of the desired biological activity of the active agent. The drug moieties often comprise cyclical carbon or heterocyclic structures and/or aromatic or polyaromatic structures substituted with one or more of the above functional groups. Also of interest as drug moieties are structures found among biomolecules, proteins, enzymes, polysaccharides, and polynucleic acids, including peptides, saccharides, fatty acids, steroids, purines, pyrimidines, derivatives, structural analogs or combinations thereof.

Suitable active agents include, but are not limited to, psychopharmacological agents, such as (1) central nervous system depressants, e.g., general anesthetics (barbiturates, benzodiazepines, steroids, cyclohexanone derivatives, and miscellaneous agents), sedative-hypnotics (benzodiazepines, barbiturates, piperidinediones and triones, quinazoline derivatives, carbamates, aldehydes and derivatives, amides, acyclic ureides, benzazepines and related drugs, phenothiazines, etc.), central voluntary muscle tone modifying drugs (anticonvulsants, such as hydantoins, barbiturates, oxazolidinediones, succinimides, acylureides, glutarimides, benzodiazepines, secondary and tertiary alcohols, dibenzazepine derivatives, valproic acid and derivatives, GABA analogs, etc.), analgesics (morphine and derivatives, oripavine derivatives, morphinan derivatives, phenylpiperidines, 2,6-methane-3-benzazocaine derivatives, diphenylpropylamines and isosteres, salicylates, p-aminophenol derivatives, 5-pyrazolone derivatives, arylacetic acid derivatives, fenamates and isosteres, etc.) and antiemetics (anticholinergics, antihistamines, antidopaminergics, etc.), (2) central nervous system stimulants, e.g., analeptics (respiratory stimulants, convulsant stimulants, psychomotor stimulants), narcotic antagonists (morphine derivatives, oripavine derivatives, 2,6-methane-3-benzoxacine derivatives, morphinan derivatives) nootropics, (3) psychopharmacologicals, e.g., anxiolytic sedatives (benzodiazepines, propanediol carbamates) antipsychotics (phenothiazine derivatives, thioxanthine derivatives, other tricyclic compounds, butyrophenone derivatives and isosteres, diphenylbutylamine derivatives, substituted benzamides, arylpiperazine derivatives, indole derivatives, etc.), antidepressants (tricyclic compounds, MAO inhibitors, etc.), (4) respiratory tract drugs, e.g., central antitussives (opium alkaloids and their derivatives); pharmacodynamic agents, such as (1) peripheral nervous system drugs, e.g., local anesthetics (ester derivatives, amide derivatives), (2) drugs acting at synaptic or neuroeffector junctional sites, e.g., cholinergic agents, cholinergic blocking agents, neuromuscular blocking agents, adrenergic agents, antiadrenergic agents, (3) smooth muscle active drugs, e.g., spasmolytics (anticholinergics, musculotropic spasmolytics), vasodilators, smooth muscle stimulants, (4) histamines and antihistamines, e.g., histamine and derivative thereof (betazole), antihistamines (H1-antagonists, H2-antagonists), histamine metabolism drugs, (5) cardiovascular drugs, e.g., cardiotonics (plant extracts, butenolides, pentadienolids, alkaloids from erythrophleum species, ionophores, adrenoceptor stimulants, etc), antiarrhythmic drugs, antihypertensive agents, antilipidemic agents (clofibric acid derivatives, nicotinic acid derivatives, hormones and analogs, antibiotics, salicylic acid and derivatives), antivaricose drugs, hemostyptics, (6) blood and hemopoietic system drugs, e.g., antianemia drugs, blood coagulation drugs (hemostatics, anticoagulants, antithrombotics, thrombolytics, blood proteins and their fractions), (7) gastrointestinal tract drugs, e.g., digestants (stomachics, choleretics), antiulcer drugs, antidiarrheal agents, (8) locally acting drugs; chemotherapeutic agents, such as (1) anti-infective agents, e.g., ectoparasiticides (chlorinated hydrocarbons, pyrethins, sulfurated compounds), anthelmintics, antiprotozoal agents, antimalarial agents, antiamebic agents, antileiscmanial drugs, antitrichomonal agents, antitrypanosomal agents, sulfonamides, antimycobacterial drugs, antiviral chemotherapeutics, etc., and (2) cytostatics, i.e., antineoplastic agents or cytotoxic drugs, such as alkylating agents, e.g., Mechlorethamine hydrochloride (Nitrogen Mustard, Mustargen, HN2), Cyclophosphamide (Cytovan, Endoxana), Ifosfamide (IFEX), Chlorambucil (Leukeran), Melphalan (Phenylalanine Mustard, L-sarcolysin, Alkeran, L-PAM), Busulfan (Mylaran), Thiotepa (Triethylenethiophosphoramide), Carmustine (BiCNU, BCNU), Lomustine (CeeNU, CCNU), Streptozocin (Zanosar) and the like; plant alkaloids, e.g., Vincristine (Oncovin), Vinblastine (Velban, Velbe), Paclitaxel (Taxol), and the like; antimetabolites, e.g., Methotrexate (MTX), Mercaptopurine (Purinethol, 6-MP), Thioguanine (6-TG), Fluorouracil (5-FU), Cytarabine (Cytosar-U, Ara-C), Azacitidine (Mylosar, 5-AZA) and the like; antibiotics, e.g., Dactinomycin (Actinomycin D, Cosmegen), Doxorubicin (Adriamycin), Daunorubicin (duanomycin, Cerubidine), Idarubicin (Idamycin), Bleomycin (Blenoxane), Picamycin (Mithramycin, Mithracin), Mitomycin (Mutamycin) and the like, and other anticellular proliferative agents, e.g., Hydroxyurea (Hydrea), Procarbazine (Mutalane), Dacarbazine (DTIC-Dome), Cisplatin (Platinol) Carboplatin (Paraplatin), Asparaginase (Elspar) Etoposide (VePesid, VP-16-213), Amsarcrine (AMSA, m-AMSA), Mitotane (Lysodren), Mitoxantrone (Novatrone), and the like. Preferred chemotherapeutic agents are those, which in the free form, demonstrate unacceptable systemic toxicity at desired doses. The general systemic toxicity associated with therapeutic levels of such agents may be reduced by their linkage to the cyclic RAP peptide. Particularly preferred are cardiotoxic compounds that are useful therapeutics but are dose limited by cardiotoxicity. A classic example is adriamycin (also known as doxorubicin) and its analogs, such as daunorubicin. Linking cyclic RAP peptide to such drugs may prevent accumulation of the active agent at the heart and associated cardiotoxicity.

Suitable active agents include, but are not limited to: Antibiotics, such as: aminoglycosides, e.g., amikacin, apramycin, arbekacin, bambermycins, butirosin, dibekacin, dihydrostreptomycin, fortimicin, gentamicin, isepamicin, kanamycin, micronomcin, neomycin, netilmicin, paromycin, ribostamycin, sisomicin, spectinomycin, streptomycin, tobramycin, trospectomycin; amphenicols, e.g., azidamfenicol, chloramphenicol, florfenicol, and theimaphenicol; ansamycins, e.g., rifamide, rifampin, rifamycin, rifapentine, rifaximin; beta.-lactams, e.g., carbacephems, carbapenems, cephalosporins, cehpamycins, monobactams, oxaphems, penicillins; lincosamides, e.g., clinamycin, lincomycin; macrolides, e.g., clarithromycin, dirthromycin, erythromycin, etc.; polypeptides, e.g., amphomycin, bacitracin, capreomycin, etc.; tetracyclines, e.g., apicycline, chlortetracycline, clomocycline, etc.; synthetic antibacterial agents, such as 2,4-diaminopyrimidines, nitrofurans, quinolones and analogs thereof, sulfonamides, sulfones;

Suitable active agents include, but are not limited to: Antifungal agents, such as: polyenes, e.g., amphotericin B, candicidin, dermostatin, filipin, fungichromin, hachimycin, hamycin, lucensomycin, mepartricin, natamycin, nystatin, pecilocin, perimycin; synthetic antifungals, such as allylamines, e.g., butenafine, naftifine, terbinafine; imidazoles, e.g., bifonazole, butoconazole, chlordantoin, chlormidazole, etc., thiocarbamates, e.g., tolciclate, triazoles, e.g., fluconazole, itraconazole, terconazole;

Suitable active agents include, but are not limited to: Antihelmintics, such as: arecoline, aspidin, aspidinol, dichlorophene, embelin, kosin, napthalene, niclosamide, pelletierine, quinacrine, alantolactone, amocarzine, amoscanate, ascaridole, bephenium, bitoscanate, carbon tetrachloride, carvacrol, cyclobendazole, diethylcarbamazine, etc.;

Suitable active agents include, but are not limited to: Antimalarials, such as: acedapsone, amodiaquin, arteether, artemether, artemisinin, artesunate, atovaquone, bebeerine, berberine, chirata, chlorguanide, chloroquine, chlorproguanil, cinchona, cinchonidine, cinchonine, cycloguanil, gentiopicrin, halofantrine, hydroxychloroquine, mefloquine hydrochloride, 3-methylarsacetin, pamaquine, plasmocid, primaquine, pyrimethamine, quinacrine, quinidine, quinine, quinocide, quinoline, dibasic sodium arsenate;

Suitable active agents include, but are not limited to: Antiprotozoan agents, such as: acranil, timidazole, ipronidazole, ethylstibamine, pentamidine, acetarsone, aminitrozole, anisomycin, nifuratel, timidazole, benzidazole, suramin, and the like.

Suitable drugs for use as active agents are also listed in: Goodman and Gilman's, The Pharmacological Basis of Therapeutics (9th Ed) (Goodman et al. eds) (McGraw-Hill) (1996); and 1999 Physician's Desk Reference (1998).

Suitable active agents include, but are not limited to: antineoplastic agents, as disclosed in U.S. Pat. Nos. 5,880,161, 5,877,206, 5,786,344, 5,760,041, 5,753,668, 5,698,529, 5,684,004, 5,665,715, 5,654,484, 5,624,924, 5,618,813, 5,610,292, 5,597,831, 5,530,026, 5,525,633, 5,525,606, 5,512,678, 5,508,277, 5,463,181, 5,409,893, 5,358,952, 5,318,965, 5,223,503, 5,214,068, 5,196,424, 5,109,024, 5,106,996, 5,101,072, 5,077,404, 5,071,848, 5,066,493, 5,019,390, 4,996,229, 4,996,206, 4,970,318, 4,968,800, 4,962,114, 4,927,828, 4,892,887, 4,889,859, 4,886,790, 4,882,334, 4,882,333, 4,871,746, 4,863,955, 4,849,563, 4,845,216, 4,833,145, 4,824,955, 4,785,085, 4,684,747, 4,618,685, 4,611,066, 4,550,187, 4,550,186, 4,544,501, 4,541,956, 4,532,327, 4,490,540, 4,399,283, 4,391,982, 4,383,994, 4,294,763, 4,283,394, 4,246,411, 4,214,089, 4,150,231, 4,147,798, 4,056,673, 4,029,661, 4,012,448;

psychopharmacological/psychotropic agents, as disclosed in U.S. Pat. Nos. 5,192,799, 5,036,070, 4,778,800, 4,753,951, 4,590,180, 4,690,930, 4,645,773, 4,427,694, 4,424,202, 4,440,781, 5,686,482, 5,478,828, 5,461,062, 5,387,593, 5,387,586, 5,256,664, 5,192,799, 5,120,733, 5,036,070, 4,977,167, 4,904,663, 4,788,188, 4,778,800, 4,753,951, 4,690,930, 4,645,773, 4,631,285, 4,617,314, 4,613,600, 4,590,180, 4,560,684, 4,548,938, 4,529,727, 4,459,306, 4,443,451, 4,440,781, 4,427,694, 4,424,202, 4,397,853, 4,358,451, 4,324,787, 4,314,081, 4,313,896, 4,294,828, 4,277,476, 4,267,328, 4,264,499, 4,231,930, 4,194,009, 4,188,388, 4,148,796, 4,128,717, 4,062,858, 4,031,226, 4,020,072, 4,018,895, 4,018,779, 4,013,672, 3,994,898, 3,968,125, 3,939,152, 3,928,356, 3,880,834, 3,668,210;

cardiovascular agents, as disclosed in U.S. Pat. Nos. 4,966,967, 5,661,129, 5,552,411, 5,332,737, 5,389,675, 5,198,449, 5,079,247, 4,966,967, 4,874,760, 4,954,526, 5,051,423, 4,888,335, 4,853,391, 4,906,634, 4,775,757, 4,727,072, 4,542,160, 4,522,949, 4,524,151, 4,525,479, 4,474,804, 4,520,026, 4,520,026, 5,869,478, 5,859,239, 5,837,702, 5,807,889, 5,731,322, 5,726,171, 5,723,457, 5,705,523, 5,696,111, 5,691,332, 5,679,672, 5,661,129, 5,654,294, 5,646,276, 5,637,586, 5,631,251, 5,612,370, 5,612,323, 5,574,037, 5,563,170, 5,552,411, 5,552,397, 5,547,966, 5,482,925, 5,457,118, 5,414,017, 5,414,013, 5,401,758, 5,393,771, 5,362,902, 5,332,737, 5,310,731, 5,260,444, 5,223,516, 5,217,958, 5,208,245, 5,202,330, 5,198,449, 5,189,036, 5,185,362, 5,140,031, 5,128,349, 5,116,861, 5,079,247, 5,070,099, 5,061,813, 5,055,466, 5,051,423, 5,036,065, 5,026,712, 5,011,931, 5,006,542, 4,981,843, 4,977,144, 4,971,984, 4,966,967, 4,959,383, 4,954,526, 4,952,692, 4,939,137, 4,906,634, 4,889,866, 4,888,335, 4,883,872, 4,883,811, 4,847,379, 4,835,157, 4,824,831, 4,780,538, 4,775,757, 4,774,239, 4,771,047, 4,769,371, 4,767,756, 4,762,837, 4,753,946, 4,752,616, 4,749,715, 4,738,978, 4,735,962, 4,734,426, 4,734,425, 4,734,424, 4,730,052, 4,727,072, 4,721,796, 4,707,550, 4,704,382, 4,703,120, 4,681,970, 4,681,882, 4,670,560, 4,670,453, 4,668,787, 4,663,337, 4,663,336, 4,661,506, 4,656,267, 4,656,185, 4,654,357, 4,654,356, 4,654,355, 4,654,335, 4,652,578, 4,652,576, 4,650,874, 4,650,797, 4,649,139, 4,647,585, 4,647,573, 4,647,565, 4,647,561, 4,645,836, 4,639,461, 4,638,012, 4,638,011, 4,632,931, 4,631,283, 4,628,095, 4,626,548, 4,614,825, 4,611,007, 4,611,006, 4,611,005, 4,609,671, 4,608,386, 4,607,049, 4,607,048, 4,595,692, 4,593,042, 4,593,029, 4,591,603, 4,588,743, 4,588,742, 4,588,741, 4,582,854, 4,575,512, 4,568,762, 4,560,698, 4,556,739, 4,556,675, 4,555,571, 4,555,570, 4,555,523, 4,550,120, 4,542,160, 4,542,157, 4,542,156, 4,542,155, 4,542,151, 4,537,981, 4,537,904, 4,536,514, 4,536,513, 4,533,673, 4,526,901, 4,526,900, 4,525,479, 4,524,151, 4,522,949, 4,521,539, 4,520,026, 4,517,188, 4,482,562, 4,474,804, 4,474,803, 4,472,411, 4,466,979, 4,463,015, 4,456,617, 4,456,616, 4,456,615, 4,418,076, 4,416,896, 4,252,815, 4,220,594, 4,190,587, 4,177,280, 4,164,586, 4,151,297, 4,145,443, 4,143,054, 4,123,550, 4,083,968, 4,076,834, 4,064,259, 4,064,258, 4,064,257, 4,058,620, 4,001,421, 3,993,639, 3,991,057, 3,982,010, 3,980,652, 3,968,117, 3,959,296, 3,951,950, 3,933,834, 3,925,369, 3,923,818, 3,898,210, 3,897,442, 3,897,441, 3,886,157, 3,883,540, 3,873,715, 3,867,383, 3,873,715, 3,867,383, 3,691,216, 3,624,126;

antimicrobial agents as disclosed in U.S. Pat. Nos. 5,902,594, 5,874,476, 5,874,436, 5,859,027, 5,856,320, 5,854,242, 5,811,091, 5,786,350, 5,783,177, 5,773,469, 5,762,919, 5,753,715, 5,741,526, 5,709,870, 5,707,990, 5,696,117, 5,684,042, 5,683,709, 5,656,591, 5,643,971, 5,643,950, 5,610,196, 5,608,056, 5,604,262, 5,595,742, 5,576,341, 5,554,373, 5,541,233, 5,534,546, 5,534,508, 5,514,715, 5,508,417, 5,464,832, 5,428,073, 5,428,016, 5,424,396, 5,399,553, 5,391,544, 5,385,902, 5,359,066, 5,356,803, 5,354,862, 5,346,913, 5,302,592, 5,288,693, 5,266,567, 5,254,685, 5,252,745, 5,209,930, 5,196,441, 5,190,961, 5,175,160, 5,157,051, 5,096,700, 5,093,342, 5,089,251, 5,073,570, 5,061,702, 5,037,809, 5,036,077, 5,010,109, 4,970,226, 4,916,156, 4,888,434, 4,870,093, 4,855,318, 4,784,991, 4,746,504, 4,686,221, 4,599,228, 4,552,882, 4,492,700, 4,489,098, 4,489,085, 4,487,776, 4,479,953, 4,477,448, 4,474,807, 4,470,994, 4,370,484, 4,337,199, 4,311,709, 4,308,283, 4,304,910, 4,260,634, 4,233,311, 4,215,131, 4,166,122, 4,141,981, 4,130,664, 4,089,977, 4,089,900, 4,069,341, 4,055,655, 4,049,665, 4,044,139, 4,002,775, 3,991,201, 3,966,968, 3,954,868, 3,936,393, 3,917,476, 3,915,889, 3,867,548, 3,865,748, 3,867,548, 3,865,748, 3,783,160, 3,764,676, 3,764,677;

anti-inflammatory agents as disclosed in U.S. Pat. Nos. 5,872,109, 5,837,735, 5,827,837, 5,821,250, 5,814,648, 5,780,026, 5,776,946, 5,760,002, 5,750,543, 5,741,798, 5,739,279, 5,733,939, 5,723,481, 5,716,967, 5,688,949, 5,686,488, 5,686,471, 5,686,434, 5,684,204, 5,684,041, 5,684,031, 5,684,002, 5,677,318, 5,674,891, 5,672,620, 5,665,752, 5,656,661, 5,635,516, 5,631,283, 5,622,948, 5,618,835, 5,607,959, 5,593,980, 5,593,960, 5,580,888, 5,552,424, 5,552,422, 5,516,764, 5,510,361, 5,508,026, 5,500,417, 5,498,405, 5,494,927, 5,476,876, 5,472,973, 5,470,885, 5,470,842, 5,464,856, 5,464,849, 5,462,952, 5,459,151, 5,451,686, 5,444,043, 5,436,265, 5,432,181, RE034918, 5,393,756, 5,380,738, 5,376,670, 5,360,811, 5,354,768, 5,348,957, 5,347,029, 5,340,815, 5,338,753, 5,324,648, 5,319,099, 5,318,971, 5,312,821, 5,302,597, 5,298,633, 5,298,522, 5,298,498, 5,290,800, 5,290,788, 5,284,949, 5,280,045, 5,270,319, 5,266,562, 5,256,680, 5,250,700, 5,250,552, 5,248,682, 5,244,917, 5,240,929, 5,234,939, 5,234,937, 5,232,939, 5,225,571, 5,225,418, 5,220,025, 5,212,189, 5,212,172, 5,208,250, 5,204,365, 5,202,350, 5,196,431, 5,191,084, 5,187,175, 5,185,326, 5,183,906, 5,177,079, 5,171,864, 5,169,963, 5,155,122, 5,143,929, 5,143,928, 5,143,927, 5,124,455, 5,124,347, 5,114,958, 5,112,846, 5,104,656, 5,098,613, 5,095,037, 5,095,019, 5,086,064, 5,081,261, 5,081,147, 5,081,126, 5,075,330, 5,066,668, 5,059,602, 5,043,457, 5,037,835, 5,037,811, 5,036,088, 5,013,850, 5,013,751, 5,013,736, 5,006,542, 4,992,448, 4,992,447, 4,988,733, 4,988,728, 4,981,865, 4,962,119, 4,959,378, 4,954,519, 4,945,099, 4,942,236, 4,931,457, 4,927,835, 4,912,248, 4,910,192, 4,904,786, 4,904,685, 4,904,674, 4,904,671, 4,897,397, 4,895,953, 4,891,370, 4,870,210, 4,859,686, 4,857,644, 4,853,392, 4,851,412, 4,847,303, 4,847,290, 4,845,242, 4,835,166, 4,826,990, 4,803,216, 4,801,598, 4,791,129, 4,788,205, 4,778,818, 4,775,679, 4,772,703, 4,767,776, 4,764,525, 4,760,051, 4,748,153, 4,725,616, 4,721,712, 4,713,393, 4,708,966, 4,695,571, 4,686,235, 4,686,224, 4,680,298, 4,678,802, 4,652,564, 4,644,005, 4,632,923, 4,629,793, 4,614,741, 4,599,360, 4,596,828, 4,595,694, 4,595,686, 4,594,357, 4,585,755, 4,579,866, 4,578,390, 4,569,942, 4,567,201, 4,563,476, 4,559,348, 4,558,067, 4,556,672, 4,556,669, 4,539,326, 4,537,903, 4,536,503, 4,518,608, 4,514,415, 4,512,990, 4,501,755, 4,495,197, 4,493,839, 4,465,687, 4,440,779, 4,440,763, 4,435,420, 4,412,995, 4,400,534, 4,355,034, 4,335,141, 4,322,420, 4,275,064, 4,244,963, 4,235,908, 4,234,593, 4,226,887, 4,201,778, 4,181,720, 4,173,650, 4,173,634, 4,145,444, 4,128,664, 4,125,612, 4,124,726, 4,124,707, 4,117,135, 4,027,031, 4,024,284, 4,021,553, 4,021,550, 4,018,923, 4,012,527, 4,011,326, 3,998,970, 3,998,954, 3,993,763, 3,991,212, 3,984,405, 3,978,227, 3,978,219, 3,978,202, 3,975,543, 3,968,224, 3,959,368, 3,949,082, 3,949,081, 3,947,475, 3,936,450, 3,934,018, 3,930,005, 3,857,955, 3,856,962, 3,821,377, 3,821,401, 3,789,121, 3,789,123, 3,726,978, 3,694,471, 3,691,214, 3,678,169, 3,624,216;

immunosuppressive agents, as disclosed in U.S. Pat. Nos. 4,450,159, 4,450,159, 5,905,085, 5,883,119, 5,880,280, 5,877,184, 5,874,594, 5,843,452, 5,817,672, 5,817,661, 5,817,660, 5,801,193, 5,776,974, 5,763,478, 5,739,169, 5,723,466, 5,719,176, 5,696,156, 5,695,753, 5,693,648, 5,693,645, 5,691,346, 5,686,469, 5,686,424, 5,679,705, 5,679,640, 5,670,504, 5,665,774, 5,665,772, 5,648,376, 5,639,455, 5,633,277, 5,624,930, 5,622,970, 5,605,903, 5,604,229, 5,574,041, 5,565,560, 5,550,233, 5,545,734, 5,540,931, 5,532,248, 5,527,820, 5,516,797, 5,514,688, 5,512,687, 5,506,233, 5,506,228, 5,494,895, 5,484,788, 5,470,857, 5,464,615, 5,432,183, 5,431,896, 5,385,918, 5,349,061, 5,344,925, 5,330,993, 5,308,837, 5,290,783, 5,290,772, 5,284,877, 5,284,840, 5,273,979, 5,262,533, 5,260,300, 5,252,732, 5,250,678, 5,247,076, 5,244,896, 5,238,689, 5,219,884, 5,208,241, 5,208,228, 5,202,332, 5,192,773, 5,189,042, 5,169,851, 5,162,334, 5,151,413, 5,149,701, 5,147,877, 5,143,918, 5,138,051, 5,093,338, 5,091,389, 5,068,323, 5,068,247, 5,064,835, 5,061,728, 5,055,290, 4,981,792, 4,810,692, 4,410,696, 4,346,096, 4,342,769, 4,317,825, 4,256,766, 4,180,588, 4,000,275, 3,759,921;

immunomodulatory agents, as disclosed in U.S. Pat. Nos. 4,446,128, 4,524,147, 4,720,484, 4,722,899, 4,748,018, 4,877,619, 4,998,931, 5,049,387, 5,118,509, 5,152,980, 5,256,416, 5,468,729, 5,583,139, 5,604,234, 5,612,060, 5,612,350, 5,658,564, 5,672,605, 5,681,571, 5,708,002, 5,723,718, 5,736,143, 5,744,495, 5,753,687, 5,770,201, 5,869,057, 5,891,653, 5,939,455, 5,948,407, 6,006,752, 6,024,957, 6,030,624, 6,037,372, 6,037,373, 6,043,247, 6,060,049, 6,087,096, 6,096,315, 6,099,838, 6,103,235, 6,124,495, 6,153,203, 6,169,087, 6,255,278, 6,262,044, 6,290,950, 6,306,651, 6,322,796, 6,329,153, 6,344,476, 6,352,698, 6,365,163, 6,379,668, 6,391,303, 6,395,767, 6,403,555, 6,410,556, 6,412,492, 6,468,537, 6,489,330, 6,521,232, 6,525,035, 6,525,242, 6,558,663, 6,572,860;

analgesic agents, as disclosed in U.S. Pat. Nos. 5,292,736, 5,688,825, 5,554,789, 5,455,230, 5,292,736, 5,298,522, 5,216,165, 5,438,064, 5,204,365, 5,017,578, 4,906,655, 4,906,655, 4,994,450, 4,749,792, 4,980,365, 4,794,110, 4,670,541, 4,737,493, 4,622,326, 4,536,512, 4,719,231, 4,533,671, 4,552,866, 4,539,312, 4,569,942, 4,681,879, 4,511,724, 4,556,672, 4,721,712, 4,474,806, 4,595,686, 4,440,779, 4,434,175, 4,608,374, 4,395,402, 4,400,534, 4,374,139, 4,361,583, 4,252,816, 4,251,530, 5,874,459, 5,688,825, 5,554,789, 5,455,230, 5,438,064, 5,298,522, 5,216,165, 5,204,365, 5,030,639, 5,017,578, 5,008,264, 4,994,450, 4,980,365, 4,906,655, 4,847,290, 4,844,907, 4,794,110, 4,791,129, 4,774,256, 4,749,792, 4,737,493, 4,721,712, 4,719,231, 4,681,879, 4,670,541, 4,667,039, 4,658,037, 4,634,708, 4,623,648, 4,622,326, 4,608,374, 4,595,686, 4,594,188, 4,569,942, 4,556,672, 4,552,866, 4,539,312, 4,536,512, 4,533,671, 4,511,724, 4,440,779, 4,434,175, 4,400,534, 4,395,402, 4,391,827, 4,374,139, 4,361,583, 4,322,420, 4,306,097, 4,252,816, 4,251,530, 4,244,955, 4,232,018, 4,209,520, 4,164,514, 4,147,872, 4,133,819, 4,124,713, 4,117,012, 4,064,272, 4,022,836, 3,966,944;

cholinergic agents, as disclosed in U.S. Pat. Nos. 5,219,872, 5,219,873, 5,073,560, 5,073,560, 5,346,911, 5,424,301, 5,073,560, 5,219,872, 4,900,748, 4,786,648, 4,798,841, 4,782,071, 4,710,508, 5,482,938, 5,464,842, 5,378,723, 5,346,911, 5,318,978, 5,219,873, 5,219,872, 5,084,281, 5,073,560, 5,002,955, 4,988,710, 4,900,748, 4,798,841, 4,786,648, 4,782,071, 4,745,123, 4,710,508;

adrenergic agents, as disclosed in U.S. Pat. Nos. 5,091,528, 5,091,528, 4,835,157, 5,708,015, 5,594,027, 5,580,892, 5,576,332, 5,510,376, 5,482,961, 5,334,601, 5,202,347, 5,135,926, 5,116,867, 5,091,528, 5,017,618, 4,835,157, 4,829,086, 4,579,867, 4,568,679, 4,469,690, 4,395,559, 4,381,309, 4,363,808, 4,343,800, 4,329,289, 4,314,943, 4,311,708, 4,304,721, 4,296,117, 4,285,873, 4,281,189, 4,278,608, 4,247,710, 4,145,550, 4,145,425, 4,139,535, 4,082,843, 4,011,321, 4,001,421, 3,982,010, 3,940,407, 3,852,468, 3,832,470;

antihistamine agents, as disclosed in U.S. Pat. Nos. 5,874,479, 5,863,938, 5,856,364, 5,770,612, 5,702,688, 5,674,912, 5,663,208, 5,658,957, 5,652,274, 5,648,380, 5,646,190, 5,641,814, 5,633,285, 5,614,561, 5,602,183, 4,923,892, 4,782,058, 4,393,210, 4,180,583, 3,965,257, 3,946,022, 3,931,197;

steroidal agents, as disclosed in U.S. Pat. Nos. 5,863,538, 5,855,907, 5,855,866, 5,780,592, 5,776,427, 5,651,987, 5,346,887, 5,256,408, 5,252,319, 5,209,926, 4,996,335, 4,927,807, 4,910,192, 4,710,495, 4,049,805, 4,004,005, 3,670,079, 3,608,076, 5,892,028, 5,888,995, 5,883,087, 5,880,115, 5,869,475, 5,866,558, 5,861,390, 5,861,388, 5,854,235, 5,837,698, 5,834,452, 5,830,886, 5,792,758, 5,792,757, 5,763,361, 5,744,462, 5,741,787, 5,741,786, 5,733,899, 5,731,345, 5,723,638, 5,721,226, 5,712,264, 5,712,263, 5,710,144, 5,707,984, 5,705,494, 5,700,793, 5,698,720, 5,698,545, 5,696,106, 5,677,293, 5,674,861, 5,661,141, 5,656,621, 5,646,136, 5,637,691, 5,616,574, 5,614,514, 5,604,215, 5,604,213, 5,599,807, 5,585,482, 5,565,588, 5,563,259, 5,563,131, 5,561,124, 5,556,845, 5,547,949, 5,536,714, 5,527,806, 5,506,354, 5,506,221, 5,494,907, 5,491,136, 5,478,956, 5,426,179, 5,422,262, 5,391,776, 5,382,661, 5,380,841, 5,380,840, 5,380,839, 5,373,095, 5,371,078, 5,352,809, 5,344,827, 5,344,826, 5,338,837, 5,336,686, 5,292,906, 5,292,878, 5,281,587, 5,272,140, 5,244,886, 5,236,912, 5,232,915, 5,219,879, 5,218,109, 5,215,972, 5,212,166, 5,206,415, 5,194,602, 5,166,201, 5,166,055, 5,126,488, 5,116,829, 5,108,996, 5,099,037, 5,096,892, 5,093,502, 5,086,047, 5,084,450, 5,082,835, 5,081,114, 5,053,404, 5,041,433, 5,041,432, 5,034,548, 5,032,586, 5,026,882, 4,996,335, 4,975,537, 4,970,205, 4,954,446, 4,950,428, 4,946,834, 4,937,237, 4,921,846, 4,920,099, 4,910,226, 4,900,725, 4,892,867, 4,888,336, 4,885,280, 4,882,322, 4,882,319, 4,882,315, 4,874,855, 4,868,167, 4,865,767, 4,861,875, 4,861,765, 4,861,763, 4,847,014, 4,774,236, 4,753,932, 4,711,856, 4,710,495, 4,701,450, 4,701,449, 4,689,410, 4,680,290, 4,670,551, 4,664,850, 4,659,516, 4,647,410, 4,634,695, 4,634,693, 4,588,530, 4,567,000, 4,560,557, 4,558,041, 4,552,871, 4,552,868, 4,541,956, 4,519,946, 4,515,787, 4,512,986, 4,502,989, 4,495,102; the disclosures of all the above of which are herein incorporated by reference.

The drug moiety of the conjugate may be the whole drug or a binding fragment or portion thereof that retains its affinity and specificity for the target of interest while having a linkage site for covalent bonding to the vector protein ligand or linker. The conjugates of such drugs may be used for the same disorders, diseases, and indications as the drugs themselves.

iii. Preferred Cancer Chemotherapeutic Active Agents

Preferred cancer chemotherapeutic agents for use in the cyclic RAP peptide conjugates of the invention include all drugs which may be useful for treating brain tumors or other neoplasia in or around the brain, either in the free form, or, if not so useful for such tumors in the free form, useful when linked to the cyclic RAP peptide. Such chemotherapeutic agents are preferably cytotoxic chemotherapeutic agents including but not limited to adriamycin (also known as doxorubicin), cisplatin, paclitaxel, analogs thereof, and other chemotherapeutic agents demonstrate activity against tumours ex vivo and in vivo. Such chemotherapeutic agents also include oalkylating agents, antimetabolites, natural products (such as vinca alkaloids, epidophyllotoxins, antibiotics, enzymes and biological response modifiers), topoisomerase inhibitors, microtubule inhibitors, spindle poisons, hormones and antagonists, and miscellaneous agents such as platinum coordination complexes, anthracendiones, substituted ureas, etc. Those of skill in the art will know of other chemotherapeutic agents.

Cytotoxic radioisotopes useful in treating cancers or neoplasias, including, but not limited to, $^{131}$I (Iodine), $^{125}$I, $^{111}$In (indium), $^{90}$Y (Yttrium), $^{67}$Cu (Copper), $^{127}$Lu (Lutetium), $^{212}$Bi (Bismuth), $^{213}$B, $^{255}$Fm (Fermium), $^{149}$Tb (Terbium), $^{223}$Rd (Radium), $^{213}$Pb (lead), $^{212}$Pb, $^{211}$At (Astatine), $^{89}$Sr (Strontium), $^{153}$Sm (Samarium), $^{166}$Ho (Holmium), $^{225}$Ac (Actinium), $^{186}$Re (Rhenium), $^{67}$Ga (Gallium), $^{68}$Ga and $^{99m}$Tc (Technetium), may be conjugated to a RAP cyclic peptide of the invention. The radioisotopes may be linked to the polypeptide using metal chelating agents common in the art for such purposes, including, but not limited to 1,4,7,10-tetraazacyclo-11 dodecane-N,N',N'',N'''-tetraacetic acid (DOTA), 1,4,8,11-tetraazacyclotetradecane N,N',N'',N'''-tetraacetic acid (TETA), diethylene triamine penta-acetate (DTPA), dimercaptosuccinic acid (DMSA), tetraazacyclotridecane-N,N',N'',N'''-tetraacetic acid (TRITA), and 1,5,9,13-tetraazacyclohexadecane-N,N',N'',N'''-tetraacetic acid (HETA), hydroxyethylidene diphosphonate (HEDP), HEXA, and ethylenediaminetetraacetic acid (EDTA), which allow "loading" of the radioisotope onto the polypeptide.

Preferred chemotherapeutic agents are those, which in the free form, demonstrate unacceptable systemic toxicity at desired doses. The general systemic toxicity associated with therapeutic levels of such agents is reduced by their linkage to a cyclic RAP peptide. Particularly preferred are cardiotoxic compounds that are useful therapeutics but are dose limited by cardiotoxicity. A classic example is adriamycin (also known as doxorubicin) and its analogs, such as daunorubicin. Linking a cyclic RAP peptide to such drugs decreases accumulation and associated cardiotoxicity at the heart.

iv. Glycoconjugates

Glycoconjugates are any molecule which includes a carbohydrate portion. Examples include, but are not limited to, glycoproteins, oligosaccharides, glycolipids and proteoglycans. Such molecules have beneficial functions such as enhancement of bioavailability of therapeutic agents or ability to block pathogenic mechanisms. For example, alpha-L-iduronidase is a glycoconjugate (glycoprotein) that is efficiently distributed throughout the body because of the oligomannose 7-bisphosphate determinant attached to the enzyme. Heparin sulfate is a carbohydrate portion of a proteoglycan that is useful for blocking coagulation pathways in humans. Attachment of suitable cyclic RAP peptide to glycoconjugates with therapeutic activities may provide a means of increasing the potency of the glycoconjugate by affecting biodistribution. Alternatively, cyclic RAP peptide glycoconjugate fusions may be engineered to act as bis-specific receptor-binding molecules with the ability to directly affect the functions of one or more receptors in specific tissues.

v. Nanoparticles

Nanoparticles are macromolecular assemblies constructed from biodegradable and non-biodegradable polymers or from other materials such as lipids. Such assemblies may be engineered to contain therapeutic molecules in cavities within the particle. Through this means, nanoparticles provide a means of altering the biodistribution, pharmacokinetics, immunogenicity and potency of drugs. Attachment of suitable cyclic RAP peptide would, in turn, provide a means of increasing the specificity of tissue distribution of these molecules.

E. Methods of Producing Cyclic RAP Peptides

RAP peptides are preferably cyclized through formation of a covalent bond, which can be formed using any methods described in the art. In some embodiments, the covalent bond is formed between an amino acid at the N-terminus and an amino acid at the C-terminus of the peptide. In some embodiments, the covalent bond is formed between the side chains of the two terminal amino acids. In other embodiments, the covalent bond is formed between the side chain of one terminal amino acid and the terminal group of the other terminal amino acid, or between the terminal groups of each terminal amino acid. For example, head-to-tail, side-chain-to-side-chain, side-chain-to-head, side-chain-to-tail, are all possible.

RAP peptides that naturally cyclize can be easily engineered by inserting two cysteines in a desired location and permitting the cysteines to naturally form a disulfide bond. A glycine or proline can be inserted internal to the cysteines (e.g. C-terminal to the N-terminal-most cysteine and N-terminal to the C-terminal-most cysteine) to minimize any structural distortion by the covalent bond of the native three-dimensional structure of the RAP peptide.

Head-to-tail cyclization coupling of the terminal amine to the terminal carboxyl group can be carried out using a number of methods, e.g., using p-nitrophenyl esters, the azide method, 2,4,5-trichlorophenyl and pentafluorophenyl esters, the mixed anhydride method, a carbodimide with catalysts such as HOBt or HONSu or HoAt or HATU, DIC, DCC, or on-resin cyclization.

In addition, the cyclic structure can be formed with a bridging group, the side chain of an amino acid residue of the peptide, or a terminal amino acid residue of the peptide. A bridging group is a chemical moiety that allows cyclization of two portions of the peptide. Nonlimiting examples of bridging groups include amides, thioethers, thioesters, disulfides, ureas, carbamates, sulfonamides, and the like. A variety of methods are known in the art for incorporation of units having such bridging groups. For example, lactam bridges (i.e., cyclic amides) can be formed via side chains of amino acids having amines and carboxylic acids, e.g., of lysine or ornithine and glutamic acid or aspartic acid. A thioester can be formed between the C-terminus and the side chain of a Cys residue. Alternatively, a thioester can be formed between via side chains of amino acids having a thiol and a carboxylic acid.

Alternatively, a cross link can be formed by incorporating a lanthionine (thio-dialanine) residue to link alanine residues that are covalently bonded together by a thioether bond. In another method, a cross-linking agent, such as a dicarboxylic acid, e.g. suberic acid (octanedioic acid), etc. can introduce a link between two functional groups of an amino acid side chain, such as a free amino, hydroxyl, thiol group, and combinations thereof.

Enzyme catalyzed cyclization can also be used. For example, it has been reported that the thioesterase domain of tyrocidine synthetase can be used to cyclize a thioester precursor, a subtilisin mutant to cyclize peptide glycolate phenylalanylamide esters, and antibody ligase 16G3 to catalyze cyclization of a p-nitrophenylester. For a review of peptide cyclization, see Davies, J. Peptide Sci., 9:471-501 (2003), incorporated herein by reference in its entirety.

F. Production of RAP Peptides i. Synthesis

The peptides of the present invention can be synthesized by solution phase solid phase, or liquid phase peptide synthesis techniques in accordance with conventional techniques. Various automatic synthesizers are commercially available and can be used in accordance with known protocols. See, for example, Stewart and Young, Solid Phase Peptide Synthesis, 2d. ed., Pierce Chemical Co., (1984); Tam et al., J. Am. Chem. Soc. 105:6442, 1983; Merrifield, Science 232:341-347, 1986; and Barany and Merrifield, The Peptides, Gross and Meienhofer, eds, Academic Press, New York, 1 284; Barany et al., Int. J. Peptide Protein Res. 30:705-739, 1987; Bodanszky, The Principles of Peptide Synthesis, 2nd ed., Springer, New York (1993); and Molina et al., Pept. Res. 9:151-5, 1996, U.S. Pat. No. 5,424,398, and Fischer et al., Journal of Peptide Science 8: 529-542, 2002, each incorporated herein by reference.

For example, solution phase techniques such as an azide process, an acid chloride process, an acid anhydride process, a mixed anhydride process, an active ester process (for example, p-nitrophenyl ester, N-hydroxy-succinimide ester, or cyanomethyl ester), a carbodiimidazole process, an oxidative-reductive process, or a dicyclohexylcarbodiimide (DCCD)/additive process can be used.

Solid phase peptide synthesis methods use a copoly(styrene-divinylbenzene) containing 0.1-1.0 mMol amines/g polymer. These methods for peptide synthesis use butyloxy-carbonyl (t-BOC) or 9-fluorenylmethyloxy-carbonyl (FMOC) protection of alpha-amino groups. Both methods involve stepwise syntheses whereby a single amino acid is added at each step starting from the C-terminus of the peptide (See, Coligan, et al., Current Protocols in Immunology, Wiley Interscience, 1991, Unit 9). On completion of chemical synthesis, the peptides can be deprotected to remove the t-BOC or FMOC amino acid blocking groups and cleaved from the polymer by treatment with acid at reduced temperature (e.g., liquid HF-10% anisole for about 0.25 to about 1 hours at 0° C.). After evaporation of the reagents, the peptides are extracted from the polymer with 1% acetic acid solution which is then lyophilized to yield the crude material. The crude material can normally be purified by such techniques as gel filtration on Sephadex G-15 using 5% acetic acid as a solvent. Lyophilization of appropriate fractions of the column will yield the homogeneous peptide or peptide derivative, which can then be characterized by such standard techniques as amino acid analysis, thin layer chromatography, high performance liquid chromatography, ultraviolet absorption spectroscopy, molar rotation, solubility, and quantitated by the solid phase Edman degradation.

Liquid phase techniques include synthetic assembly of polypeptide chains reversibly linked to polyethylene glycol which is a hybrid between traditional solution and solid-phase chemistries. The process may be carried out using the N-fluorenylmethoxycarbonyl techniques commonly used in solid-phase peptide synthesis and fluoride ions used in place of conventional organic base piperidine for the repetitive amino-deprotection step. See Fischer et al., Journal of Peptide Science 8: 529-542, 2002.

ii. Host Cells

Host cells used to produce chimeric proteins are bacterial, yeast, insect, non-mammalian vertebrate, or mammalian cells; the mammalian cells include, but are not limited to, hamster, monkey, chimpanzee, dog, cat, bovine, porcine, mouse, rat, rabbit, sheep and human cells. The host cells can be immortalized cells (a cell line) or non-immortalized (primary or secondary) cells and can be any of a wide variety of cell types, such as, but not limited to, fibroblasts, keratinocytes, epithelial cells (e.g., mammary epithelial cells, intestinal epithelial cells), ovary cells (e.g., Chinese hamster ovary or CHO cells), endothelial cells, glial cells, neural cells, formed elements of the blood (e.g., lymphocytes, bone marrow cells), muscle cells, hepatocytes and precursors of these somatic cell types. Host cells can include mutants of CHO cells that do not express LRP such as CHO13-5-1 (FitzGerald et al., J. Biol. Chem., 129 (6):1533-41, 1995).

Cells that contain and express DNA or RNA encoding the chimeric protein are referred to herein as genetically modified cells. Mammalian cells that contain and express DNA or RNA encoding the chimeric protein are referred to as genetically modified mammalian cells. Introduction of the DNA or RNA into cells is by a known transfection method, such as electroporation, microinjection, microprojectile bombardment, calcium phosphate precipitation, modified calcium phosphate precipitation, cationic lipid treatment, photoporation, fusion methodologies, receptor mediated transfer, or polybrene precipitation. Alternatively, the DNA or RNA can be introduced by infection with a viral vector. Methods of producing cells, including mammalian cells, which express DNA or RNA encoding a chimeric protein are described in U.S. Pat. Nos. 6,048,729, 5,994,129, and 6,063,630. The teachings of each of these applications are expressly incorporated herein by reference in their entirety.

iii. Nucleic Acid Constructs

A nucleic acid construct used to express the chimeric protein can be one which is expressed extrachromosomally (episomally) in the transfected mammalian cell or one which integrates, either randomly or at a pre-selected targeted site through homologous recombination, into the recipient cell's genome. A construct which is expressed extrachromosomally comprises, in addition to chimeric protein-encoding sequences, sequences sufficient for expression of the protein in the cells and, optionally, for replication of the construct. It typically includes a promoter, chimeric protein-encoding DNA and a polyadenylation site. The DNA encoding the chimeric protein is positioned in the construct in such a manner that its expression is under the control of the promoter. Optionally, the construct may contain additional components such as one or more of the following: a splice site, an enhancer sequence, a selectable marker gene under the control of an appropriate promoter, and an amplifiable marker gene under the control of an appropriate promoter.

In those embodiments in which the DNA construct integrates into the cell's genome, it need include only the chimeric protein-encoding nucleic acid sequences. Optionally, it can include a promoter and an enhancer sequence, a polyadenylation site or sites, a splice site or sites, nucleic acid sequences which encode a selectable marker or markers, nucleic acid sequences which encode an amplifiable marker and/or DNA homologous to genomic DNA in the recipient cell to target integration of the DNA to a selected site in the genome (targeting DNA or DNA sequences).

iv. Cell Culture Methods

Mammalian cells containing the chimeric protein-encoding DNA or RNA are cultured under conditions appropriate for growth of the cells and expression of the DNA or RNA. Those cells which express the chimeric protein can be identified, using known methods and methods described herein, and the chimeric protein isolated and purified, using known methods and methods also described herein; either with or without amplification of chimeric protein production. Identification can be carried out, for example, through screening genetically modified mammalian cells displaying a phenotype indicative of the presence of DNA or RNA encoding the chimeric protein, such as PCR screening, screening by Southern blot analysis, or screening for the expression of the chimeric protein. Selection of cells having incorporated chimeric protein-encoding DNA may be accomplished by including a selectable marker in the DNA construct and culturing transfected or infected cells containing a selectable marker gene under conditions appropriate for survival of only those cells that express the selectable marker gene. Further amplification of the introduced DNA construct can be affected by culturing genetically modified mammalian cells under conditions appropriate for amplification (e.g., culturing genetically modified mammalian cells containing an amplifiable marker gene in the presence of a concentration of a drug at which only cells containing multiple copies of the amplifiable marker gene can survive).

Genetically modified mammalian cells expressing the chimeric protein can be identified, as described herein, by detection of the expression product. For example, mammalian cells expressing chimeric protein in which the carrier is a cyclic RAP peptide can be identified by a sandwich enzyme immunoassay. The antibodies can be directed toward the RAP portion or the active agent portion of the conjugate.

v. Purification of RAP Peptides

RAP peptides can be purified via reversed phase high performance liquid chromatography (RP-HPLC) using methods well known in the art. See, for example, "The Handbook of Analysis and Purification of Peptides and Proteins by Reversed-Phase HPLC", $3^{rd}$ ed., Grace Vydac, W.R. Grace & Co., Columbia, Md. (2002). Gradients of acetonitrile and water with trifluoroacetic acid are frequently used as eluent. Preparative RP-HPLC is routinely used to purify synthetic peptides in milligram and gram quantities, and to purify mg to kg quantities of recombinantly produced polypeptides for therapeutic use.

RAP peptides may also be produced and purified as described in WO 2006/138343 (Zankel et al.), hereby incorporated by reference in its entirety.

RAP peptides can also be purified by affinity chromatography on agarose beads coupled to appropriate CR pairs. This technique can be used alone or as a further step following RP-HPLC purification. Fragments of CR-containing protein comprising CR pairs or triplets are prepared as follows. DNA fragments encoding each CR pair or triplet are PCR amplified from human cDNA (BD Biosciences Marathon-Ready®) using HotStart PfuTurbo® polymerase and reagents (Stratagene). Each amplified fragment is sequentially digested with BamHI and HindIII and then ligated into similarly digested pET30(+)a (EMD Biosciences). The resulting plasmids encode protein fragments consisting of N-terminal hexahistidine and S-peptides fused to the CR fragment. All expression constructs are sequenced to verify insert integrity. Each plasmid is then used to transform BL21(DE3) CodonPlus-RIPL® cells (Stratagene). The CR fragment is expressed and refolded as previously described, and purified by Ni-NTA chromatography according to manufacturer protocols (Qiagen). Activated agarose beads (AffiGel 15, Bio-Rad) are transferred to a 10 mL fritted, plastic column (Pierce). Beads are washed twice with three volumes of 10 mM HEPES, 100 mM NaCl supplemented with 5 mM CaCl2 buffer. CR fragment (2.5 mg/mL packed beads in five column-volumes of same buffer) is then added and the mixture incubated overnight with mixing at room temperature. Beads are then washed with buffer until no further protein was present in the eluate as measured by Bradford assay. Beads are stored in 20% ethanol until use. RAP peptides in TBS are added to equilibrated CR-linked beads (1 mg/mL packed beads) and incubated with mixing at room temperature for 2 hours. Beads are washed with the same buffer and bound peptides are eluted in TBS supplemented with 100 mM EDTA.

G. Characterization of RAP Conjugates i. Labels

In some embodiments, the cyclic RAP peptide or conjugate thereof is labeled to facilitate its detection. A "label" or a "detectable moiety" is a composition detectable by spectroscopic, photochemical, biochemical, immunochemical, chemical, or other physical means. For example, labels suitable for use in the present invention include, for example, radioactive labels (e.g., 32P), fluorophores (e.g., fluorescein), electron dense reagents, enzymes (e.g., as commonly used in an ELISA), biotin, digoxigenin, or haptens and proteins which can be made detectable, e.g., by incorporating a radiolabel into the hapten or peptide, or used to detect antibodies specifically reactive with the hapten or peptide.

As noted above, depending on the screening assay employed, the active agent, the linker or the cyclic RAP peptide portion of a conjugate may be labeled. The particular label or detectable group used is not a critical aspect of the invention, as long as it does not significantly interfere with the biological activity of the conjugate. The detectable group can be any material having a detectable physical or chemical property. Thus, a label is any composition detectable by spectroscopic, photochemical, biochemical, immunochemical, electrical, optical or chemical means.

Examples of labels suitable for use in the present invention include, but are not limited to, fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and colorimetric labels such as colloidal gold or colored glass or plastic beads (e.g., polystyrene, polypropylene, latex, etc.).

The label may be coupled directly or indirectly to the desired component of the assay according to methods well known in the art. Preferably, the label in one embodiment is covalently bound to the biopolymer using an isocyanate reagent for conjugating an active agent according to the invention. In one aspect of the invention, the bifunctional isocyanate reagents of the invention can be used to conjugate a label to a biopolymer to form a label biopolymer conjugate without an active agent attached thereto. The label biopolymer conjugate may be used as an intermediate for the synthesis of a labeled conjugate according to the invention or may be used to detect the biopolymer conjugate. As indicated above, a wide variety of labels can be used, with the choice of label depending on sensitivity required, ease of conjugation with the desired component of the assay, stability requirements, available instrumentation, and disposal provisions. Non-radioactive labels are often attached by indirect means. Generally, a ligand molecule (e.g., biotin) is covalently bound to the molecule. The ligand binds to another molecules (e.g., streptavidin) molecule, which is either inherently detectable or covalently bound to a signal system, such as a detectable enzyme, a fluorescent compound, or a chemiluminescent compound.

The conjugates can also be conjugated directly to signal generating compounds, e.g., by conjugation with an enzyme or fluorophore. Enzymes suitable for use as labels include, but are not limited to, hydrolases, particularly phosphatases, esterases and glycosidases, or oxidotases, particularly peroxidases. Fluorescent compounds, i.e., fluorophores, suitable for use as labels include, but are not limited to, fluorescein and its derivatives, rhodamine and its derivatives, dansyl, umbelliferone, etc. Further examples of suitable fluorophores include, but are not limited to, eosin, TRITC-amine, quinine, fluorescein W, acridine yellow, lissamine rhodamine, B sulfonyl chloride erythroscein, ruthenium (tris, bipyridinium), Texas Red, nicotinamide adenine dinucleotide, flavin adenine dinucleotide, etc. Chemiluminescent compounds suitable for use as labels include, but are not limited to, luciferin and 2,3-dihydrophthalazinediones, e.g., luminol. For a review of various labeling or signal producing systems that can be used in the methods of the present invention, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by the use of electronic detectors such as charge coupled devices (CCDs) or photomultipliers and the like. Similarly, enzymatic labels may be detected by providing the appropriate substrates for the enzyme and detecting the resulting reaction product. Colorimetric or chemiluminescent labels may be detected simply by observing the color associated with the label. Other labeling and detection systems suitable for use in the methods of the present invention will be readily apparent to those of skill in the art. Such labeled modulators and ligands may be used in the diagnosis of a disease or health condition.

ii. Screening Assays for Conjugates and Modulators of their Delivery

The present invention provides a screening assay for cyclic RAP peptide conjugates, wherein the conjugates are tested for their ability to influence a measurable activity of a specific receptor which can be situated in a whole cell, a cell extract, semi-purified, purified or any other format that allows for measurement of its activity. The activity can be any activity in the expression, function or degradation of CR-containing protein including, for example, the amount or timing of such activities. Such activities include, for example, transcription, transcript processing, translation or transcript stability of the receptor gene sequence or mRNA transcript. Such activities include, for example, the synthesis of new receptor, the subcellular localization of the receptor and activation of receptor biological activity. Such activities include, for example, the ability of the receptor to bind substances, adopt conformations, catalyze reactions, bind known ligands and the like. Such activities include, for example, the amount or stability of the receptor, the processing and removal or degradation of the receptor and the like. In preferred embodiments, the cyclic RAP peptide used is one which has been modified or naturally has a higher binding affinity for the targeted receptor than for any other receptor.

The invention contemplates a variety of different screening formats. Some designs are considered low throughput and test only one or a few compounds in series or in parallel. High throughput screening assays are suitable for screening tens of thousands or hundreds of thousands of compounds in a matter of weeks or months. "In silico" screening formats employ computer-aided rational design techniques to identify potential modulators of biological activity.

H. Pharmaceutical Compositions, and their Administration

The conjugates and modulators may be administered by a variety of routes. For oral preparations, the conjugates can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The conjugates and modulators can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The conjugates, modulators, and LDLR ligands can be utilized in aerosol formulation to be administered via inhalation. The compounds of the present invention can be formulated into pressurized acceptable propellants such as dichlorodifluoromethane, propane, nitrogen and the like.

Furthermore, the conjugates and modulators can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms of the conjugate, modulator, and LDLR ligand for oral or rectal administration such as syrups, elixirs, and suspensions may be provided wherein each dosage unit, for example, teaspoonful, tablespoonful, tablet or suppository, contains a predetermined amount of the composition containing active agent. Similarly, unit dosage forms for injection or intravenous administration may comprise the conjugate in a composition as a solution in sterile water, normal saline or another pharmaceutically acceptable carrier.

In practical use, the conjugate, modulator, and LDLR ligand according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

With respect to transdermal routes of administration, methods for transdermal administration of drugs are disclosed in Remington's Pharmaceutical Sciences, 17th Edition, (Gennaro et al. Eds. Mack Publishing Co., 1985). Dermal or skin patches are a preferred means for transdermal delivery of the conjugates, modulators, and LRP ligands of the invention. Patches preferably provide an absorption enhancer such as DMSO to increase the absorption of the compounds. Other methods for transdermal drug delivery are disclosed in U.S. Pat. Nos. 5,962,012, 6,261,595, and 6,261,595. Each of which is incorporated by reference in its entirety.

In specific embodiments, it is contemplated that the therapeutic administering of the conjugates described herein will be administered intrathecally into the CSF. The intrathecal administration of the present invention may comprise introducing the pharmaceutical composition into a cerebral ventricle. Alternatively, the intrathecal administration may comprise introducing the pharmaceutical composition into the lumbar area. In yet another alternative, the intrathecal administration comprises introducing the pharmaceutical composition into the cisterna magna. Any such administration is preferably via a bolus injection. Depending on the severity of the symptoms and the responsiveness of the subject to the therapy, such a bolus injection may be administered once per week, once per month, once every 6 months or annually. In other embodiments, the intrathecal administration is achieved by use of an infusion pump. The pharmaceutical could of course be intrathecally administered continually over a period of at least several days or alternatively, the intrathecal administration is continually over a period of at least four weeks. Of course, where the administration is via a continuous infusion, the rate of dose administration of the enzyme replacement therapy may be greatly reduced as compared to the bolus injection administration. In preferred embodiments, the active agent of the conjugate is iduronidase and it is delivered in an amount that comprises about 1 mg iduronidase/20 kg of body weight of the mammal being treated for MPS. In particular embodiments, the above dose is delivered to 15 cc CSF. At such a concentration it is contemplated that the enzyme concentration will be 18,000 units per ml of CSF. It should be understood that the aforementioned dosage is merely an exemplary dosage and those of skill in the art will understand that this dosage may be varied.

The methods and compositions of the invention may be combined with methods and compositions of inducing antigen specific tolerance prior to the enzyme replacement therapy. Such methods include inducing antigen specific tolerance comprises administration of an immunosuppressive agent, such as e.g., cyclosporine A and may further comprise administration of an antiproliferative agent, including but not limited to a nucleotide analog or an anti-metabolite. The antiproliferative agent may be azathioprine. Further methods are described in e.g., U.S. patent application Ser. No. 10/141,668, published as U.S. Publication No. 20030211113; and U.S. patent application Ser. No. 10/429,314 published as U.S. Publication No. 20040009906, each incorporated herein by reference.

Pharmaceutically acceptable excipients, such as vehicles, adjuvants, carriers or diluents, are commercially available. Moreover, pharmaceutically acceptable auxiliary substances, such as pH adjusting and buffering agents, tonicity adjusting agents, stabilizers, wetting agents and the like, are commercially available.

Those of skill will readily appreciate that dose levels can vary as a function of the specific compound, the severity of the symptoms and the susceptibility of the subject to side effects. Preferred dosages for a given compound are readily determinable by those of skill in the art by a variety of means, including, but not limited to dose response and pharmacokinetic assessments conducted in patients, test animals, and in vitro.

In each of these aspects, the compositions include, but are not limited to, compositions suitable for oral, rectal, topical, parenteral (including subcutaneous, intramuscular, and intravenous), pulmonary (nasal or buccal inhalation), or nasal administration, although the most suitable route in any given case will depend in part on the nature and severity of the conditions being treated and on the nature of the active ingredient. Exemplary routes of administration are the oral and intravenous routes. The compositions may be conveniently presented in unit dosage form and prepared by any of the methods well-known in the art of pharmacy.

In practical use, the modulators or according to the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. The percentage of an active compound in these compositions may, of course, be varied and may conveniently be between about 2 percent to about 60 percent of the weight of the unit.

The conjugates, modulators, and ligands of the invention are useful for therapeutic, prophylactic and diagnostic intervention in animals, and in particular in humans. As described herein, the conjugates show preferential accumulation and/or release of the active agent in any target organ, compartment, or site depending upon the biopolymer used.

Compositions of the present invention may be administered encapsulated in or attached to viral envelopes or vesicles, or incorporated into cells. Vesicles are micellular particles which are usually spherical and which are frequently lipidic. Liposomes are vesicles formed from a bilayer membrane. Suitable vesicles include, but are not limited to, unilamellar vesicles and multilamellar lipid vesicles or liposomes. Such vesicles and liposomes may be made from a wide range of lipid or phospholipid compounds, such as phosphatidylcholine, phosphatidic acid, phosphatidylserine, phosphatidylethanolamine, sphingomyelin, glycolipids, gangliosides, etc. using standard techniques, such as those described in, e.g., U.S. Pat. No. 4,394,448. Such vesicles or liposomes may be used to administer compounds intracellularly and to deliver compounds to the target organs. Controlled release of a p97-composition of interest may also be achieved using encapsulation (see, e.g., U.S. Pat. No. 5,186,941).

Any route of administration that delivers the cyclic RAP peptide active agent conjugate or modulator composition into the blood stream, or preferably at least outside of the blood-brain barrier, may be used. Preferably, the composition is administered peripherally, most preferably intravenously or by cardiac catheter. Intrajugular and intracarotid injections are also useful. Compositions may be administered locally or regionally, such as intraperitoneally or subcutaneously on intramuscularly. In one aspect, compositions are administered with a suitable pharmaceutical diluent or carrier.

Dosages to be administered will depend on individual needs, on the desired effect, the active agent used, the biopolymer and on the chosen route of administration. Preferred dosages of a conjugate range from about 0.2 pmol/kg to about 25 nmol/kg, and particularly preferred dosages range from 2-250 pmol/kg; alternatively, preferred doses of the conjugate may be in the range of 0.02 to 2000 mg/kg. These dosages will be influenced by the number of active agent or drug moieties associated with the biopolymer. Alternatively, dosages may be calculated based on the active agent administered.

In preferred embodiments the conjugate comprises a cyclic RAP peptide. For instance, doses of cyclic RAP peptide-adriamycin comprising from 0.005 to 100 mg/kg of adriamycin are also useful in vivo. Particularly preferred is a dosage of cyclic RAP peptide-adriamycin comprising from 0.05 mg/kg to 20 mg/kg of adriamycin. Those skilled in the art can determine suitable doses for compounds linked to a cyclic RAP peptide based in part on the recommended dosage used for the free form of the compound. Conjugation of the active agent to a cyclic RAP peptide generally reduces the amount of drug needed to obtain the same effect.

The conjugates and modulators of the invention are useful for therapeutic, prophylactic and diagnostic intervention in animals, and in particular in humans. Cyclic RAP peptide compounds may show preferential accumulation in particular tissues. Preferred medical indications for diagnostic uses include, for example, any condition associated with a target organ of interest (e.g., lung, liver, kidney, spleen). In particularly preferred embodiments, the target organ of interest in the brain.

The subject methods find use in the treatment of a variety of different disease conditions. In certain embodiments, of particular interest is the use of the subject methods in disease conditions where an active agent or drug having desired activity has been previously identified, but in which the active agent or drug is not adequately delivered to the target site, area or compartment to produce a fully satisfactory therapeutic result. With such active agents or drugs, the subject methods of conjugating the active agent to a cyclic RAP peptide can be used to enhance the therapeutic efficacy and therapeutic index of active agent or drug.

A variety of hosts or subjects are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

EXAMPLES

The following example(s) is included to demonstrate preferred embodiments of the invention. It should be appreciated by those of skill in the art that the techniques disclosed in the example(s) that follows represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention. The following examples provide exemplary protocols for generating, isolating and characterizing the interaction of cyclic RAP peptides with their preferred receptors.

Example 1

Generation and Analysis of RAP Variants

Materials and Methods
Materials

The M13 phage display vector was from Maxim Biotechnology. Expression vector pET30(+)a and S-tag purification reagents were from EMD Biosciences. Anti-RAP antibodies were produced at BioMarin Pharmaceutical, Inc. Restriction enzymes and T4 DNA ligase were from New England Biolabs. An ABI 3100 Avant automated DNA sequencer was used for sequence data generation and analysis. Hexahistidine tag purification reagents were from Qiagen. The anti-RAP polyclonal antibody was described previously (49).

Expression, Refolding and Purification of CR Proteins

Others have elegantly demonstrated that CR proteins can be expressed, purified and refolded to their native form in vitro (45, 50-54). For the work described here, the following CR sequences were selected for this process: A CR triplet from LRP6 (CR1-3), the two CR pairs from LRP6 within the triplet (CR1 and 2, termed CR12, CR2 and 3, termed CR23), a CR triplet from human VLDLR (CR6-8), a CR pair from VLDLR (CR78), a CR triplet from LRP2 (CR34-36), two CR pairs from LRP2 (CR89, CR3435), three CR pairs from matriptase/ST14/TADG-15 (CR12, CR23 and CR34), a CR triplet from LRP1 (CR3-5) and the CR pair from FDC-8D6 antigen. DNA fragments encoding each were PCR amplified from human cDNA (BD Biosciences Marathon-ready™ or from a previously-cloned LRP6 cDNA (9) using HotStart PfuTurbo™ (Stratagene) and the primers:

LRP6CR1F:
(SEQ ID NO: 3)
5'-GCGATAGGATCCCCAACATGTTCTCCTCAGCAGTTTACTTGTTTCAC
GGGGGAAATTGACTGTATC-3';

LRP6CR2R:
(SEQ ID NO: 4)
5'-GCGATAAAGCTTTTATCAAAGCACTTCACAGTTCTTCTCATCTGATT
TGTCCTGGCAGTTTGCATCTCCA-3';

LRP6CR2F:
(SEQ ID NO: 5)
5'-GCGATAGGATCCCCTGTATGCTCAGAGTCCCAGTTCCAGTGTGCCAG
TGGGCAGTGTATTGATGG-3';

LPR6CR3R:
(SEQ ID NO: 6)
5'-GCGATAAAGCTTTCACTAAGTCGGATAACAATCCAGTTCATCTGACT
TGTCACTGCAATCCAC-3';

VLDLRCR6F:
(SEQ ID NO: 7)
5'-GCGATAGGATCCCACACCAAGTGTCCAGCCAGCGAAATCCAGTGCGG
CTCTGGCGAGTGC-3';

VLDLRCR7F:
(SEQ ID NO: 8)
5'-GCGATAGGATCCACTTGCCGACCTGACCAATTTGAATGTGAGGATGG
CAGC-3';

VLDLRCR8R:
(SEQ ID NO: 9)
5'-GCGATAAAGCTTTTATCATTCGTTTATATGACACTCTTTCAGGGGCT
CATCACTCCAGTCCCTG-3';

LRP2CR8F:
(SEQ ID NO: 10)
5'-GCGATAGGATCCCCCACGGAGCAGTGTGGCTTATTTTCCTTCCCCTG
TAAAAATGGC-3';

LRP2CR9R:
(SEQ ID NO: 11)
5'-GCGATAAAGCTTTTATCATGCGTGGGTGGGGCAGTTGTGCTCATCAC
TGCCATCCACACAGTCGTTGCGTTTG-3';

LRP2CR34F:
(SEQ ID NO: 12)
5'-GCGATAGGATCCGATGGTGCATACTGCCAGGCTACTATGTTCGAATG
CAAAAACCATGTTTGTATCCCGC-3';

LRP2CR35F:
(SEQ ID NO: 13)
5'-GCGATAGGATCCGATGTTCCCTGTAATTCACCAAACCGTTTCCGGTG
TGACAACAATCGCTGC-3';

LRP2CR36R:
(SEQ ID NO: 14)
5'-GCGATAAAGCTTTTATCATATATTTTCAGCACATGTTCTTTCTTTTC
CTTTATTGCAACCCAGTTCATCG-3';

ST14F1:
(SEQ ID NO: 15)
5'-GCGATAGGATCCCCATGCCCGGGGCAGTTCACGTGCCGCACGGGGCG
GTGTATC-3';

ST14F2:
(SEQ ID NO: 16)
5'-GCGATAGGATCCTGCGACGCCGGCCACCAGTTCACGTGCAAGAACAA
GTTCTGC-3';

ST14F3:
(SEQ ID NO: 17)
5'-GCGATAGGATCCAGTTGTCCGGCCCAGACCTTCAGGTGTTCCAATGG
GAAGTG-3';

ST14R1:
(SEQ ID NO: 18)
5'-GCGATAAAGCTTTTATCAACCCCTGCTCGTCGCTGTTGTCTCCGCAG
TCGTTCACACTG-3';

ST14R2:
(SEQ ID NO: 19)
5'-GCGATAAAGCTTTTATCAACTGCACCCCTGCTCGTCGCTGTTG-3';

ST14R3:
(SEQ ID NO: 20)
5'-GCGATAAAGCTTTTATCAGTCGCAGTCCTTCTCATCTGAGCCGTCGC
TACAGTCCTCCTTCCCG-3';

LRP1CR3F:
(SEQ ID NO: 21)
5'-GCGATAGGATCCCCCCAGTGCCAGCCAGGCGAGTTTGCC-3';

LRP1CR5R:
(SEQ ID NO: 22)
5'-GCGATAAGCTTTCAATAGGCACACGAAGCAGACTCATCAGAGCGG-3'

```
8D6AF:
                                             (SEQ ID NO: 23)
5'-GCGATAGGATCCTCGTGCCCACCCACCAAGTTCCAGTGCCGCACCAG
TGGCTTATG-3'

8D6SAR:
                                             (SEQ ID NO: 24)
5'-GCGATAAAGCTTTTATCATCCACAGCCGAGCTCGTCGCTGGAGTCGG
GAC-3'.
```

Each amplified fragment was sequentially digested with BamHI and HindIII and then ligated into similarly digested pET30(+)a. The resulting plasmids encode proteins consisting of N-terminal hexahistidine and S-peptides fused to the CR fragment. Ligation reactions were transformed into XL-Blue MRF' (Stratagene) by electroporation and plasmids isolated from single colonies. Three mutations, Y1040W, V1047D and R1088D, were introduced into the LRP2 CR89 expression plasmid both singly and in combination using Stratagene QuikChange II XL reagents and the primers:

```
CR89YWF:
                                             (SEQ ID NO: 25)
5'-GTGCCCAATTACTGGCTCTGTGATGGAG-3';

CR89YWR:
                                             (SEQ ID NO: 26)
5'-CTCCATCACAGAGCCAGTAATTGGGCAC-3';

CR89V1047DF:
                                             (SEQ ID NO: 27)
5'-CTCTGTGATGGAGACGATGATTGTCATGATA-3';

CR89V1047DR:
                                             (SEQ ID NO: 28)
5'-TATCATGACAATCATCGTCTCCATCACAGAG-3';

CR89R1088DF:
                                             (SEQ ID NO: 29)
5'-CACACTGGCGCTGTGACAAAGACAACGACTGTGTGGATGGC-3';

CR89R1088DR:
                                             (SEQ ID NO: 30)
5'-GCCATCCACACAGTCGTTGTCTTTGTCACAGCGCCAGTGTG-3'.
```

All expression constructs were sequenced to verify insert sequences and the junctions with the expression vector. Each plasmid was then used to transform BL21(DE3) CodonPlus-RIPL™ cells (Stratagene). Expression of the CR proteins was induced in logarithmic growth-phase cells grown in LB supplemented with 34 µg/mL chloramphenicol, 12.5 µg/mL tetracycline and 15 µg/mL kanamycin by addition of 2 mM IPTG, followed by reduction in incubator temperature to 32° C. and incubation for 4 hours with agitation at 250×g. Cells were pelleted and resuspended, at 3.5% of the initial culture volume in 10 mM Tris-HCl pH 8, 100 mM NaH$_2$PO$_4$, 8M Urea. Resuspended cells were then frozen in liquid nitrogen, rapidly thawed to 37° C. and sonicated for 10 seconds at an amplitude setting of 60 using a Cole-Parmer CP-130 ultrasonic processor connected to a 3 mm probe. This procedure was repeated three times to effect complete lysis of the cells. Lysates were clarified by spinning twice at 10,000×g in a Sorvall RC-5 centrifuge for 20 minutes at 15° C. Ni-NTA columns (Qiagen Superflow™, 1.5 mL packed bed) were used to purify the CR proteins. Briefly, the resin was equilibrated with two column volumes of lysis buffer. The clarified lysate was then supplemented to 20 mM with imidazole and incubated with the equilibrated Ni-NTA resin overnight at 4° C. The flow-through was discarded. Columns were washed once with one column volume of lysis buffer and then three times with one column volume of TBS pH 8 supplemented with 20 mM imidazole. CR-loaded beads were then removed from the column and CR proteins eluted by incubating at room temperature for 30 minutes with one column volume of the same buffer containing 200 mM imidazole. This step was repeated once and the eluates pooled. Eluted CR protein solutions were then supplemented to 2 M urea, 10 mM CaCl$_2$ and 5 mM DTT. Purified, denatured CR protein solutions were transferred to 3,500 MWCO Slide-A-Lyzer™ (Pierce) cassettes and sequentially dialyzed against a 200-fold excess of 50 mM Tris-HCl pH 8.5, 10 mM CaCl$_2$, 1 mM reduced glutathione, 0.5 mM oxidized glutathione at room temperature overnight and then against TBS supplemented with 5 mM CaCl$_2$ at 4° C. overnight. Protein concentrations were determined by Bradford assay and purity confirmed by SDS-PAGE with Coomassie Brilliant Blue staining.

Preparation of a RAP Phage Display Library

The phage display phagemid pHage 3.2 was modified to remove PflMI and HindIII sites within the pIII leader sequence using QuikChange II™ reagents (Stratagene). In addition, the polylinker of pHage 3.2 was modified by ligation to a double-stranded linker containing BamHI, NotI and AgeI sites. The resulting modified phagemid was called pHage 3.6. A previously described vector for expression of a fusion between RAP and human α-L-iduronidase, pc3B-RAPIDU (49), was digested with BamHI and AgeI to obtain a DNA fragment encoding the human RAP sequence. This sequence begins at nucleotide 102 of the RAP cDNA and ends at nucleotide 1059. The encoded RAP protein lacks both the RAP signal peptide at the N-terminus and the HNEL endoplasmic reticulum retention signal at the C-terminus (SEQ ID NO: 108). In addition, there is an in-frame BamHI site at the 5'-end and an in-frame sequence encoding the peptide AEA-ETG (SEQ ID NO: 112), including an AgeI site, at the 3'-end. The RAP sequence was ligated into similarly digested pHage 3.6, creating a fusion between the M13 pIII leader peptide, the RAP sequence and the pIII sequence. This construct was termed pHage 3.6 RAP. Next, two positions within the third domain of RAP (RAP d3 K256 and K270) that had been previously reported to be important for receptor binding were mutagenized (55). These two positions were saturated by separate PCR amplification of the 5' and 3'-halves of RAP d3 using pairs of normal and mutagenic primers:

```
RAP2KXF:
                                             (SEQ ID NO: 31)
5'-CCCTCGGACGTCAGCGACATCAAGGGCAGCGTCCTG-3';

RAP2KX2:
                                             (SEQ ID NO: 32)
5'-CTCCAGCTGCTTCTGGTAGTGGTTGTGVNNCTCCTCGATTTTGGCTT
CGAAGTGCTTGAGCTCCT-3';

RAP2KX1:
                                             (SEQ ID NO: 33)
5'-AAGCAGCTGGAGATTGCGCACGAGNNBCTGAGGCACGCAGAGAGCGT
GGGCGAACGGC-3';
and RAPmut1R:
                                             (SEQ ID NO: 34)
5'-GGTGCGGGGCCTCACCGGT-3').
```

The fragments were amplified from pc3B-RAPIDU. Each mutagenic primer replaces one of the selected lysine codons with one of 47 other codons or with one of the three possible stop codons. This substitution creates a pool of 2304 possible combinations of nucleotides and 441 possible combinations of amino acids (or termination codons). Both the RAP d3 5' and RAP d3 3'-PCR fragments were digested with PvuII at a common site and then combined in a ligation reaction with T4

DNA ligase. A heterodimeric ligation product consisting of the 5'- and 3'-fragments fused at the PvuII site was resolved on FMC NuSieve GTG™ agarose gels and purified using Amersham GFX™ reagents. The heterodimer was quantified by UV spectroscopy and subjected to further rounds of mutagenesis by error-prone PCR using the GeneMorph II EZ Clone™ reagents (Stratagene) and the primers RAPKXF and RAPmut1R (described above). The heterodimer concentration was kept below 400 pg for each 50 μL reaction to maximize the final mutation frequency. Mutagenized DNA was digested with AgeI, purified by GFX, quantified by UV spectroscopy and used for ligase-free cloning into pHage 3.6 RAP using Stratagene EZclone™ reagents. Ligase-free cloning reaction products were purified using Qiagen MinElute™ columns. Aliquots of the purified ligase-free cloning products (3 μL) were used to transform 50 μL aliquots of XL10-Gold™ chemically-competent cells. Aliquots of the transformed cells were serially-diluted and plated on LB plates containing 100 μg/mL carbenicillin to determine the number of primary transformants. The remaining transformed cells were plated on Nunclon 25×25 cm dishes. A total of 119,500 primary transformant colonies were recovered from the dishes with the aid of 350 mL of Qiagen GigaPrep™ P1 buffer. Plasmid DNA was prepared using Qiagen reagents and protocols. The plasmid preparation was quantified and digested with BamHI and AgeI to confirm the presence of appropriately-sized insert.

Preparation of a RAP d3 Mutant Library

A RAP d3 mutant library was prepared by PCR using PfuUltra enzyme and reagents (Stratagene). The 5' and 3' halves of the d3 coding sequence were separately amplified using HPLC-purified primers

```
MORPHF4:
                                        (SEQ ID NO: 35)
5'-GGCCCAGATCTACCGGTTTCTGCCTCGGC-3';

D3HALFR2:
                                        (SEQ ID NO: 36)
5'-GTGCGCAATCTCGAGCTGCTTCTGGTAGTGGTTGTGVNNCTGATTT
TGGCVNNGAAGTGCTTGAGCTCCTCCCGG-3';

D3HALFF2:
                                        (SEQ ID NO: 37)
5'-CCACTACCAGAAGCAGCTCGAGATTGCGCACGAGNNBCTGAGGCACG
CAGAGAGCGTGGGCGACGGC-3';

MORPHR3:
                                        (SEQ ID NO: 38)
5'-GAGTGCGGCCGCAAGCTTATCTTCTGCCTCGGC-3'.
```

The primers replace codons at positions 251, 256 and 270 with NNB, resulting all possible amino acids at these positions. In addition, a PvuII site within the RAP d3 coding sequence was ablated with a single, silent, base substitution. Amplified fragments were purified using Amersham GFX reagents and then assembled by primer-less PCR using PfuUltra. The assembled pool of RAP d3 variants sequences was then quantified and subject to mutagenesis using GeneMorph II reagents (Stratagene). Mutagenized DNA was sequentially digested with BamHI, PvuII and AgeI with purification using GFX reagents after each reaction. The digested RAP d3 variant fragment pool was then ligated into similarly digested pHage 3.6 (see above). A plasmid library was prepared by transformation of XL10-Gold cells (Stratagene) and plating on 25×25 cm dishes of LB supplemented with carbenicillin. Colonies were recovered from the dishes and plasmid DNA prepared as above.

Preparation of Phage

Plasmid libraries (10 ng) were used to transform XL-Blue MRF' by electroporation. Following incubation for 1 hour at 37° C. in 1 mL of 2×YT supplemented with 2% glucose, cultures of transformed cells were supplemented to 100 μg/mL with carbenicillin and grown an additional 6 hours. Following this interval the 1 mL culture was used to innoculate 10 mL of 2×YT supplemented with 2% glucose, 100 μg/mL carbenicillin and $10^8$ pfu/mL M13K07 helper phage (New England Biolabs) in a 50 mL Erlenmeyer flask. This culture was shaken at 250×g for 2 hours at 37° C., and then centrifuged in a Sorvall RC-5 centrifuge at 2,000×g for 10 minutes to pellet the cells. Cells were resuspended in 10 ml 2×YT with 100 μg/ml carbenicillin and 100 μg/ml kanamycin and shaken overnight at 37° C. Cultures were clarified by centrifugation twice at 10,000×g and supernatants collected. Phage were precipitated by combining the supernatant with one volume of cold TBS and 0.2 volumes of 2% PEG 8000 (Sigma), 2.5 M NaCl, collected by centrifugation at 10,000×g and resuspended in TBS. Phage titer was determined by serially-diluting phage samples, incubating with logarithmic phase XL-Blue MRF' and plating on 2×YT agar supplemented with 100 μg/mL carbenicillin.

Phage Panning

Purified, folded CR proteins were used to coat Nunc MaxiSorp™ 96-well plates at 1 μg/well overnight at 4° C. in TBS supplemented with 5 mM $CaCl_2$. Wells were rinsed and blocked with TBS Superblock™ (Pierce) supplemented with 5 mM $CaCl_2$ prior to addition of phage. Purified phage libraries of $10^9$ cfu ($10^{10}$ cfu/mL) in TBS Superblock™ supplemented with 5 mM $CaCl_2$ and 0.05% Tween-20 were added to coated wells and incubated for 2 hours at room temperature. Wells were then washed fifteen times with TBSTC (20 mM Tris-HCl pH 7.4, 150 mM NaCl supplemented with 5 mM $CaCl_2$ and 0.05% Tween-20). Bound phage were eluted in 0.2 M glycine-HCl pH 2.2 with 1 mg/ml BSA and transferred to tubes containing 0.2 volumes of 1M Tris-HCl pH 9.1 to bring the pH to neutrality. Eluted phage were recovered by mixing eluate with log-phase XL-Blue MRF' cells. Rescued phage were amplified by growing cells in liquid culture at 30° C. overnight (16 hours). In addition, aliquots of transformed cells were titered by serially diluting the samples and plating on 2×YT agar containing 100 μg/mL carbenicillin. Phage were purified and concentrated from media supernatants by PEG precipitation.

Expression of RAP d3 Proteins

RAP d3 sequences were PCR amplified using d3 Rescue F: 5'-G C G A T A G G A T C C C T G G A C C G C C T G C G C A G G G T C A G C C A C C-3' (SEQ ID NO: 39) and d3 Rescue R: 5'-G C G A T A A A G C T T T T A T C A A G A T C T A C C G G T T T C T G C C T C G G C-3' (SEQ ID NO: 40), digested with BamHI and HindIII and ligated into similarly digested pET30(+)a. RAP d3 proteins were expressed in BL21(DE3) CodonPlus-RIPL™ and purified by Ni-NTA chromatography as described above. Protein concentrations were measured by Bradford assay and purity was assessed by SDS-PAGE.

Sequential Reversion of Mutant RAP d3 and Forward Mutation of Wild-Type RAP d3

Each mutation within the affinity-selected RAP d3 variant was individually reverted to wild-type using Stratagene QuickChange II XL™ reagents and primers

```
V2AR1:
                                        (SEQ ID NO: 41)
5'-AGGGTCAGCCACCAGGGCTACAGCACTGAGGCTAAGTTCGAGGAGCC
```

```
CAGGGTGAT-3';

V2AR2:
                                        (SEQ ID NO: 42)
5'-CAGCCACCAGGGCTACACCACTGAGGCTGAGTTCGAGGAGCCCAGGG
TGATTGACC-3';

V2AR3:
                                        (SEQ ID NO: 43)
5'-GGAGGCGTTCCGGGAGGAGCTCAAGCACTTCAAAGCCAAAATTGAGG
CCCACAACC-3';

V2AR4:
                                        (SEQ ID NO: 44)
5'-CGTTCCGGGAGGAGCTCAAGTACTTCGAAGCCAAAATTGAGGCCCAC
AACCACTAC-3';

V2AR5:
                                        (SEQ ID NO: 45)
5'-GCTCAAGTACTTCAAAGCCAAAATTGAGAAGCACAACCACTACCAGA
AGCAGCTGGAG-3';

V2AR6:
                                        (SEQ ID NO: 46)
5'-AGAAGCAGCTGGAGATTGCGCACGAGAAGCTGAGGCACGCAGAGAGC
GTGGGCGACGG-3';

V2ARR1:
                                        (SEQ ID NO: 47)
5'-ATCACCCTGGGCTCCTCGAACTTAGCCTCAGTGCTGTAGCCCTGGTG
GCTGACCCT-3';

V2ARR2:
                                        (SEQ ID NO: 48)
5'-GGTCAATCACCCTGGGCTCCTCGAACTCAGCCTCAGTGGTGTAGCCC
TGGTGGCTG-3';

V2ARR3:
                                        (SEQ ID NO: 49)
5'-GGTTGTGGGCCTCAATTTTGGCTTTGAAGTGCTTGAGCTCCTCCCGG
AACGCCTCC-3';

V2ARR4:
                                        (SEQ ID NO: 50)
5'-GTAGTGGTTGTGGGCCTCAATTTTGGCTTCGAAGTACTTGAGCTCCT
CCCGGAACG-3';

V2ARR5:
                                        (SEQ ID NO: 51)
5'-CTCCAGCTGCTTCTGGTAGTGGTTGTGCTTCTCAATTTTGGCTTTGA
AGTACTTGAGC-3';

V2ARR6:
                                        (SEQ ID NO: 52)
5'-CCGTCGCCCACGCTCTCTGCGTGCCTCAGCTTCTCGTGCGCAATCTC
CAGCTGCTTCT-3'.
```

Wild-type RAP d3 was mutagenized using the same method and the following primers:

```
K256AF:
                                        (SEQ ID NO: 53)
5'-CTTCGAAGCCAAAATCGAGGCGCACAACCACTACCAGAAGC-3';

K256AR:
                                        (SEQ ID NO: 54)
5'-GCTTCTGGTAGTGGTTGTGCGCCTCGATTTTGGCTTCGAAG-3';

K270EF:
                                        (SEQ ID NO: 55)
5'-GCTGGAGATTGCGCACGAGGAGCTGAGGCACGCAGAGAG-3';

K270ER:
                                        (SEQ ID NO: 56)
5'-CTCTCTGCGTGCCTCAGCTCCTCGTGCGCAATCTCCAGC-3';

d3E251KF:
                                        (SEQ ID NO: 57)
5'-GAGGAGCTCAAGCACTTCAAAGCCAAAATCGAGAAGCACAAC-3';

d3E251KR:
                                        (SEQ ID NO: 58)
5'-GTTGTGCTTCTCGATTTTGGCTTTGAAGTGCTTGAGCTCCTC-3';

d3E217KF:
                                        (SEQ ID NO: 59)
5'-CAGGGCTACAGCACTGAGGCTAAGTTCGAGGAGCCCAGGGTG-3';

d3E217KR:
                                        (SEQ ID NO: 60)
5'-CACCCTGGGCTCCTCGAACTTAGCCTCAGTGCTGTAGCCCTG-3';

d3H249YF:
                                        (SEQ ID NO: 61)
5'-GTTCCGGGAGGAGCTCAAGTACTTCGAAGCCAAAATCGAG-3';

d3H249YR:
                                        (SEQ ID NO: 62)
5'-CTCGATTTTGGCTTCGAAGTACTTGAGCTCCTCCCGGAAC-3'.
```

Solid Phase Binding Assays

Purified, refolded CR protein (1 μg) was bound to Nunc Maxisorp™ 96-well plates in TBS pH 8 supplemented with 5 mM $CaCl_2$ (TBSC) overnight at 4° C. Wells were washed with TBSC and then blocked with TBSC containing 2% bovine serum albumin (BSA). RAP ligands were then incubated with the immobilized receptor at a range of concentrations for 2 hours in the above blocking buffer supplemented with 0.05% Tween-20 at room temperature. Control wells contained no added ligand. As an additional control, to determine whether the absence of calcium affected binding, 10 mM EGTA was included in the incubation medium for some samples. Wells were washed with TBSTC and bound ligands detected with polyclonal anti-RAP (BP41/42, 1:1,000, BioMarin). Excess primary antibody was removed and wells washed before incubation with the secondary antibody, HRP-conjugated goat anti rabbit IgG (Bio-Rad). After washing, TMB substrate solutions (Bio-Rad) were added to detect HRP. Color development was stopped with 1N HCl. Absorption at 450 nm was measured with a microplate spectrophotometer (Molecular Devices). Data were plotted and $K_d$ values derived by non-linear regression with the assumption of single-site binding (GraphPad Prism).

Results

In order to identify tandem CR pairs within the human proteome and to analyze those positions within the pairs that had been previously implicated in binding to RAP, sequences of 190 non-redundant human CR sequences identified in the Pfam database (pfam.wustl.edu) were transferred to a spreadsheet. Tandem pairs of CR sequences were then identified, with the only requirement for assignment as a pair being that the two CR sequences be immediately adjacent to each other within the primary sequence of the protein in which they were found. Imposition of a 75 amino acid limit on the distance between the first amino acids of each CR sequence, as defined in the Pfam database, adequately tested for this condition. The assumption of the requirement for a tandem arrangement was made since the preponderance of historical data on the binding of RAP to defined CR sequences involves such pairs. Overlapping pairs were included such that a linear array of three CR sequences comprised two CR pairs. There were 149 tandem CR pairs identified in this way. Sequence conservation in the area of the calcium-binding loop facilitated the next step in the analysis, extraction of four amino acids tied directly to RAP binding in previous studies (56, 57). These are equivalent to A and C from the AxcBxCxD motif of each CR sequence of a CR pair. The amino acid identities at positions A and C from the first CR sequence of each pair, along with the amino acids at positions A and C from the second CR sequence of each pair (henceforth, A' and C') were then concatamerized into a single, tetrameric text string (ACA'C') for the purposes of comparison. The text strings for each CR pair were compared to those for all other CR pairs and the frequency of each counted. Of the 149 non-redundant human tandem CR pair sequences that were identified in this analysis, the most common combination of amino acids at A, C, A' and C' was WDWD, which was found 16 times. In addition, there were a total of four CR pairs with the WEWD signature, two with WEWE and six with WDWE, for a total of 28 fitting our definition of canonical CR pairs. The canonical CR pair signatures were found only in the LDLR family, specifically in VLDLR, LRP1, LRP1B, LRP2, LRP4, apoER2 and SorLA. All of these receptors have been previously shown to bind RAP with high affinity. In addition to redundant combinations of lower frequency, 101 unique combinations were identified, with all CR pair-containing proteins having at least one. Each tetrameric combination of amino acids at A, C, A' and C' was then generalized by assigning amino acids to one of six groups based on the approximate physico-chemical properties of their side-chains. Hydrophobic aliphatic amino acids were assigned to group 1 (I, L, M, V), small, hydrophilic amino acids to group 2 (A, C, G, P, S, T), basic amino acids to group 3 (H, K, R), acidic amino acids to group 4 (D, E), carboxamide amino acids to group 5 (N, Q) and aromatic amino acids to group 6 (F, W, Y). As before, each generalized combination was then compared to all other such combinations and their frequencies counted. The most common generalized combination was found to be 6464, with aromatic amino acids at A and A' and acidic amino acids at C and C'. This group included all 28 of the specific canonical combinations, and accounted for 44 of the 149 CR pair combinations. Representatives of this class of CR pairs were found in ten proteins, including two outside of the LDLR family, corin and perlecan. A total of 57 of the generalized combinations were unique and, as before, at least one unique combination could be found in each LDLR receptor ectodomain, except for the VLDLR. Other proteins containing CR pairs with unique generalized combinations of amino acids at the selected positions included the transmembrane serine protease matriptases 1, 2 and 3 (MT-SP1, ST14, TADG-15), FDC-8D6 antigen, corin, complement factor I and the heparin sulfate proteoglycan protein, perlecan (25, 58).

Figure 2:
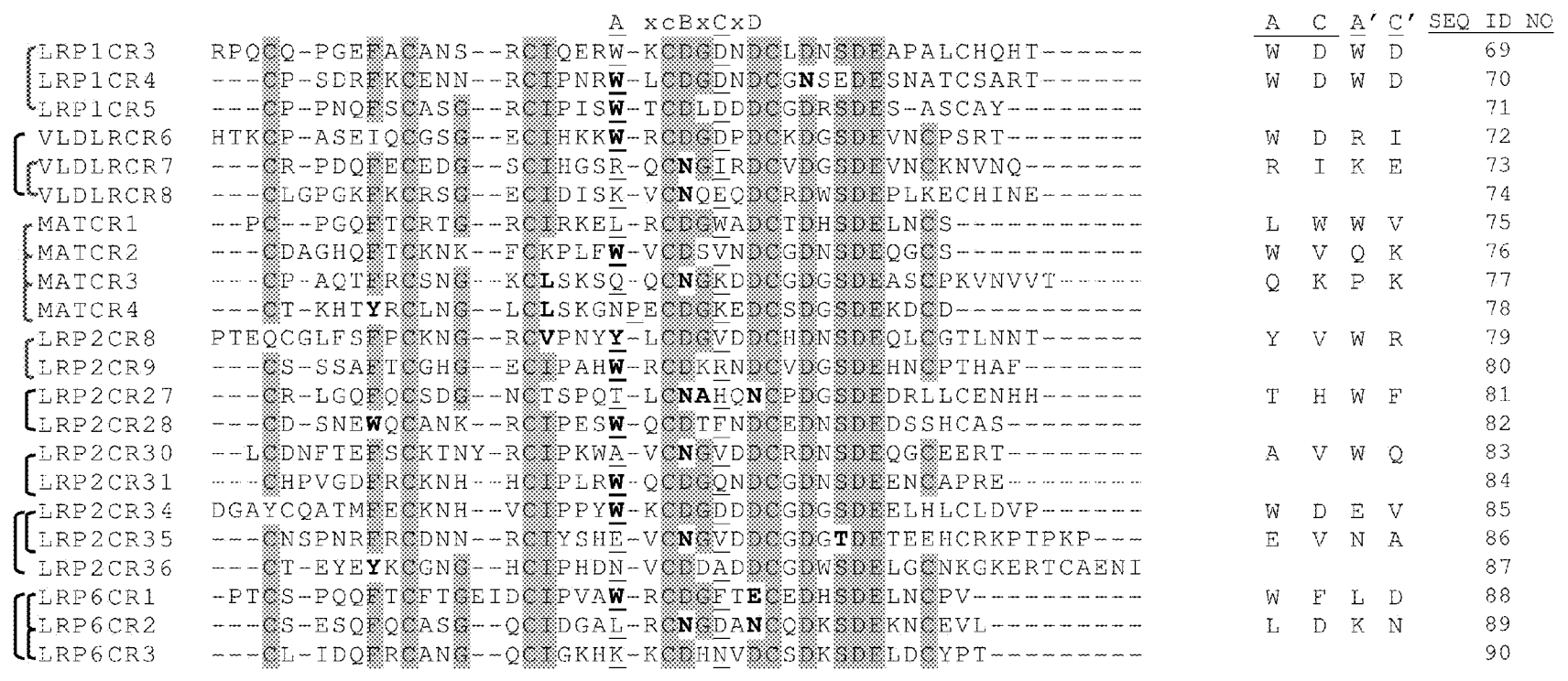

From the large number of CR pairs with unique combinations of amino acids at A, C, A' and C' within the calcium-binding loop of each CR, CR pairs or triplets were selected to test their binding to RAP d3 (FIG. 2). An additional pair derived from the FDC-8D6 protein was tested, designated 8D6 CR12, having the sequence (GSSCPPTKFQCRTSGLCVPLTWRCDRDLDCSDGSDEEECRIEPCTQKGQCPP PPGLPCPCTGVSDCSGGTDKKLRNCSRLACLAGELRCTLSDDCIPLTWRCDGH PDCPDSSDELGCG) (SEQ ID NO: 91). The selected receptor fragments comprise single pairs or two overlapping pairs (triplets) of CR sequences and were meant to reflect the range of amino acid combinations at the selected positions. Taking into account that overlapping pairs might fold less efficiently than isolated pairs, one or both overlapping pairs making up each triplet were also expressed in some cases. Sequences included an LRP6 CR triplet, equivalent to amino acids 1247-1363 of full-length human LRP6 (Uniprot accession O75581), termed LRP6 CR1-3; both overlapping CR pairs comprising the LRP6 triplet, LRP6 CR12 and LRP6 CR23, amino acids 1247-1322 and 1323-1363; a fragment of the VLDLR, amino acids 235-358 (Uniprot accession P98155), termed VLDLR CR6-8; a CR pair within the VLDLR triplet, termed VLDLR CR78, containing amino acids 295-358; three CR pairs from the transmembrane serine protease matriptase, termed MAT CR12 (ST14 CR12), amino acids 452-524, MAT CR23 (ST14 CR23), amino acids 487-566 (Uniprot accession Q8WVC1) and MAT CR34 (ST14 CR34), amino acids 525-602; the CR pair from FDC-8D6 antigen, amino acids 53-168 (Uniprot accession Q9NPF0) (SEQ ID NO: 94) and, a triplet from LRP1, termed LRP1 CR3-5, comprising amino acids 852-973 (Uniprot accession P98157). LRP1 CR3-5 consists of two, overlapping canonical CR pairs with the WDWD signature, each of which has previously been demonstrated to bind to RAP d3 with high-affinity (56).

A number of previous studies have demonstrated that CR pairs and triplets can be expressed in bacteria and refolded in vitro into native structures (45, 50-54, 56, 57, 59-62). Each purified, refolded CR protein was expressed and analyzed by SDS-PAGE under both reducing and non-reducing conditions (FIG. 3). CR mobility was consistent with predicted molecular weight under reducing conditions, and each protein was judged to be >90% pure. Under non-reducing conditions, each CR protein migrated through the gel more quickly than expected for the predicted molecular weight. This observation is consistent with a compact folded structure dependent on intramolecular disulfide bond formation. While a number of possible disulfide bond combinations are possible, the studies cited above demonstrate that the native disulfide-bonding pattern is favored during refolding, especially in the presence of calcium. In most cases, and taking into account the relatively low resolution of the electrophoretic analysis, the folded form of the CR protein appeared to be a single band (FIG. 3).

Figure 4:
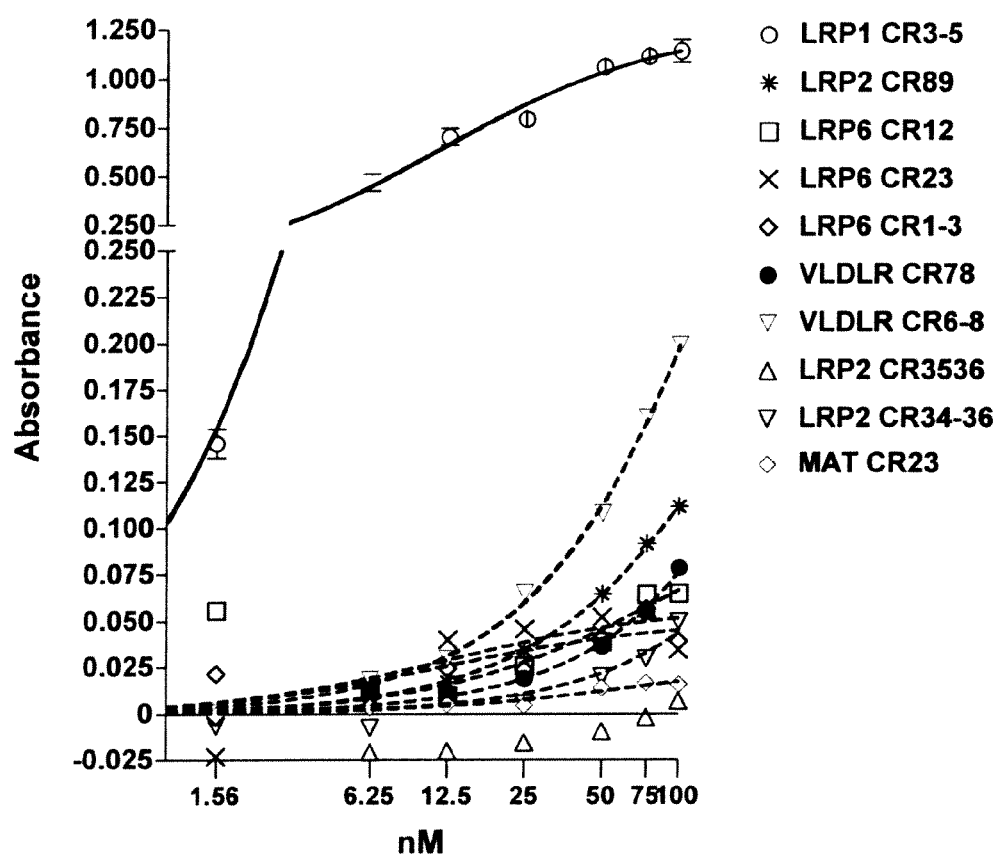
FIG. 4 depicts binding of RAP d3 to selected CR proteins using a dilution series of RAP d3 was prepared from 100-1.25 nM.

The binding of wild-type RAP d3 to each CR pair or set of overlapping pairs was then measured by solid-phase assay (FIG. 4). The apparent $K_d$ for binding of RAP d3 to LRP1 CR3-5 in this assay was 11 nM, in the same range as values previously reported (56, 57, 63). RAP d3 binding to LRP6 CR12, LRP6 CR23, LRP6 CR1-3, VLDLR CR78, LRP2 CR3536, LRP2 CR34-36 and MAT CR23 was less than 5% of that for LRP1 CR3-5 at the highest ligand concentrations tested. Binding of RAP d3 to MAT CR12 and CR34, measured in a separate set of experiments, was also undetectable. RAP d3 binding to VLDLR CR6-8 and LRP2 CR89 was slightly higher, allowing curves to be reliably fitted to the binding isotherms. Nevertheless, apparent dissociation constants for binding of RAP d3 to these receptor fragments were over 300 nM.

Having established that RAP d3 does not bind to CR pairs containing unique combinations of amino acids within the calcium-binding loop, an affinity-selection system for mutants of RAP d3 that are able to bind such pairs was developed. Fusions of RAP to other proteins have been expressed in both mammalian and bacterial cells and have been demonstrated to retain the receptor-binding behavior of native RAP (49, 64, 65). Therefore, libraries of full-length RAP fused N-terminally to the M13 pIII structural protein were created, as has been previously done with other proteins (66). To create a pool of RAP mutants, two mutagenic procedures were applied to the third domain within the full-length RAP coding sequence. The codons for two positions previously demonstrated to participate directly in receptor binding, K256 and K270, were first subjected to saturation mutagenesis. Additional mutations were then randomly introduced into RAP d3 using error-prone PCR. Following these procedures, a total of 38 randomly-selected clones were sequenced to determine the mutation frequency. Ten clones (26%) had base insertions, deletions or substitutions that resulted in stop codons within the RAP sequence. Recombinant phage encoding such sequences will be favored during the processes of phage assembly and infection since only wild-type pIII becomes incorporated into the phage capsid. An additional four clones (11%) were found to encode wild-type RAP. The remaining 24 clones (63%) of the RAP phage-pIII fusions encoded RAP proteins with mutations in d3. None of these clones had the same combination of amino acids at positions 256 and 270, indicating that a range of substitutions had occurred as expected at these sites. The average mutation frequency exclusive of positions 256 and 270 was 2.4 amino acid substitutions within the last 110 amino acids of RAP (RAP d3). One of the 38 clones had an in-frame deletion of 7 codons while another had an in-frame insertion of unidentified sequence partly replacing the 3'-end of RAP d3. No mutations were found within d1 or d2 of RAP.

A second phage display library was prepared encoding only RAP d3. This library was generated in a similar fashion to the full-length RAP library, except that an additional position, 251, was subjected to saturation mutagenesis based the apparent importance of this site in a variant from an earlier screen (see below). Apart from positions 251, 256 and 270, the RAP d3 mutant library had an average mutation frequency of 2 amino acid substitutions within the last 110 amino acids of RAP. There was no apparent over-representation of wild-type RAP sequences in this library.

To test whether the phage panning system could be used to isolate RAP sequences based on affinity, a preparation of phage expressing wild-type RAP was diluted one thousand-fold into a preparation of phage expressing a mutant RAP (K256D, K270D) that was expected to have diminished CR pair-binding ability (55). Panning was performed as described in Methods. Recovered phage were amplified and titered. The RAP d3 sequence from ten recovered colonies was sequenced. After a single round of panning, two of the ten colonies from the panning experiment contained wild-type RAP, an enrichment of 200-fold from the starting pool. As an additional test of the system using a more complex pool of sequences, RAP phage libraries in which positions 256 and 270 had been randomized were panned on LRP1 CR3-5. In the initial phage library, the wild-type RAP sequence was encoded by approximately one of 10 phage (based on sequencing of random clones prior to selection). Following the first round of panning, the wild-type RAP sequence was encoded by 7 of 10 phage. This result demonstrates a 7-fold enrichment for the selected sequence from a complex pool of sequences after one round of panning.

Concluding that RAP sequences could be isolated from phage display libraries by affinity selection, we first chose a CR pair that was not bound by wild-type RAP, LRP2 CR89, and used it as a panning substrate with the doubly-mutagenized full-length RAP phage library. After four rounds of panning, three of eight randomly chosen clones were identical. The common sequence had seven mutations: V175L, S213T, E217K, H249Y, E251K, K256A, K270E. A second group of four clones had identical substitutions at positions 256 and 270 (K256A, K270R), but had variable substitution patterns outside of these two sites. After a fifth round of panning, seven of eight randomly chosen clones had the previously-observed V175L, S213T, E217K, H249Y, E251K, K256A, K270E mutation set. All mutations for this sequence, termed RAPv2A or MegaRAP1 (SEQ ID NO: 93) were in the region specifically mutagenized to make the variant library.

To confirm that library resolution had occurred as a result of affinity selection, RAP and MegaRAP1 phage were prepared and assayed for binding to LRP2 CR89. With identical starting titers, 2.6-fold more colony forming units (cfu) were recovered by panning with MegaRAP1 phage than with wild-type RAP phage. Similar results were obtained when bound phage were detected with an anti-pIII antibody, indicating that differences in infectivity between the two phage were not responsible for differences in the titers of recovered phage. By conducting the binding reaction in the presence of 50 mM EDTA, MegaRAP1 binding was determined to be dependent on calcium, consistent with the requirement for an ordered CR fold as the receptor. Since both RAP and MegaRAP1 phage had identical d1 sequences and d2 sequences that differed by a single, conservative substitution (V175L), we hypothesized that differences in d3 were responsible for improvements in binding to LRP2 CR89. Accordingly, RAP d3 and MegaRAP1 d3 were subcloned and expressed for subsequent binding analyses. Since the d3 regions expressed for further study comprised amino acids 201-319 of mature RAP, the effect of the V175L mutation on the binding behavior of RAPv2A was not determined.

Figure 5A:
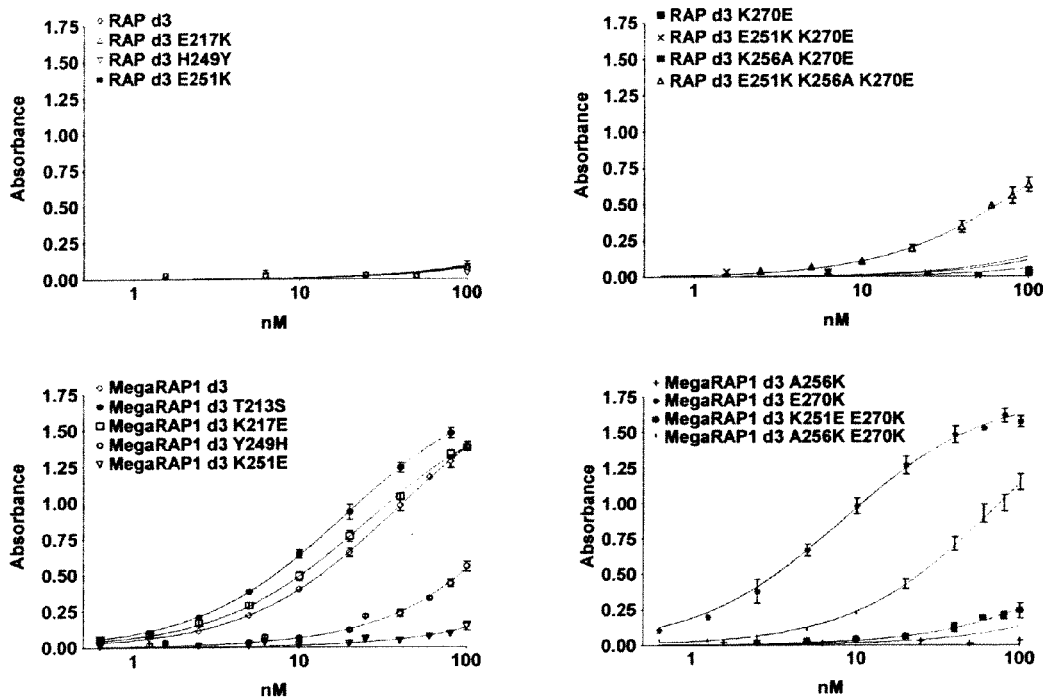

Next, the binding of RAP d3 and MegaRAP1 d3 proteins to LRP1 CR3-5 and LRP2 CR89 was assessed. In order to understand the relative contributions of each MegaRAP1 d3 mutation to differences in affinity, we also prepared a number of MegaRAP1 d3 revertants and RAP d3 forward mutants, all comprising sequence variants intermediate between MegaRAP1 d3 and wild-type RAP d3 (lacking the 4 amino acid C-terminal retention signal (SEQ ID NO: 92) (FIGS. 5A and 5B, Table 2). In all cases, 10 mM EGTA prevented binding of both RAP d3 and MegaRAP1 d3 to CR proteins. Since calcium was the only divalent metal ion present in the binding buffer, this observation is consistent with both RAP d3 and MegaRAP1 d3 binding to calcium-loaded CR pairs. RAP d3 bound LRP1 CR3-5 with a dissociation constant of 16 nM and showed no significant affinity for LRP2 CR89, consistent with the data represented in FIG. 4. Conversely, MegaRAP1 d3 bound LRP2 CR89 with an apparent dissociation constant of 38 nM but with no significant affinity for LRP1 CR3-5. Therefore, wild-type RAP d3 and MegaRAP1 d3 have inverted binding preferences for these two receptor fragments. Two MegaRAP1 d3 revertants, T213S and K217E had slightly improved affinities for LRP2 CR89 and remained unable to detectably bind LRP1 CR3-5. Three MegaRAP1 d3 revertants, Y249H, K251E and A256K, failed to bind either receptor fragment, indicating that the mutations were important for the interaction between MegaRAP1 d3 and LRP2 CR89 and were not individually responsible for disrupting binding to LRP1 CR3-5. Interestingly, the E270K revertant bound both receptor fragments with higher affinity than MegaRAP1 d3, giving apparent dissociation constants of 8 nM for LRP2 CR89 and 142 nM for LRP1 CR3-5. Since the MegaRAP1 d3 mutant was selected based on affinity for LRP2 CR89, this result is consistent with the diversity of the starting library being insufficient to account for all possible sequence variants. Alternatively, the affinity differences between MegaRAP1 d3 and MegaRAP1 d3 E270K may have been insufficient to allow the latter to predominate upon iterative panning. A double revertant, T213S, E270K, had binding behavior that was not distinguishable from MegaRAP1 d3 in our assays. Since the two single-site revertants at these positions appeared to show improved affinity for LRP2 CR89, and in the case of E270K, LRP1 CR3-5 also, this result indicates a lack of additivity for binding effects resulting from these reversions or a lack of accuracy within this affinity range in our assays. The binding behavior of the K251E, E270K double revertant implies a strong dependence of the affinity of MegaRAP1 d3 for LRP2 CR89 on the E251K mutation. The difference in LRP2 CR89 affinity between this revertant and the single-site E270K revertant is almost 20-fold. The A256K, E270K double revertant results in a 2-fold loss of affinity for LRP2 CR89, implying a moderately positive effect that the K256A MegaRAP1 d3 mutation has on affinity for this fragment. However, the most striking difference between this double revertant and the E270K single-site revertant is the nearly 30-fold improvement in affinity for LRP1 CR3-5. Therefore, the K256A mutation in MegaRAP1 d3 is a crucial determinant of the ability of this variant to discriminate between the two receptor fragments, exerting its effect by negatively impacting affinity for LRP1 CR3-5 while at the same time improving affinity for LRP2 CR89.

Of the RAP d3 forward mutants tested, only the combination of E251K, K256A and K270E resulted in measurable affinity for LRP2 CR89. The apparent dissociation constant for binding of this triple mutant to LRP2 CR89 was 114 nM, still relatively high compared to MegaRAP1 d3. This affinity difference would presumably close further with the addition of the H249Y mutation. Single-site RAP d3 mutants at 217, 249 and 251 had minimal effects on binding LRP1 CR3-5 and did not bring affinity for LRP2 CR89 into the measurable range. The K270E mutation, either alone or in combination with E251K, K256A or both, failed to measurably bind LRP1 CR3-5. The significant negative impact of K256A or K270E on binding of RAP d3 to LRP1 have been previously reported in a study on loss-of-function RAP mutants (55). The results reported here are consistent with this work. Overall, the positive contributions of the mutations at 249, 251 and 256 in MegaRAP1 d3 toward binding of LRP2 CR89 and the negative contributions of mutations at 256 and 270 on binding to LRP1 CR3-5 seem to primarily account for the differences between MegaRAP1 d3 and wild-type RAP d3 in binding to the two receptor fragments.

Figure 6:
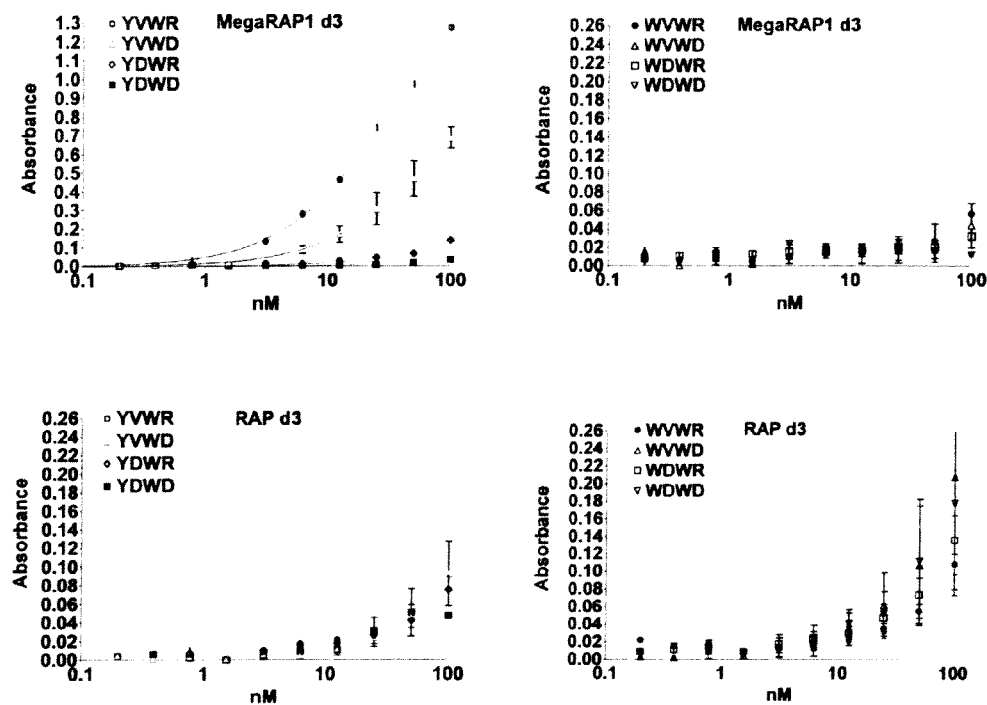
FIG. 6 shows binding of MegaRAP1 d3 and RAP d3 to LRP2 CR89 variants. Abbreviations used in the figure: LRP2 CR89 Y1042W (WVWR), LRP2 CR89 V1047D (YDWR), LRP2 CR89 R1088D (YVWD), LRP2 CR89 V1047D R1088D (YDWD), LRP2 CR89 Y1042W V1047D R1088D (WDWD), LRP2 CR89 Y1042W V1047D (WDWR), LRP2 CR89 Y1042W R1088D (WVWD).

One premise of this work was that amino acids at A, C, A' and C' within the calcium-binding loops of a CR pair were key determinants of binding affinity for RAP and would be similarly important for binding of RAP variants. To test this idea, mutant LRP2 CR89 were prepared in which the native, non-canonical residues at these positions were sequentially substituted with the non-native, canonical residues. As defined above, the A, C, A', C' string for LRP2 CR89 is YVWR. Mutants included LRP2 CR89 Y1042W (WVWR), LRP2 CR89 V1047D (YDWR), LRP2 CR89 R1088D (YVWD), LRP2 CR89 V1047D R1088D (YDWD), LRP2 CR89 Y1042W V1047D R1088D (WDWD), LRP2 CR89 Y1042W V1047D (WDWR), LRP2 CR89 Y1042W R1088D (WVWD). Binding to both RAP d3 and MegaRAP1 d3 were measured for each LRP2 CR89 mutant by solid-phase assay. Only the YVWD mutant retained significant binding to MegaRAP1 d3, with an approximate 2-fold loss of affinity relative to LRP2 CR89 (FIG. 6 and Table 3). The position C mutant, with the tetrameric sequence string of YDWR failed to bind measurably to MegaRAP1 d3 as did all other single mutations or combinations of mutations involving either A or C. Interestingly, the nominally conservative Y1042W mutation alone was sufficient to prevent binding of MegaRAP1 d3. The A' position in LRP2 CR89 is a tryptophan, the canonical residue for wild-type RAP d3 binding, and was not mutated in our studies. While substitution of amino acids at A, C and C' had a strong negative impact on binding of MegaRAP1 d3, these substitutions did not greatly improve affinity for RAP d3, despite substitution with amino acids preferred by RAP d3 in other CR pairs such as LRP1 CR56. We did see a small increase in binding of RAP d3 to the WVWD and WDWD combinations at A, C, A' and C'. These results suggest that while some amino acids in the calcium-binding loop are important for defining RAP and RAPv2A binding behavior, they are not sufficient to do so alone.

As a test of the generality of the screening method phage library panning experiments were performed on additional CR proteins. Isolated variant sequences are depicted in Table 4 and FIG. 8. Initially VLDLR CR6-8, constituting the last three CR domains of human VLDLR, was used as a substrate for panning using a phage-display library encoding mutants of RAP d3 alone. Following five rounds of panning, five of eight randomly chosen clones had the same mutation set: R205S, E251R, K256L, K270E, R296L, G313D. This sequence variant, VRAP1) d3 was expressed for solid-phase binding studies. Binding of VRAP1 d3, MegaRAP1 d3 and RAP d3 to LRP1 CR3-5, LRP2 CR89 and VLDLR CR6-8 was compared. A similar variant sequence, E251T, K256I, K270E, R296L, was selected on VLDLR CR78. We also panned on three CR pairs from human matriptase, MAT CR12, MAT CR23 and MAT CR34 using the same d3 library. Phage libraries were resolved to predominant sequences by the sixth round of panning on the matriptase pairs. The predominant sequence selected on MAT CR23 was E251G, K256R, K270W. This variant was name MatRAP1 (RAP vMA). The predominant sequence selected on MAT CR34 was S232P, E239G, E246G, E251L, K256P, I266T, A267V, H268R, K270P, H273Y, R287H, H290Y, K298R, S312F. This variant was named MatRAP2 (RAP vMB). Panning experiments were also performed on the CR pair from FDC-8D6 antigen. The predominant variant selected was K256S, K270S, L271M, D279Y, V283M, K305T, K306M. This variant was named 320RAP1.

To test the extent to which the length of a RAP d3 sequence variant could be minimized, sequentially-truncated sections of MatRAP1 were prepared by PCR, expressed, purified and tested for binding as described above (FIG. 9). Removal of 10 amino acids slightly diminished affinity but removal of 31 and 42 amino acids from the N-terminus resulted in incremental increases in affinity up to 3-fold over the full-length d3 variant. Further N-terminal truncations, beginning with an additional 10 amino acids (52 total), resulted in a complete loss of binding. Subsequent C-terminal truncation of the best N-terminally truncated variant (MatRAP1 N-42) resulted in further, significant increases in binding affinity, starting with a 2-fold increase (6-fold from full-length) with removal of the C-terminal linker and affinity tag and then a 4-fold increase (12-fold over full-length) after removal of an additional 6 amino acids from the C-terminus. Further C-terminal truncations, beginning with an additional 19 amino acids, resulted in a complete loss of binding. The best truncated variant consisted of amino acids 243-313 (71 amino acids). To test the generality of this modification in improving affinity, we made identical truncations to 320RAP1. The resulting truncated form of this variant bound with a 3.5-fold improvement in affinity for the FDC-8D6 antigen pair as compared to the full-length variant (FIG. 10).

Figure 7:
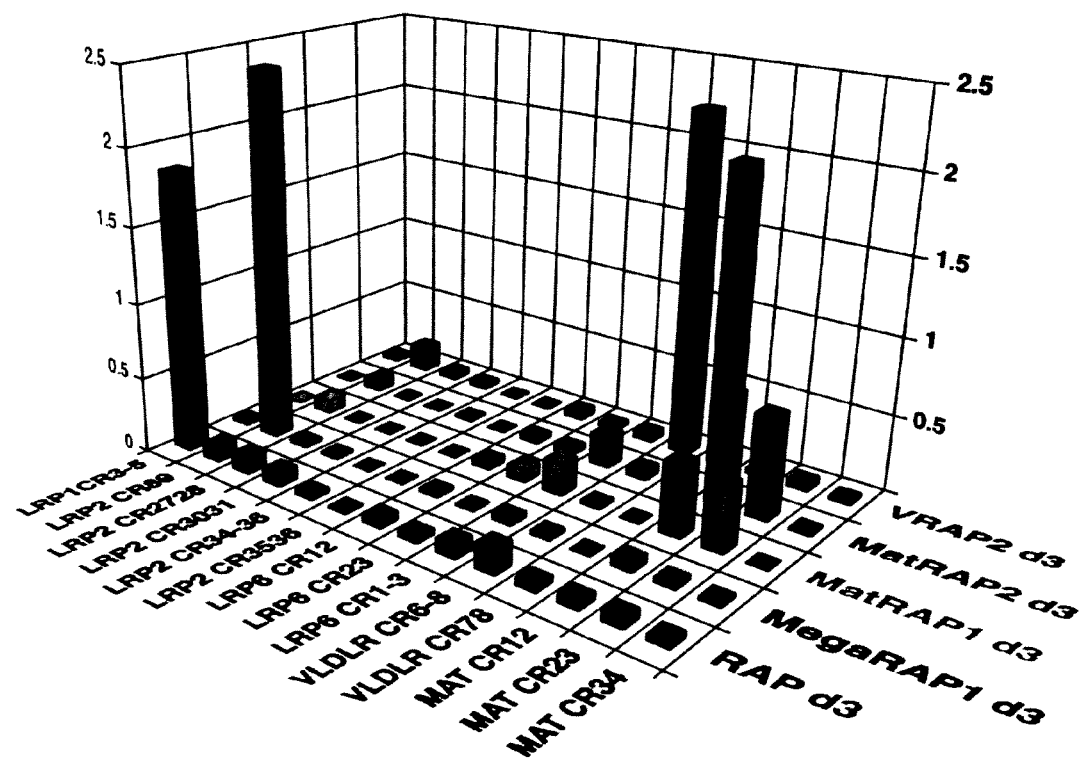
FIG. 7 shows binding of RAP d3 variants to CR pairs. RAP d3, MegaRAP1 d3, VRAP2 d3, MatRAP1 d3 and MatRAP2 d3 were each incubated at 80 nM concentrations with LRP1 CR3-5, LRP6 CR12, LRP6 CR23, LRP6 CR1-3, LRP2 CR89, LRP2 CR2728, LRP2 CR3031, LRP2 CR3435, LRP2 CR34-36, VLDLR CR78, VLDLR CR6-8, MAT CR12, MAT CR23 and MAT CR34. Samples were tested twice, in duplicate, and values combined. Means and standard deviations were then calculated. Blank values obtained from wells incubated in the absence of ligand were used to correct absorbance data. Coefficients of variance (CV) did not exceed 20% (mean of 6%) for any condition tested and are not shown.
Figure 11A:
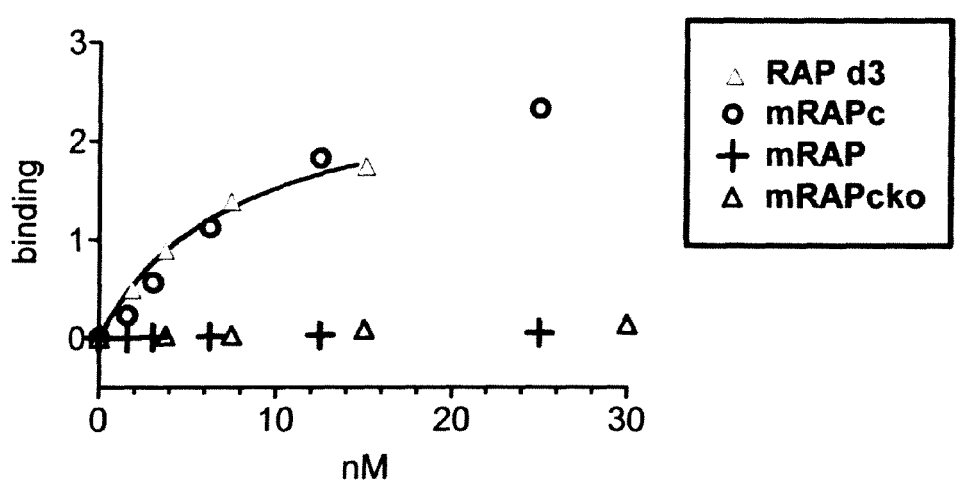
FIGS. 11A and 11B show the relative binding of RAP peptides to rhLRP1 cluster 2 and to rmVLDLR ectodomain, respectively.
Figure 11B:
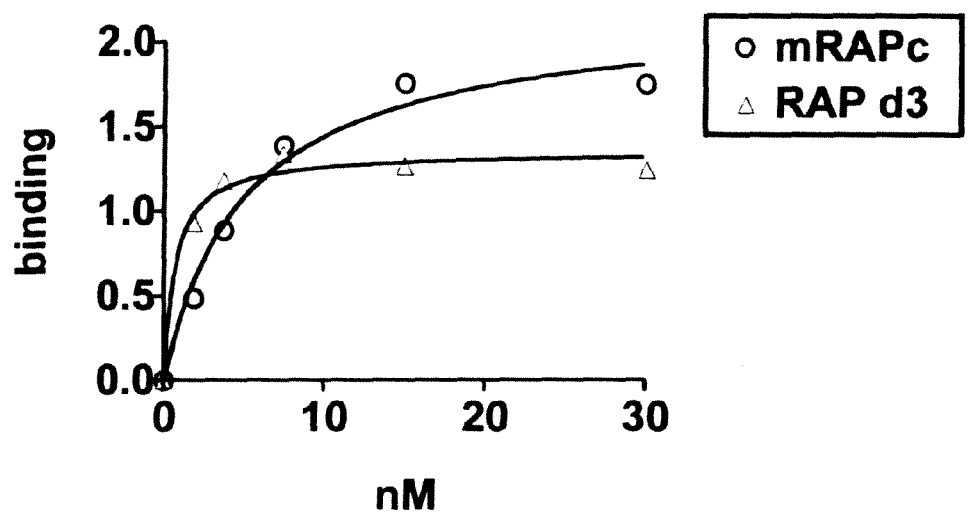

The apparent dissociation constant for binding of VRAP1 d3 to VLDLR CR78 was determined to be 44±9 nM. We then compared binding of RAP d3, MegaRAP1 d3, VRAP1 d3, MatRAP1 d3 and MatRAP2 d3, each at a concentration of 80 nM, to fourteen CR pairs or triplets, including LRP1 CR3-5, LRP2 CR89, LRP2 CR2728, LRP2 CR3031, LRP2 CR34-36, LRP2 CR3536, VLDLR CR78, VLDLR CR6-8, LRP6 CR1-3, LRP6 CR12, LRP6 CR23, MAT CR12, MAT CR23 and MAT CR34 (FIG. 7). As before, RAP d3 only bound to LRP1 CR3-5. MegaRAP1 d3 bound only to LRP2 CR89. VRAP1 d3 bound to both VLDLR CR78 and VLDLR CR6-8, a triplet that includes the CR78 pair. MatRAP1 and MatRAP2 bound to both MAT CR12 and MAT CR23 but not appreciably to the other CR pairs.

In addition to panning on CR pairs and triplets, whole, CR pair-containing human proteins were used as targets for the RAP d3 variant phage panning procedure. These commercially-available proteins included the ectodomains of corin, LRP6, FDC-8D6 antigen and complement factor I. Panning was performed exactly as described for isolated CR pairs and triplets.

Example 2

Evaluation of RAP Variants or CR-Specific Antibody Using In Vitro and In Vivo Assays RAP variants or CR-specific antibodies are useful as therapeutic agents or to transport therapeutic or diagnostic agents across the blood-brain barrier or other types of tissue membranes to treat a variety of human conditions or disorders. In vitro activity or transport assays and in vivo measurement of RAP variant activity or distribution are examples of methods to assess the efficacy of RAP variants. Examples of such assays are disclosed below.

Preparation of Cr-specific antibodies binding to any of the repeated Cr domains described herein may be carried out using any means known in the art, and antibodies thus prepared may be screened for relatively higher binding to the desired CR pairs compared to other CR pairs. Antibodies thus selected will then be tested for binding to the desired CR-containing protein compared to one or more other CR-containing proteins in the family. Antibodies that meet these criteria can then be assayed, alone or conjugated to other active agents, for ability to target to desired tissues, alteration of receptor activity, and/or prevention or treatment of disease in exemplary assays as described below.

In Vivo Anti-Tumor Assays Using Matriptase-Selective RAP Variants

To assess the antagonistic effect that matriptase-selective RAP variants or a CR-specific antibody have on tumor formation and progression, at least two in vivo models can be used. The first model utilizes nude mice innoculated with human tumor cell lines and is well-described in the literature. This system is useful for testing the ability of RAP variants or a CR-specific antibody to slow tumor progression. The second model utilizes a transgenic mouse model that overexpresses mouse matriptase under control of the keratin promoter, restricting expression to epithelial tissues. This model has also been described previously (List et al., Genes and Development, 2005, 19:1934-1950).

In Vitro Transport Assays of LRP2 and VLDLR-Selective RAP Using Recombinant MDCK Cells To assess the transport of RAP variants or CR-specific antibodies across cell membranes, in vitro transport assays are used. Stably-transfected MDCK cells expressing a mini-receptor of human LRP2 (LB2) and full-length human VLDLR are cultured in vitro. These cells are plated on Transwell polyacetate membrane inserts (Costar, Cambridge, Mass.) having a uniform pore size of 0.4 μm. Cells are seeded at a density of $2 \times 10^5$/ml and cultured in DMEM supplemented with 10% FBS. Medium is changed every three days. The cells are maintained in a 5% $CO_2$ incubator at 37° C. Transcytosis studies are performed in triplicate. Twenty minutes before the transport assay, the Transwell insert is equilibrated in transport buffer (Hank's balanced salt solution with 25 mM HEPES and 0.1% albumin) at 37° C. Transport is initiated by addition of $^{125}$I-RAP variant (1 μCi/ml) and $^{99}$mTc-albumin (2 μCi/ml) to the upper or lower chambers. The plate is maintained at 37° C. with gentle agitation at 130 rpm during the entire procedure. At 5, 10, 15, 20, 30, 40, 50, and 60 minutes following addition of labeled protein, a 10 μl of sample is collected from the lower chamber and upper chambers of each well. At 60 minutes, the entire solution in the upper and lower chambers is transferred to separate test tubes on ice. The total radioactivity from $^{125}$I and $^{99}$mTc is measured simultaneously in a γ-counter with a dual-channel program. The amount of intact RAP and albumin after transport is measured by acid precipitation and comparison of radioactive counts in the soluble and insoluble fractions of the sample.

Measurement of Tissue Distribution of RAP and RAP Variants in Mice

To determine the ability of the RAP variants or CR-specific antibodies to transcytose tissue in vivo, the tissue distribution of RAP variants or CR-specific antibodies in tissue samples from treated animals is measured.

Male CD1 mice, weighing 25-35 grams (Charles River Laboratories), are anesthetized by intraperitoneal injection of pentobarbital 30 mg/kg and ketamine 30 mg/kg. Each mouse receives a bolus injection of $^{125}$I-RAP or RAP variant or CR-specific antibody and $^{131}$I-albumin as a vascular space marker (1 μCi of each labeled protein in lactated Ringers with 1% albumin) through the left jugular vein. At designated intervals (1-60 minutes after injection), blood is collected by cutting the right common carotid artery, and the mouse was decapitated. Brain and peripheral tissue samples are collected and assayed for weight and radioactivity. Volumes of distribution are calculated as using techniques well-known in the art. A decrease in radioactivity in tissue samples indicates that the RAP variant is competing for binding with the labeled wild-type RAP and is internalized instead of wild-type RAP.

Measurement of the Anti Proliferative Effects of LRP6-Selective RAP Variants in Cell Proliferation Assays LRP6 overexpression has been correlated with increased tumorigienicity. RAP protein is a potent binder of LRP6, and variants of RAP may be useful to inhibit RAP/LRP6 interaction, or to deliver drug to LRP6 expressing cells. To examine the ability of RAP variants to modulate LRP6-mediated cell-proliferation, cell proliferation assays are performed.

HT1080 cells transfected with an LRP6 expression construct (Li, (2004) Oncogene 23, 9129-9135) seeded into 6-well plates ($5 \times 10^4$ cells per well). RAP variants and other test compounds are included in the growth medium at 5-50 nM. Medium is changed and cells harvested each day. Cells are counted and scored for viability using a Vi-Cell cell analysis system. Doubling times under the various test conditions are obtained by non-linear regression using GraphPad Prism software. A decrease in cell proliferation in the presence of RAP variants indicates the RAP variants are effective inhibitors of LRP6 induced cell proliferation. Similar assays can be carried out with CR-specific antibodies.

Measurement of the Anti-Proliferative Effects of LRP6-Selective RAP Variants in Soft Agar Colony Assays HT1080 cells transfected with an LRP6 expression construct are cultured in 6-well plates coated with an agar layer (DMEM medium with 0.5% agar and 5% FBS). Cell are seeded within a second layer containing $2 \times 10^3$ cells in DMEM with 0.33% agar and 5% FBS. The agar and cells are overlaid with medium to prevent drying. Test compounds, including RAP variants, are added directly to the medium and allowed to incubate with the cells. Medium is exchanged every three days. Triplicate wells are prepared for each cell line. After 3 weeks of incubation, colonies larger than 0.1 mm in diameter are scored. A decrease in colony formation in the presence of RAP variants indicates that RAP variants are effective inhibitors of LRP6 induced cell proliferation.

Measurement of the Anti-Tumor Effects of LRP6-Selective, Matriptase-Selective and FDC-8D6-Selective RAP Variants in a Nude Mouse Model of Tumorigenicity To examine the effects of RAP variants on LRP6, matriptase or FDC-8D6 antigen inhibition in vivo, experimental animal models of tumorigenicity are used. Similar assays can be carried out with CR-specific antibodies.

Female athymic nude mice (4-5 weeks old) (Harlan Sprague-Dawley) (Indianapolis, Ind.). are injected subcutaneously in the flank (9) with HT1080 cells transfected with an LRP6 expression construct ($6\times10^6$ cells in 200 µL of serum free DMEM with 50% Matrigel matrix (BD Biosciences)), CWR22R prostate carcinoma cells (matriptase) (67) or L3055 Burkitt's lymphoma cells (FDC-8D6 antigen) (36). Selective RAP variants, or vehicle alone, are administered by tail vein injection in sterile PBS every other day to mice receiving tumor cells or control animals. Tumor size are measured every 7 days, and tumor volumes calculated using width (a) and length (b) measurements (a2×b/2, where a<b).

Measurement of the Effects of RAP Variants on LRP5-Dependent Wnt Signaling in Cultured Osteoblasts Wnt signaling through LRP5 has been demonstrated to increase osteoblast differentiation, inhibit osteoclast activity and enhance bone deposition (Westendorf, (2004) Gene 341, 19-39; Zhang, et al., (2004) Mol Cell Biol 24, 4677-4684; Mizuguchi, et al., (2004) J Hum Genet. 49, 80-86). Because RAP binds to CR in LRP5, RAP variants may be useful to modulate Wnt signaling through the receptor. The ability of RAP variants to modulate Wnt signaling is measured using cultured osteoblasts. Similar assays can be carried out with CR-specific antibodies.

Osteoblast cell lines MG63 expresses large amounts of LRP1 and no VLDLR. SAOS-2 cells express large amounts of VLDLR and almost no LRP1 (American Type Culture Collection (ATCC) Accession #HTB-85. MG63 and SAOS-2 cells are grown in DMEM supplemented with 10% FBS at 37° C. in 10% CO2. Media are supplemented with Wnt7a to induce the Wnt signaling pathway, along with buffer, DKK-1, Mesd, RAP or RAP variants. After washing in ice-cold PBS, cells are collected and homogenized in a glass Dounce homogenizer with 100 mM Tris-HCl, pH 7.4, 140 mM NaCl, 2 mM DTT, 2 mM PMSF, and 1× Complete™ protease inhibitors (500 µl/well). The homogenate is centrifuged for 10 minutes at 500×g, and the supernatant is further centrifuged at 100,000×g at 4° C. for 90 minutes. The β-catenin levels are measured in the clarified supernatant by Western blotting using β-catenin-specific antibody from Cell Signaling Technology. The immunoreactive proteins are detected using the ECL system. Alternatively, cells are first transfected with 0.5 µg of the TOP-FLASH TCF luciferase construct (Upstate Biotechnology) along with 0.5 µg of β-catenin-expressing vector, 0.5 µg of Wnt1-expressing vector, or empty pcDNA3 vector. A β-galactosidase-expressing vector (Promega, Madison, Wis.) is included as an internal control for transfection efficiency. After 48 hours, media is changed and either buffer, DKK-1, Mesd, RAP or RAP variants is added. After incubating for an addition 6 hours, cells are lysed and both luciferase and β-galactosidase activities determined with enzyme assay kits (Promega). The luciferase activity is determined with a luminometer using the Dual Luciferase Assay system (Promega). Luciferase activity is normalized to the activity of the β-galactosidase.

Example 3

Production and Characterization of Cyclic RAP Peptides

Cyclic RAP peptides were produced and characterized for binding affinity as follows. RAP peptides were manufactured by Abgent (San Diego). Peptides were purified by HPLC and characterized by mass spectrometry. NS0-expressed and purified recombinant mouse VLDLR ectodomain and recombinant human LRP1 ligand binding cluster II were purchased from R&D Systems (Minneapolis). Tag-free RAP d3 was expressed and purified by GeneScript (San Diego). Human RAP was obtained from Dr. Guojun Bu (Washington University in St. Louis, School of Medicine). Bradford assays were used for protein quantification.

Solid phase binding assays were carried out as follows. Recombinant murine VLDLR ectodomain (aa 1-798, C-terminal hexahistidine, 1 µg) or rhLRP1 cluster II (aa 786-1165, C-terminal Fc, 1 µg) were bound to Nunc Maxisorp™ 96-well plates in TBS pH 8 supplemented with 5 mM $CaCl_2$ (TBSC) overnight at 4° C. Wells were washed with TBSC and then blocked with TBSC containing 2% BSA. Peptides were then incubated with the immobilized receptor at a range of concentrations for 2 hours in the above blocking buffer supplemented with 0.05% Tween-20 at room temperature. Identical binding reactions were done in the presence of 50 mM EDTA to provide a measure of non-specific binding. Control wells contained no added peptide. Additional controls established absence of cross-reactivity between antibodies and receptors. Wells were washed with TBSTC and bound peptides detected with streptavidin-HRP (Pierce) or polyclonal anti-RAP (1:1,000, Raptor Pharmaceutical). Binding of the anti-RAP polyclonal antibody to test peptides was qualitatively confirmed by Western blotting (data not shown). Excess streptavidin-HRP or primary antibody was removed and wells washed before incubation with the secondary antibody, when necessary, HRP-conjugated goat anti rabbit IgG (Bio-Rad). Color was developed using TMB reagents (Bio-Rad). Absorption at 450 nm was measured with a microplate spectrophotometer (Molecular Devices). Absorption obtained in the presence of EDTA was subtracted from absorption obtained in the presence of calcium prior to analysis. Data were plotted and $K_d$ values derived by non-linear regression with the assumption of single-site binding (GraphPad Prism).

A bacterially-expressed, purified, tag-free RAP d3 peptide comprising amino acids 201-319 of mature, human RAP was purchased from GeneScript. This peptide lacks the C-terminal HNEL tetrapeptide (SEQ ID NO: 108). A unique cysteine was included at the C-terminus to facilitate affinity tagging. The RAP d3 peptide was linked to maleimide-$PEO_2$-biotin (Pierce) and the resulting conjugate purified by desalting and trapping of unreacted peptide with activated thiol Sepharose beads (GE Biosciences). All other peptides were made by solid-phase peptide synthesis. Inspection of structural data for the complex between RAP d3 and LDLR CR3 and 4 suggested that significant truncation of RAP d3 could be performed without removal of residues that make up the contact surface with CR pairs. Since some of the sequences flanking the contact surface have been implicated in fold stabilization, we reasoned that a non-native disulfide could be introduced as a means of stabilizing the folded structure in their absence. To create a minimized version of RAP d3, mRAPc (SEQ ID NO: 99), closely opposed pairs of residues located N-terminally to H249 on helix 1 and C-terminal to T303 on helix 2 in the structure of the RAP d3 LDLR CR3 and 4 complex were identified and replaced with glycines. These substitutions were A242G and R314G. Introduction of glycines at these sites was intended to allow a break in the helix for an adjacent non-native inter-helical disulfide bond. Two cysteines were then substituted before and after G242 and G314 in helix 1 and 2, respectively, to allow the formation of a disulfide bond. These substitutions were E241C and I315C.

No additional residues were included C-terminally to C315 in helix 2. The sequence biotin-GGSGG (SEQ ID NO: 102) was added N-terminally to E241C in helix 1 to allow efficient detection with streptavidin-reporter conjugates. The peptide was cyclized through intramolecular disulfide bond formation during solid-phase synthesis. For a linearized control of the mRAPc peptide, termed mRAP, both cysteines were substituted with serines. As an additional control for mRAPc, an otherwise identical peptide with the mutations K256A and K270E was made, mRAPcko. These mutations have been previously shown to significantly lower the affinity of RAP d3 for LRP1.

The binding affinity of the peptides for LRP1 and VLDLR, another receptor in the LDLR family, was measured as follows. NS0-expressed and purified hrLRP1 or mVLDLR (R&D Systems) were use to coat wells in 96-well plates. Various dilutions of the test peptides were incubated with the immobilized receptors in the presence and absence of 50 mM EDTA in triplicate. Bound peptides were detected with streptavidin-HRP after extensive washing. Binding values measured in the presence of EDTA were subtracted from values measured in the absence of EDTA in order to determine calcium-dependent binding levels. Corrected values were plotted and fitted by non-linear regression with the assumption of a single-binding site using GraphPad Prism. Results are displayed in FIGS. 12A and 12B.

While mRAP (SEQ ID NO: 107) and mRAPcko had no measurable affinity for hrLRP1 cluster II, mRAPc bound with high-affinity in a calcium-dependent fashion with a $K_d$ of 10±2 nM. This binding affinity was not distinguishable from that of full-length RAP d3 in this system (8±1 nM). In addition, the binding of the peptides to the entire ectodomain of mouse VLDLR was measured. Binding affinities were again comparable, with dissociation constants of 5±1 nM for mRAPc and 1±0.2 for full-length RAP d3.

Example 4

Characterization of Additional Cyclic RAP Peptides

Additional cyclic RAP peptides were developed as described above and tested for their ability to bind to the LRP1 receptor.

To generate the mRAP-8c peptide, the truncated RAP peptide sequence from amino acids 246 to 312 was utilized, and amino acid substitutions were made as follows: E246C, L247G and L311G and S312C. The mRAP-8c peptide is set out in SEQ ID NO: 100. To generate a further truncated peptide, mRAP-14c, a truncated RAP starting at position 250 and ending at position 309 was used. Amino acid substitutions were made for mRAP-14c as follows: F250C and L308G and Q309C. No glycine was substituted after the cysteine in the case of mRAP-14c because the F250C sidechain from helix 1 is already pointed directly at helix 2 in the structure of the complex. The sequence of mRAP-14c is set out in SEQ ID NO: 101. Another truncated, cyclized peptide, Heptide, was developed. The Heptide sequence is derived from amino acids 246 to 313 of RAP. Amino acid substitutions were made to generate Heptide as follows: E246C, L247G, G280A, L311A, and S312C. The sequence of Heptide is set out in SEQ ID NO: 103.

Binding of the mRAP-8c and mRAP-14c peptides to the LRP1 and VLDLR receptors was assessed as above. mRAp-8c bound to the LRP1 (cluster II) receptor with approximately 4 to 6 nM affinity (in two separate assays) while mRAP-14c bound with an affinity of approximately 21 nM. The Heptide cyclic peptide bound to LRP1 with an affinity of approximately 3.5 nM.

These results demonstrate that several different cyclic RAP peptides are able to bind the LRP1 receptor with high affinity.

Example 5

Binding of Cyclic RAP Peptides to Cells In Vitro

In order to determine the ability of the cyclic RAP peptides to bind receptor on the surface of a cell, binding was assessed in the presence of cultured cell lines. To determine whether cyclic RAP peptides could be bound and endocytosed by full-length LRP1 expressed on cells in culture, an endocytosis-dependent toxicity assay was used. Two cell-lines were used, Chinese hamster ovary CHO-K1 cells expressing only one high-affinity RAP-receptor, LRP1, and a mutant CHO-K1 lacking LRP1 expression was used as control. Cells were cultured in BioWhittaker UltraCHO medium (Lonza, Basel, Switzerland) supplemented with 2.5% fetal bovine serum. Cells were seeded in 12-well tissue culture plates. The biotinylated mRAPc was combined with equimolar amounts of a conjugate between streptavidin and the bacterial toxin saporin (ZAP, Advanced Targeting Systems, San Diego, Calif.). The mixture was diluted in MEM without phenol red (Mediatech, Manassas, Va.) supplemented with 10% FBS to 100 nM. Conjugated mRAPc (100 nM) and control agents (mRAPc alone, 100 nM, streptavidin-saporin alone, 100 nM, saporin alone, 1 mM) were cultured with confluent cells and cell death was assayed 48 hours later via MTT assay (Invitrogen, San Diego, Calif.).

Figure 12:
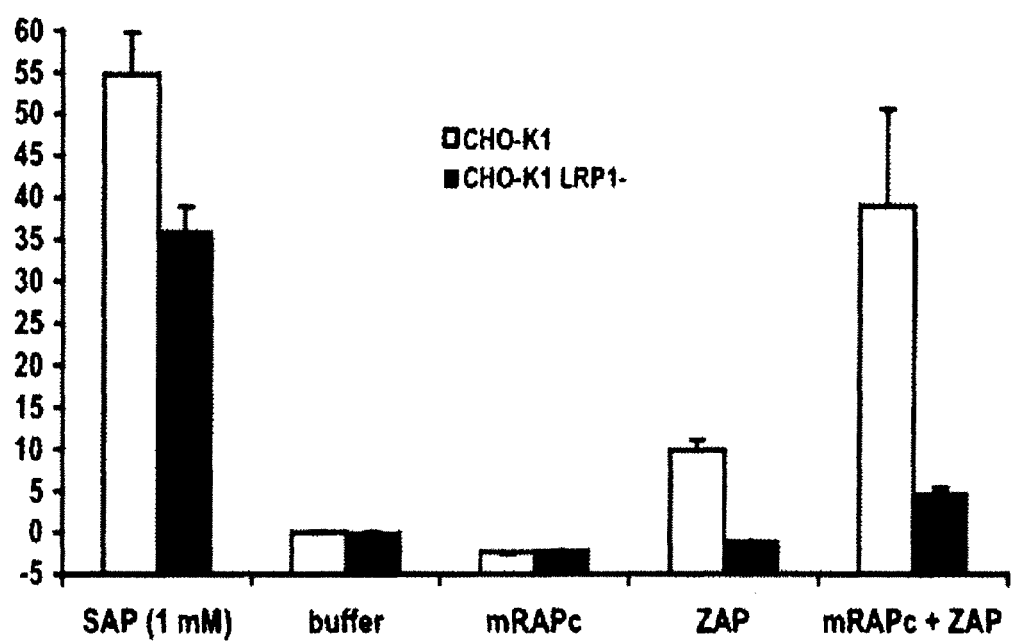
FIG. 12 shows the effect of toxin-conjugated mRAPc on cell viability of LRP-expressing and LRP-deficient CHO cells.

Results are set out in FIG. 12. The mRAPc peptide alone had no effect on cell survival, regardless of the cell-type used. The streptavidin-saporin conjugate alone reduced viable cell number by approximately 10% for wild-type CHO-K1 cells with no effect on the LRP-deficient cells. The combination of mRAPc and the cytotoxic conjugate reduced viable cell number by nearly 40% for wild-type CHO-K1 with only a 5% loss for the LRP-deficient cells.

These data suggest that the mRAPc peptide can significantly enhance the toxicity of the cytotoxic conjugate in a receptor dependent manner by internalizing the toxin through the LRP1 endocytic pathway.

Binding inhibition assays were also carried out to determine the ability of the mRAPc peptide to interfere with RAP d3 binding to LRP1 (cluster II), as well as binding of LRP ligands α-2-macroglobulin and uPA/PAI-1. To allow complexation with streptavidin or an anti-biotin antibody, the mRAPc peptide was fitted with an N-terminal biotin residue separated from the RAP sequence by a pentapeptide linker (GGSGG). Solid phase binding assays were performed using recombinant human LRP1 cluster II (amino acids 786-1165, with C-terminal Fc tag, 1 µg, R&D Systems, Minneapolis, Minn.) to coat Nunc MAXISORP™ 96-well plates in TBS pH 8 supplemented with 5 mM $CaCl_2$ (TBSC) overnight at 4° C. Data was generated by ELISA assay. Wells were washed with TBSC and blocked with TBSC containing 2% BSA. In assays involving complexes between streptavidin and biotinylated peptide, LRP1 ligands (RAP d3 (2 nM), trypsin-activated α-2-macroglobulin (1 nM) or uPA/PAI-1 (10 nM) were incubated with the immobilized receptor, in the presence or absence of inhibitors, for 2 hours in the above blocking buffer supplemented with 0.05% Tween-20 at room temperature. In assays involving complexes of the anti-biotin antibody and biotinylated peptide, all inhibitor solutions were pre-incubated with immobilized LRP1-C2 prior to washing and subsequent incubation with ligand. Since the ligand binding competence of CR pairs requires calcium, identical binding reactions were done in the presence of 50 mM EDTA to provide a measure of non-specific binding. Control wells contained no added inhibitor. Wells were washed with TBS supplemented with 5 mM $CaCl_2$ and 0.05% Tween-20. Bound ligand was detected with either anti-S-peptide-HRP conjugate (Abcam, Cambridge, Mass.), anti-α-2-macroglobulin-HRP or anti-PAI-1-HRP. Excess HRP conjugate was removed and wells washed. Color was developed using TMB reagents (BioRad, Hercules, Calif.). Absorption at 450 nm was measured with a microplate spectrophotometer (Molecular Devices, Palo Alto, Calif.).

Figure 14A:
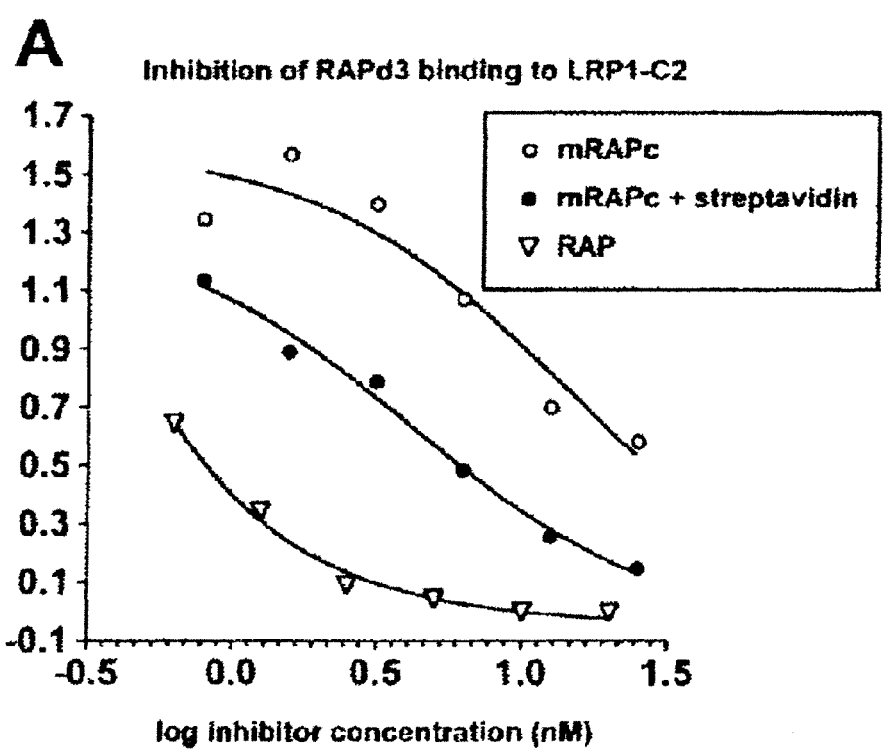
FIGS. 14A, 14B and 14C shows the inhibition of RAP, and uPA-PAI-1 binding to LRP1 receptor by mRAPc peptide and mRAP conjugated to streptavidin.

The ability of mRAPc, in the presence and absence of either streptavidin or anti-biotin antibody, to inhibit binding of recombinant RAP d3 to LRP1-C2 was measured. The degree of inhibition ($EC_{50}$) for the monomeric peptide was 32±12 nM (FIG. 14A). The $EC_{50}$ for mRAPc combined with one half mole equivalent of streptavidin, but under otherwise identical conditions, was 4±2 nM, a near 8-fold improvement over peptide alone (FIG. 14). Mature RAP had an $EC_{50}$ of 0.5±2 nM, 64-fold better than monomeric mRAPc peptide and about 8-fold better than peptide assembled on streptavidin. The streptavidin alone had no inhibitory effect. The multifold enhancement of inhibition seen in the presence of streptavidin is consistent with an improvement in avidity upon multimerization of the minimized RAP domain.

Figure 14B:
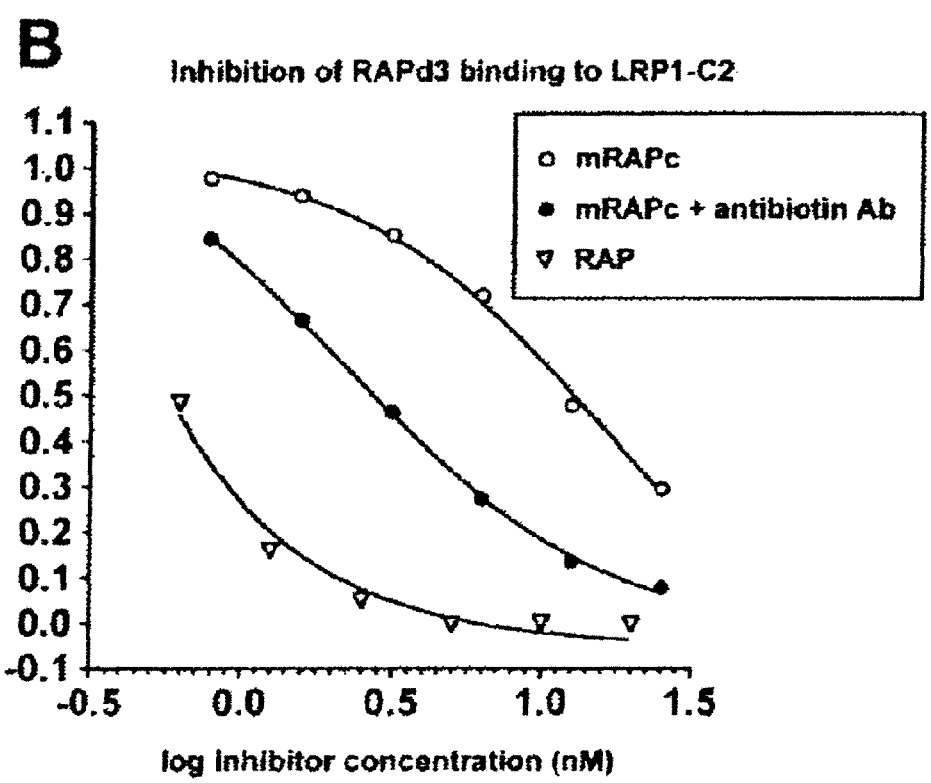
Figure 14C:
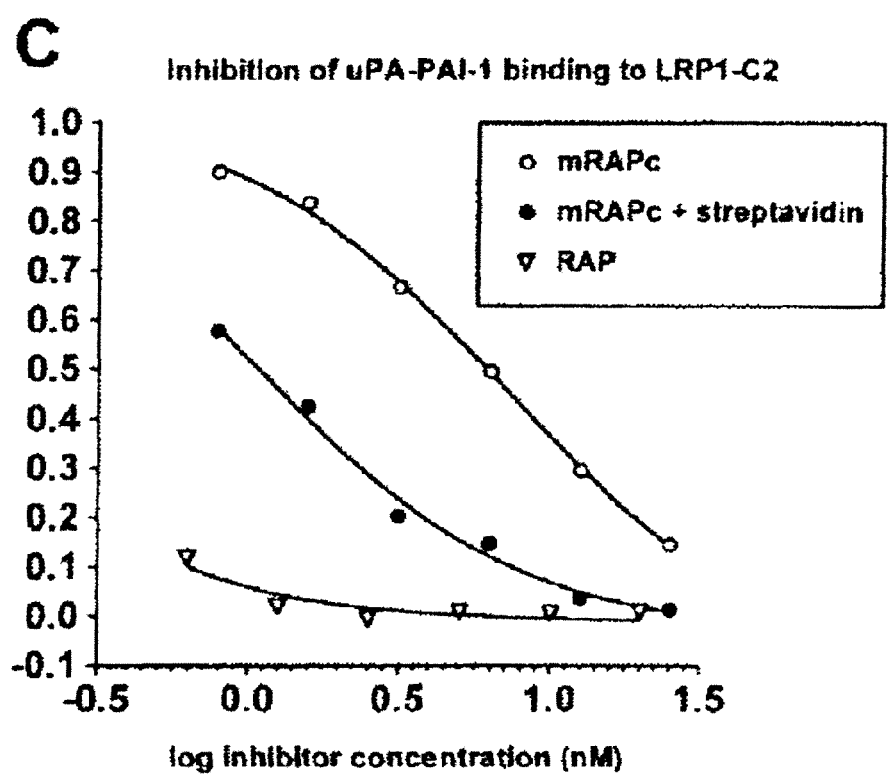

Given the relatively weak monovalent affinity of the anti-biotin antibody for biotin (low nanomolar KD), it was hypothesized that preassembly of a multivalent complex consisting of two, suitably proximate, receptor-bound peptides and a single antibody would stabilize the peptide-antibody complex. Therefore, the antibody and peptide, in a molar ratio of one to three, was incubated with the immobilized receptor prior to washing and subsequent addition of the RAP d3 ligand. The same procedure was performed for the controls; peptide alone, antibody alone and RAP. Using this method, an $EC_{50}$ was derived for the mRAPc peptide alone of 17±1 nM (FIG. 14B). Combination of mRAPc with the anti-biotin antibody yielded an $EC_{50}$ of 2±1 nM. Full-length RAP gave an $EC_{50}$ of 0.3±7 nM. Antibody alone had no inhibitory effect. As was the case with tetravalent streptavidin, addition of the bivalent antibody significantly improved the ability of the peptide to inhibit binding of RAP d3 to LRP1-C2. Next the effect of the multimerized mRAPc was determined. The multimerized mRAPc was compared to the mRAPc monomer and full-length RAP in the inhibition of binding of two other ligands to LRP1-C2, trypsin-activated α-2-macroglobulin and the uPA/PAI-1 complex, at a single ligand concentration. The complex of streptavidin and mRAPc inhibited binding of the heterologous ligand with as $EC_{50}$ of 1±1 nM, 7-fold better than monomeric peptide alone, at 7±1 nM (FIG. 14C). In both cases, the complex of streptavidin and mRAPc inhibited binding with an $EC_{50}$ approximately midway between RAP and the mRAPc monomer.

These results demonstrate that the avidity advantage of multivalent RAP in binding multivalent receptors. The results show that a synthetic peptide sequence multimerized on streptavidin or an immunoglobulin is capable of partially recapitulating the inhibitory potency of full-length RAP against three LRP1 ligands.

Example 6

Administration of Cyclic RAP Peptides In Vivo

The previous results demonstrate that the truncated, cyclized RAP peptides efficiently bind LRP1 receptors on the surface of cells in vitro. In order to measure the efficacy of the cyclic RAP peptides in vivo, biodistribution assays were performed.

Studies were performed at Charles River Laboratories in Montreal, Canada. Biotinylated mRAPc peptide, biotinylated RAP protein or buffer were combined with $^{35}$S-SLR-streptavidin (0.7 mCi/mL, 300 Ci/mmol, GE Healthcare) and dialyzed against phosphate-buffered saline (PBS) with D-TUBE™ dialysis cassettes (14 kD MWCO, EMD Biosciences/Merck, Darmstadt, Germany). Male Sprague-Dawley rats (6-8 weeks) were injected with test materials (2 µL/g; ~20 µCi/rat) through a tail vein. Animals were sacrificed thirty minutes post-injection with pentobarbital (200 mg/kg). All subjects were treated in accordance with the guidelines set by the Canadian Council on Animal Care for the humane treatment of laboratory animals. Carcasses were frozen, embedded in carboxymethycellulose and sectioned for analysis by semi-quantitative whole-body autoradioluminography (QWBA) using a Fuji BAS-2500 phosphorimager. Clearly delineated areas within assayed organs for each animal were selected for luminescence analysis (Fuji Image Reader v1.1 and Fuji Image Gauge v3.12). Values are reports in units of photostimulated luminescence per unit area (PSL/mm2).

Given the potency of multimeric mRAPc in the inhibition of binding to LRP1-C2, the efficacy of the multimeric peptide and its ability to would mimic the in vivo biodistribution behavior of full-length RAP following intravenous injection was determined. This behavior is characterized by primary accumulation in the liver (Warshawsky et al., J Clin Invest 92:937-944, 1993), where blood access to LRP1 on hepatocytes is high (Beisiegel et al., Nature 341:162-164, 1989; Moestrup et al., Cell Tissue Res 269:375-382, 1992). A preparation of $^{35}$S-labeled streptavidin was combined with the biotinylated mRAPc peptide, in a molar ratio of twenty to one, or with in vivo biotinylated RAP, in a molar ratio of five to one, and injected intravenously into rats. Labeled streptavidin alone was used as a control. Streptavidin has been reported to accumulate in kidney, but not significantly in liver, following intravenous injection (Wilbur et al., Bioconjug Chem 9:100-107, 1998; Rosebrough et al., J Nucl Med 37:1380-1384, 1996).

Figure 15:
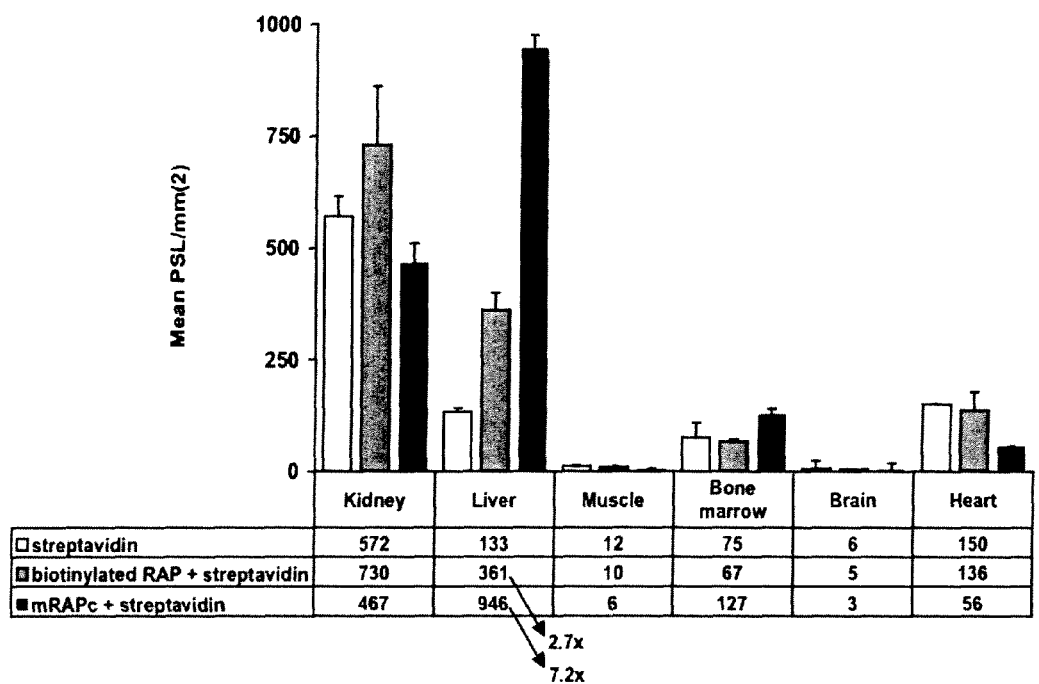
FIG. 15 illustrates the biodistribution of cyclic RAP peptide after intravenous administration in animals.

The preparation of biotinylated RAP distributed to liver at levels 2.7-fold greater than that of streptavidin alone, and at similar or lower levels in all other tissues tested (FIG. 15). The mRAPc peptide, pre-assembled on labeled streptavidin, distributed to the liver at levels over 7-fold greater than that of streptavidin alone, and with similar or lower levels compared to control in all other tissues tested (FIG. 15). It is notable that high levels of competing LRP1 ligands in the blood were apparently unable to block liver uptake of the peptide complex, an observation made previously, as well as here, for intravenously-administered full-length RAP. (See Isbell et al., Biochem Biophys Res Comm 364:614-619, 2007).

The results of the biodistribution data suggest that smaller, peptide-based, versions of RAP may prove useful in the development of pharmacological agents targeting the liver.

Example 7

Conjugates of Cyclic RAP Peptides

The RAP peptides and cyclic RAP peptides can be conjugated to various cytotoxic agents or other agents for delivery of the agents to a cell expressing a RAP receptor. Peptide conjugates are made using techniques well-known in the art.

Figure 13A:
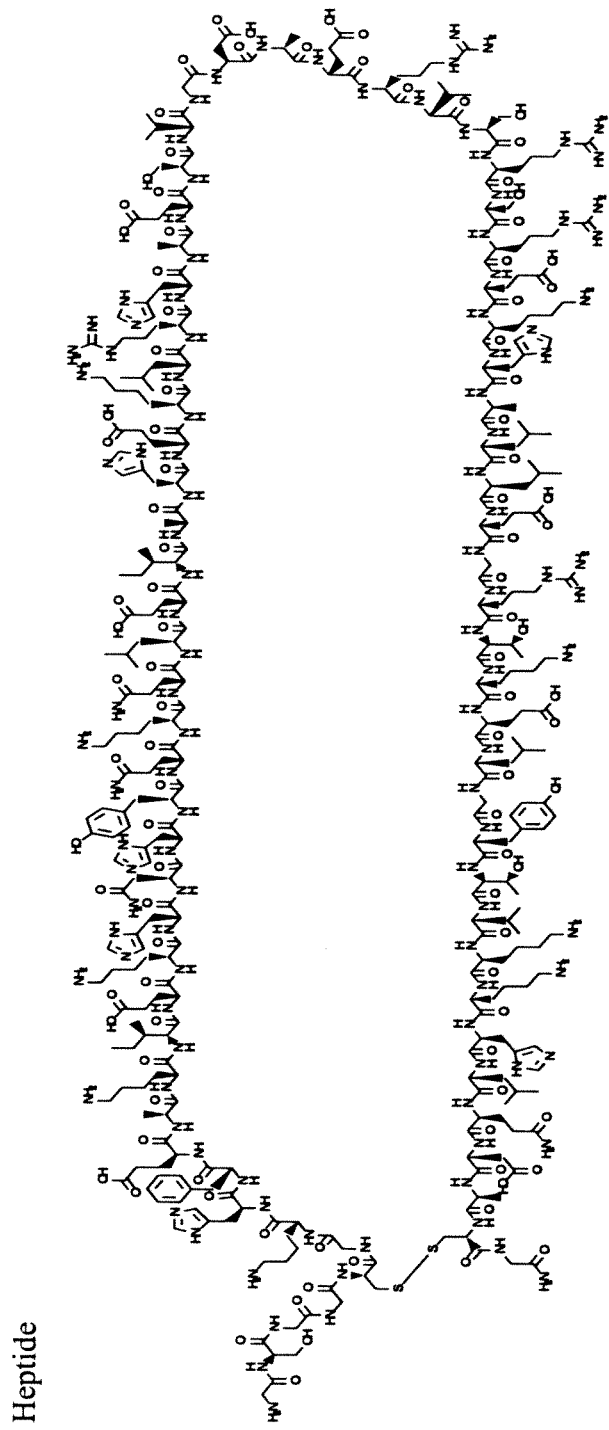
FIGS. 13A, 13B and 13C illustrate the chemical structures of the cyclic RAP peptide, Heptide, conjugated to different cytotoxic agents.
Figure 13B:
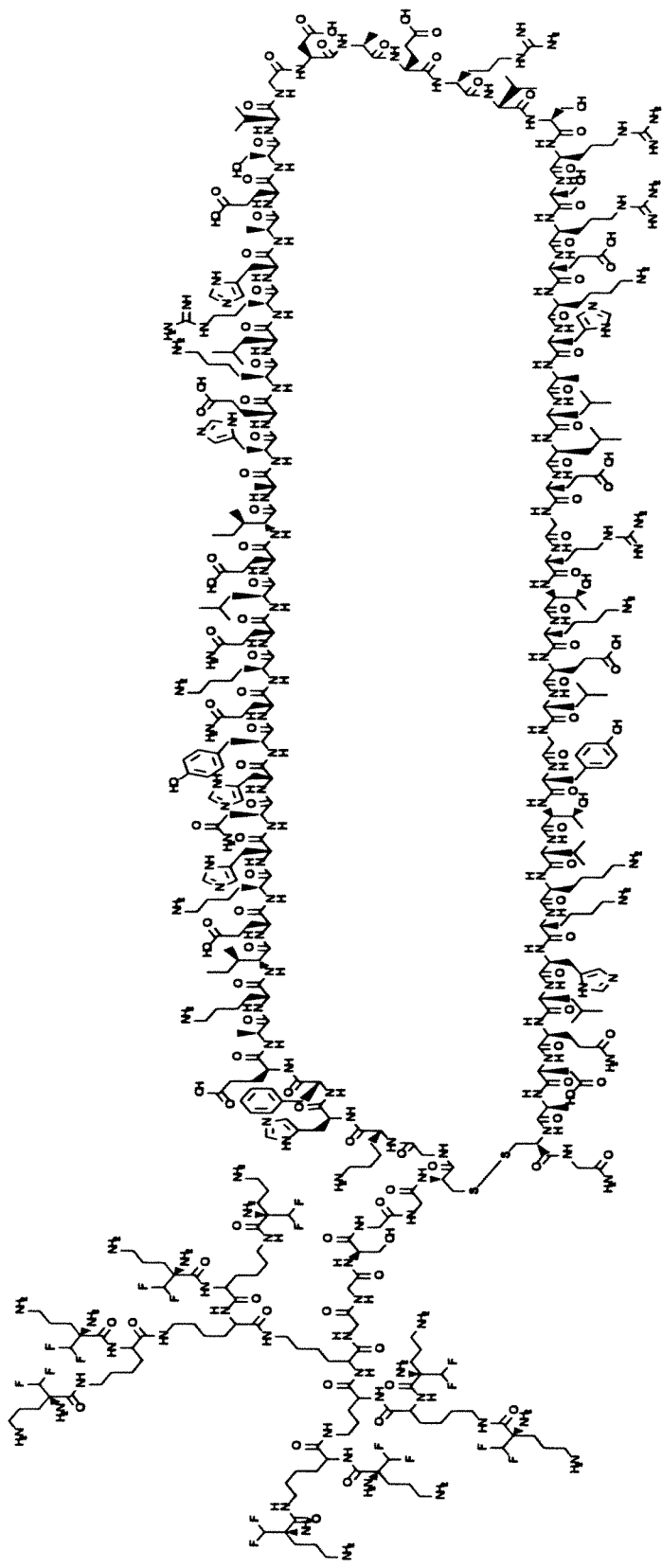
Figure 13C:
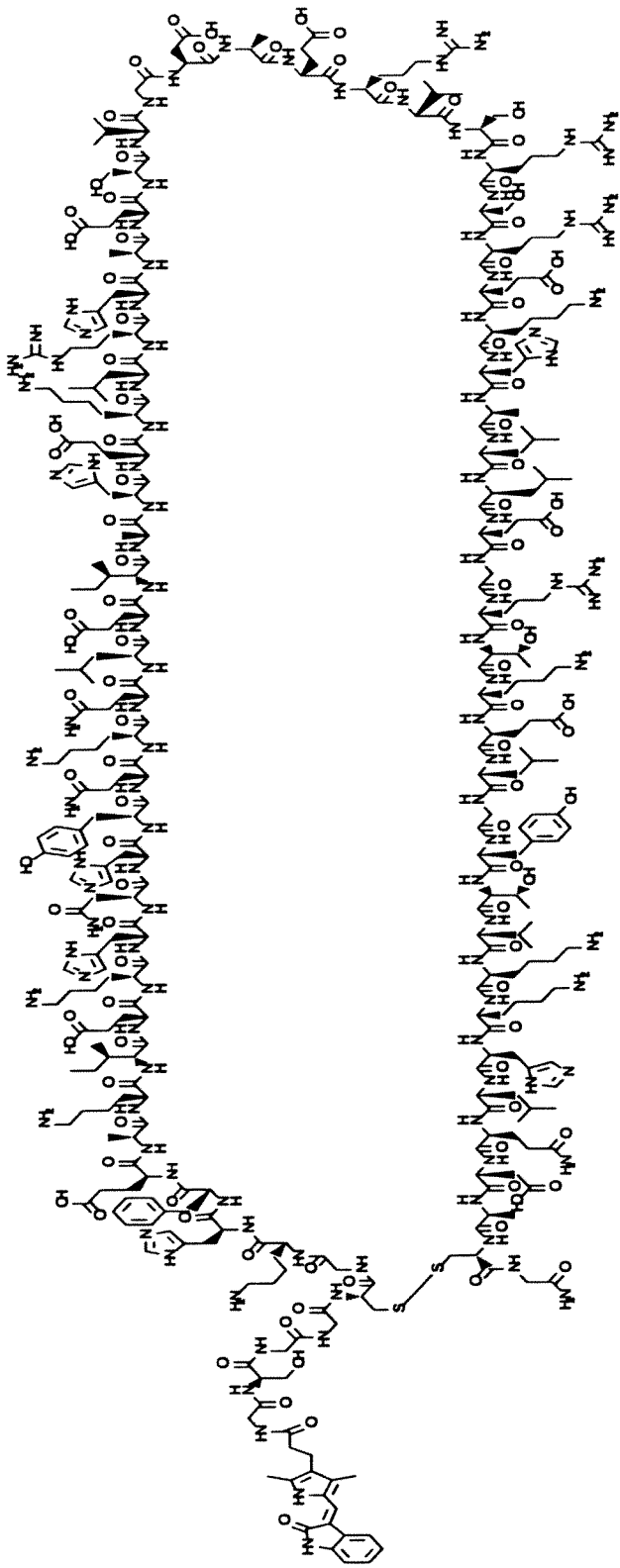

Exemplary cyclic RAP peptide conjugates are described in FIG. 13, which illustrate Heptide conjugated to difluoromethylornithine (Heptide-Octa-difluoromethylornithine) and Heptide conjugated to the tyrosine kinase inhibitor SU6668 (Heptide-mono-SU6668). The Heptide peptide in FIG. 13A (SEQ ID NO: 104) includes the pentapeptide linker GGSGG (SEQ ID NO: 102). The Heptide-mono-SU6668 is generated by conjugation of the SU6668 moiety to the N-terminal glycine on the heptide (FIG. 13C, SEQ ID NO: 105). The Heptide-Octa-difluoromethylornithine (DMFO) is generated by addition of a lysine to the N-terminal glycine of the peptapeptide. This N-terminal lysine is modified by addition of a lysine ($K_1$) further connected to two lysines ($K_2$, $K_3$), each conjugated to two DMFO moieties. The first lysine ($K_1$) is also connected to an ornithine residue comprising two DMFO moities, and further connected to a final lysine residue ($K_4$) conjugated to two DMFO residues (FIG. 13B and SEQ ID NO: 106).

Additional conjugates may be made by one of ordinary skill in the art using any of the agents described herein or known in the art.

Example 8

Administration of Conjugated Cyclic RAP Peptides In Vitro

Hepatocyte cell lines are used to assess the cell surface binding of cyclic RAP peptides as well as cyclic RAP peptides conjugated to a chemical agent.

Hepatcellular carcinoma (HCC) cell lines, such as Heb3B, HepG2 and Huh-7, or normal human hepatocyte cell lines, such as THLE-5b or primary hepatocytes (see e.g., Shimizu et al., Metabolism. 56:1478-85, 2007; Agrawal et al., Stem Cells. 2008 Feb. 21), are cultured according to techniques known in the art. Cultured cells are treated with cyclic RAP peptide conjugated with cytotoxic agents such as difluoromethylornithine (cyclic RAP peptide-octa-difluoromethylornithine) or SU6668 (cyclic RAP peptide-mono-SU6668), cyclic RAP peptide alone, or difluoromethylornitihine or SU6668 alone. Cells are treated with reagent within the following concentrations: 0.05 to 50 µM cyclic RAP peptide-octa-difluoromethylornithine, 0.2 to 200 µM cyclic RAP peptide-mono-SU6668, 0.05 to 200 µM cyclic RAP peptide alone, 0.05 to 50 µM difluoromethylornitihine or 0.2 to 200 µM SU6668. The conjugated cyclic RAP peptides are assessed for their cytostatic and cytotoxic effect on the hepatocyte cultures.

After treatment with the cyclic RAP peptide or conjugated cyclic RAP peptides, cytotoxic and cytostatic effects are measured according to techniques known in the art (see e.g., Elmore et al., In Vitr Mol. Toxicol. 14:191-207, 2001; Miret et al., J Biomol Screen. 11:184-93, 2006), and the extent of cell growth or cell death in the presence of the test agents is determined.

The ability of the conjugated cyclic RAP peptide to reduce growth of cells in culture indicates that the cyclic peptides bind to the receptor on the surface of the cells and are an effective means to deliver agents into cells resulting in a biologically measurable effect.

Example 9

Administration of Cyclic RAP Peptides In Vivo

In order to assess receptor binding of cyclic RAP peptides in vivo, as well as assess the ability of the molecule to deliver cytotoxic compounds to cells in vivo, orthotopic models of human hepatocellular carcinoma are used.

To generate orthotopic tumors in animals, human hepatocarcinoma cell lines are implanted into nude mice, rats, or other appropriate animal and the tumor cells allowed to grow in vivo. HCC cell lines useful for orthotopic models include, but are not limited to, those cell lines described above, such as Heb3B, HepG2 and Huh-7. Orthotopic tumor models of HCC are known in the art and are described in, for example, Okubo et al. (J Gastroenterol Hepatol. 2007 22:423-8); Armengol et al., (Clin Cancer Res. 2004 10:2150-7); and Yao et al., (Clin Cancer Res. 2003 9:2719-26).

To first establish a dose range for administration of the conjugated cyclic RAP peptides and controls in vivo, a small does range study is carried out using 5 mice per group, receiving conjugated cyclic RAP peptide, (e.g., either cyclic RAP peptide-octa-difluoromethylornithine (up to 200 mg/kg/day), cyclic RAP peptide-mono-SU6668 (up to 200 mg/kg/day)), cyclic RAP peptide alone (up to 200 mg/kg/day), difluoromethylornitihine or SU6668 alone. The test agents are administered either intravenously or intraperitoneally daily for two weeks (QD×14) and the subject animals tested for change in body weight, any clinical observations, and clinical pathology and tissue histopathology at study endpoint.

To carry out an efficacy study, 8 to 10 mice per group are used, and 3 test dose ranges of the compounds above (cyclic RAP peptide-octa-difluoromethylornithine, cyclic RAP peptide-mono-SU6668, cyclic RAP peptide alone, difluoromethylornitihine or SU6668) are administered to the animals receiving human HCC cells and control animals. Test agents are administered either intravenously or intraperitoneally and are administered at an appropriate frequency, e.g., daily for 4 weeks (QD×28), daily for 3 weeks (QD×21) or daily for 2 weeks (QD×14). Subject animals are then assessed for any changes in body weight, clinical observations, and in vivo efficacy measurements, such as tumor volume, liver histopathology, and general clinical pathology, using techniques known in the art.

The ability of the conjugated cyclic RAP peptides to reduce growth of hepatocellular carcinoma cells in vivo demonstrates that the cyclic peptides bind to the cellular receptor on the surface of the tumor cell and are an effective means to deliver agents into cells resulting in a biologically measurable effect. Demonstration of efficient tumor death in animal models suggests that conjugated cyclic RAP peptides are an efficient method for delivering cytotoxic agents to tumor cells in humans suffering from hepatocarcinoma or other conditions in which RAP receptors are associated.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

The references cited herein throughout, to the extent that they provide exemplary procedural or other details supplementary to those set forth herein, are all specifically incorporated herein by reference.

REFERENCES

1. MAY, P., BOCK, H. H., AND HERZ, J. (2003) *SCI STKE* 2003, PE12.
2. HERZ, J., AND WILLNOW, T. E. (1995) *ATHEROSCLEROSIS* 118 *SUPPL*, S37-41.
3. TAKAHASHI, S., SAKAI, J., FUJINO, T., MIYAMORI, I., AND YAMAMOTO, T. T. (2003) *MOL. CELL. BIOCHEM.* 248, 121-7.
4. HERZ, J., AND BOCK, H. H. (2002) *ANNU. REV. BIOCHEM.* 71, 405-34.
5. HAHN-DANTONA, E., RUIZ, J. F., BORNSTEIN, P., AND STRICKLAND, D. K. (2001) *J. BIOL. CHEM.* 276, 15498-503.
6. NEELS, J. G., BOVENSCHEN, N., VAN ZONNEVELD, A. J., AND LENTING, P. J. (2000) *TRENDS CARDIOVASC MED* 10, 8-14.
7. MARTIN, S., VINCENT, J. P., AND MAZELLA, J. (2003) *J. NEUROSCI.* 23, 1198-205.
8. SCHNEIDER, W. J., AND NIMPF, J. (2003) *CELL MOL LIFE SCI* 60, 892-903.
9. LI, Y., LU, W., HE, X., SCHWARTZ, A. L., AND BU, G. (2004) *ONCOGENE* 23, 9129-35.
10. HOANG, B. H., KUBO, T., HEALEY, J. H., SOWERS, R., MAZZA, B., YANG, R., HUVOS, A. G., MEYERS, P. A., AND GORLICK, R. (2004) *INT. J. CANCER* 109, 106-11.
11. VERDAGUER, N., FITA, I., REITHMAYER, M., MOSER, R., AND BLAAS, D. (2004) *NAT STRUCT MOL BIOL* 11, 429-34.
12. PFISTERMUELLER, D. M., BLAAS, D., AND HODITS, R. A. (1996) *FEBS LETT.* 396, 14-20.
13. HOE, H. S., HARRIS, D. C., AND REBECK, G. W. (2005) *J. NEUROCHEM.* 93, 145-55.
14. QIU, Z., CRUTCHER, K. A., HYMAN, B. T., AND REBECK, G. W. (2003) *NEUROSCIENCE* 122, 291-303.
15. BASU, S., BINDER, R. J., RAMALINGAM, T., AND SRIVASTAVA, P. K. (2001) *IMMUNITY* 14, 303-13.
16. BENCHENANE, K., BEREZOWSKI, V., ALI, C., FERNANDEZ-MONREAL, M., LOPEZ-ATALAYA, J. P., BRILLAULT, J., CHUQUET, J., NOUVELOT, A., MACKENZIE, E. T., BU, G., CECCHELLI, R., TOUZANI, O., AND VIVIEN, D. (2005) *CIRCULATION* 111, 2241-9.
17. DEHOUCK, B., FENART, L., DEHOUCK, M. P., PIERCE, A., TORPIER, G., AND CECCHELLI, R. (1997) *J. CELL BIOL.* 138, 877-89.
18. FILLEBEEN, C., DESCAMPS, L., DEHOUCK, M. P., FENART, L., BENAISSA, M., SPIK, G., CECCHELLI, R., AND PIERCE, A. (1999) *J. BIOL. CHEM.* 274, 7011-7.
19. PAN, W., KASTIN, A. J., ZANKEL, T. C., VAN KERKHOF, P., TERASAKI, T., AND BU, G. (2004) *J. CELL SCI. PT.*
20. MOESTRUP, S. K., AND VERROUST, P. J. (2001) *ANNU REV NUTR* 21, 407-28.
21. MARINO, M., ZHENG, G., CHIOVATO, L., PINCHERA, A., BROWN, D., ANDREWS, D., AND MCCLUSKEY, R. T. (2000) *J. BIOL. CHEM.* 275, 7125-37.
22. DEANE, R., WU, Z., SAGARE, A., DAVIS, J., DU YAN, S., HAMM, K., XU, F., PARISI, M., LARUE, B., HU, H. W., SPIJKERS, P., GUO, H., SONG, X., LENTING, P. J., VAN NOSTRAND, W. E., AND ZLOKOVIC, B. V. (2004) *NEURON* 43, 333-44.
23. MIZUGUCHI, T., FURUTA, I., WATANABE, Y., TSUKAMOTO, K., TOMITA, H., TSUJIHATA, M., OHTA, T., KISHINO, T., MATSUMOTO, N., MINAKAMI, H., NIIKAWA, N., AND YOSHIURA, K. (2004) *J HUM GENET* 49, 80-6.
24. BOUCHER, P., GOTTHARDT, M., LI, W. P., ANDERSON, R. G., AND HERZ, J. (2003) *SCIENCE* 300, 329-32.
25. TANIMOTO, H., SHIGEMASA, K., TIAN, X., GU, L., BEARD, J. B., SAWASAKI, T., AND O'BRIEN, T. J. (2005) *BR J CANCER* 92, 278-83.
26. KATAOKA, H., TANAKA, H., NAGAIKE, K., UCHIYAMA, S., AND ITOH, H. (2003) *HUM CELL* 16, 1-14.
27. JOHNSON, M. D., OBERST, M. D., LIN, C. Y., AND DICKSON, R. B. (2003) *EXPERT REV MOL DIAGN* 3, 331-8.
28. SANTIN, A. D., CANE, S., BELLONE, S., BIGNOTTI, E., PALMIERI, M., DE LAS CASAS, L. E., ANFOSSI, S., ROMAN, J. J., O'BRIEN, T., AND PECORELLI, S. (2003) *CANCER* 98, 1898-904.
29. OBERST, M., ANDERS, J., XIE, B., SINGH, B., OSSANDON, M., JOHNSON, M., DICKSON, R. B., AND LIN, C. Y. (2001) *AM J PATHOL* 158, 1301-11.
30. LEE, J. W., YONG SONG, S., CHOI, J. J., LEE, S. J., KIM, B. G., PARK, C. S., LEE, J. H., LIN, C. Y., DICKSON, R. B., AND BAE, D. S. (2005) *HUM PATHOL* 36, 626-33.
31. HOANG, C. D., D'CUNHA, J., KRATZKE, M. G., CASMEY, C. E., FRIZELLE, S. P., MADDAUS, M. A., AND KRATZKE, R. A. (2004) *CHEST* 125, 1843-52.
32. SANTIN, A. D., ZHAN, F., BELLONE, S., PALMIERI, M., CANE, S., BIGNOTTI, E., ANFOSSI, S., GOKDEN, M., DUNN, D., ROMAN, J. J., O'BRIEN, T. J., TIAN, E., CANNON, M. J., SHAUGHNESSY, J., JR., AND PECORELLI, S. (2004) *INT J CANCER* 112, 14-25.
33. OBERST, M. D., JOHNSON, M. D., DICKSON, R. B., LIN, C. Y., SINGH, B., STEWART, M., WILLIAMS, A., AL-NAFUSSI, A., SMYTH, J. F., GABRA, H., AND SELLAR, G. C. (2002) *CLIN CANCER RES* 8, 1101-7.
34. NAGAIKE, K., KOHAMA, K., UCHIYAMA, S., TANAKA, H., CHIJIIWA, K., ITOH, H., AND KATAOKA, H. (2004) *CANCER SCI* 95, 728-35.
35. SUZUKI, M., KOBAYASHI, H., KANAYAMA, N., SAGA, Y., LIN, C. Y., DICKSON, R. B., AND TERAO, T. (2004) *J BIOL CHEM* 279, 14899-908.
36. LI, L., YOON, S. O., FU, D. D., ZHANG, X., AND CHOI, Y. S. (2004) *BLOOD* 104, 815-21.
37. LI, L., ZHANG, X., KOVACIC, S., LONG, A. J., BOURQUE, K., WOOD, C. R., AND CHOI, Y. S. (2000) *J. EXP. MED.* 191, 1077-84.
38. POSTINA, R., SCHROEDER, A., DEWACHTER, I., BOHL, J., SCHMITT, U., KOJRO, E., PRINZEN, C., ENDRES, K., HIEMKE, C., BLESSING, M., FLAMEZ, P., DEQUENNE, A., GODAUX, E., VAN LEUVEN, F., AND FAHRENHOLZ, F. (2004) *J. CLIN. INVEST.* 113, 1456-64.
39. POLLACK, A. (2005) *NY TIMES (PRINT)*, C1, C2.
40. IRIE, S., AND TAVASSOLI, M. (1991) *CELL BIOL REV* 25, 317-33, 340-1.
41. BICKEL, U., YOSHIKAWA, T., AND PARDRIDGE, W. M. (2001) *ADV DRUG DELIV REV* 46, 247-79.
42. TSUZUKI, S., MURAI, N., MIYAKE, Y., INOUYE, K., HIRAYASU, H., IWANAGA, T., AND FUSHIKI, T. (2005) *BIOCHEM J* 388, 679-87.
43. OBERST, M. D., WILLIAMS, C. A., DICKSON, R. B., JOHNSON, M. D., AND LIN, C. Y. (2003) *J BIOL CHEM* 278, 26773-9.

44. HUNG, R. J., HSU I A, W., DREILING, J. L., LEE, M. J., WILLIAMS, C. A., OBERST, M. D., DICKSON, R. B., AND LIN, C. Y. (2004) *AM J PHYSIOL CELL PHYSIOL* 286, C1159-69.
45. SIMONOVIC, M., DOLMER, K., HUANG, W., STRICKLAND, D. K., VOLZ, K., AND GETTINS, P. G. (2001) *BIOCHEMISTRY* 40, 15127-34.
46. THOMPSON, J. D., HIGGINS, D. G., AND GIBSON, T. J. (1994) *NUCLEIC ACIDS RES.* 22, 4673-80.
47. RUDENKO, G., HENRY, L., HENDERSON, K., ICHTCHENKO, K., BROWN, M. S., GOLDSTEIN, J. L., AND DEISENHOFER, J. (2002) *SCIENCE* 298, 2353-8.
48. FISHER, C., BEGLOVA, N., AND BLACKLOW, S. C. (2006) *MOL CELL* 22, 277-83.
49. PRINCE, W. S., MCCORMICK, L. M., WENDT, D. J., FITZPATRICK, P. A., SCHWARTZ, K. L., AGUILERA, A. I., KOPPAKA, V., CHRISTIANSON, T. M., VELLARD, M. C., PAVLOFF, N., LEMONTT, J. F., QIN, M., STARR, C. M., BU, G., AND ZANKEL, T. C. (2004) *J. BIOL. CHEM.* 279, 35037-46.
50. WANG, Q. Y., DOLMER, K., HUANG, W., GETTINS, P. G., AND RONG, L. (2001) *J. VIROL.* 75, 2051-8.
51. HUANG, W., DOLMER, K., AND GETTINS, P. G. (1999) *J. BIOL. CHEM.* 274, 14130-6.
52. DOLMER, K., HUANG, W., AND GETTINS, P. G. (2000) *J. BIOL. CHEM.* 275, 3264-9.
53. DOLMER, K., HUANG, W., AND GETTINS, P. G. (1998) *BIOCHEMISTRY* 37, 17016-23.
54. VASH, B., PHUNG, N., ZEIN, S., AND DECAMP, D. (1998) *BLOOD* 92, 3277-85.
55. MIGLIORINI, M. M., BEHRE, E. H., BREW, S., INGHAM, K. C., AND STRICKLAND, D. K. (2003) *J. BIOL. CHEM.* 278, 17986-92.
56. ANDERSEN, O. M., CHRISTENSEN, L. L., CHRISTENSEN, P. A., SORENSEN, E. S., JACOBSEN, C., MOESTRUP, S. K., ETZERODT, M., AND THOGERSEN, H. C. (2000) *J. BIOL. CHEM.* 275, 21017-24.
57. ANDERSEN, O. M., SCHWARZ, F. P., EISENSTEIN, E., JACOBSEN, C., MOESTRUP, S. K., ETZERODT, M., AND THOGERSEN, H. C. (2001) *BIOCHEMISTRY* 40, 15408-17.
58. OLSEN, B. R. (1999) *J. CELL BIOL.* 147, 909-12.
59. ANDERSEN, O. M., PETERSEN, H. H., JACOBSEN, C., MOESTRUP, S. K., ETZERODT, M., ANDREASEN, P. A., AND THOGERSEN, H. C. (2001) *BIOCHEM. J.* 357, 289-96.
60. ANDERSEN, O. M., VORUM, H., HONORE, B., AND THOGERSEN, H. C. (2003) *BMC BIOCHEM* 4, 7.
61. HORN, I. R., VAN DEN BERG, B. M., VAN DER MEIJDEN, P. Z., PANNEKOEK, H., AND VAN ZONNEVELD, A. J. (1997) *J. BIOL. CHEM.* 272, 13608-13.
62. ANDERSEN, O. M., CHRISTENSEN, P. A., CHRISTENSEN, L. L., JACOBSEN, C., MOESTRUP, S. K., ETZERODT, M., AND THOGERSEN, H. C. (2000) *BIOCHEMISTRY* 39, 10627-33.
63. MEDVED, L. V., MIGLIORINI, M., MIKHAILENKO, I., BARRIENTOS, L. G., LLINAS, M., AND STRICKLAND, D. K. (1999) *J. BIOL. CHEM.* 274, 717-27.
64. ZHENG, G., BACHINSKY, D. R., STAMENKOVIC, I., STRICKLAND, D. K., BROWN, D., ANDRES, G., AND MCCLUSKEY, R. T. (1994) *J. HISTOCHEM. CYTOCHEM.* 42, 531-42.
65. ORLANDO, R. A., EXNER, M., CZEKAY, R. P., YAMAZAKI, H., SAITO, A., ULLRICH, R., KERJASCHKI, D., AND FARQUHAR, M. G. (1997) *PROC. NATL. ACAD. SCI. U.S.A.* 94, 2368-73.
66. SIDHU, S. S., LOWMAN, H. B., CUNNINGHAM, B. C., AND WELLS, J. A. (2000) *METHODS ENZYMOL.* 328, 333-63.
67. GALKIN, A. V., MULLEN, L., FOX, W. D., BROWN, J., DUNCAN, D., MORENO, O., MADISON, E. L., AND AGUS, D. B. (2004) *PROSTATE* 61, 228-35.

What is claimed is:

1. A cyclic receptor associated protein (RAP) peptide that is less than or about 85 amino acids in length, comprising 50 contiguous amino acids that are at least 70% identical to SEQ ID NO: 97, and which binds to a complement repeat (CR)-containing protein with a binding affinity Kd of about $1\times10^{-8}$ M or less.

2. The cyclic RAP peptide of claim 1 that binds to lipoprotein receptor 1 (LRP1) with a Kd of about $1\times10^{-8}$ M or less.

3. The cyclic RAP peptide of claim 1 comprising a mutation at any one of positions 251, 256, 257, 266, 270, 279, 280, 296 or 305 of mature RAP set out in SEQ ID NO: 95.

4. The cyclic RAP peptide of claim 3 that contains at least one additional mutation within positions 271-319 of mature RAP set out in SEQ ID NO: 95.

5. The cyclic RAP peptide according to claim 3, wherein said mutation is the replacement of an acidic amino acid with a basic amino acid.

6. The cyclic RAP peptide according to claim 3, wherein said mutation is the replacement of a basic amino acid with an acidic amino acid.

7. The cyclic RAP peptide according to claim 3, wherein said mutation is the replacement of an amino acid selected from the group consisting of A, C, D, E, G, I, K, L, M, N, P, Q, R, S, T, and V with an amino acid selected from the group consisting of F, Y, W, and H.

8. The cyclic RAP peptide of claim 1 that binds selectively to matriptase.

9. The cyclic RAP peptide of claim 8 comprising a mutation at any one of positions 251, 256, 257, 266, 270, or 280 of mature RAP set out in SEQ ID NO: 95.

10. The cyclic RAP peptide of claim 1 that binds selectively to a very low density lipoprotein receptor (VLDLR) protein.

11. The cyclic RAP peptide of claim 10 which comprises a mutation at any one of positions 251, 256, 270 or 296 of mature RAP set out in SEQ ID NO: 95.

12. The cyclic RAP peptide of claim 1 that binds selectively to an FDC-8D6 (CD320) protein.

13. The cyclic RAP peptide of claim 12 which comprises a mutation at any one of positions 251, 256, 270, 279 or 305 of mature RAP set out in SEQ ID NO: 95.

14. The cyclic RAP peptide of claim 1 that comprises SEQ ID NO: 97.

15. The cyclic RAP peptide of claim 1 that contains at least one mutation within positions 205-250 of mature RAP set out in SEQ ID NO: 95.

16. The cyclic RAP peptide of claim 1 that comprises a mutation at three or more of the following positions: 213, 217, 226, 230, 232, 239, 241, 242, 246, 247, 249, 250, 251, 256, 257, 261, 266, 267, 268, 270, 273, 279, 280, 287, 290, 294, 296, 297, 298, 305, 308, 311, 312, 313, 314, or 315 of mature RAP set out in SEQ ID NO: 95.

17. The cyclic RAP peptide of claim 1 that comprises a mutation at three or more of the following positions: 217, 249, 251, 256, 257, 266, 270, 294, 296, 297, 305 of mature RAP set out in SEQ ID NO: 95.

18. The cyclic RAP peptide of claim 1 that comprises three or more of the following mutations: S213T, E217K, L226M, H249Y, A230V, S232P, E239G, E246G, E251L, E251K, E251T, E251G, E251P, E251N, E251R, K256R, K256V, K256A, K256I, K256P, K256L, I266F, I266T, H257Y, Q261R, A267V, H268R, K270P, K270D, K270N, K270G, K270E, K270W, L271M, H273Y, D279Y, V283M, R287H, H290Y, H290L, E294V, R296L, T297I, K298R, K305T, K306M, S312F, G313D, E246C, L247G, G280A, L311A, S312C, Q309C, F250C, L308G, L311G, E241C, and I315C of mature RAP set out in SEQ ID NO: 95.

19. A pharmaceutical composition comprising a cyclic RAP peptide of claim 1 in a pharmaceutically acceptable carrier, diluent or excipient.

20. The cyclic RAP peptide of claim 1, wherein the peptide comprises a RAP peptide having the following mutations, H249Y, E251K, K256A and K270E of mature RAP set out in SEQ ID NO: 95.

* * * * *

UNITED STATES PATENT AND TRADEMARK OFFICE
CERTIFICATE OF CORRECTION

PATENT NO. : 8,440,629 B2  Page 1 of 1
APPLICATION NO. : 12/600786
DATED : May 14, 2013
INVENTOR(S) : Starr et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 664 days.

Signed and Sealed this
Eighth Day of September, 2015

Michelle K. Lee
*Director of the United States Patent and Trademark Office*